(12) United States Patent
Mo et al.

(10) Patent No.: US 10,930,857 B2
(45) Date of Patent: Feb. 23, 2021

(54) HETEROCYCLIC COMPOUND AND ORGANIC LIGHT EMITTING DEVICE USING SAME

(71) Applicant: LT MATERIALS CO., LTD., Yongin (KR)

(72) Inventors: Jun-Tae Mo, Osan-si (KR); Yong-Geun Jung, Seoul (KR); Won-Jang Jeong, Hwaseong-si (KR); Dae-Hyuk Choi, Yongin-si (KR); Joo-Dong Lee, Seongnam-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 290 days.

(21) Appl. No.: 15/780,402

(22) PCT Filed: Dec. 1, 2016

(86) PCT No.: PCT/KR2016/014019
§ 371 (c)(1),
(2) Date: May 31, 2018

(87) PCT Pub. No.: WO2017/095157
PCT Pub. Date: Jun. 8, 2017

(65) Prior Publication Data
US 2018/0366652 A1  Dec. 20, 2018

(30) Foreign Application Priority Data
Dec. 1, 2015 (KR) .................... 10-2015-0170140

(51) Int. Cl.
*H01L 51/52* (2006.01)
*H01L 51/50* (2006.01)
(Continued)

(52) U.S. Cl.
CPC ........ *H01L 51/0067* (2013.01); *C07D 215/04* (2013.01); *C07D 401/14* (2013.01);
(Continued)

(58) Field of Classification Search
CPC ............. H01L 51/0081; H01L 51/5004; H01L 51/5012; H01L 51/56; H01L 51/0067;
(Continued)

(56) References Cited

U.S. PATENT DOCUMENTS 4,356,429 A   10/1982  Tang
7,063,901 B2 *  6/2006  Igarashi ................. C09K 11/06
                                                                        204/296
(Continued)

OTHER PUBLICATIONS

"Chemical Abstract Compund, STN express. RN: 181050-60-2 (Sep. 20, 1996), 181050-59-9 (Sep. 20, 1996), 181050-57-7 (Sep. 20, 1996), 181050-54-4 (Sep. 20, 1996), 181050-51-1 (Sep. 20, 1996)", 4 pages.
(Continued)

*Primary Examiner* — Golam Mowla
(74) *Attorney, Agent, or Firm* — Birch, Stewart, Kolasch & Birch, LLP

(57) ABSTRACT

The present application provides a hetero-cyclic compound which may significantly improve the service life, efficiency, electrochemical stability, and thermal stability of an organic light emitting device, and an organic light emitting device in which the hetero-cyclic compound is contained in an organic compound layer.

6 Claims, 19 Drawing Sheets

(51) Int. Cl.
*H01L 51/56* (2006.01)
*H01L 51/00* (2006.01)
*C07D 401/14* (2006.01)
*C07D 471/04* (2006.01)
*C09K 11/06* (2006.01)
*C09B 57/00* (2006.01)
*C07D 215/04* (2006.01)
*C07D 519/00* (2006.01)

(52) U.S. Cl.
CPC ......... *C07D 471/04* (2013.01); *C07D 519/00* (2013.01); *C09B 57/00* (2013.01); *C09K 11/06* (2013.01); *H01L 51/0052* (2013.01); *H01L 51/0054* (2013.01); *H01L 51/0072* (2013.01); H01L 51/001 (2013.01); H01L 51/0081 (2013.01); H01L 51/0085 (2013.01); H01L 51/5004 (2013.01); H01L 51/5012 (2013.01); H01L 51/5056 (2013.01); H01L 51/5072 (2013.01); H01L 51/5088 (2013.01); H01L 51/5092 (2013.01); H01L 51/5096 (2013.01); H01L 51/5278 (2013.01); *H01L 51/56* (2013.01); H01L 2251/552 (2013.01); H01L 2251/558 (2013.01)

(58) Field of Classification Search
CPC ............... H01L 51/001; H01L 51/5278; H01L 51/0052; H01L 51/0085; H01L 51/0054; H01L 51/5088; H01L 51/5056; H01L 51/5096; H01L 51/5092; H01L 51/5072
See application file for complete search history.

(56) References Cited

U.S. PATENT DOCUMENTS

| 10,177,321 | B2* | 1/2019 | Namanga | H01L 51/0085 |
| 2005/0244673 | A1* | 11/2005 | Satoh | C07F 13/005 |
| | | | | 428/690 |
| 2006/0058524 | A1* | 3/2006 | Falcou | C08G 61/02 |
| | | | | 544/294 |
| 2006/0076537 | A1* | 4/2006 | Christou | H01L 51/0084 |
| | | | | 252/301.16 |
| 2007/0043222 | A1* | 2/2007 | Yoshimoto | C07D 339/06 |
| | | | | 549/15 |
| 2007/0148491 | A1* | 6/2007 | Hsu | H01L 51/5012 |
| | | | | 428/690 |

OTHER PUBLICATIONS

Hancock et al., "Block Co-oligomers for Organic Electronics and Optoelectronics: Synthesis, Photophysics, Electroluminescence, and Field-Effect Charge Transport of Oligothiophene-b-oligoquinoline-b-oligothiophene Triblock Co-oligomers", Macromolecules, vol. 41, 2008, pp. 3588-3597.
Hu et al., "Friedländer Approach for the Incorporated of 6-Bromoquinoline into Novel Chelating Ligands", Organic Letters, vol. 5, No. 13, 2003, pp. 2251-2253.
International Search Report for PCT/KR2016/014019 (PCT/ISA/210) dated Mar. 10, 2017.
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Materials, vol. 6, No. 9. 1994, pp. 677-679.

* cited by examiner

[Figure 1]
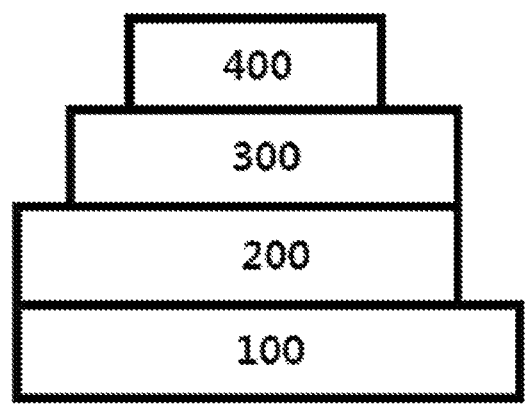
[Figure 2]
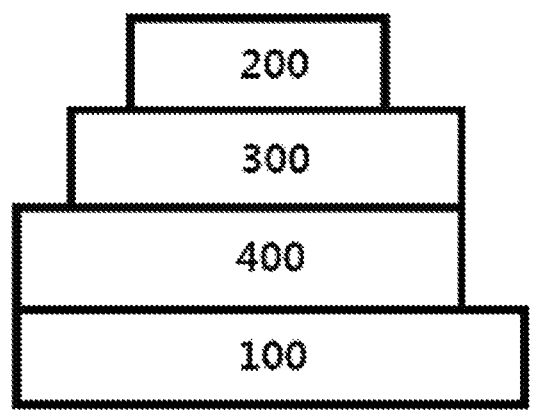

[Figure 3]
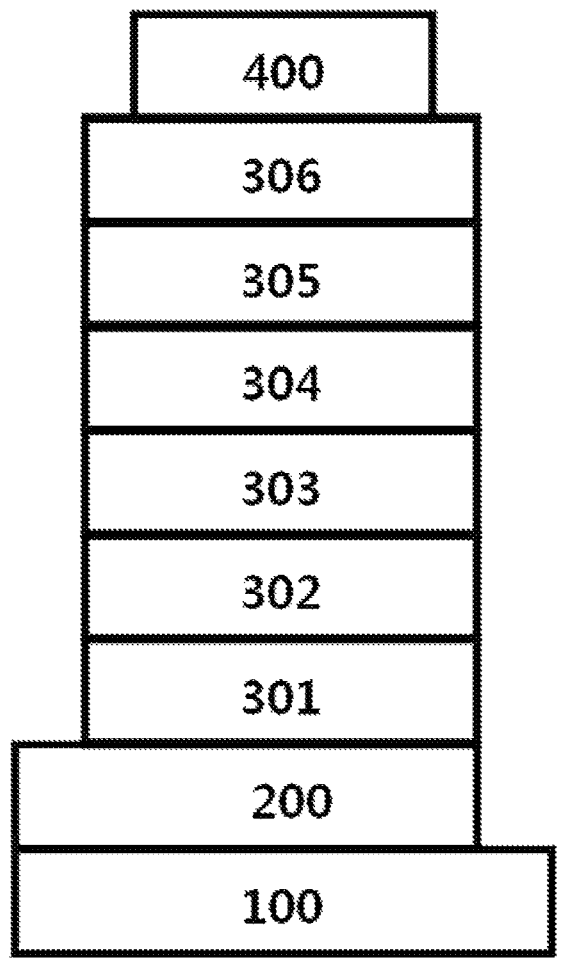

[Figure 4]
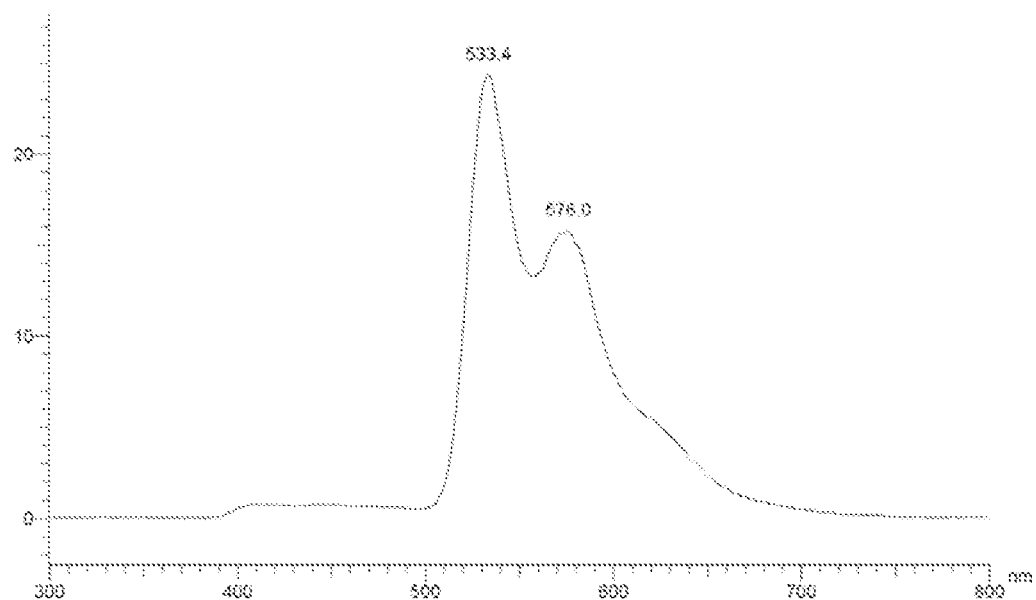
[Figure 5]
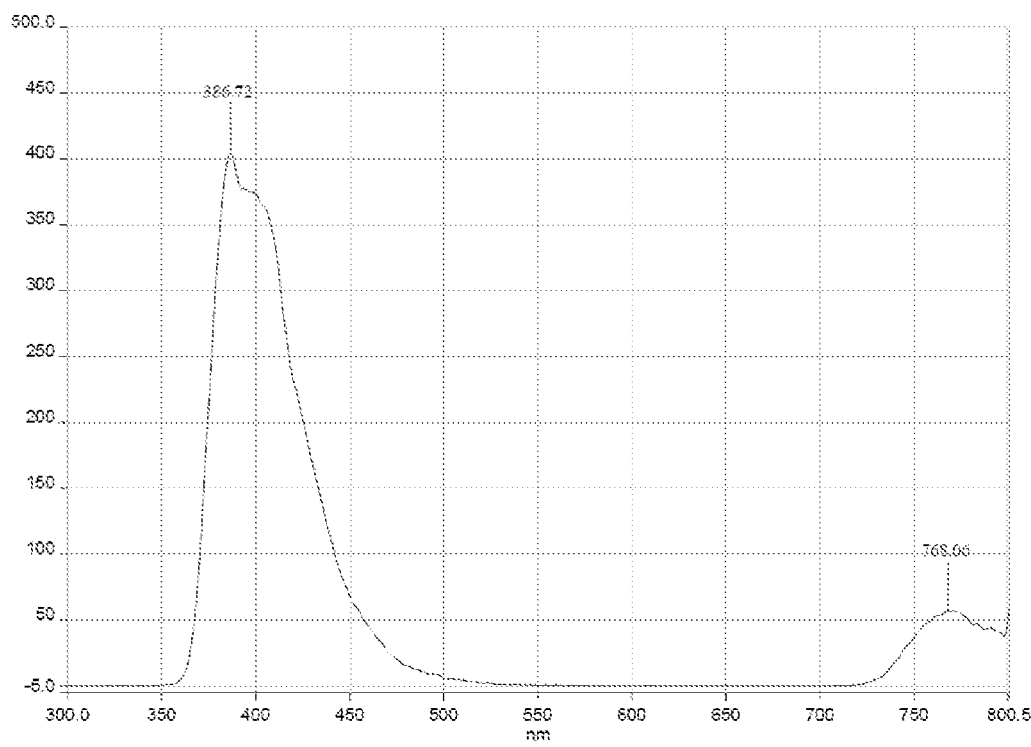

[Figure 6]
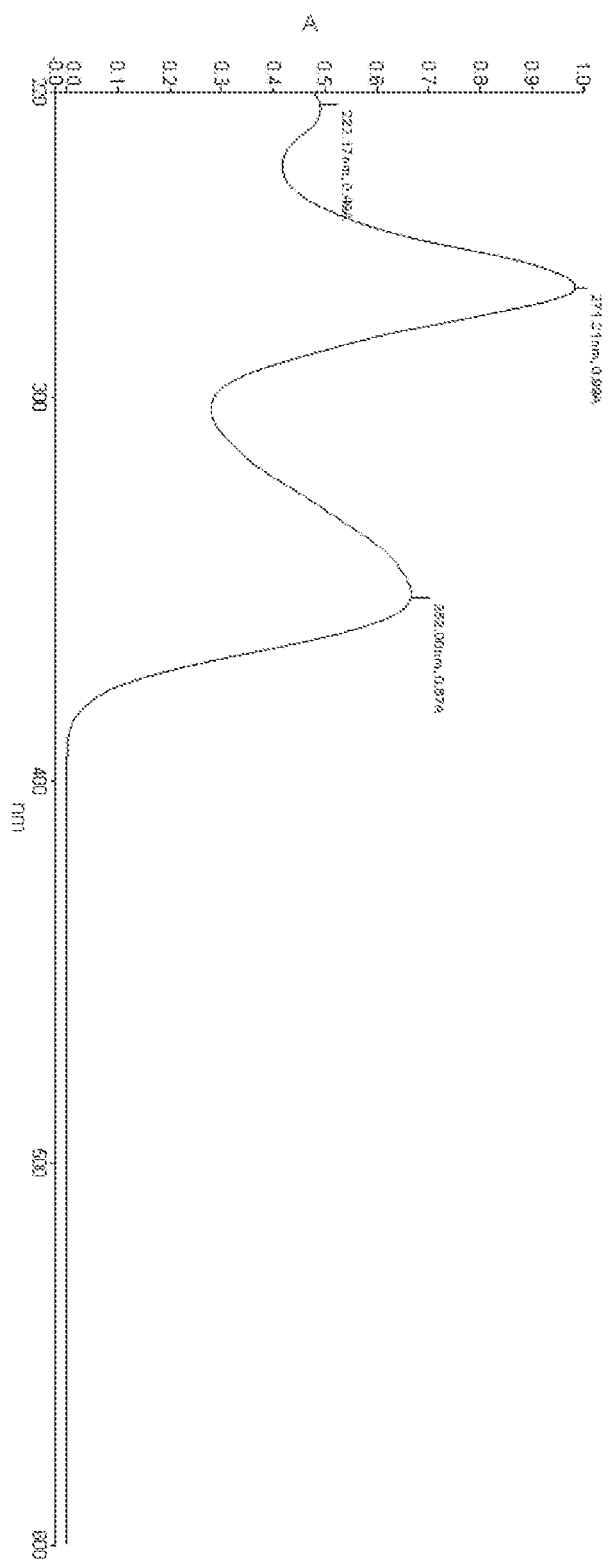

[Figure 7]
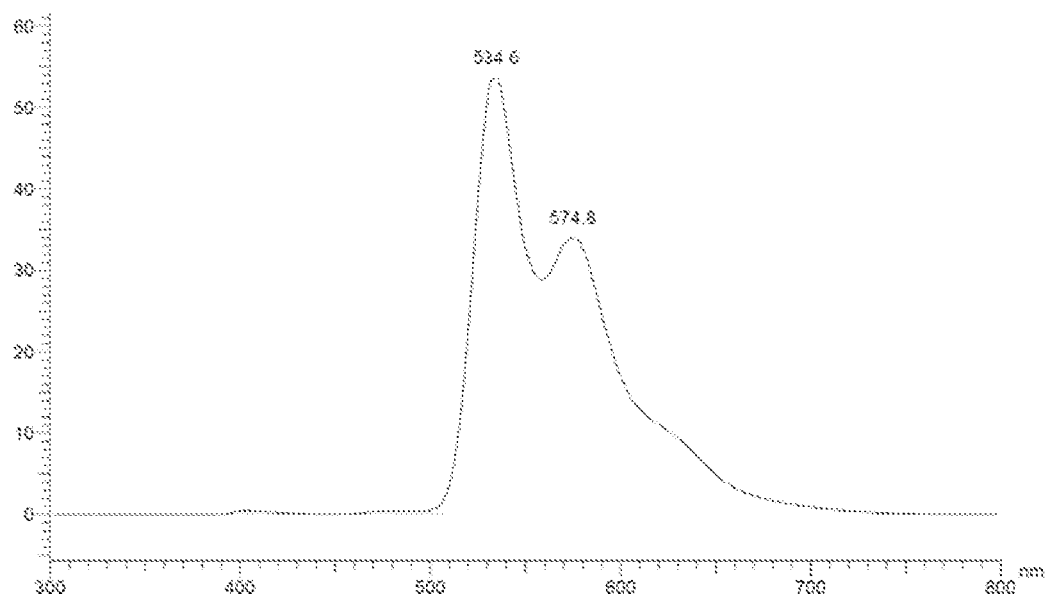

[Figure 8]
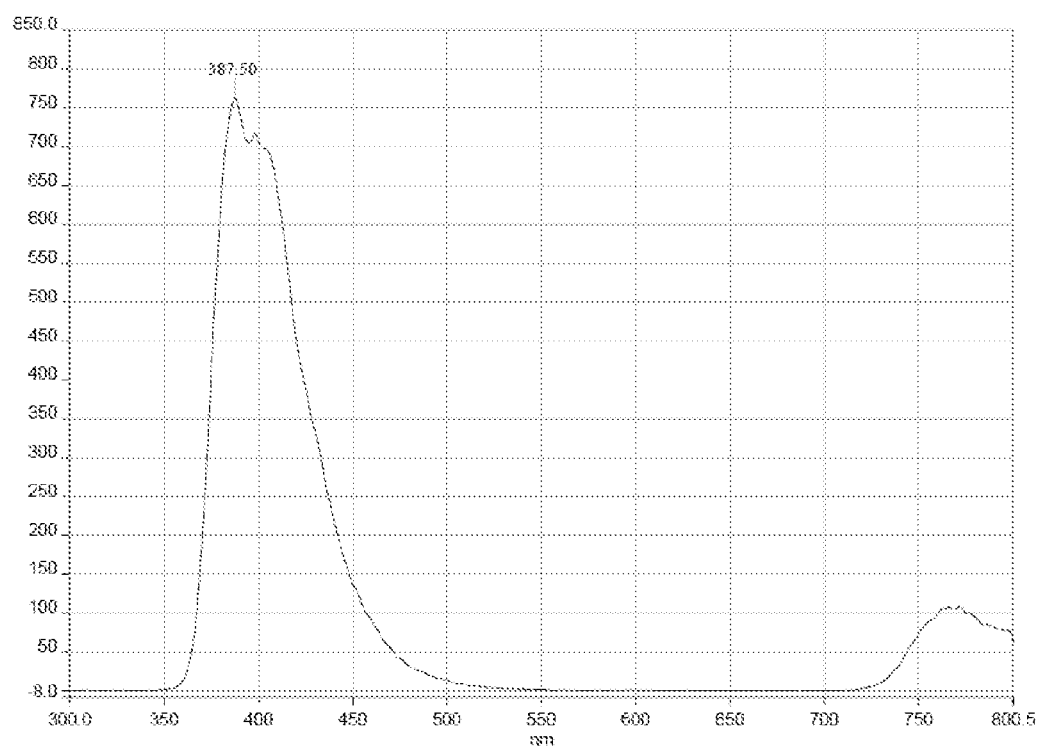

[Figure 9]
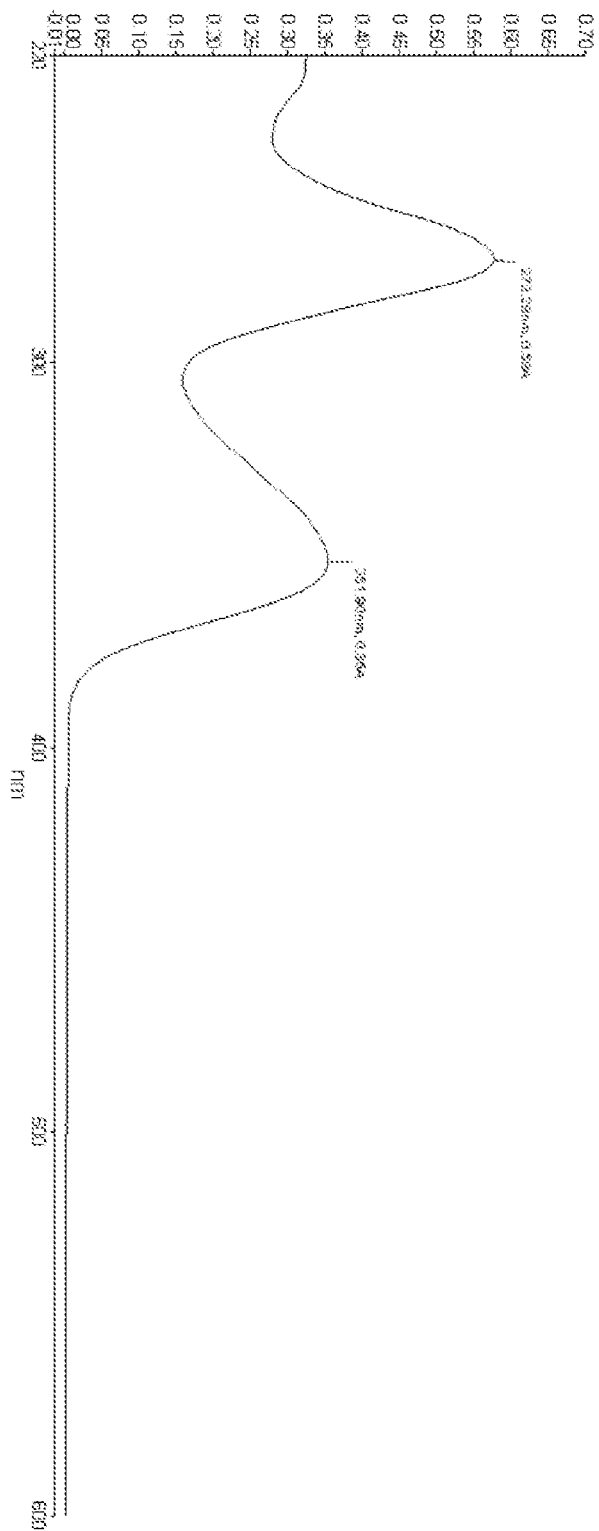

[Figure 10]
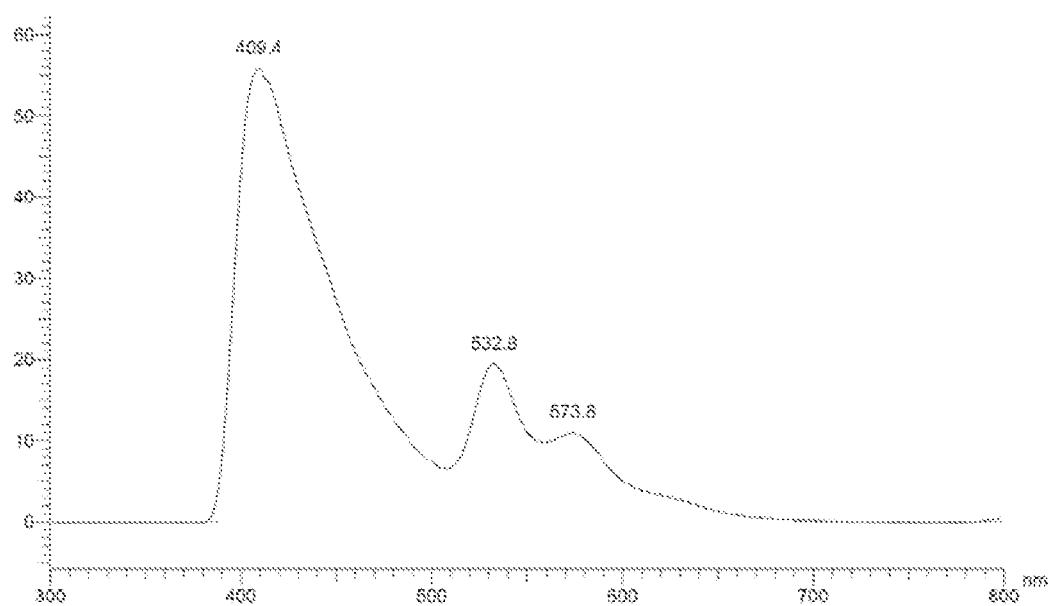

[Figure 11]
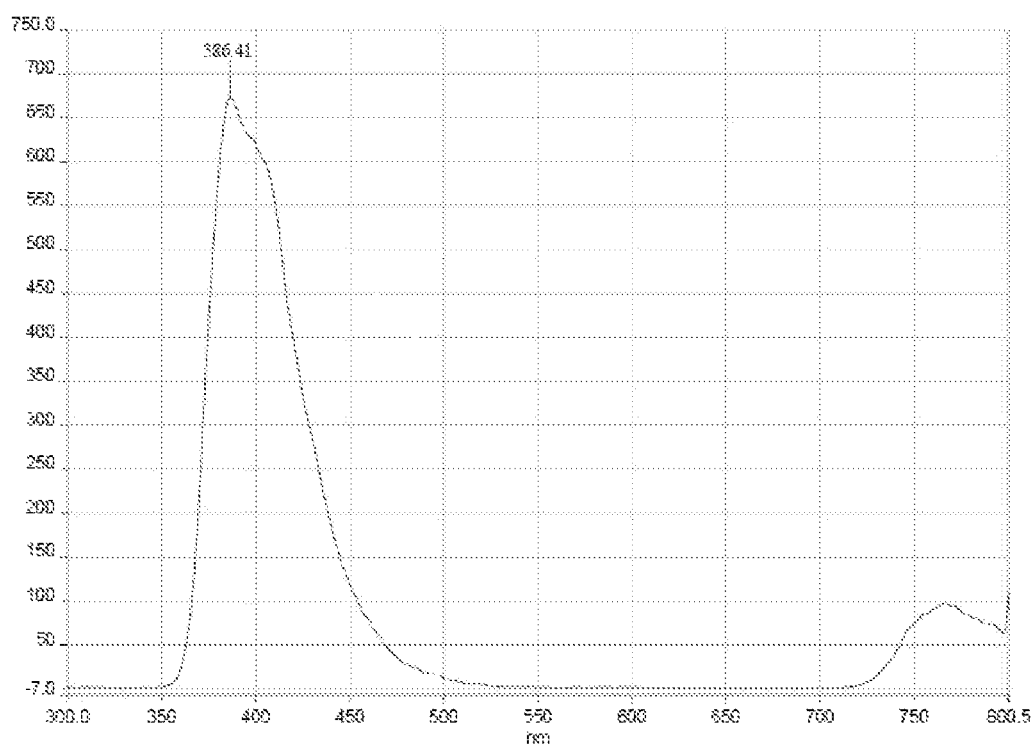

[Figure 12]
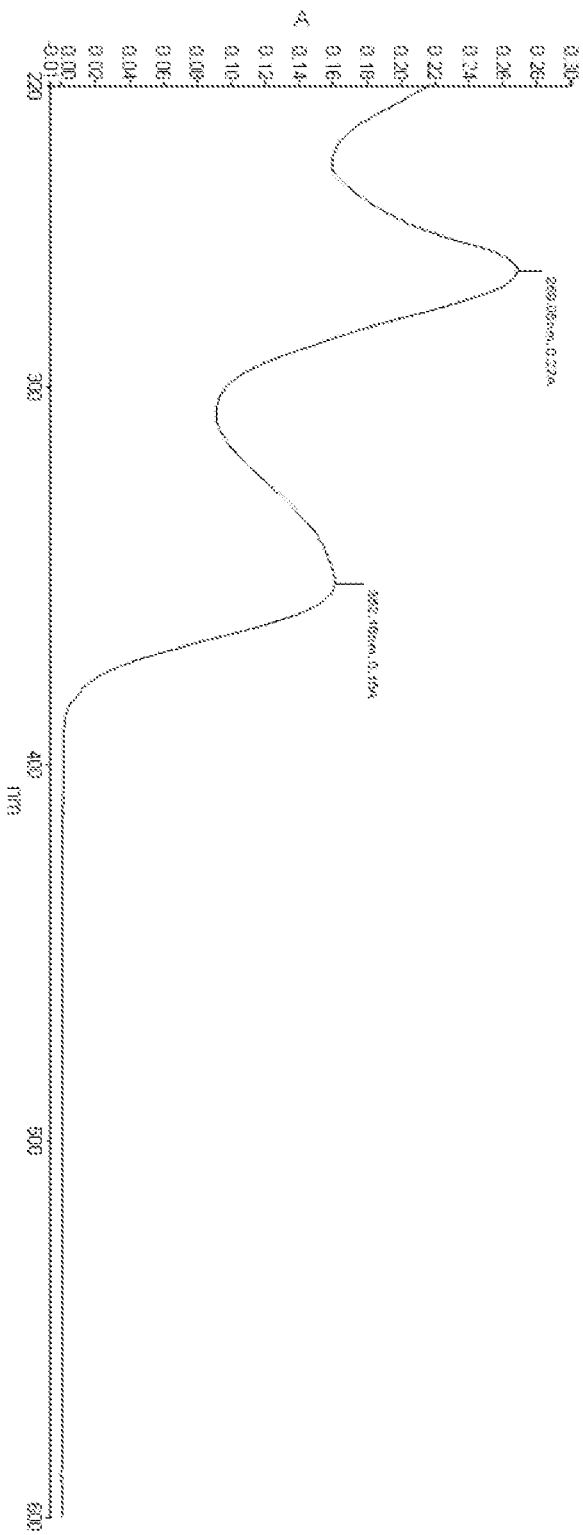

[Figure 13]
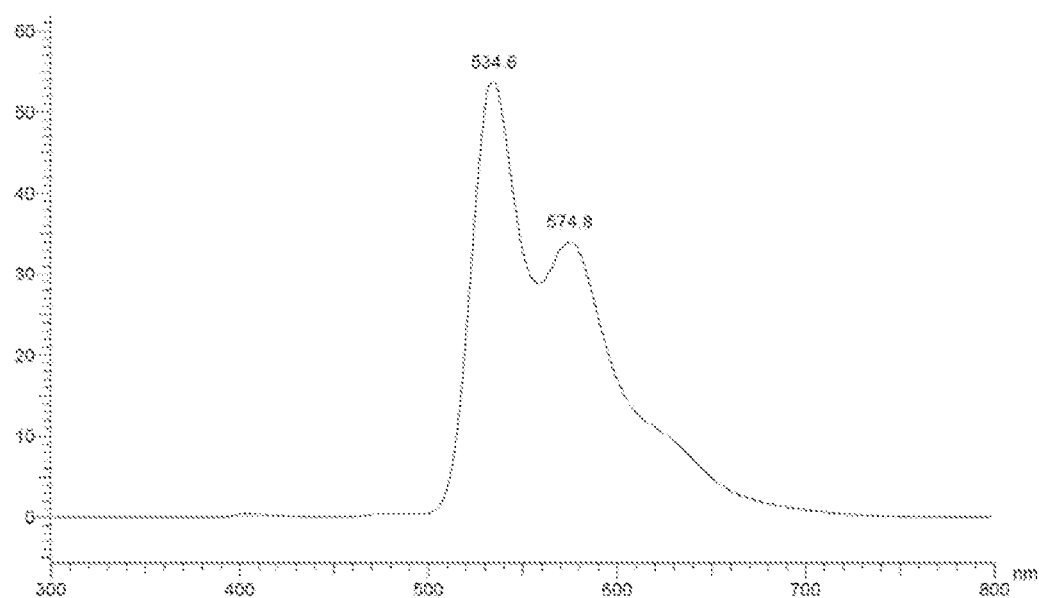

[Figure 14]
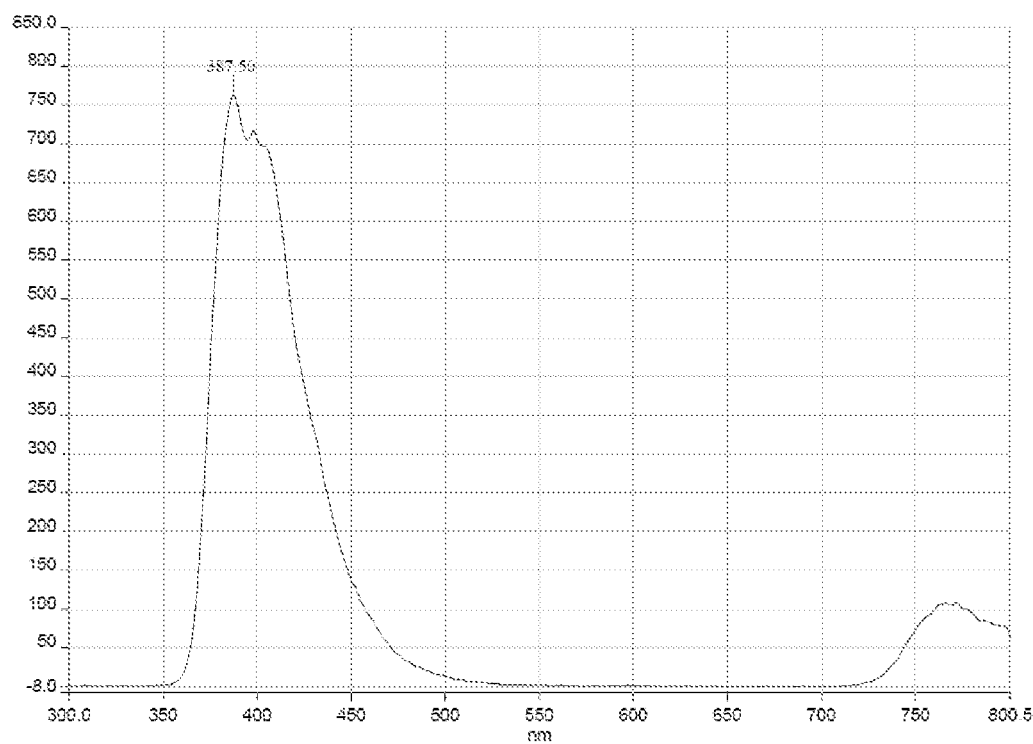

[Figure 15]
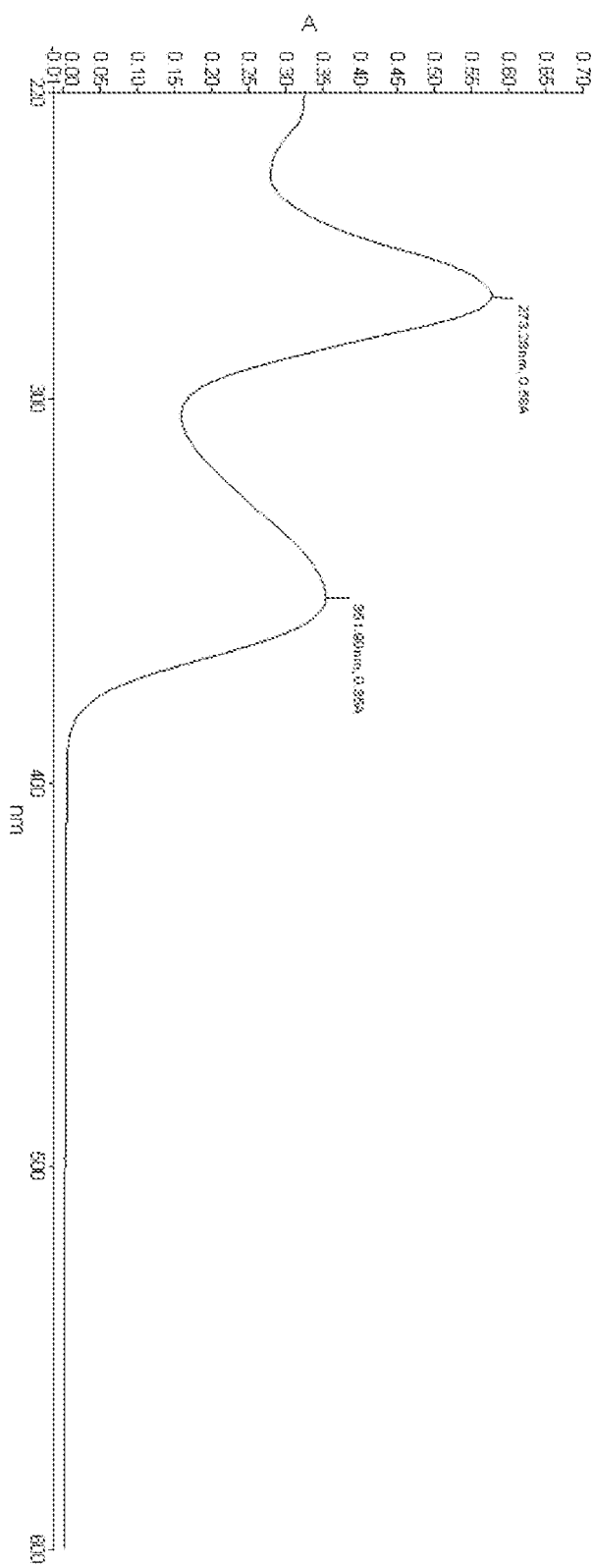

[Figure 16]
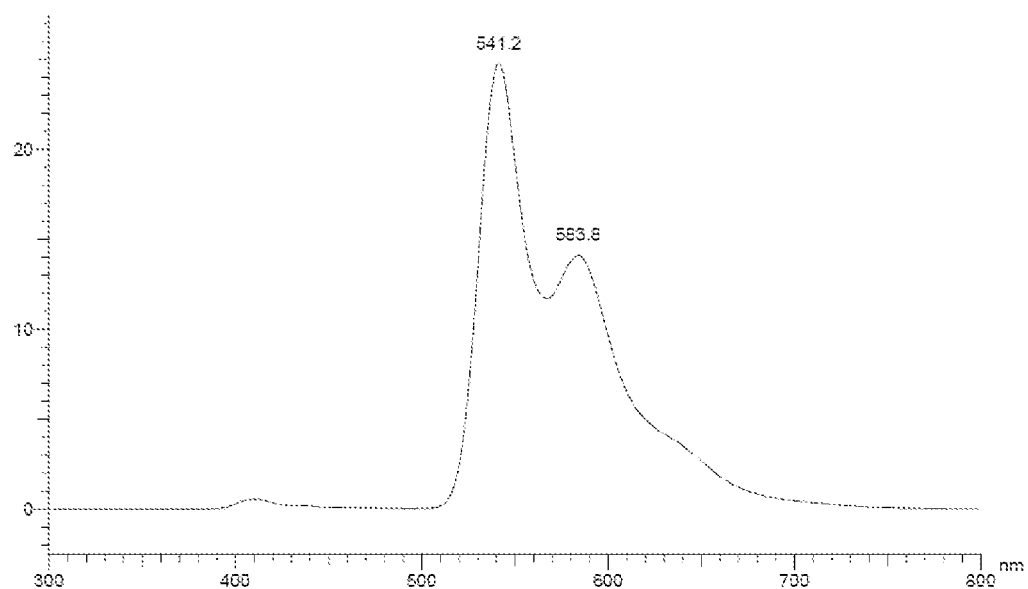

[Figure 17]
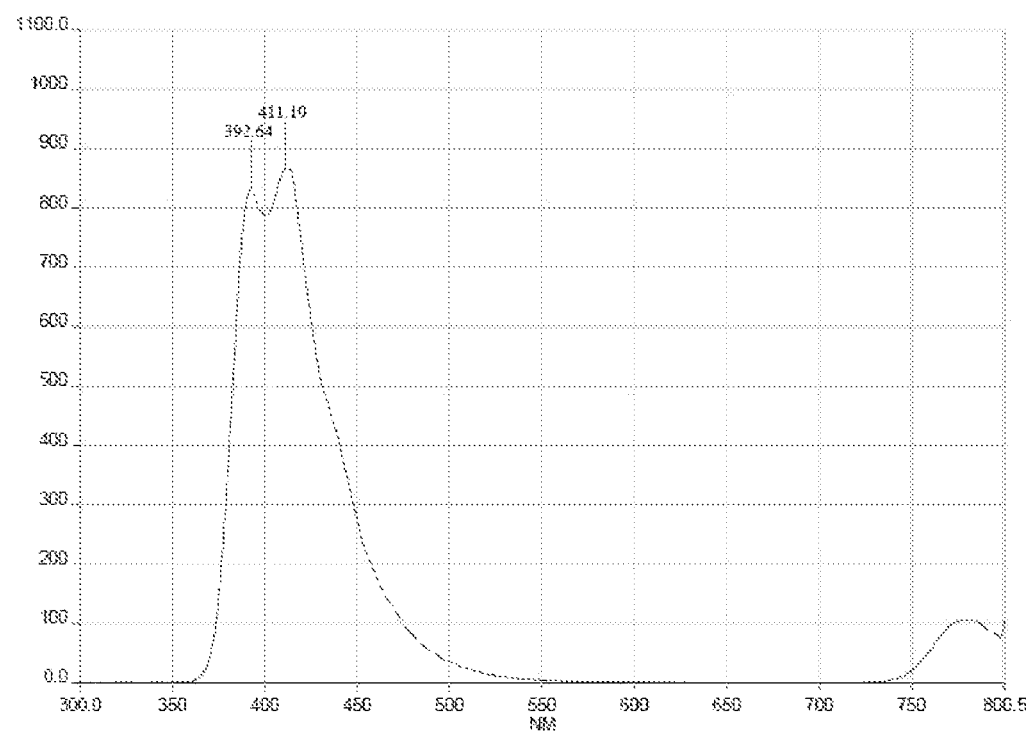

[Figure 18]
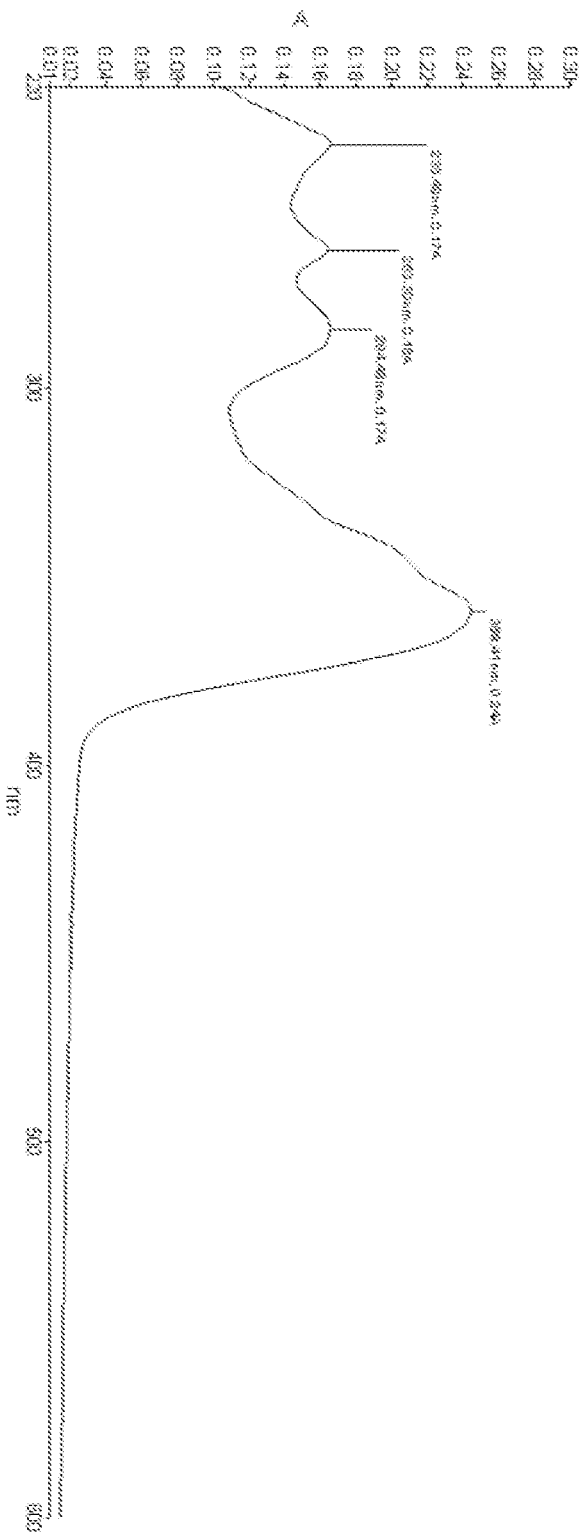

[Figure 19]
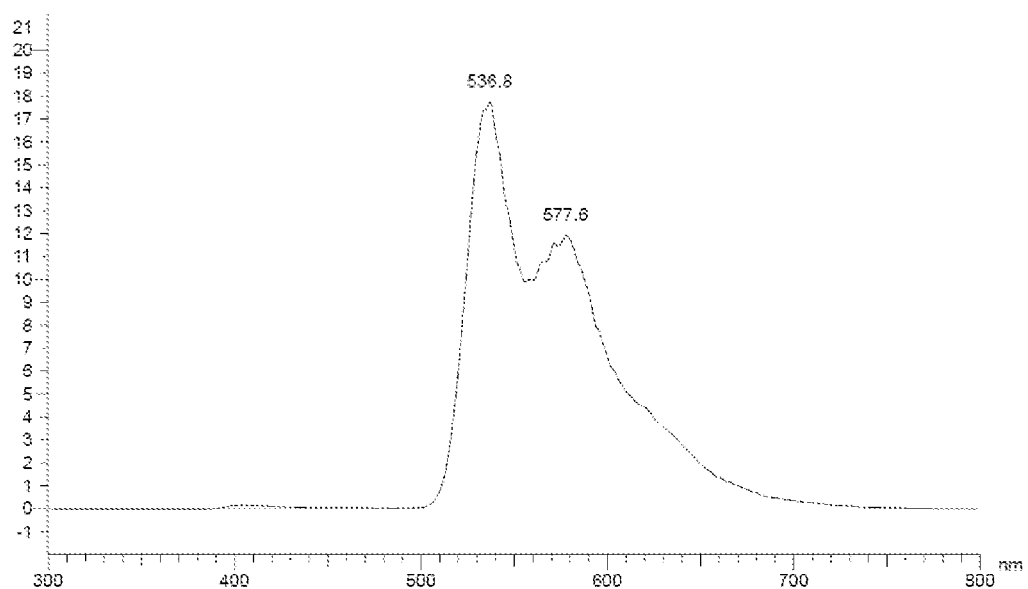

[Figure 20]
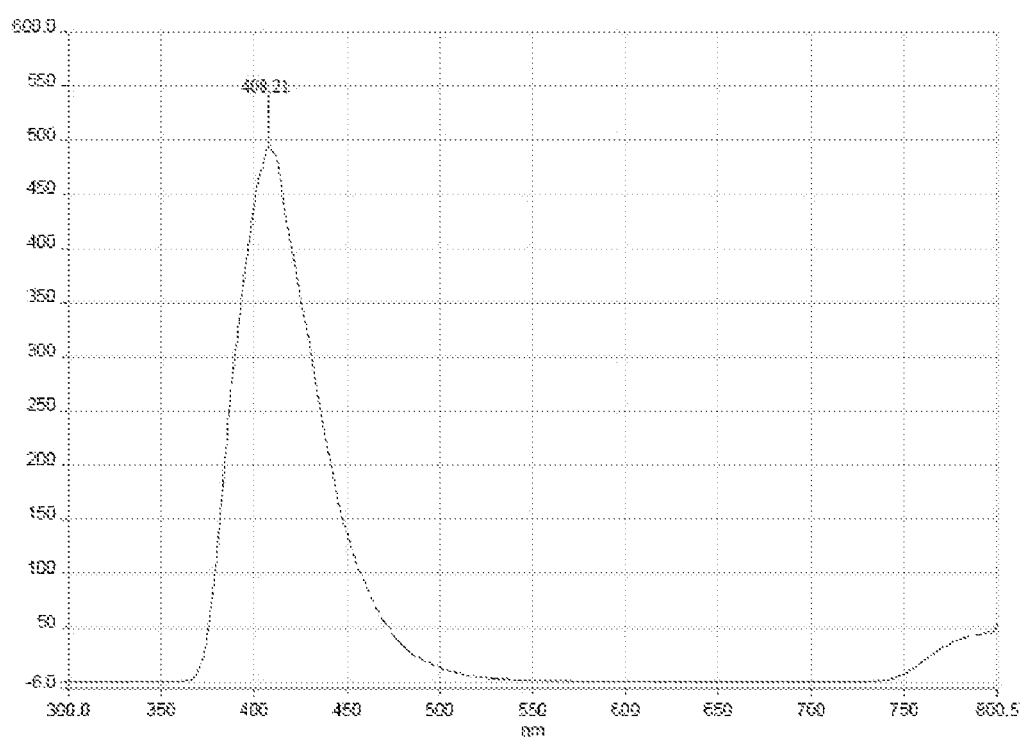

[Figure 21]
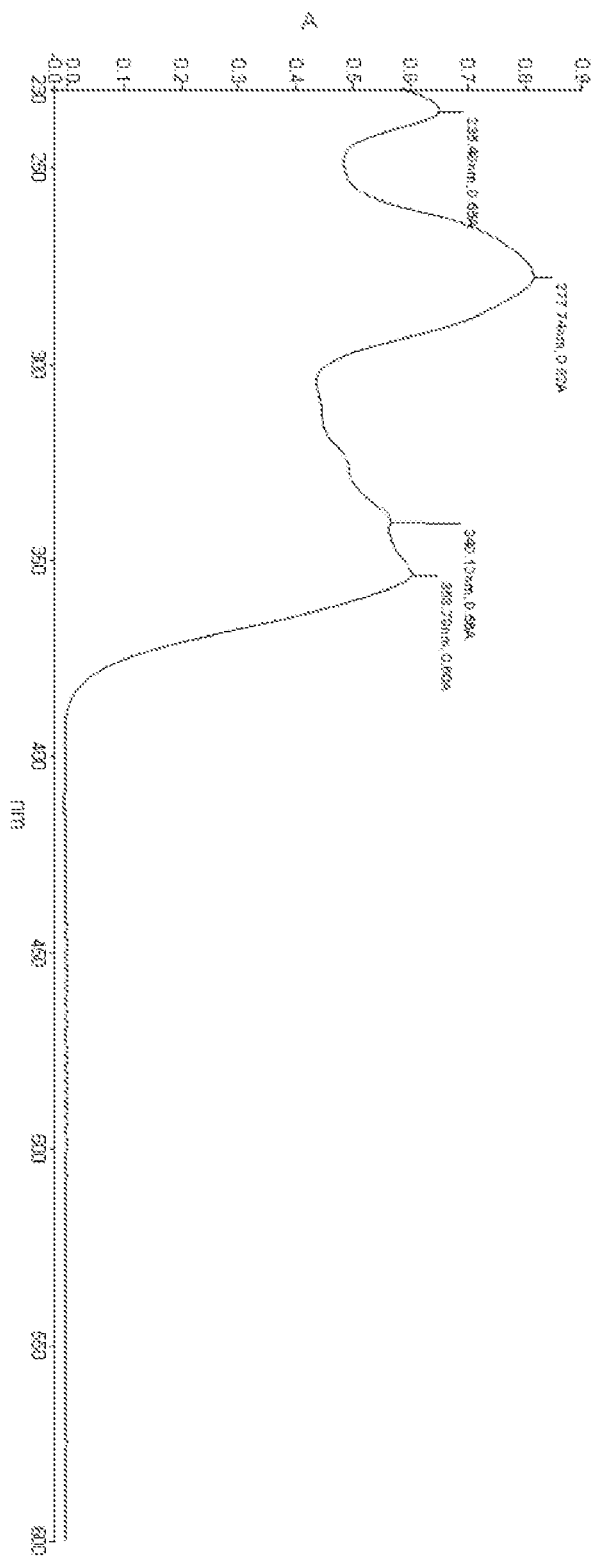

HETEROCYCLIC COMPOUND AND ORGANIC LIGHT EMITTING DEVICE USING SAME

TECHNICAL FIELD

This application claims priority to and the benefit of Korean Patent Application No. 10-2015-0170140 filed in the Korean Intellectual Property Office on Dec. 1, 2015, the entire contents of which are incorporated herein by reference.

The present application relates to a hetero-cyclic compound and an organic light emitting device using the same.

BACKGROUND ART

An electroluminescence device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

DISCLOSURE

Technical Problem

It is necessary to perform studies on an organic light emitting device comprising a compound having a chemical structure, which may satisfy conditions required for a material which is available for the organic light emitting device, for example, appropriate energy levels, electrochemical stability, thermal stability, and the like, and may perform various functions required for the organic light emitting device according to the substituent.

Technical Solution

An exemplary embodiment of the present application provides a hetero-cyclic compound represented by the following Chemical Formula 1:

[Chemical Formula 1]

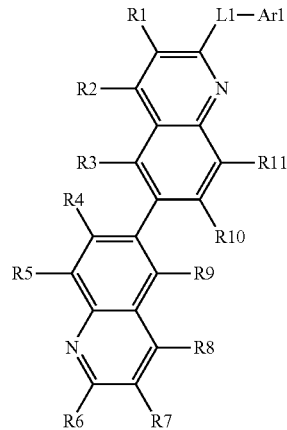

In Chemical Formula 1,

L1 is a direct bond; or a substituted or unsubstituted $C_6$ to $C_{60}$ arylene group, Ar1 comprises at least one of N, O, and S, and is a substituted or unsubstituted $C_2$ to $C_{60}$ heteroaryl group, R1 to R11 are the same as or different from each other, and are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups are bonded to each other to form a substituted or unsubstituted aliphatic or aromatic hydrocarbon ring, and R, R', and R'' are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

Further, another exemplary embodiment of the present application provides an organic light emitting device comprising a positive electrode, a negative electrode, and an organic material layer having one or more layers disposed between the positive electrode and the negative electrode, in which one or more layers of the organic material layer comprise the hetero-cyclic compound.

Advantageous Effects

A hetero-cyclic compound according to an exemplary embodiment of the present application may be used as a material for an organic material layer of an organic light emitting device. The hetero-cyclic compound may be used as a material for a hole injection layer, a hole transporting layer, a light emitting layer, an electron transporting layer, an electron injection layer, a charge producing layer, and the like in an organic light emitting device. In particular, the hetero-cyclic compound represented by Chemical Formula 1 may be used as a material for an electron transporting layer, a hole transporting layer, or a light emitting layer of an organic light emitting device. In addition, when the hetero-cyclic compound represented by Chemical Formula 1 is used for an organic light emitting device, the driving voltage of the device may be lowered, the light efficiency of the device may be improved, and the service life characteristics of the device may be improved due to the thermal stability of the compound.

DESCRIPTION OF DRAWINGS

FIGS. 1 to 3 each are a view schematically illustrating a stacking structure of an organic light emitting device according to an exemplary embodiment of the present application.

FIG. 4 illustrates a measurement graph of LTPL of Compound 6 at a wavelength of 270 nm.

FIG. 5 illustrates a measurement graph of PL of Compound 6 at a wavelength of 271 nm.

FIG. 6 illustrates a measurement graph of UV of Compound 6.

FIG. 7 illustrates a measurement graph of LTPL of Compound 7 at a wavelength of 352 nm.

FIG. 8 illustrates a measurement graph of PL of Compound 7 at a wavelength of 273 nm.

FIG. 9 illustrates a measurement graph of UV of Compound 7.

FIG. 10 illustrates a measurement graph of LTPL of Compound 11 at a wavelength of 270 nm.

FIG. 11 illustrates a measurement graph of PL of Compound 11 at a wavelength of 270 nm.

FIG. 12 illustrates a measurement graph of UV of Compound 11.

FIG. 13 illustrates a measurement graph of LTPL of Compound 12 at a wavelength of 352 nm.

FIG. 14 illustrates a measurement graph of PL of Compound 12 at a wavelength of 273 nm.

FIG. 15 illustrates a measurement graph of UV of Compound 12.

FIG. 16 illustrates a measurement graph of LTPL of Compound 13 at a wavelength of 359 nm.

FIG. 17 illustrates a measurement graph of PL of Compound 13 at a wavelength of 284 nm.

FIG. 18 illustrates a measurement graph of UV of Compound 13.

FIG. 19 illustrates a measurement graph of LTPL of Compound 16 at a wavelength of 354 nm.

FIG. 20 illustrates a measurement graph of PL of Compound 16 at a wavelength of 354 nm.

FIG. 21 illustrates a measurement graph of UV of Compound 16.

EXPLANATION OF REFERENCE NUMERALS AND SYMBOLS

100: Substrate
200: Positive electrode
300: Organic material layer
301: Hole injection layer
302: Hole transporting layer
303: Light emitting layer
304: Hole blocking layer
305: Electron transporting layer
306: Electron injection layer
400: Negative electrode

BEST MODE

Hereinafter, the present application will be described in detail.

A hetero-cyclic compound according to an exemplary embodiment of the present application is represented by Chemical Formula 1. More specifically, the hetero-cyclic compound represented by Chemical Formula 1 may be used as a material for an organic material layer of an organic light emitting device by the structural characteristics of the core structure and the substituent as described above.

According to an exemplary embodiment of the present application, Ar1 of Chemical Formula 1 may be represented by any one of the following Chemical Formulae 2 to 6.

[Chemical Formula 2]

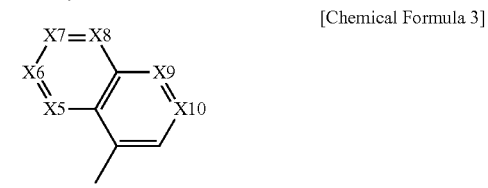

[Chemical Formula 3]

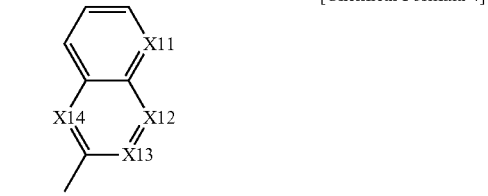

[Chemical Formula 4]

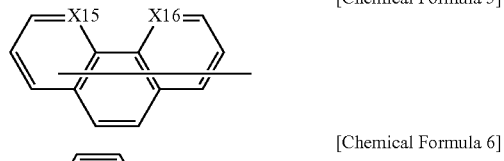

[Chemical Formula 5]

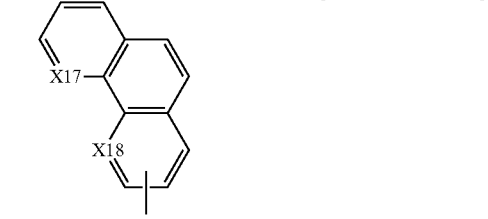

[Chemical Formula 6]

In Chemical Formulae 2 to 6, at least one of X1 to X4 is N, O, or S, and the others are CR12, at least one of X5 to X10 is N, O, or S, and the others are CR13, at least one of X11 to X14 is N, O, or S, and the others are CR14, at least one of X51 and X16 is N, O, or S, and the other is CR15, at least one of X17 and X18 is N, O, or S, and the other is CR16, R12 to R16 are the same as or different from each other, and are each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group which is unsubstituted or substituted with a $C_1$ to $C_{20}$ alkyl group, a substituted or unsubstituted $C_6$ to $C_{60}$ aryl group, or a $C_2$ to $C_{60}$ heteroaryl group, or two or more adjacent groups are bonded to each other to form a substituted or unsubstituted aliphatic or aromatic hydrocarbon ring, and R, R', and R" are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to an exemplary embodiment of the present application, R6 of Chemical Formula 1 is -(L2)m-(Z)n, L2 is a substituted or unsubstituted $C_6$ to $C_{60}$ arylene; or a substituted or unsubstituted $C_2$ to $C_{60}$ heteroarylene, Z is a substituted or unsubstituted $C_6$ to $C_{60}$ aryl group; or a substituted or unsubstituted $C_2$ to $C_{60}$ heteroaryl group, m is an integer from 0 to 5, and n is an integer from 1 to 3.

When m and n each are an integer of 2 or more, a plurality of L2 and Z are each the same as or different from each other.

In an exemplary embodiment of the present application, R1 to R5 and R7 to R11 of Chemical Formula 1 may be hydrogen or deuterium.

In the present application, the substituents of Chemical Formula 1 will be more specifically described as follows.

In the present specification, "substituted or unsubstituted" means being unsubstituted or substituted with one or more substituents selected from the group consisting of deuterium; a halogen group; —CN; a $C_1$ to $C_{60}$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R"; —P(=O)RR'; a $C_1$ to $C_{20}$ alkylamine group; a $C_6$ to $C_{60}$ arylamine group; and a $C_2$ to $C_{60}$ heteroarylamine group, being unsubstituted or substituted with a substituent to which two or more substituents among the substituents are bonded, or being unsubstituted or substituted with a substituent to which two or more substituents selected among the substituents are linked. For example, "the substituent to which two or more substituents are linked" may be a biphenyl group. That is, the biphenyl group may also be an aryl group, and may be interpreted as a substituent to which two phenyl groups are linked. The additional substituents may also be additionally substituted. R, R', and R" are the same as or different from each other, and are each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to an exemplary embodiment of the present application, the "substituted or unsubstituted" means being unsubstituted or substituted with one or more substituents selected from the group consisting of deuterium, a halogen group, —CN, SiRR'R", P(=O)RR', a $C_1$ to $C_{20}$ straight or branched alkyl group, a $C_6$ to $C_{60}$ aryl group, and a $C_2$ to $C_{60}$ heteroaryl group, and R, R', and R" are the same as or different from each other, and are each independently hydrogen; deuterium; —CN; a $C_1$ to $C_{60}$ alkyl group which is unsubstituted or substituted with deuterium, a halogen group, —CN, a $C_1$ to $C_{20}$ alkyl group, a $C_6$ to $C_{60}$ aryl group, and a $C_2$ to $C_{60}$ heteroaryl group; a $C_3$ to $C_{60}$ cycloalkyl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group; a $C_6$ to $C_{60}$ aryl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group; or a $C_2$ to $C_{60}$ heteroaryl group which is unsubstituted or substituted with deuterium, halogen, —CN, a $C_1$ to $C_{20}$ alkyl group, a $C_6$ to $C_{60}$ aryl group, and a $C_2$ to $C_{60}$ heteroaryl group.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the halogen may be fluorine, chlorine, bromine or iodine.

In the present specification, the alkyl group comprises a straight-chain or branched-chain having 1 to 60 carbon atoms, and may be additionally substituted with another substituent. The number of carbon atoms of the alkyl group may be 1 to 60, specifically 1 to 40, and more specifically 1 to 20. Specific examples thereof include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group, and the like, but are not limited thereto.

In the present specification, the alkenyl group comprises a straight-chain or branched-chain having 2 to 60 carbon atoms, and may be additionally substituted with another substituent. The number of carbon atoms of the alkenyl group may be 2 to 60, specifically 2 to 40, and more specifically 2 to 20. Specific examples thereof include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group, and the like, but are not limited thereto.

In the present specification, the alkynyl group comprises a straight-chain or branched-chain having 2 to 60 carbon atoms, and may be additionally substituted with another substituent. The number of carbon atoms of the alkynyl group may be 2 to 60, specifically 2 to 40, and more specifically 2 to 20.

In the present specification, the cycloalkyl group comprises a monocycle or polycycle having 3 to 60 carbon atoms, and may be additionally substituted with another substituent. Here, the polycycle means a group in which a cycloalkyl group is directly linked to or fused with another cyclic group. Here, another cyclic group may also be a cycloalkyl group, but may also be another kind of cyclic group, for example, a heterocycloalkyl group, an aryl group, a heteroaryl group, and the like. The number of carbon atoms of the cycloalkyl group may be 3 to 60, specifically 3 to 40, and more specifically 5 to 20. Specific examples thereof include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, the heterocycloalkyl group comprises O, S, Se, N, or Si as a heteroatom, includes a monocycle or polycycle having 2 to 60 carbon atoms, and may be additionally substituted with another substituent. Here, the polycycle means a group in which a heterocycloalkyl group is directly linked to or fused with another cyclic group. Here, another cyclic group may also be a heterocycloalkyl group, but may also be another kind of cyclic group, for example, a cycloalkyl group, an aryl group, a heteroaryl group, and the like. The number of carbon atoms of the heterocycloalkyl group may be 2 to 60, specifically 2 to 40, and more specifically 3 to 20.

In the present specification, the aryl group comprises a monocycle or polycycle having 6 to 60 carbon atoms, and may be additionally substituted with another substituent. Here, the polycycle means a group in which an aryl group is directly linked to or fused with another cyclic group. Here, another cyclic group may also be an aryl group, but may also be another kind of cyclic group, for example, a cycloalkyl group, a heterocycloalkyl group, a heteroaryl group, and the like. The aryl group includes a spiro group. The number of carbon atoms of the aryl group may be 6 to 60, specifically 6 to 40, and more specifically 6 to 25. Specific examples of the aryl group include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof, and the like, but are not limited thereto.

In the present specification, the spiro group is a group comprising a spiro structure, and may have 15 to 60 carbon atoms. For example, the spiro group may include a structure in which a 2,3-dihydro-1H-indene group or a cyclohexane group is spiro-bonded to a fluorenyl group. Specifically, the spiro group may include any one of the groups of the following structural formulae.

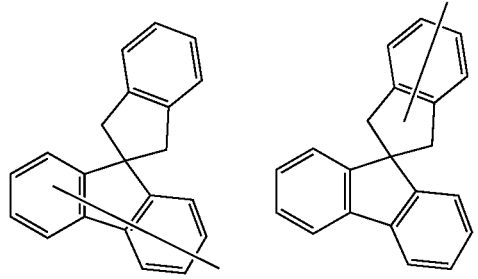

-continued

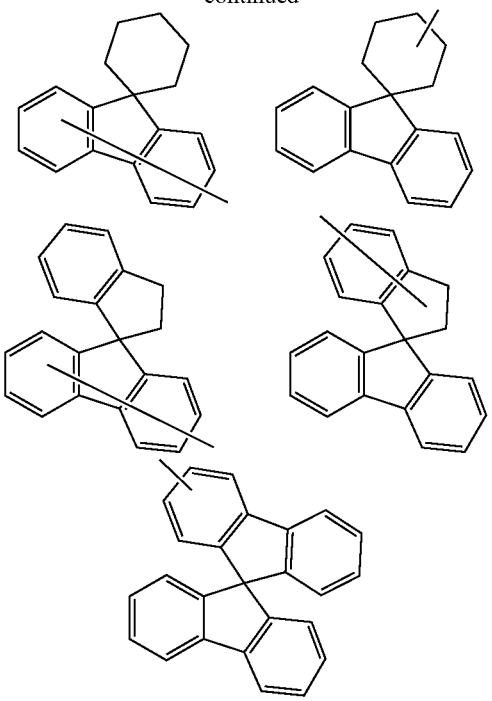

In the present specification, the heteroaryl group comprises S, O, Se, N, or Si as a heteroatom, comprises a monocycle or polycycle having 2 to 60 carbon atoms, and may be additionally substituted with another substituent. Here, the polycycle means a group in which a heteroaryl group is directly linked to or fused with another cyclic group. Here, another cyclic group may also be a heteroaryl group, but may also be another kind of cyclic group, for example, a cycloalkyl group, a heterocycloalkyl group, an aryl group, and the like. The number of carbon atoms of the heteroaryl group may be 2 to 60, specifically 2 to 40, and more specifically 3 to 25. Specific examples of the heteroaryl group comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinozolilyl group, a naphthyridyl group, an acridinyl group, a phenanthridinyl group, an imidazopyridinyl group, a diaza naphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi (dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b] carbazolyl group, an indolinyl group, a 10,11-dihydrodibenzo[b,f]azepin group, a 9,10-dihydroacridinyl group, a phenanthrazinyl group, a phenothiazinyl group, a phthalazinyl group, a naphthylidinyl group, a phenanthrolinyl group, a benzo[c][1,2,5]thiadiazolyl group, a 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group, and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and the number of carbon atoms thereof is not particularly limited, but is preferably 1 to 30. Specific examples of the amine group comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group, and the like, but are not limited thereto.

In the present specification, the arylene group means that there are two bonding positions in an aryl group, that is, a divalent group. The above-described description on the aryl group may be applied to the arylene group, except for a divalent arylene group. Further, the heteroarylene group means that there are two bonding positions in a heteroaryl group, that is, a divalent group. The above-described description on the heteroaryl group may be applied to the heteroarylene group, except for a divalent heteroarylene group.

According to an exemplary embodiment of the present application, Chemical Formula 1 may be represented by any one of the following compounds, but is not limited thereto.

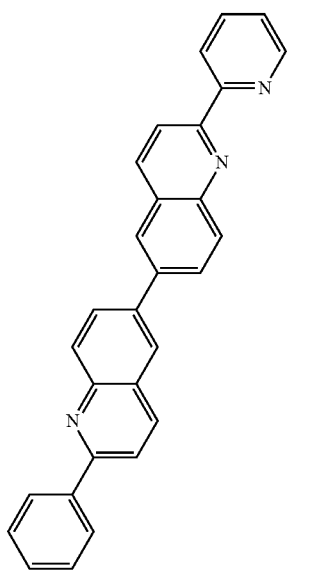

1

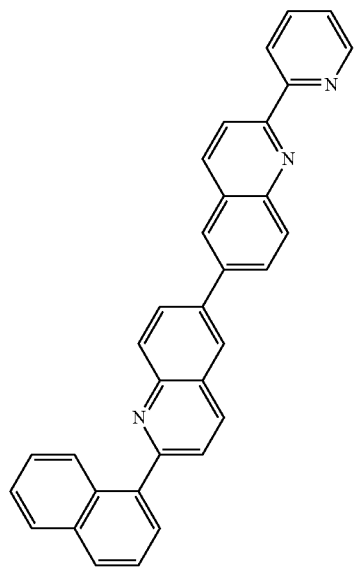

2

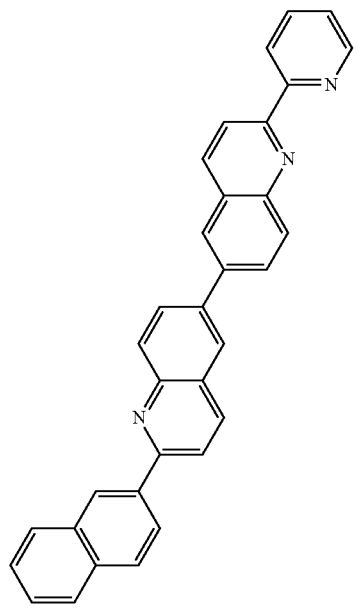

3

4
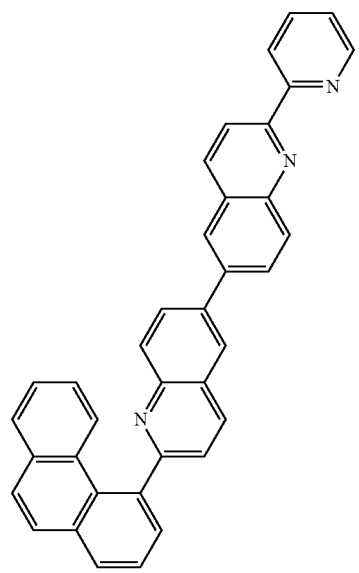
5
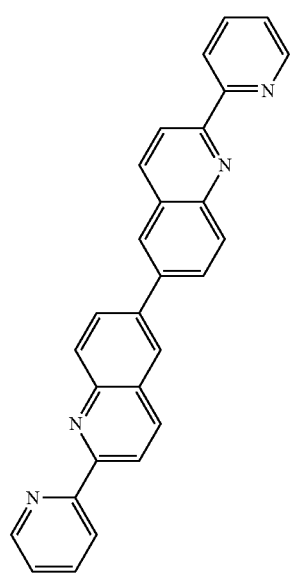
6
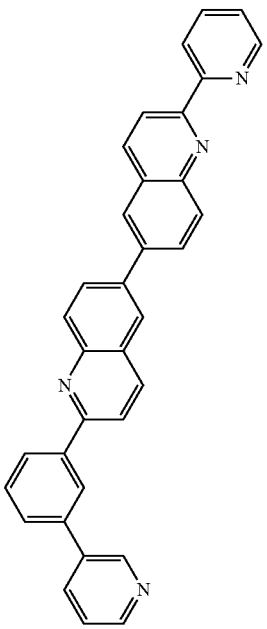
7
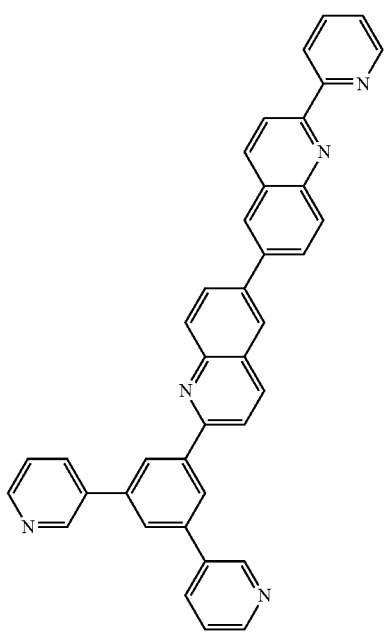

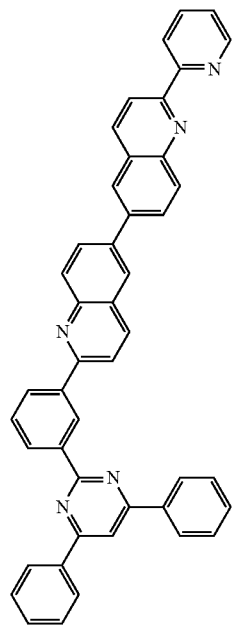
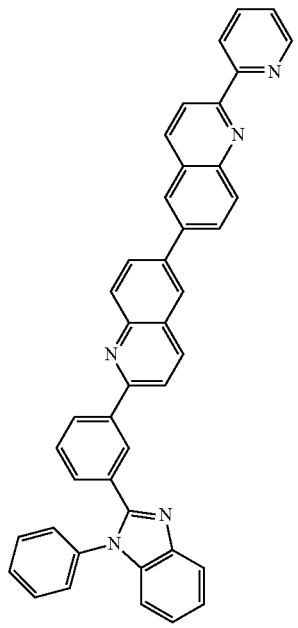

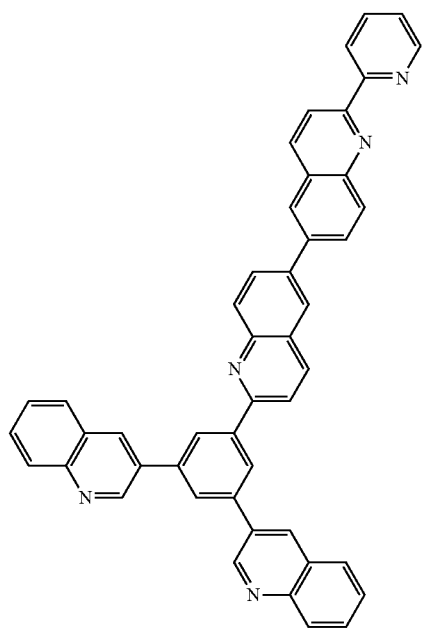
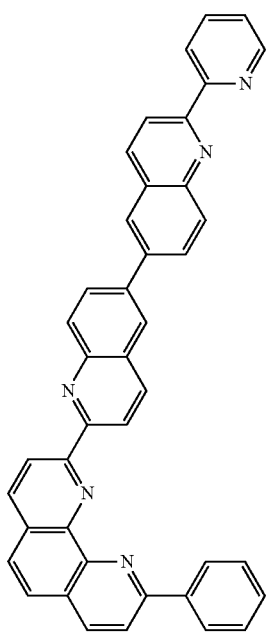
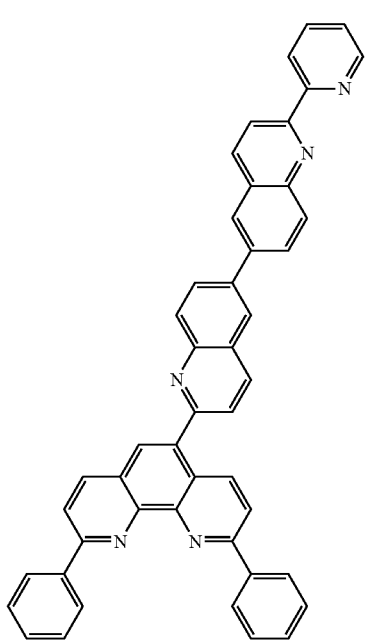

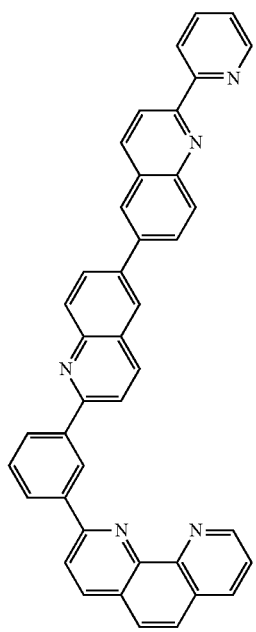
16
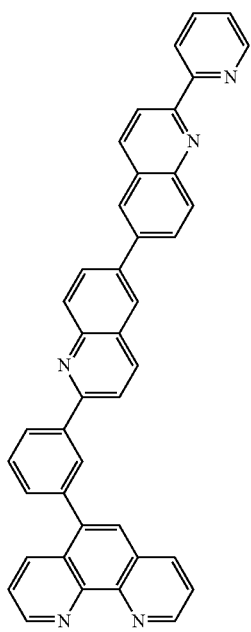
18
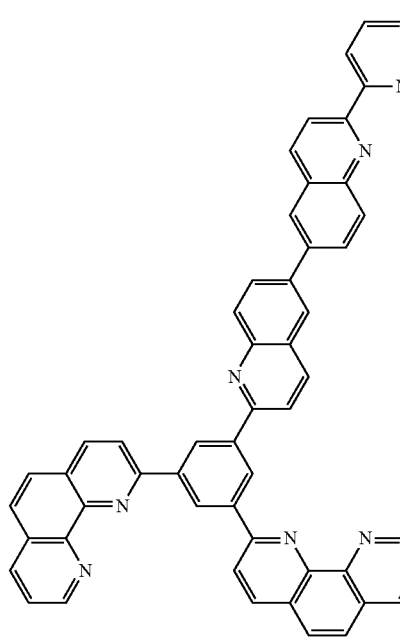
17

20
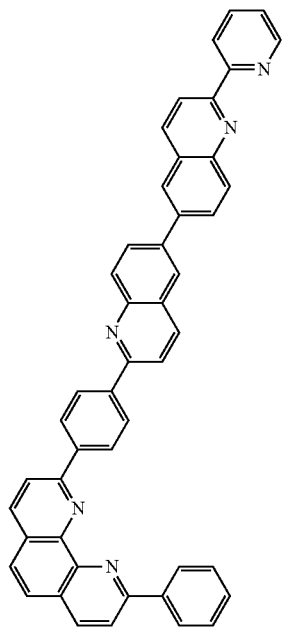
21
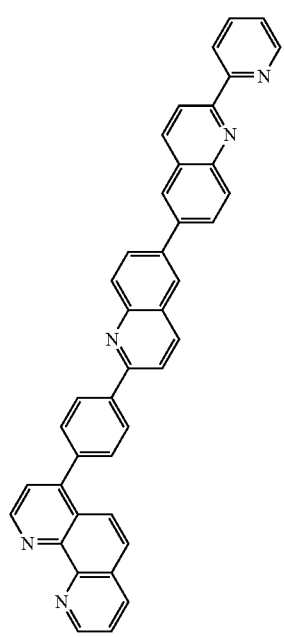
22
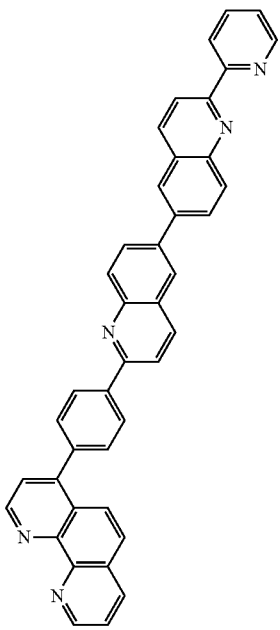
23
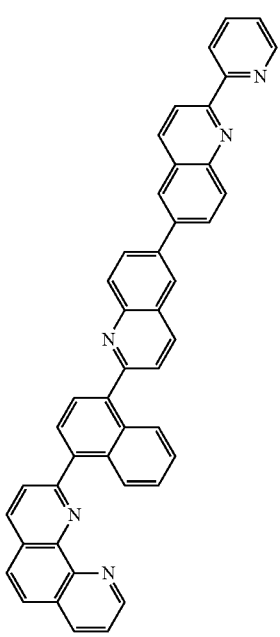

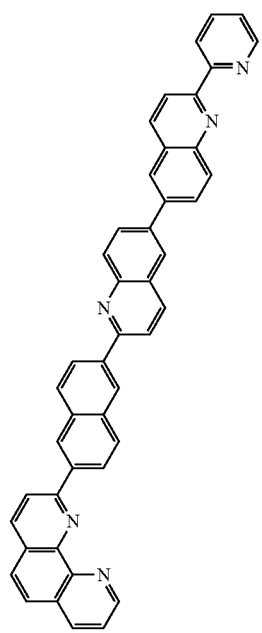
24
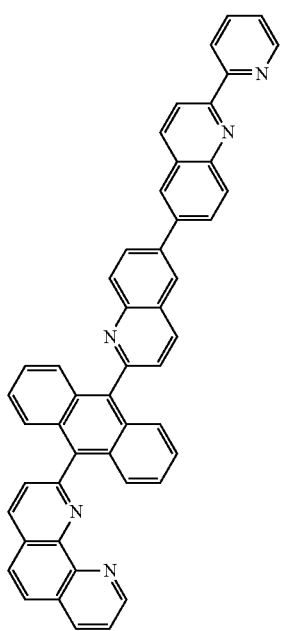
25
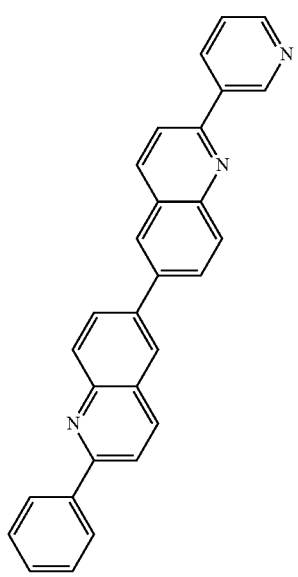
26
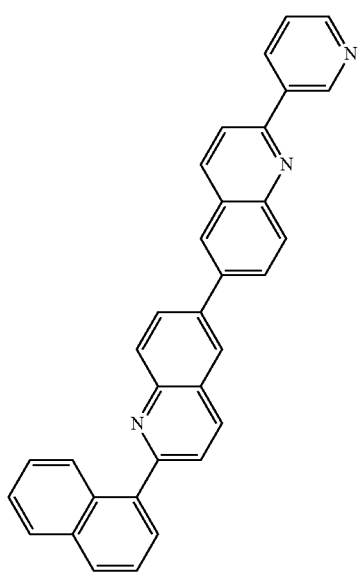
27

28
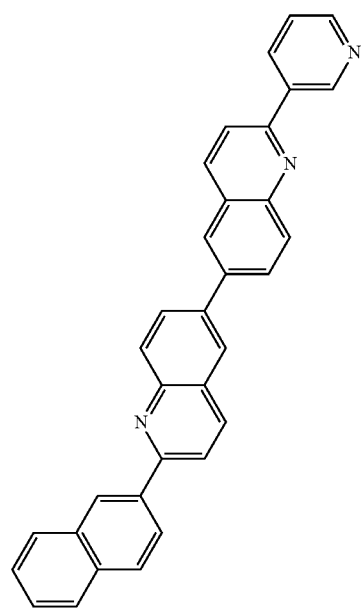
29
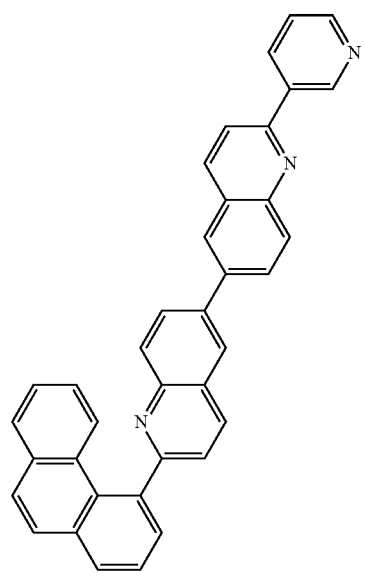
30
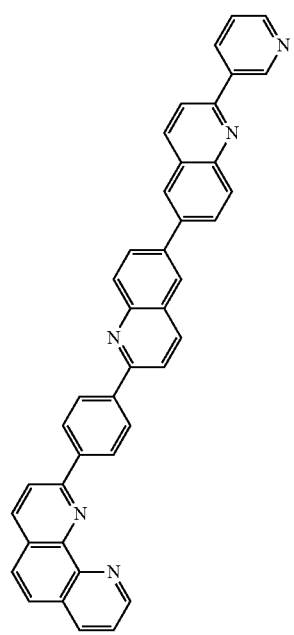
31
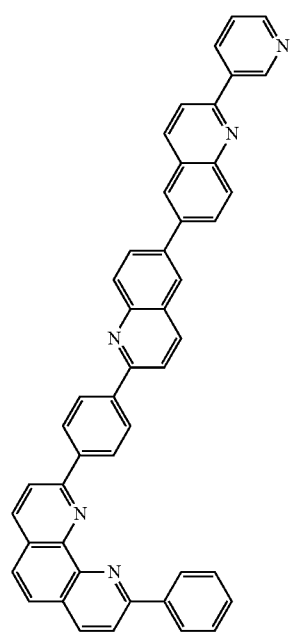

32
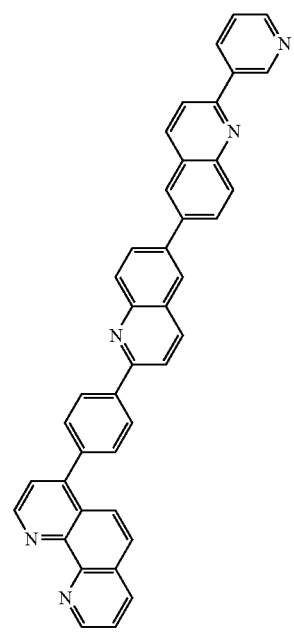
33
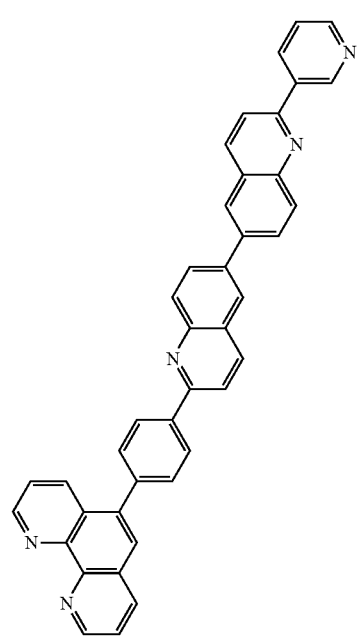
34
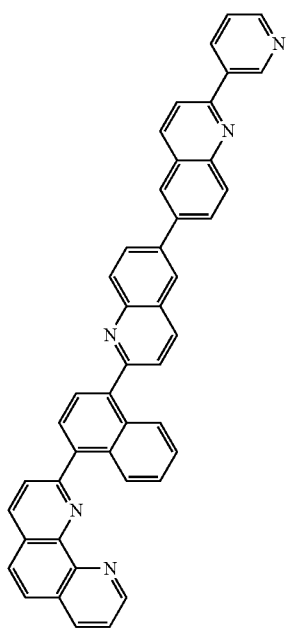
35
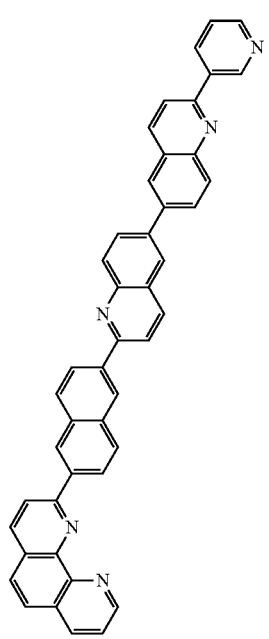

36
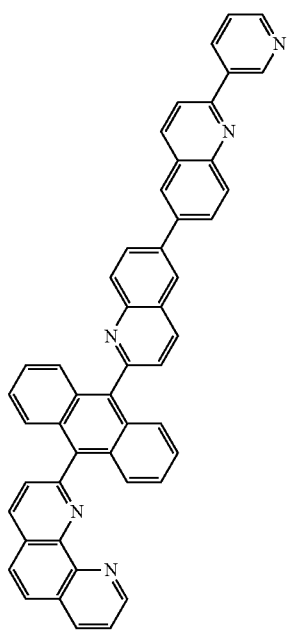
37
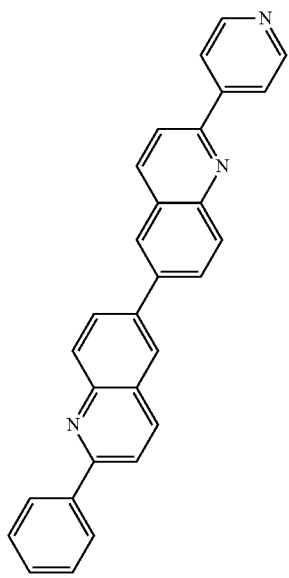
38
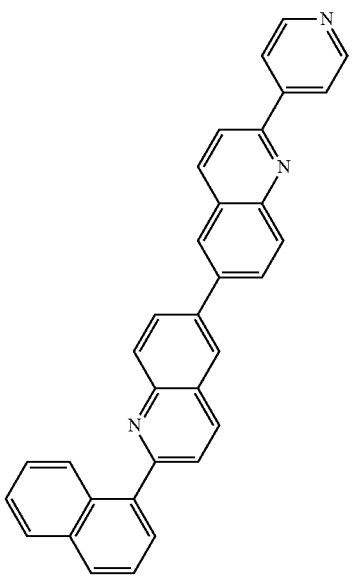
39
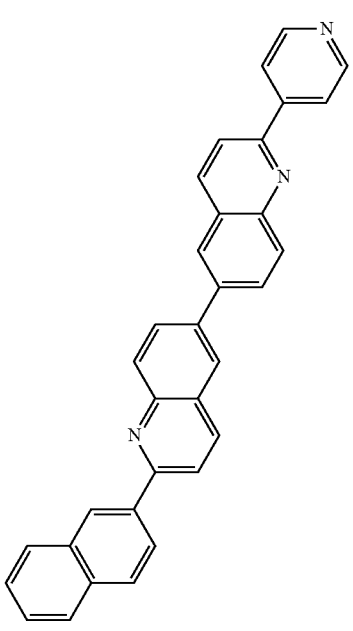

40
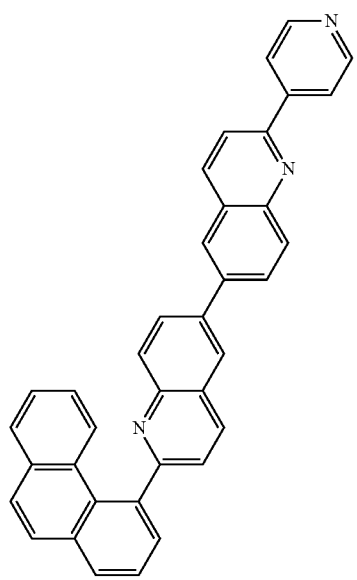
42
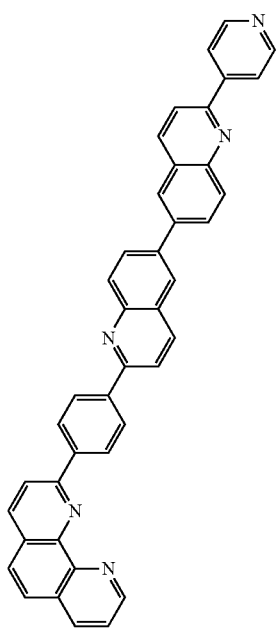
41
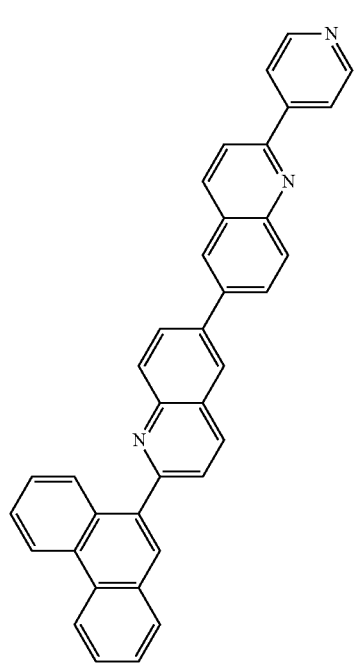
43
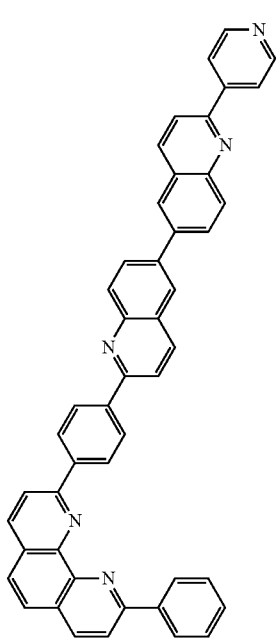

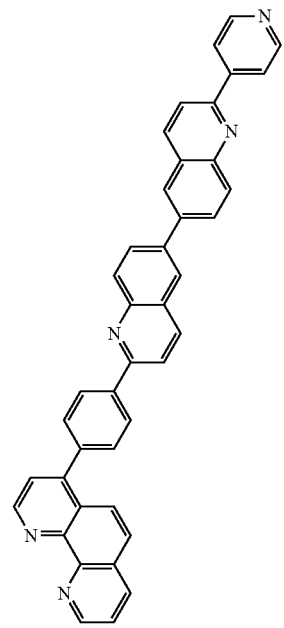
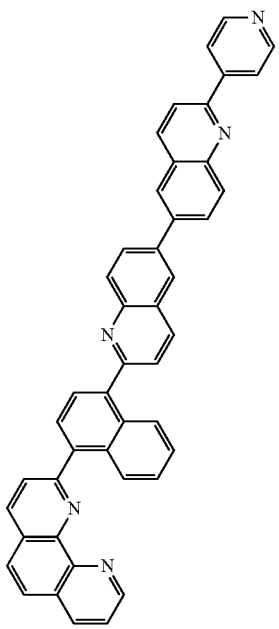
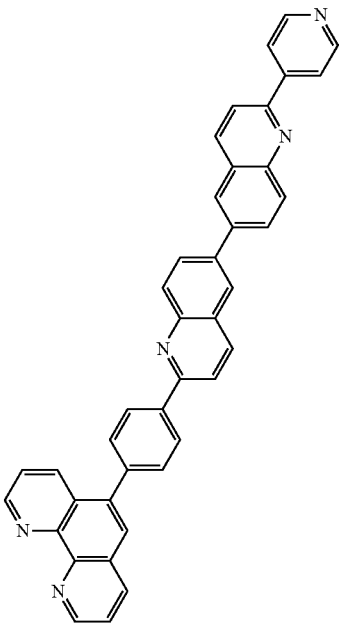
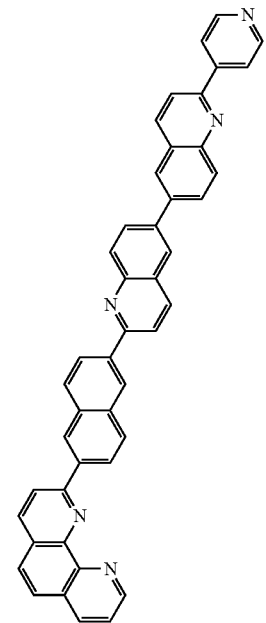

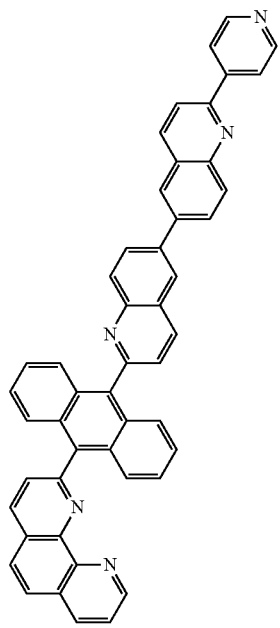
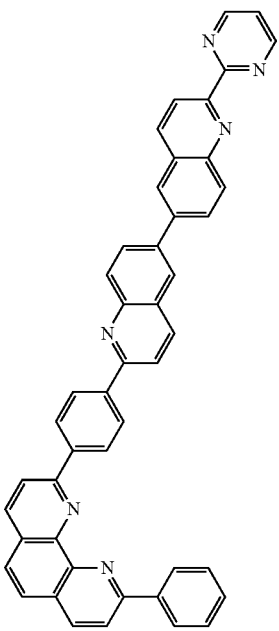

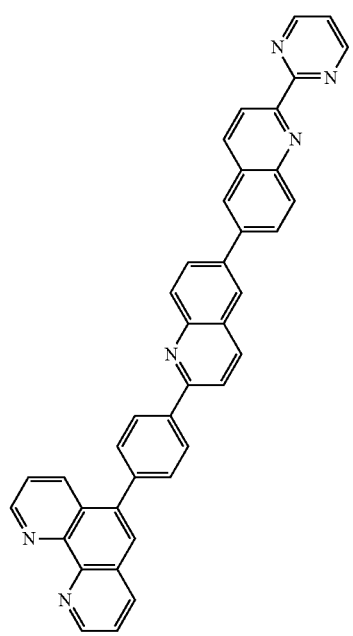
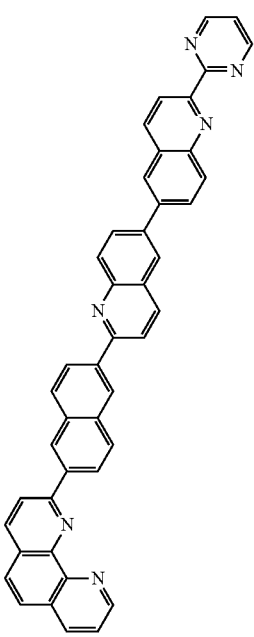

56
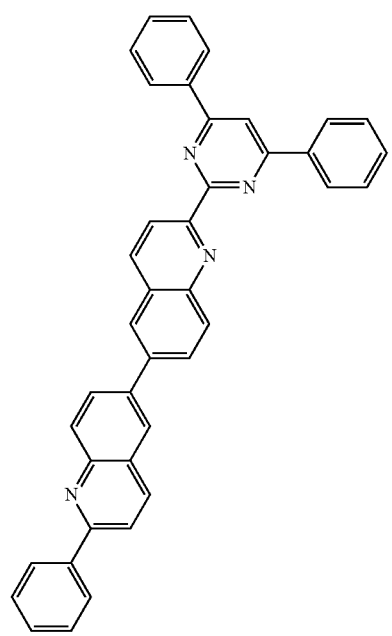
57
58
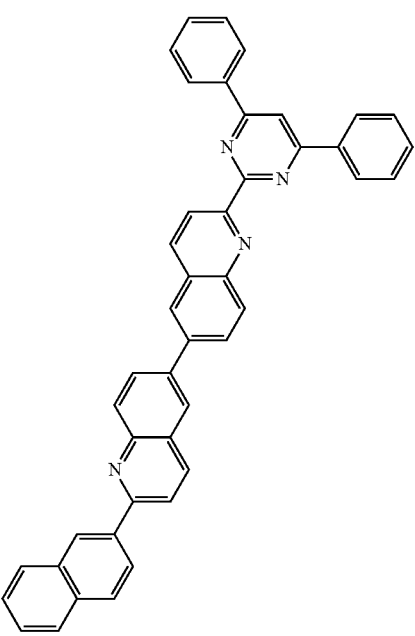
59

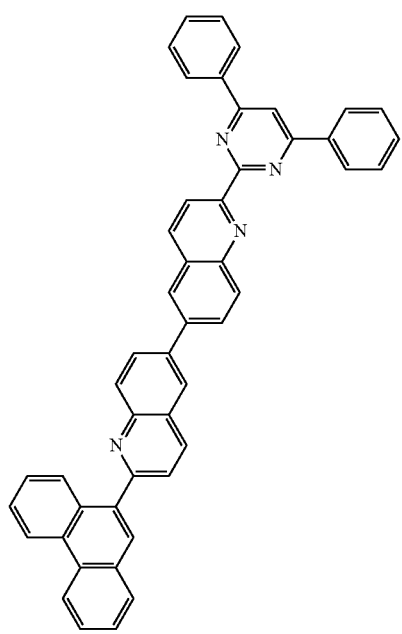
60
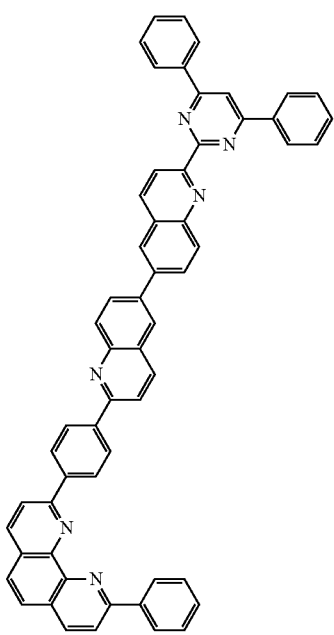
62
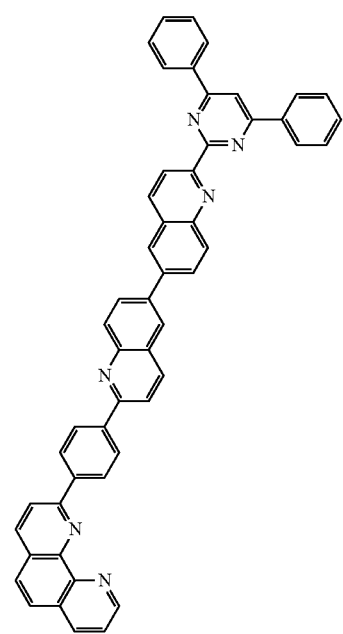
61

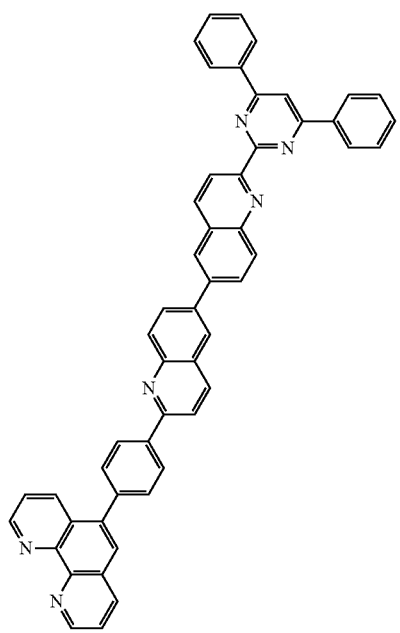
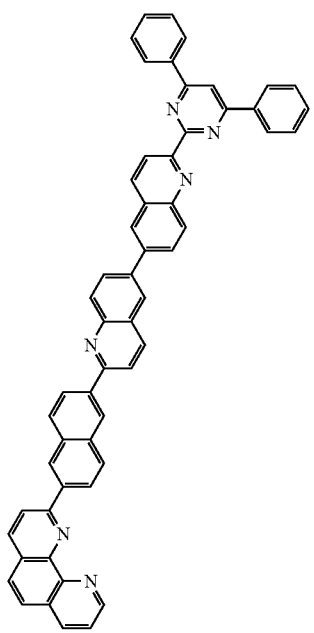

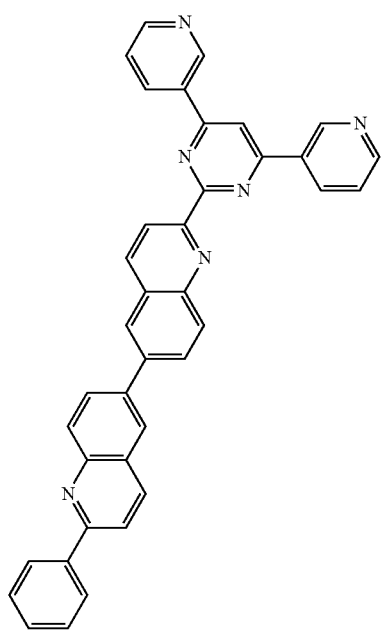
68
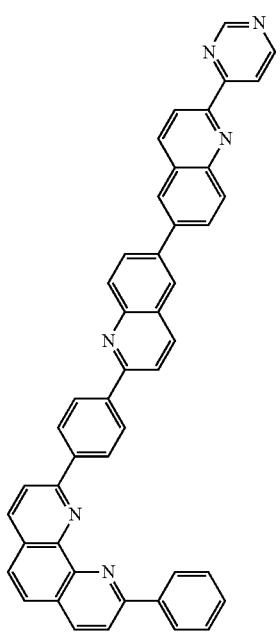
70
69
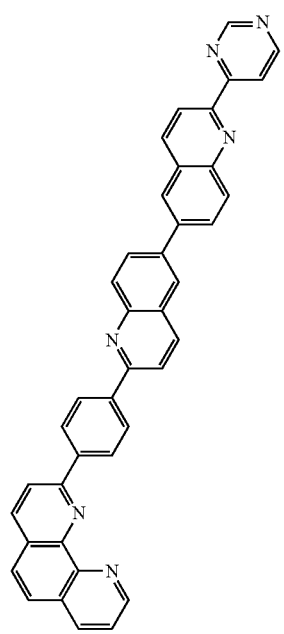
71

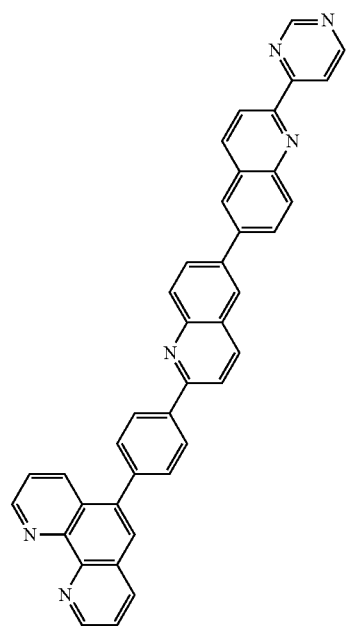
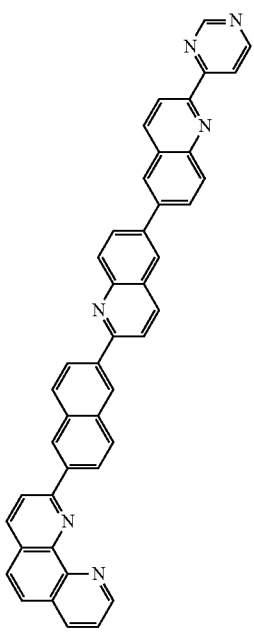

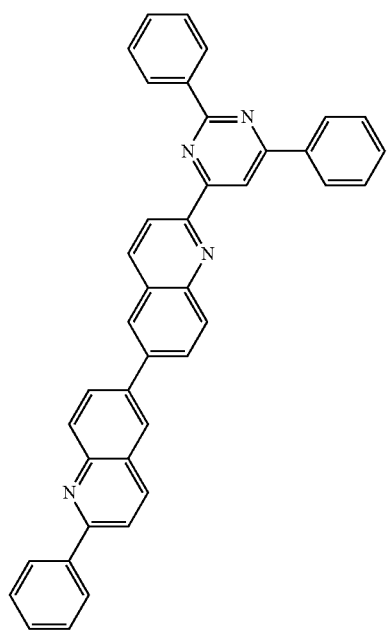
76
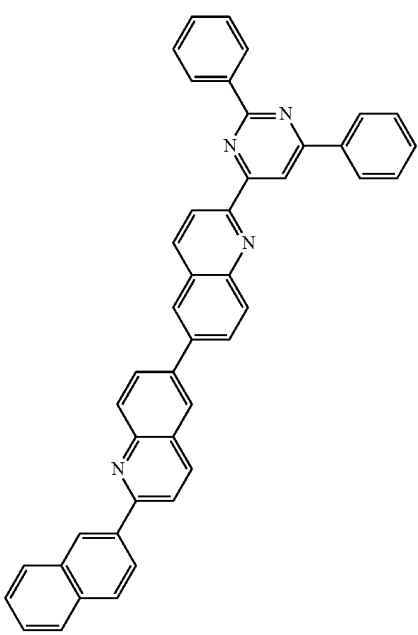
78
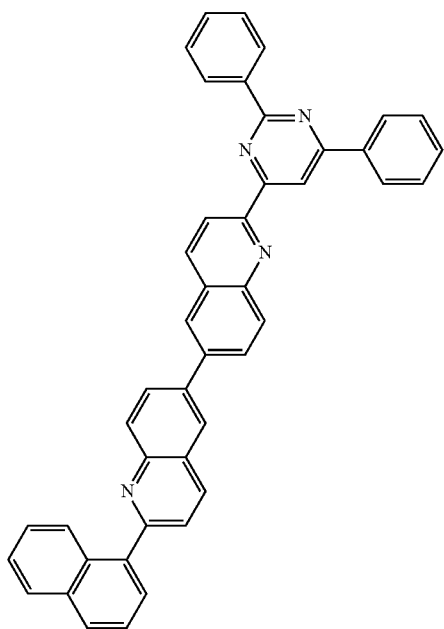
77

80
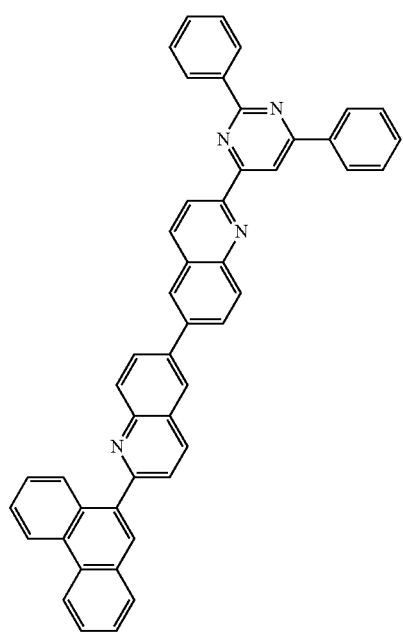
82
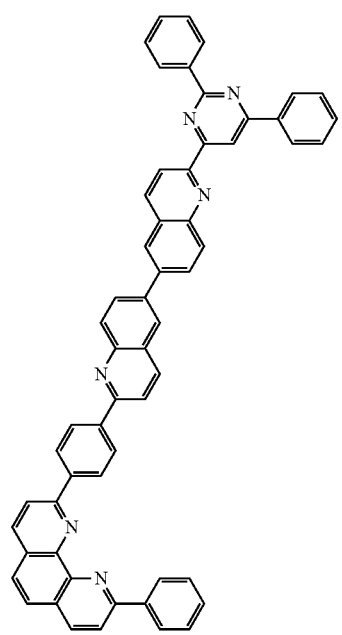
81
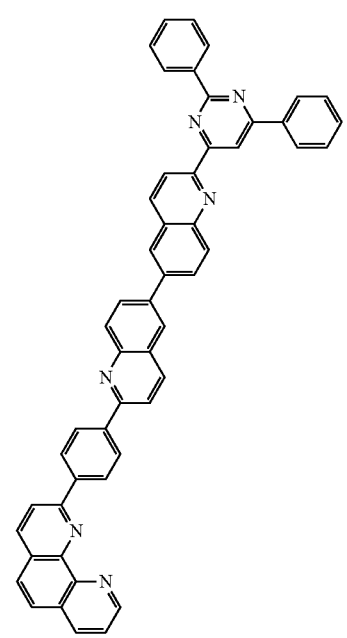
83
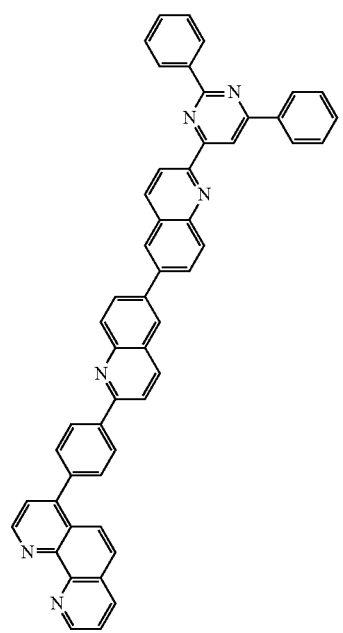

84
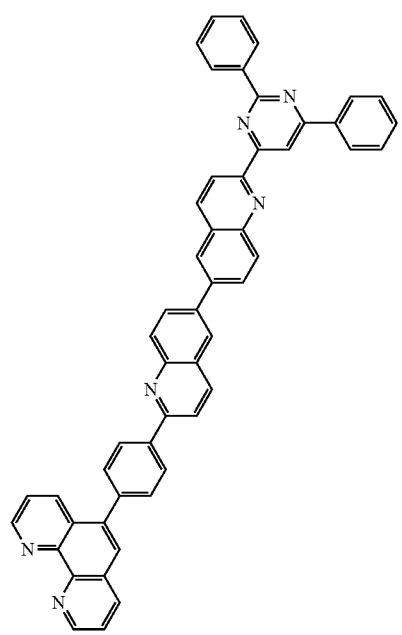
86
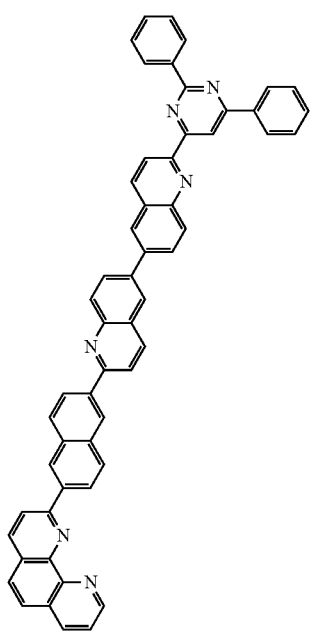
85
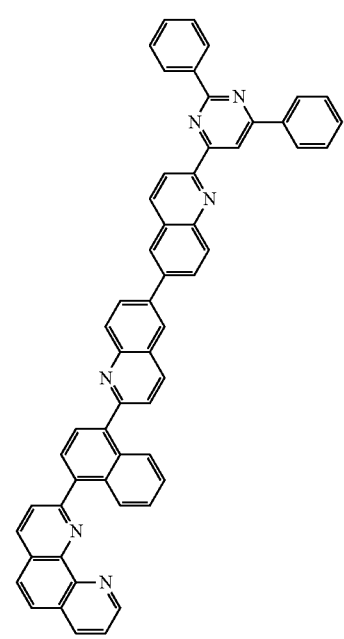
87
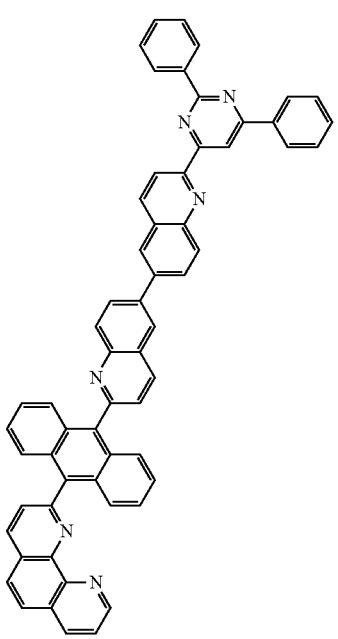

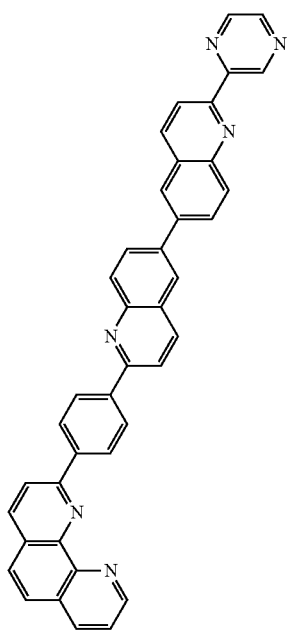
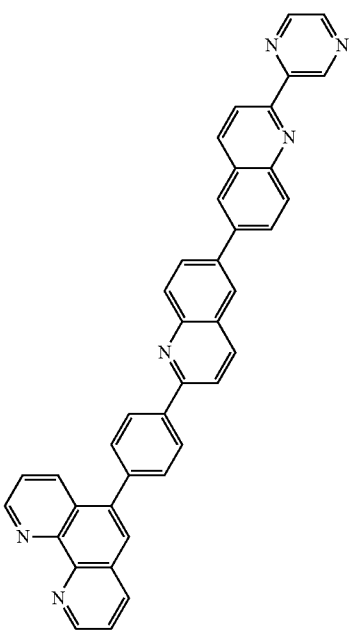

92
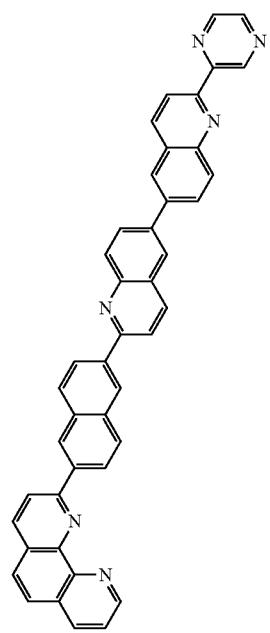
93
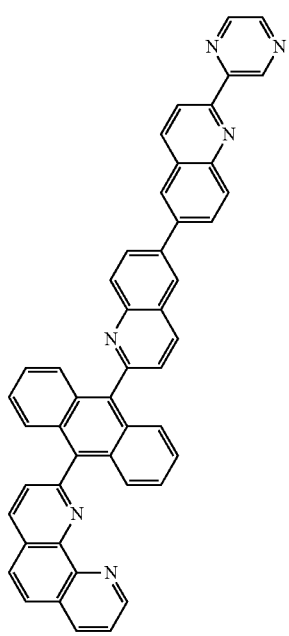
94
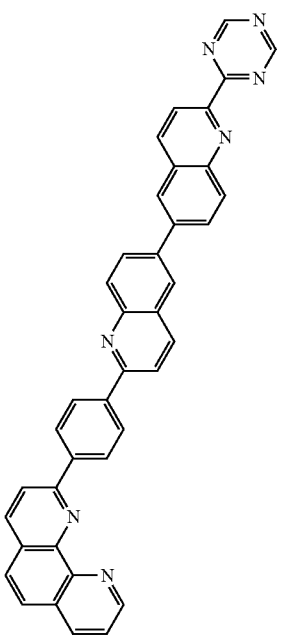
95
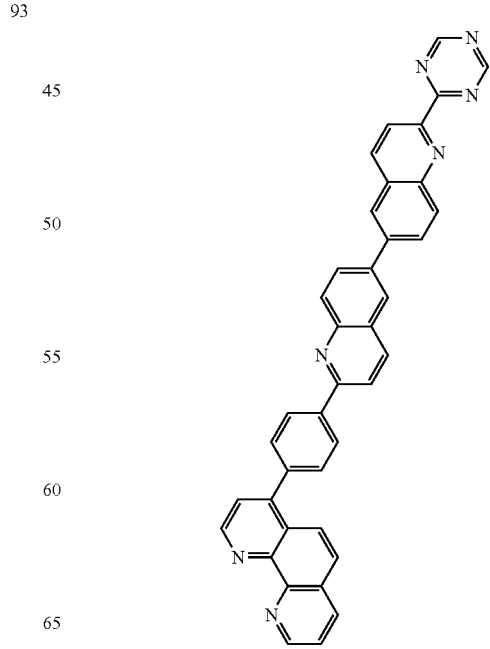

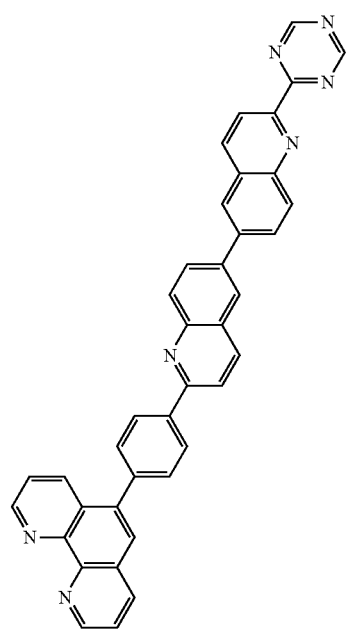
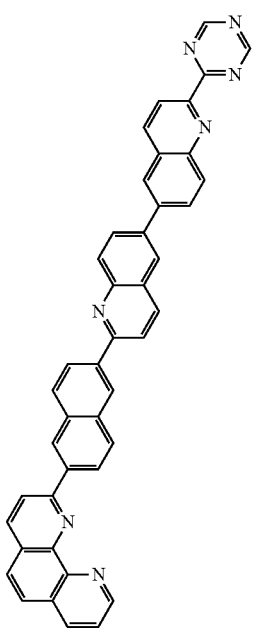

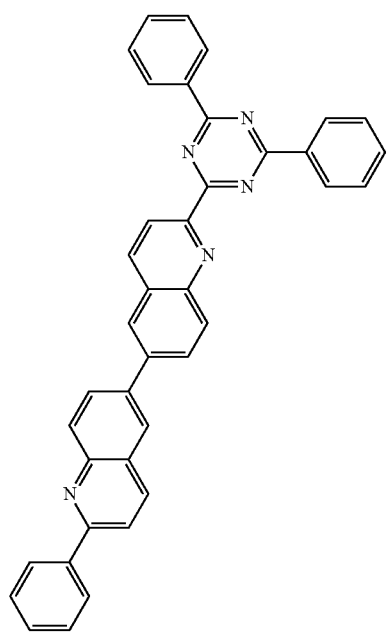
100
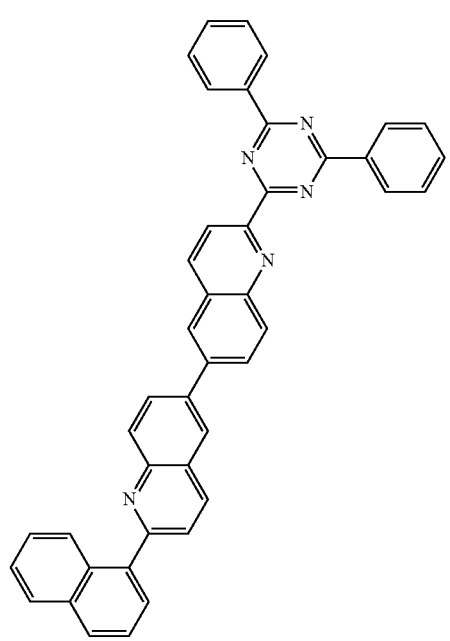
101
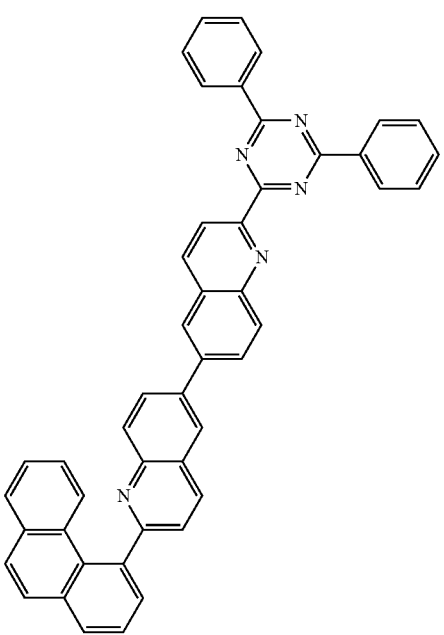
102
103

104
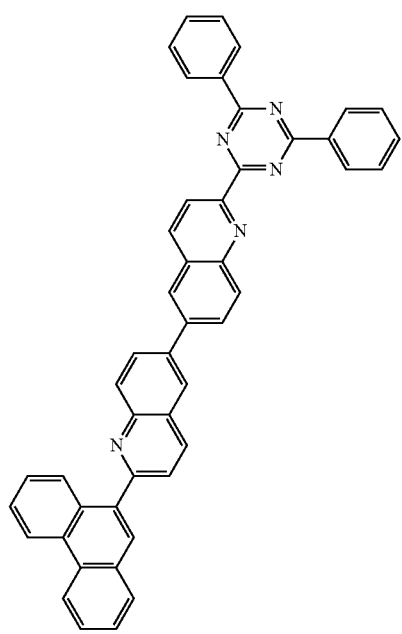
105
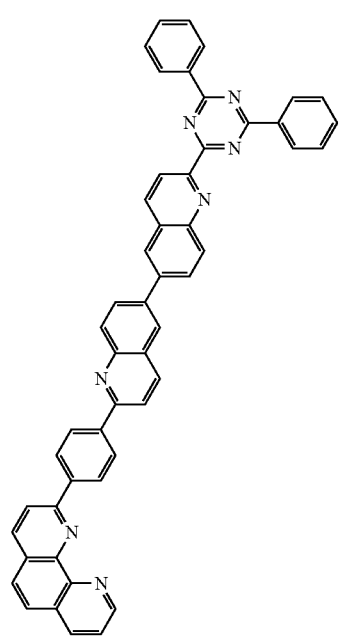
106
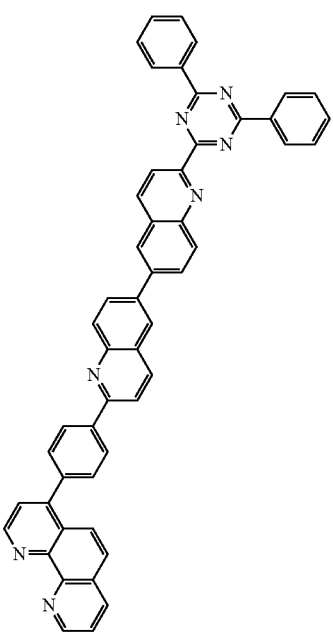
107
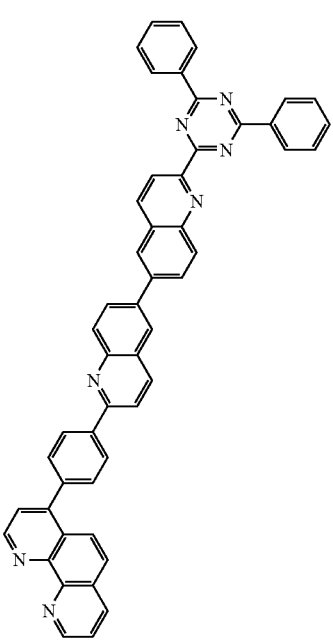

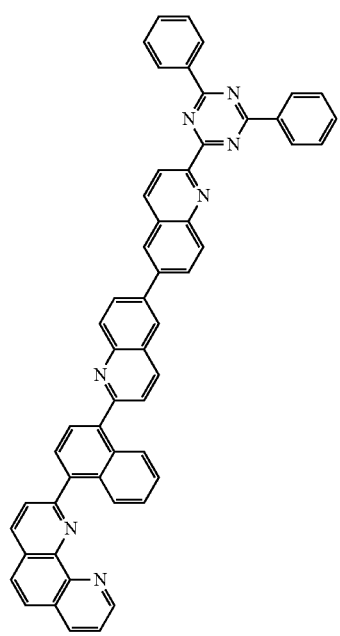
108
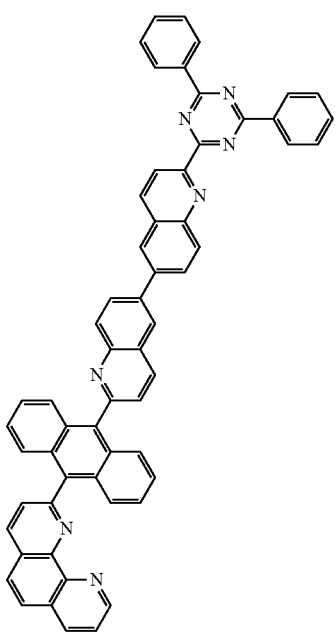
110
109
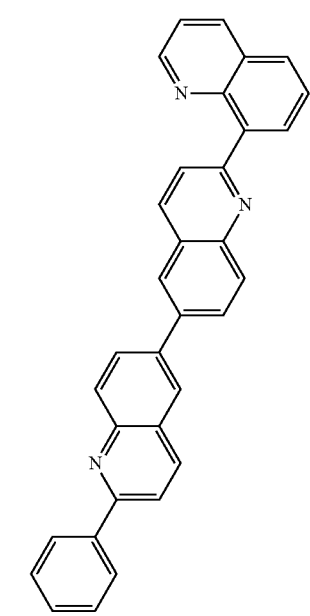
111

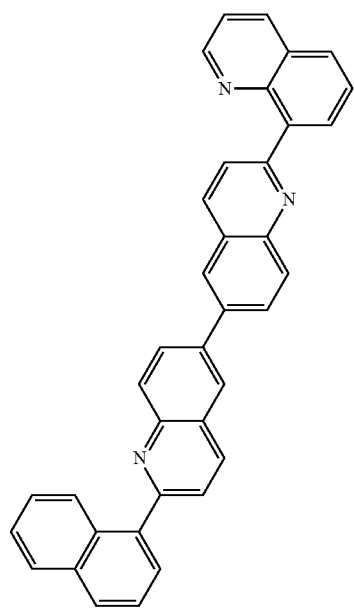
112
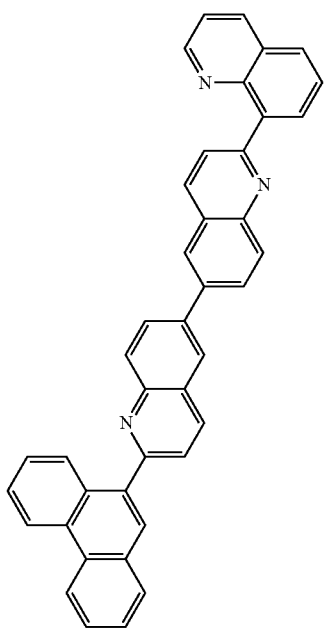
114
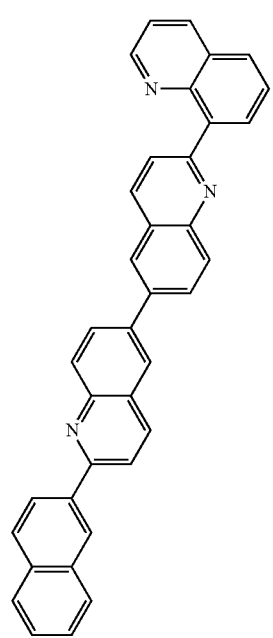
113
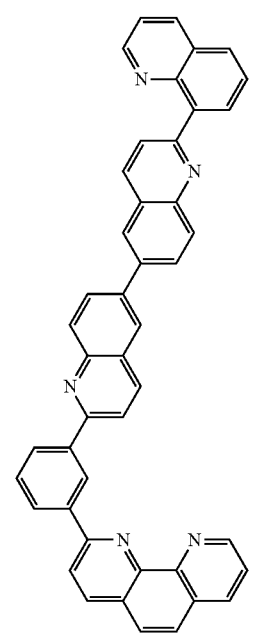
115

116
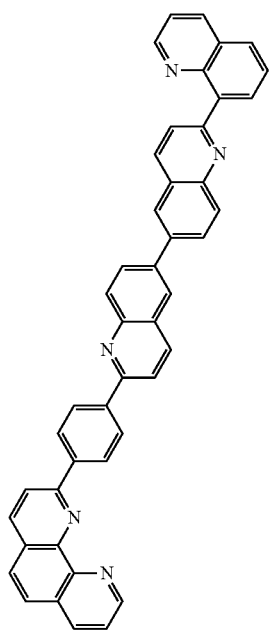
117
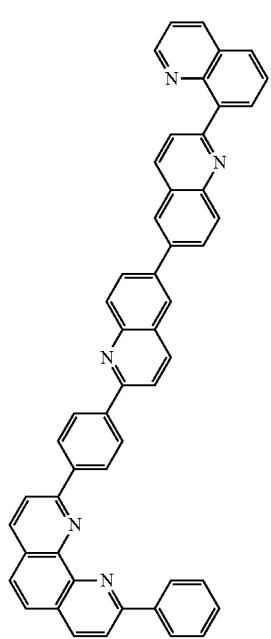
118
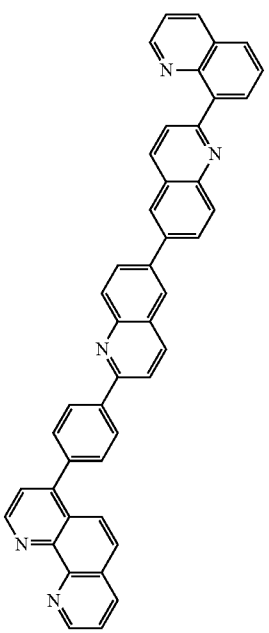
119
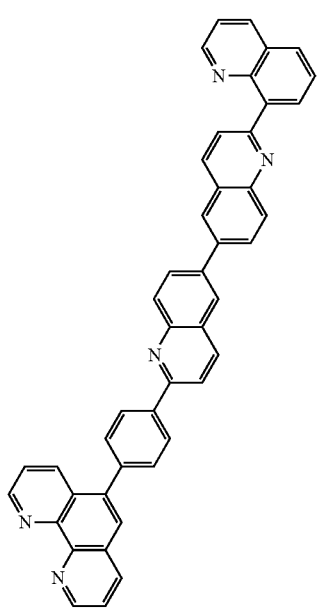

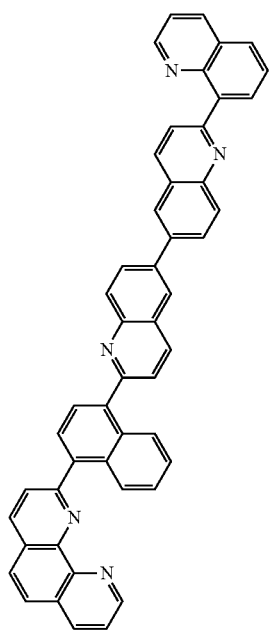
120
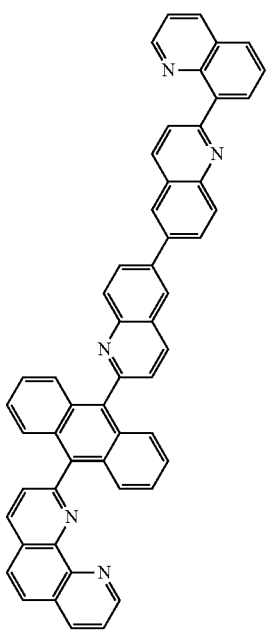
122
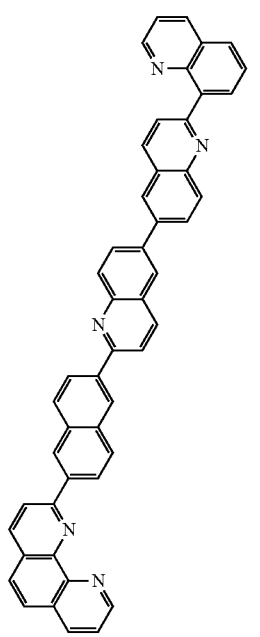
121

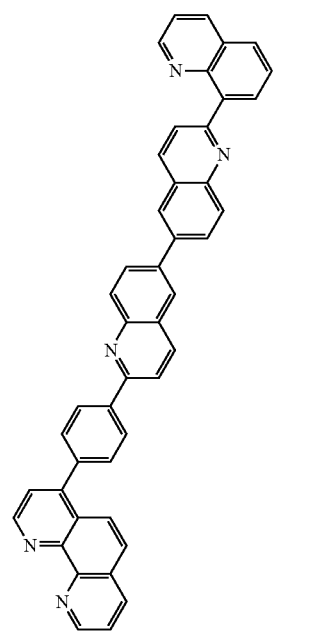
124
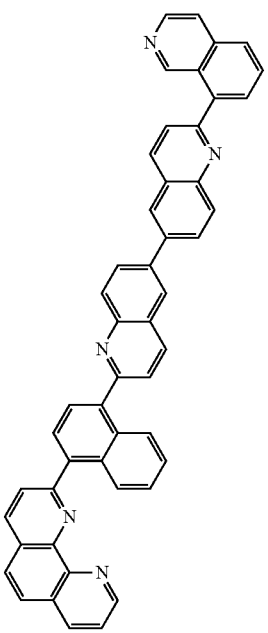
126
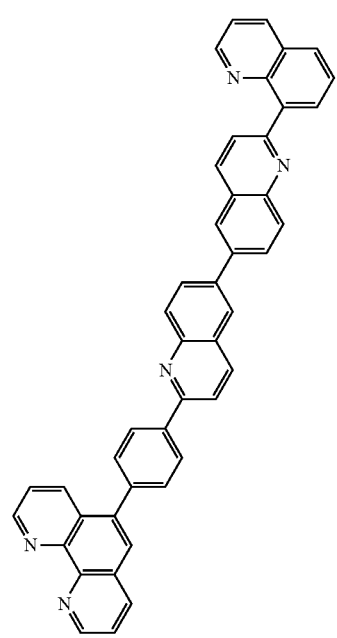
125
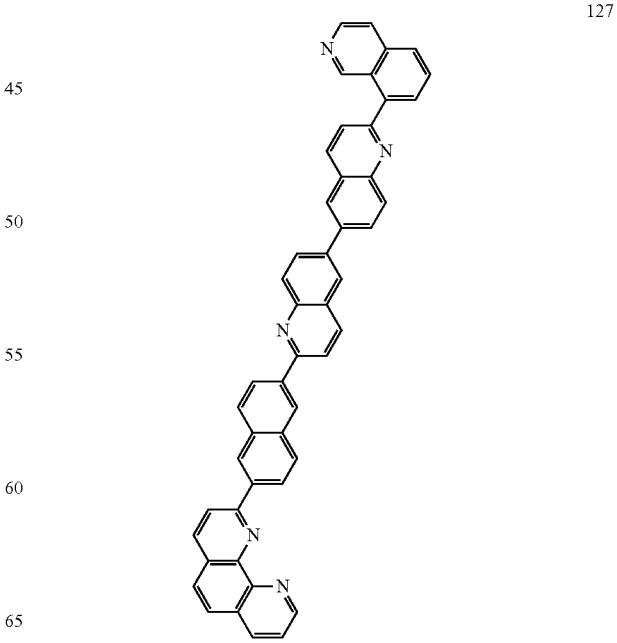
127

128
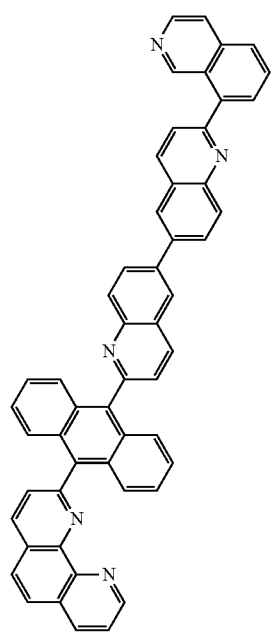
130
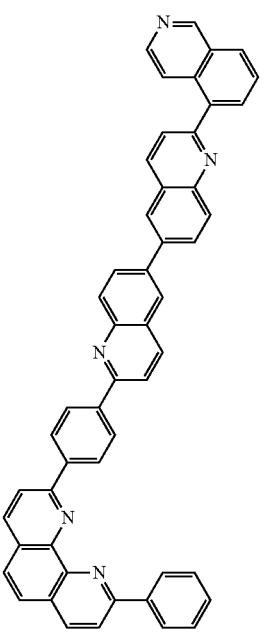
129
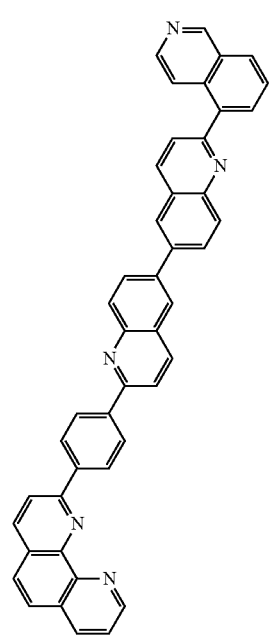
131
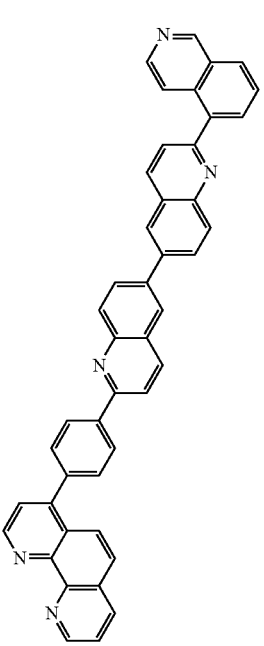

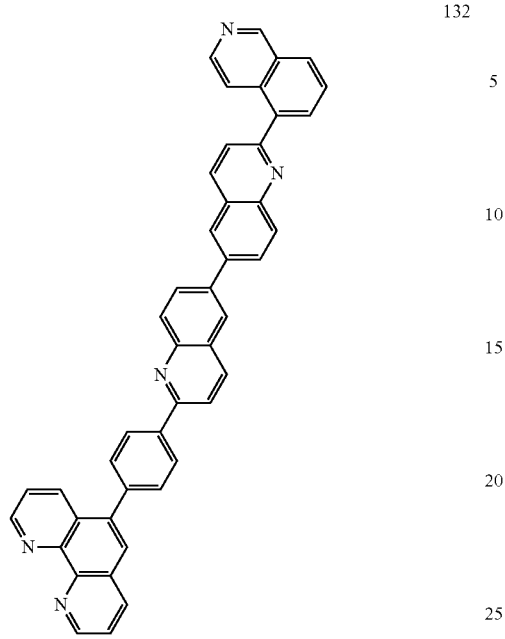
132
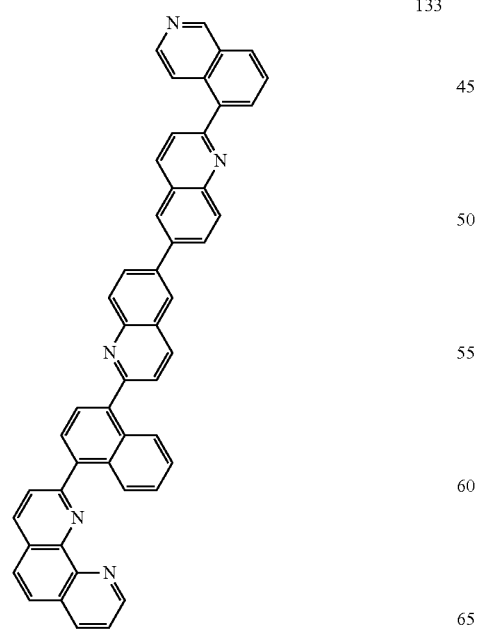
133
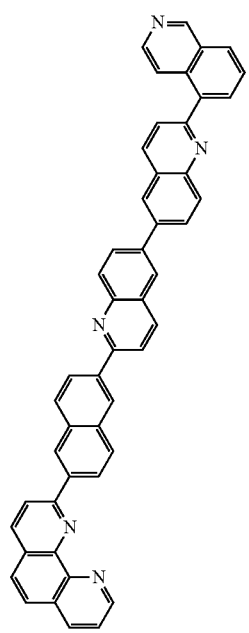
134
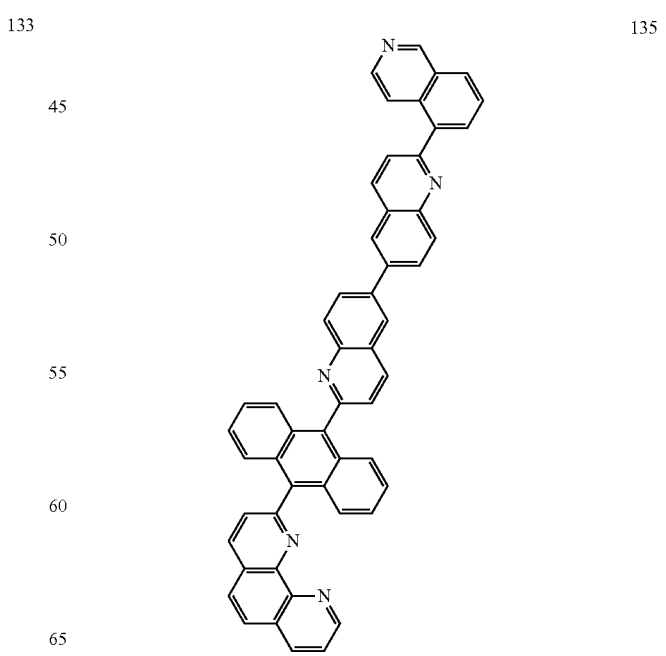
135

-continued
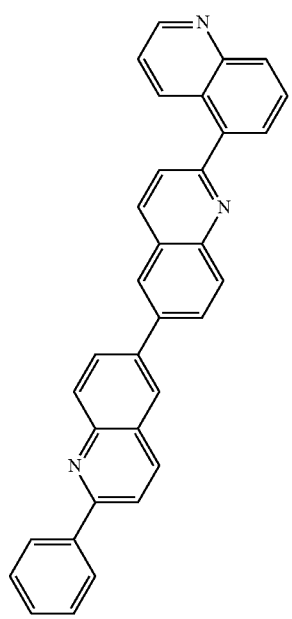
136
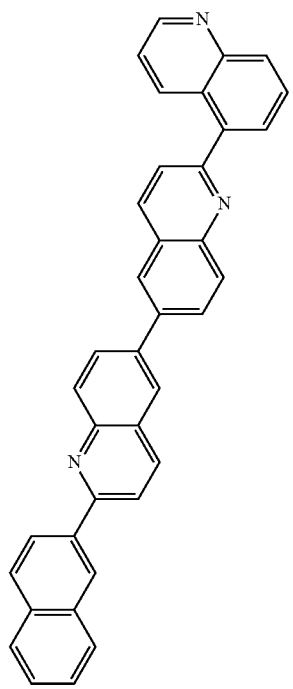
138
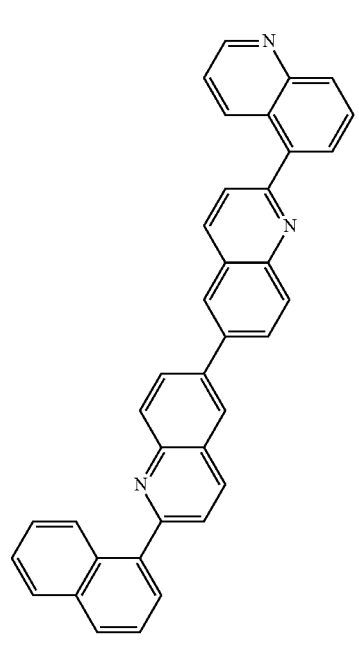
137
139

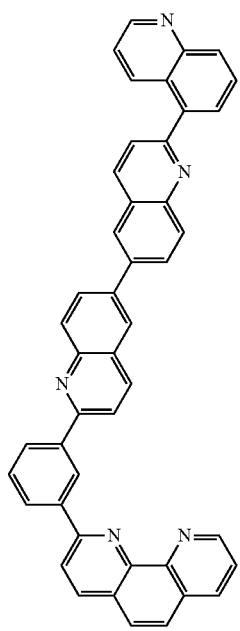
140
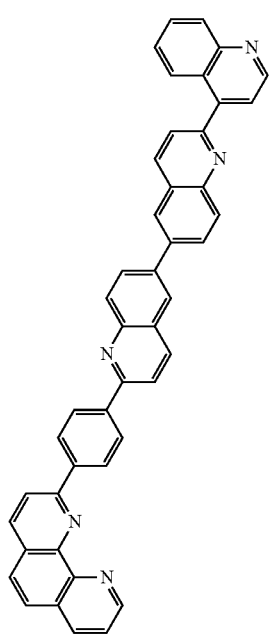
141
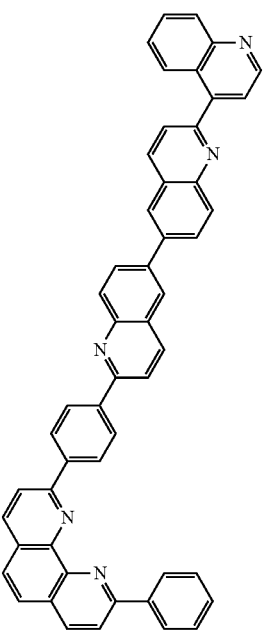
142
143

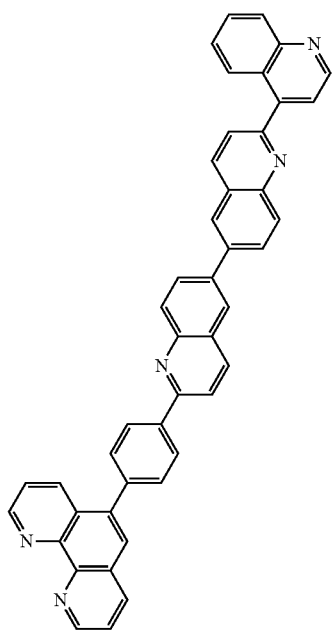
144
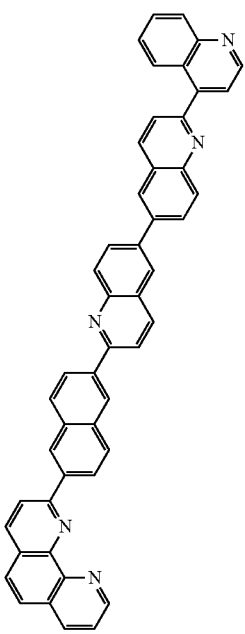
146
145
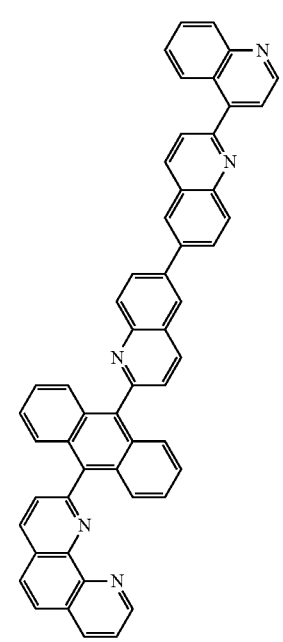
147

148
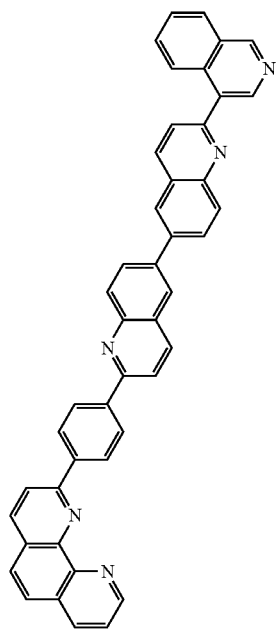
149
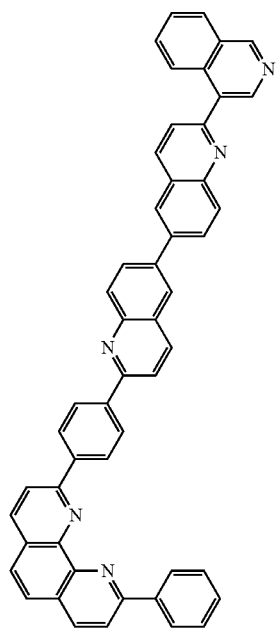
150
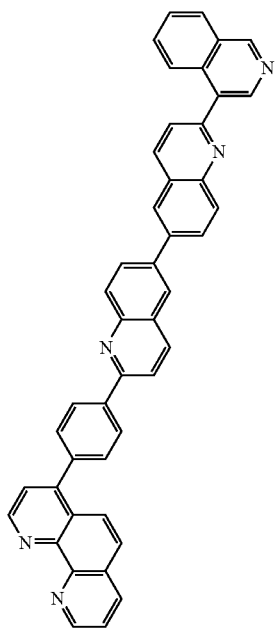
151
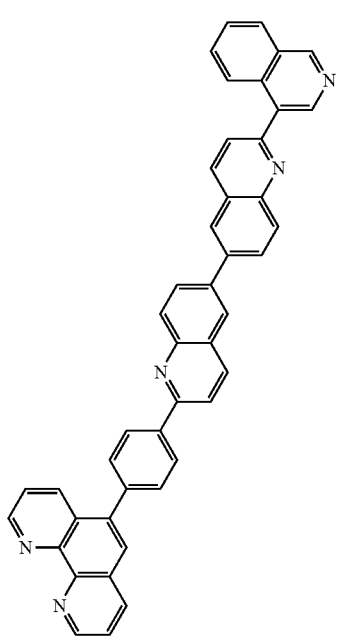

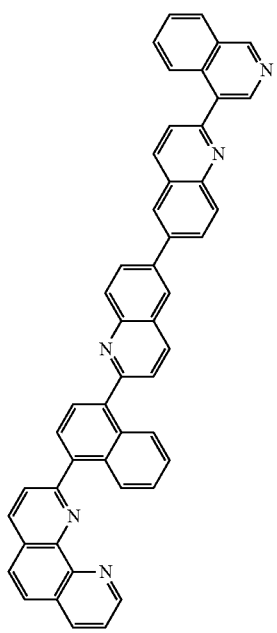
152
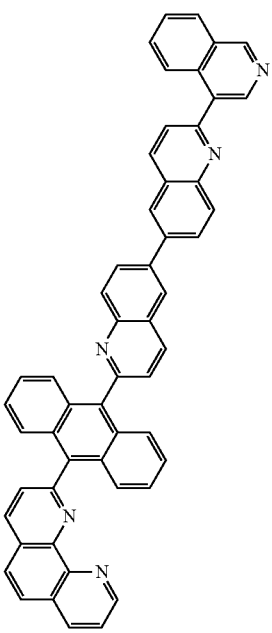
154
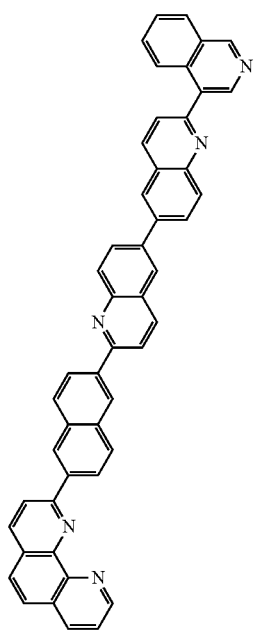
153
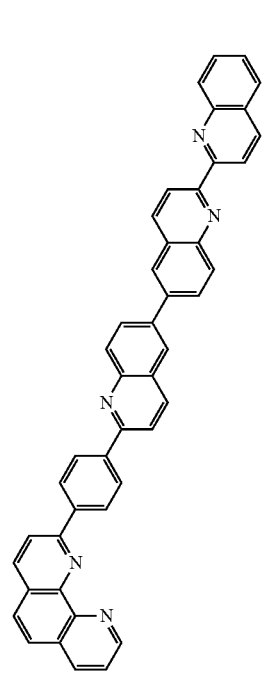
155

156
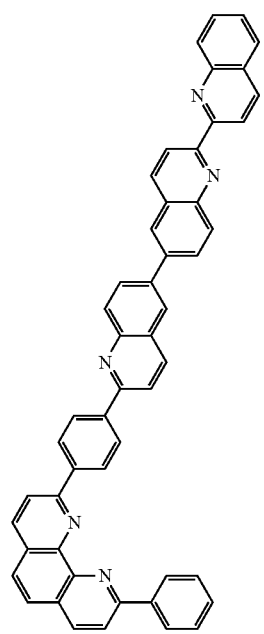
157
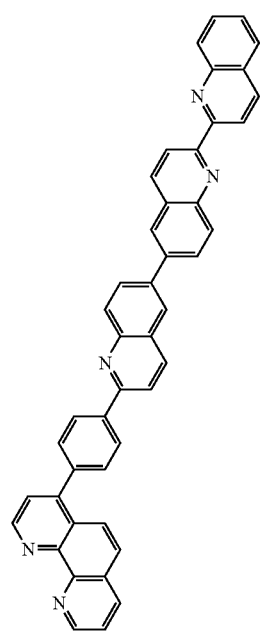
158
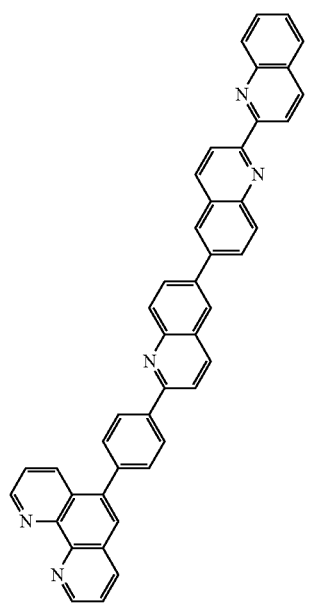
159
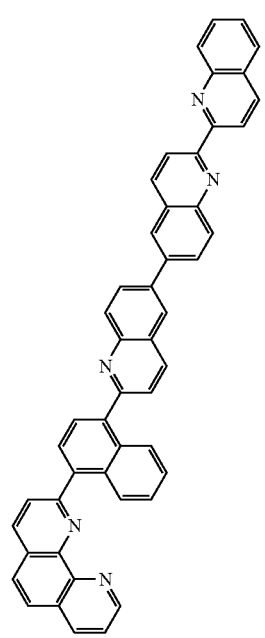

160
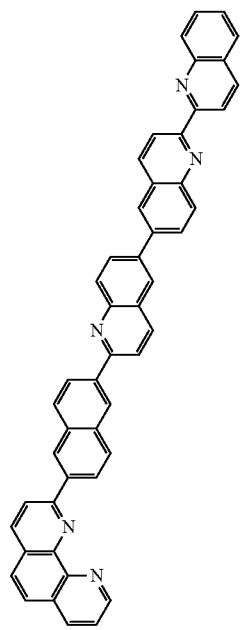
161
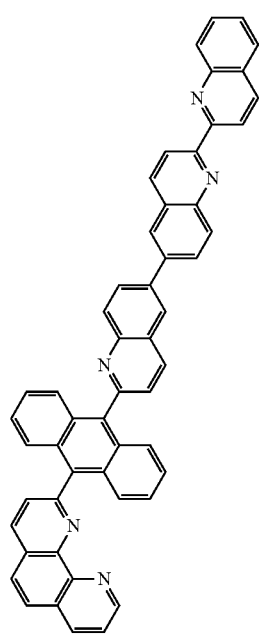
162
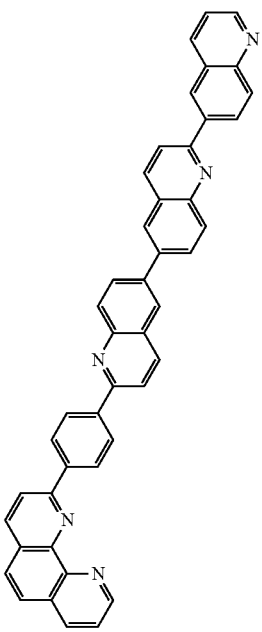
163

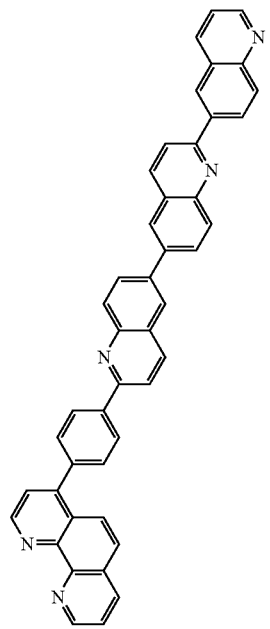
164
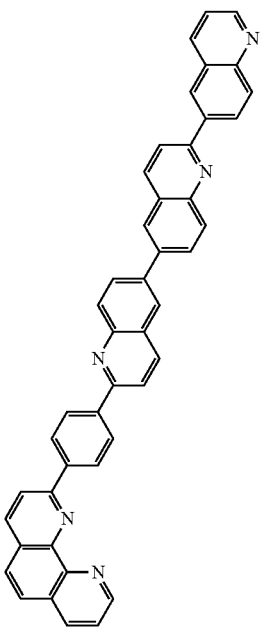
166
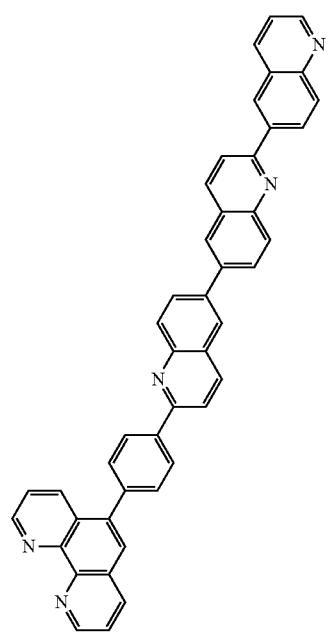
165
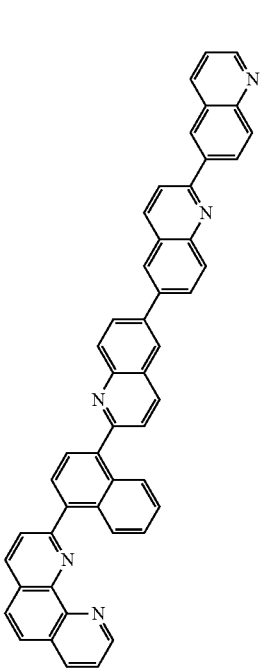
167

168
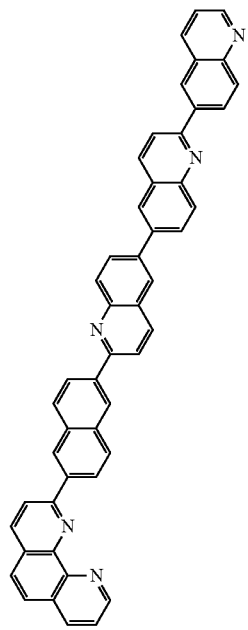
169
170
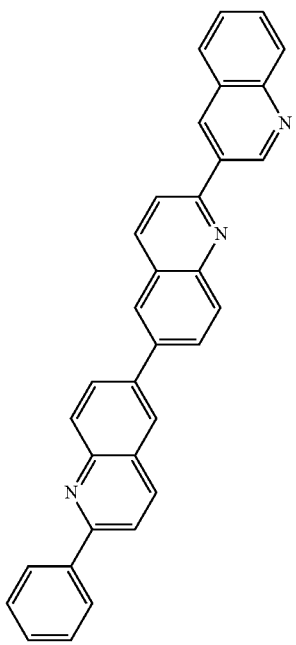
171
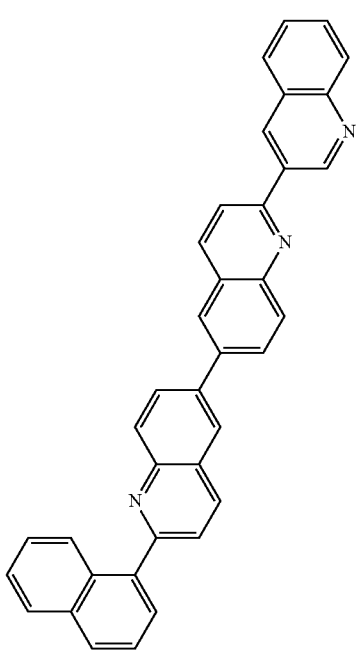

172
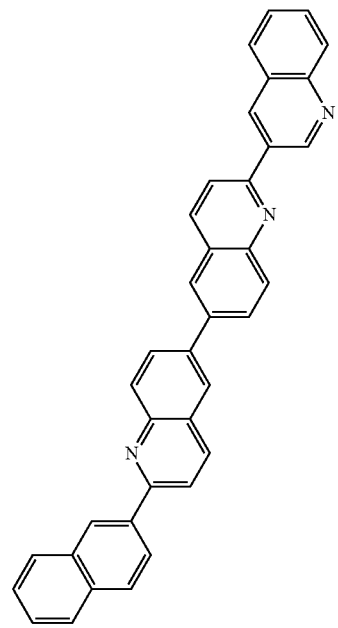
173
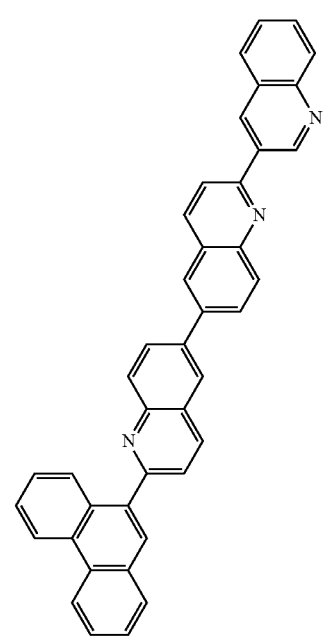
174
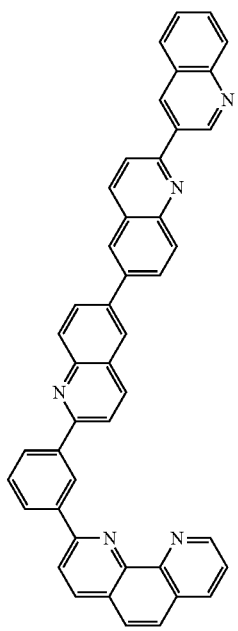
175
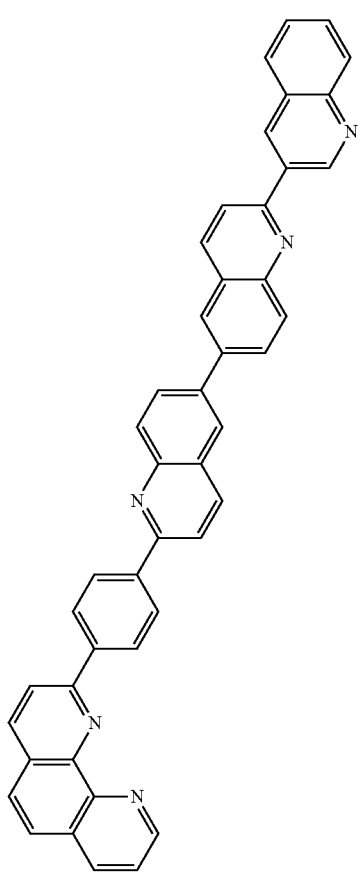

176 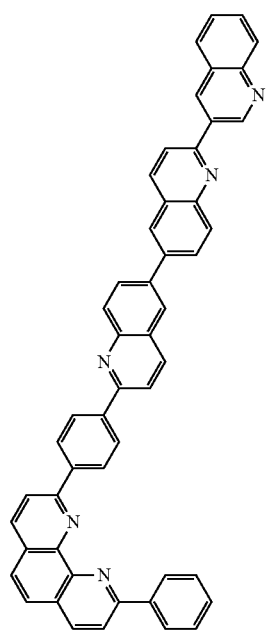
177 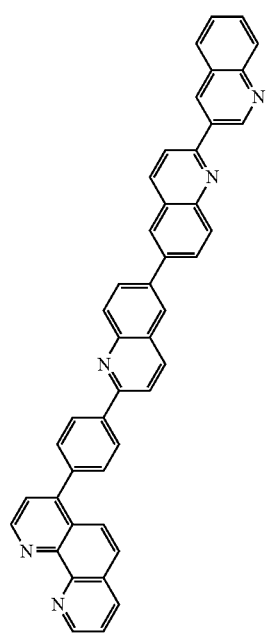
178 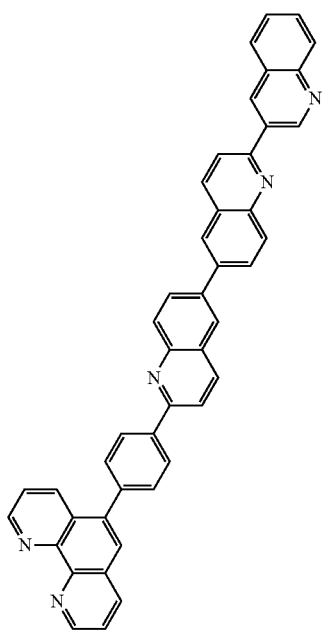
179 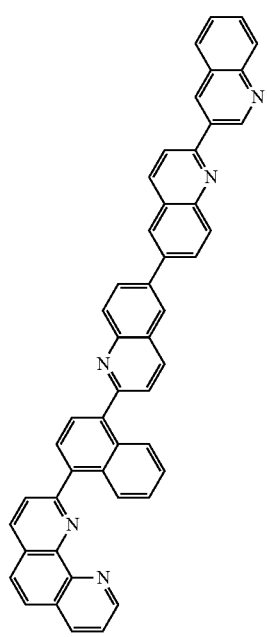

180
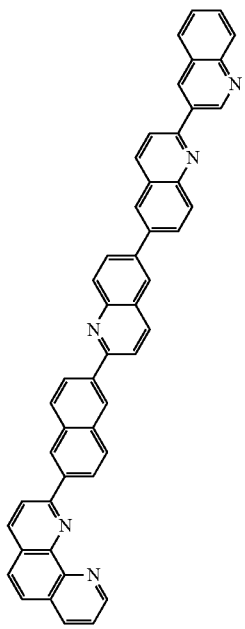
181
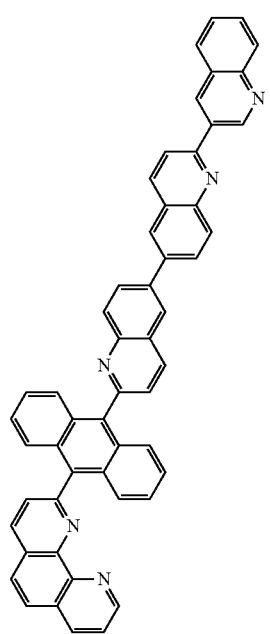
182
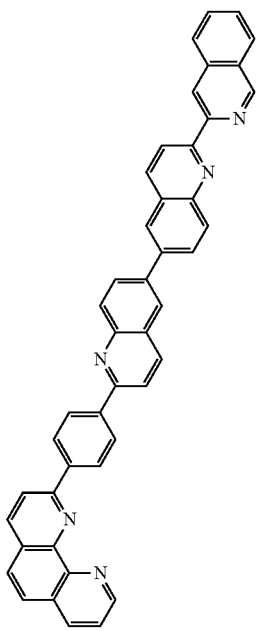
183
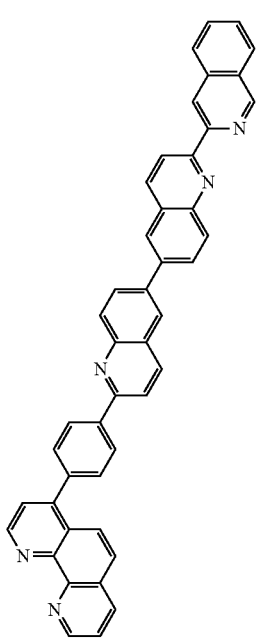

184
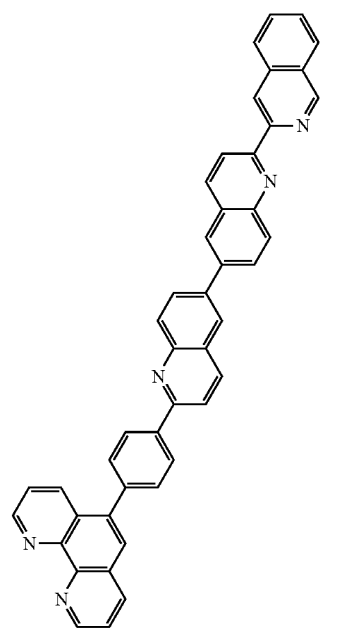
185
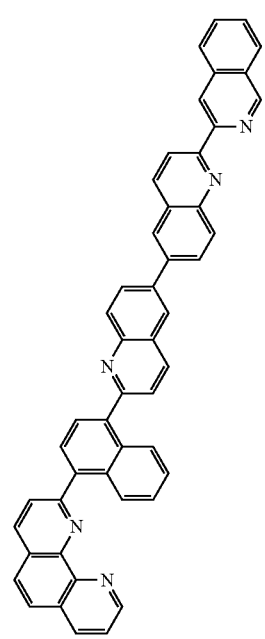
186
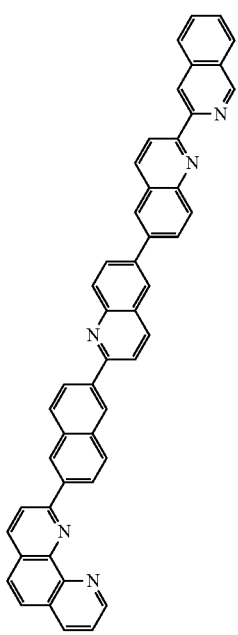
187
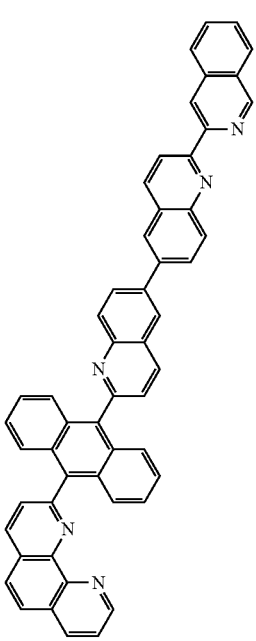

-continued
188
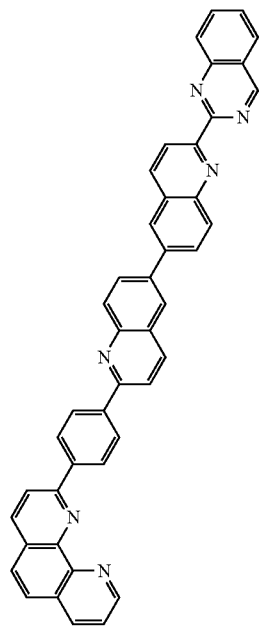
189
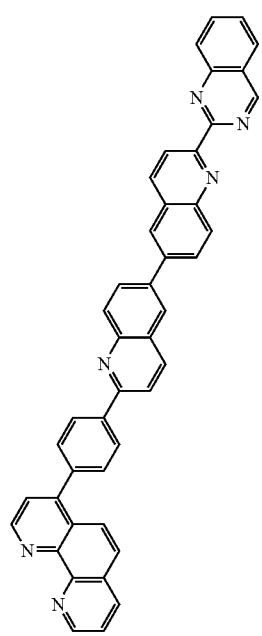
-continued
190
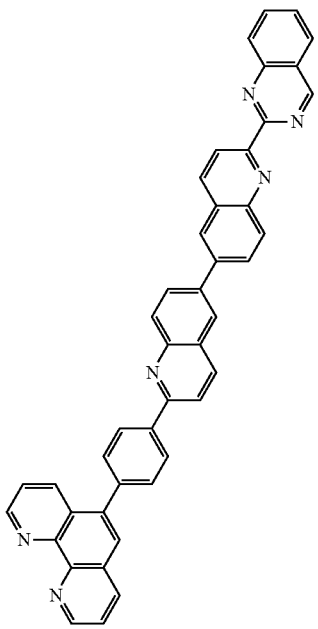
191
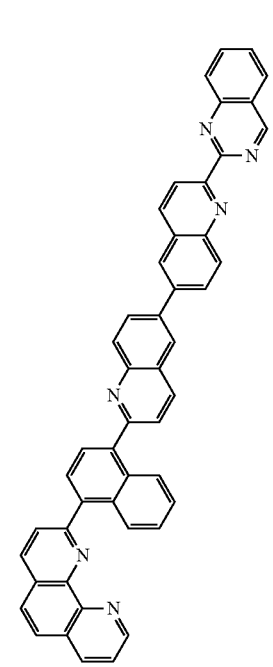

192
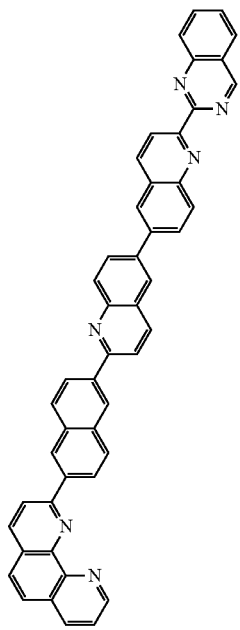
193
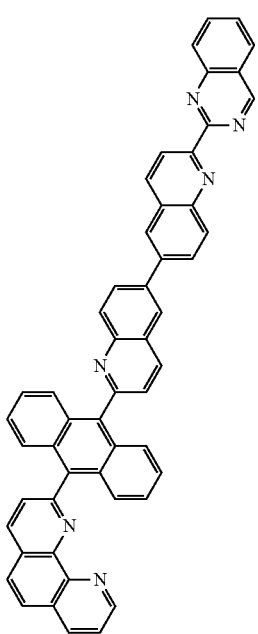
194
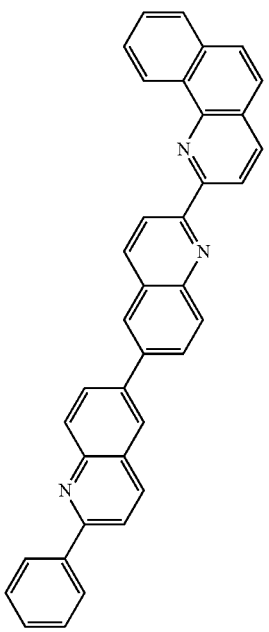
195
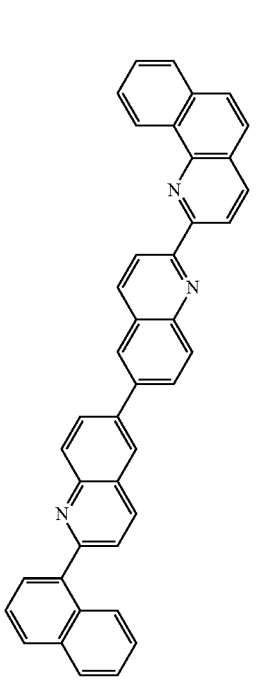

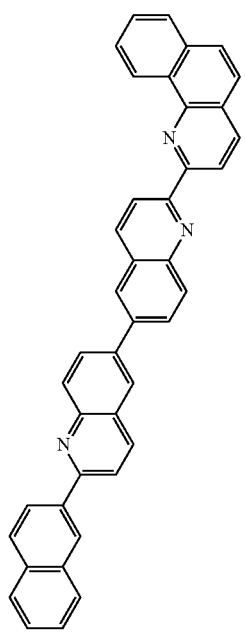
196
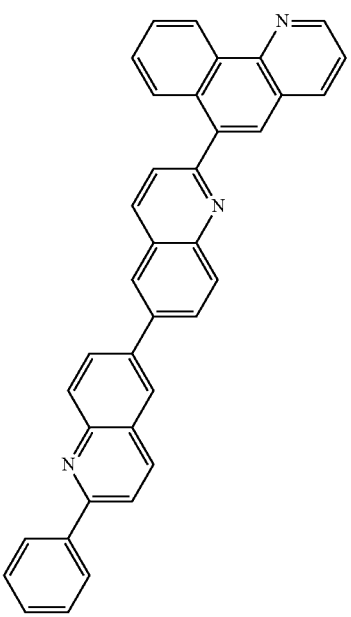
198
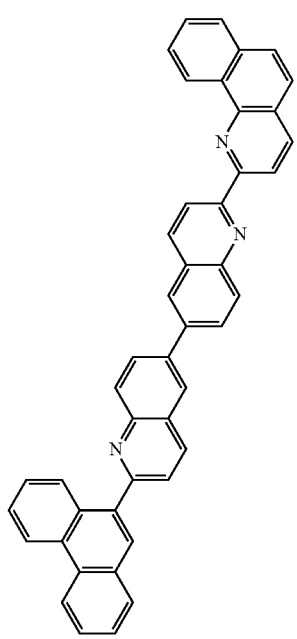
197
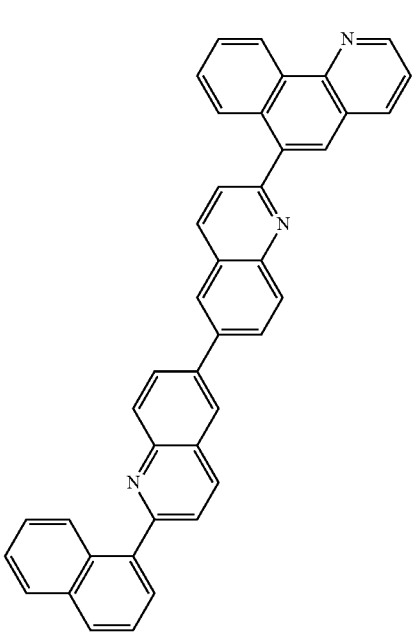
199

-continued
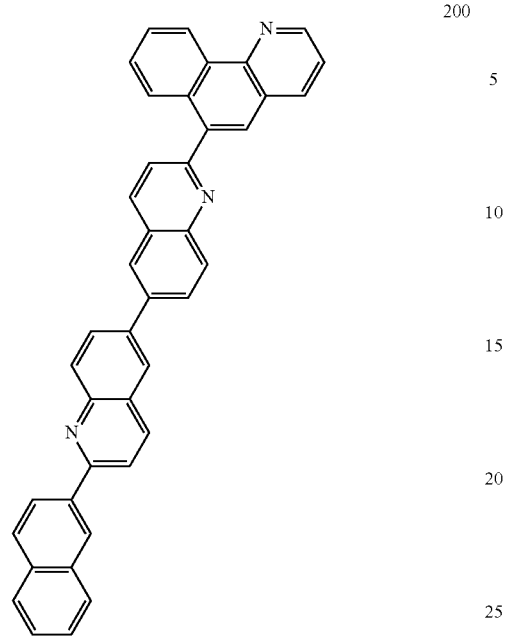
200
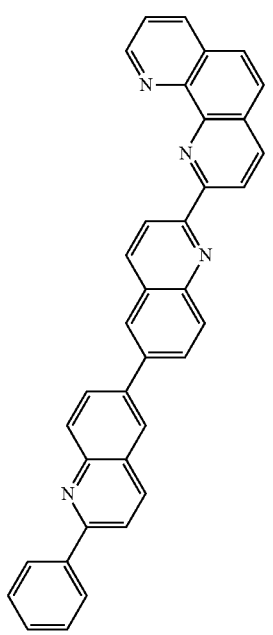
202
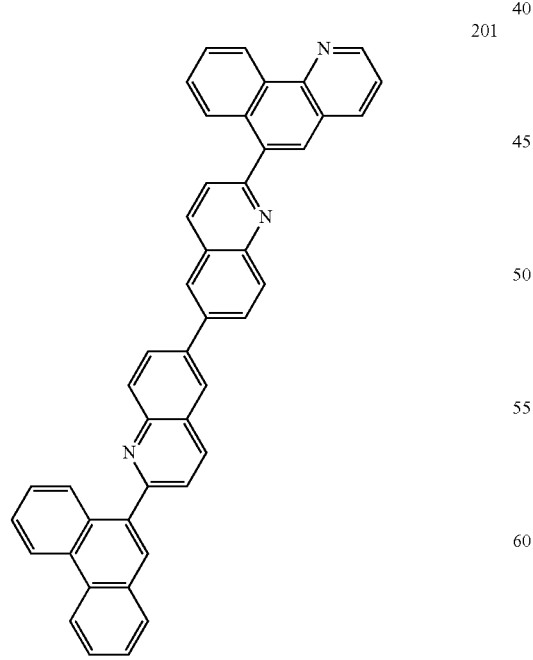
201
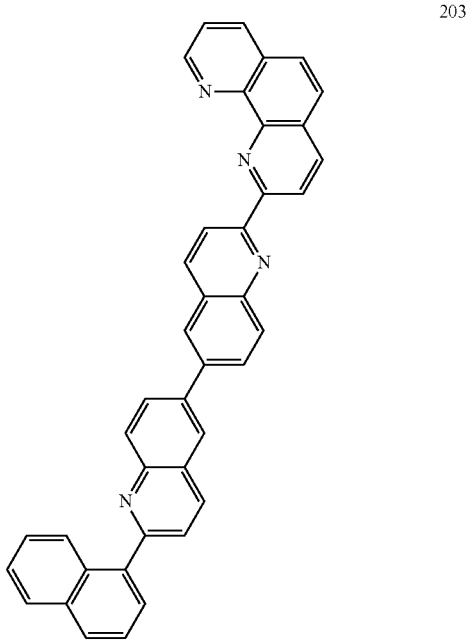
203

204
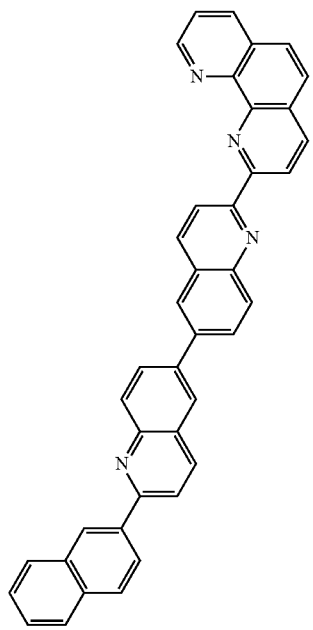
205
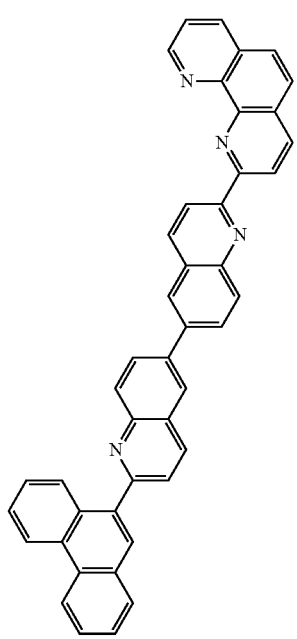
206
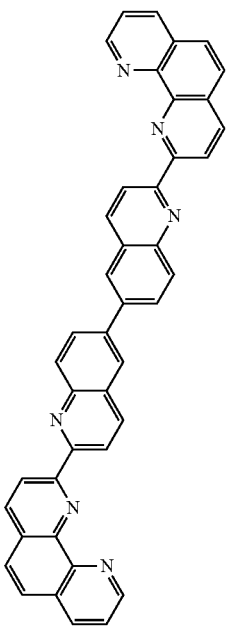
207
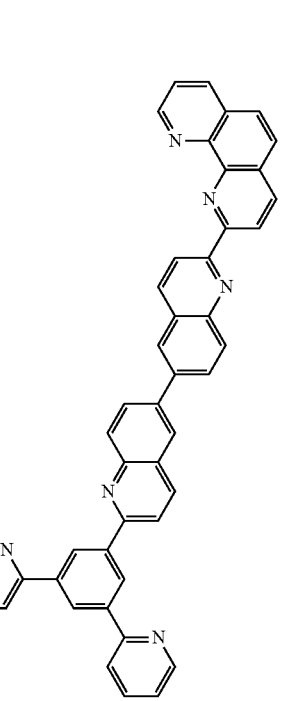

208
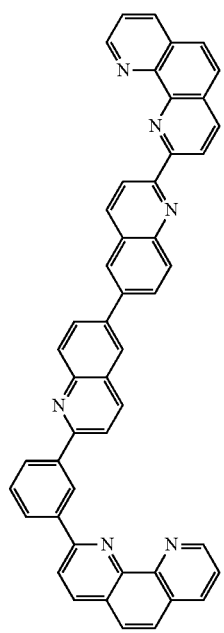
209
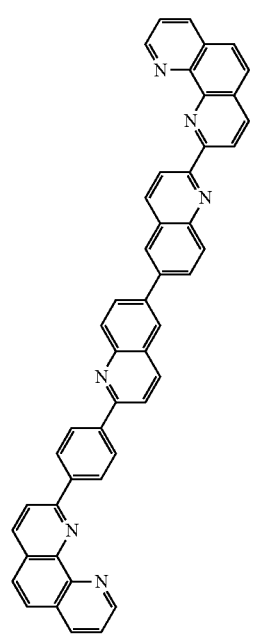
210
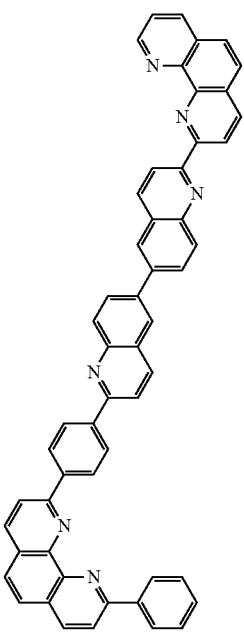
211
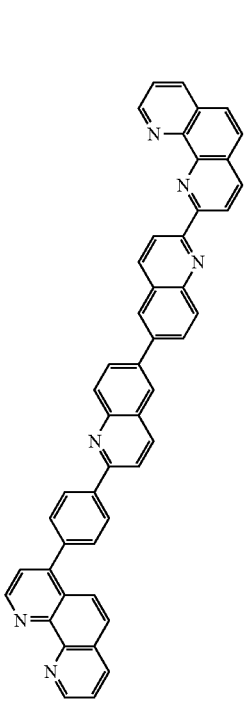

-continued
212
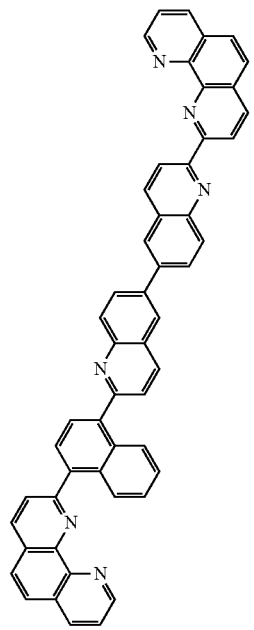
213
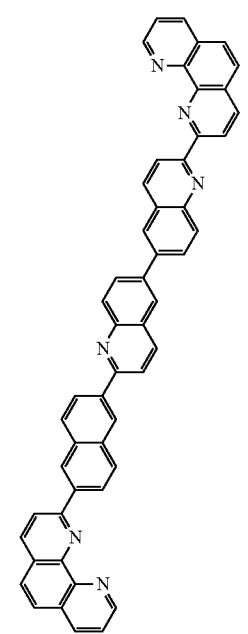
214
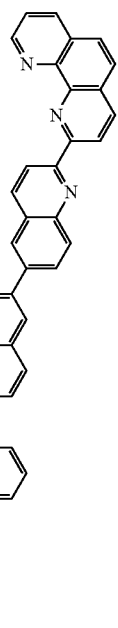
215
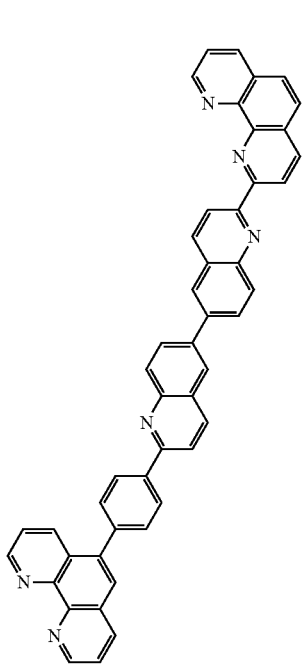

117
-continued
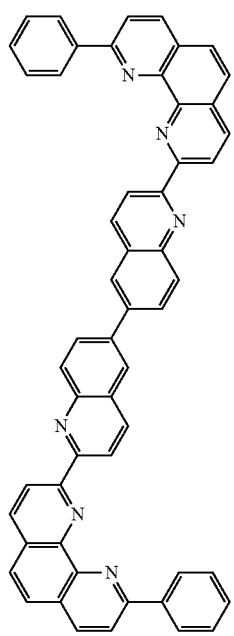
216
118
-continued
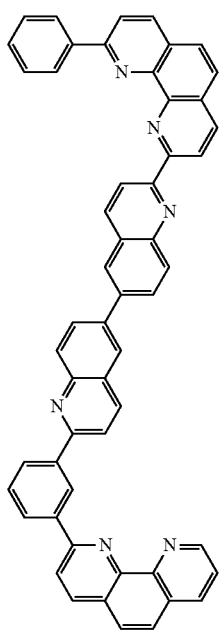
218
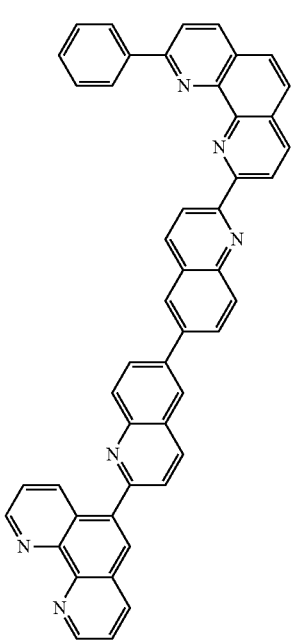
217
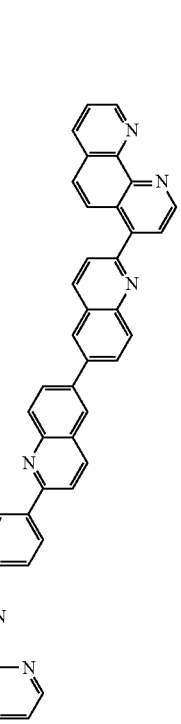
219

-continued
220
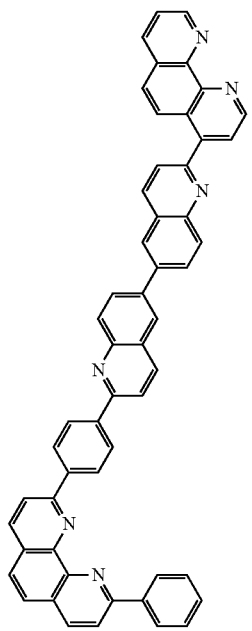
221
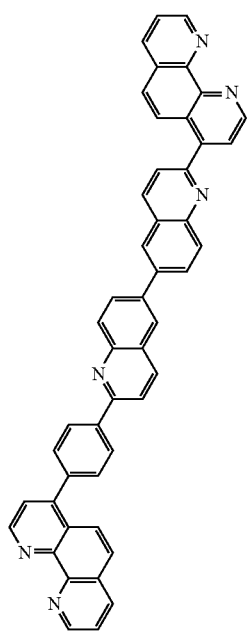
-continued
222
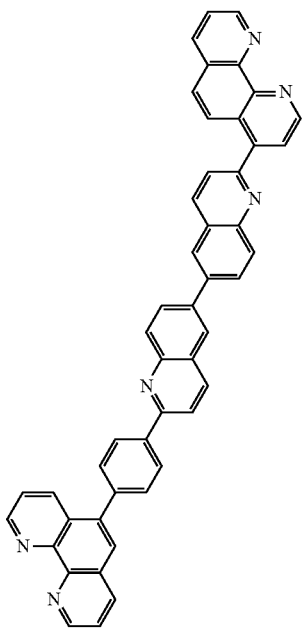
223

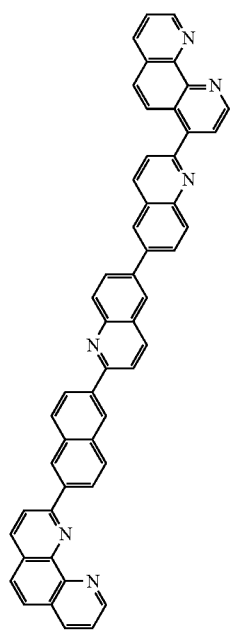
224
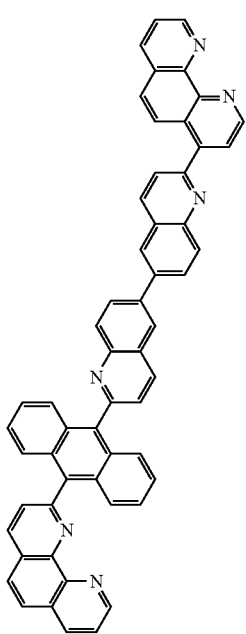
225
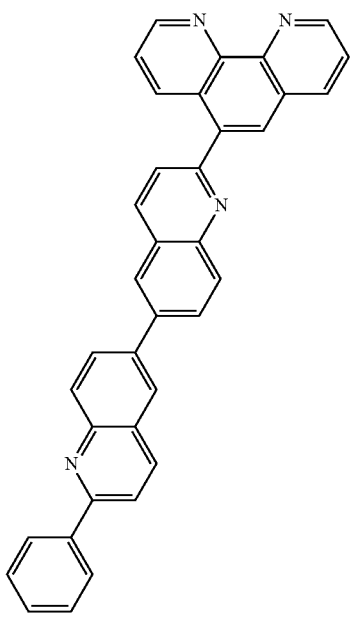
226
227

-continued
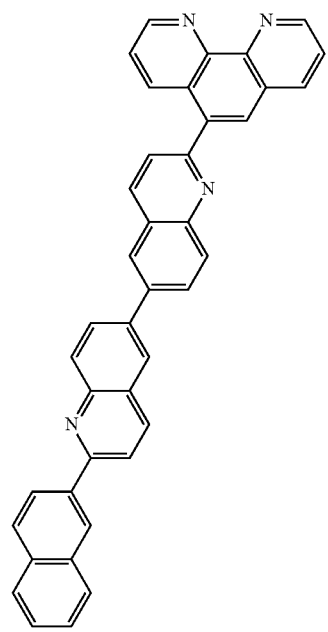
228
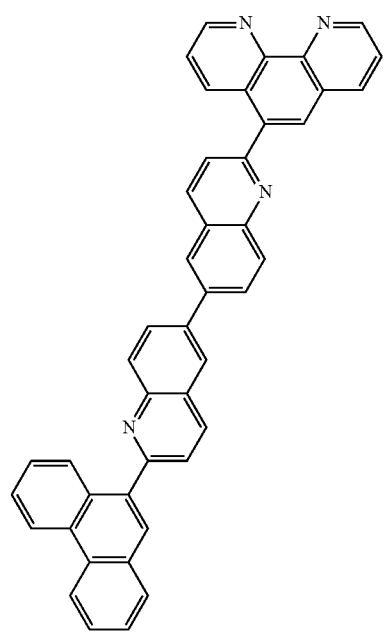
229
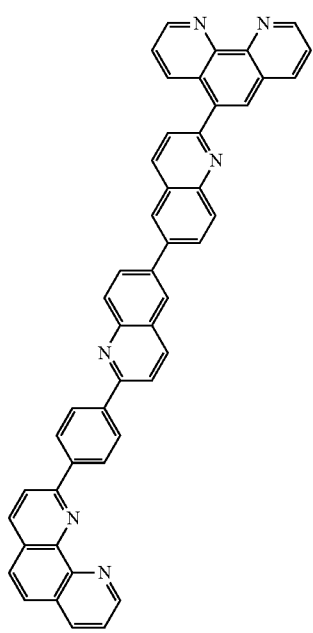
230
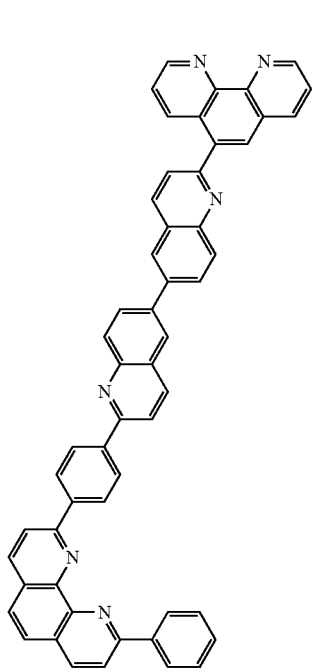
231

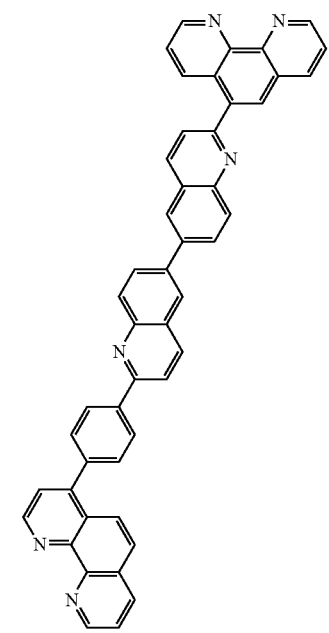
232
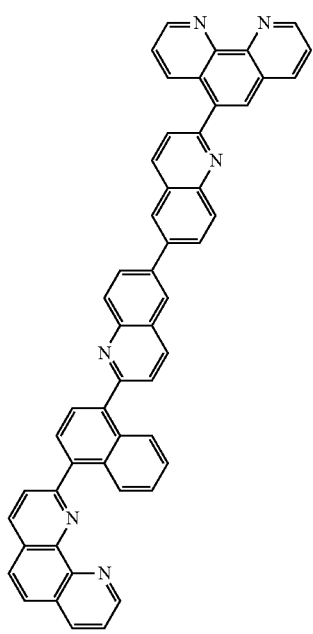
234
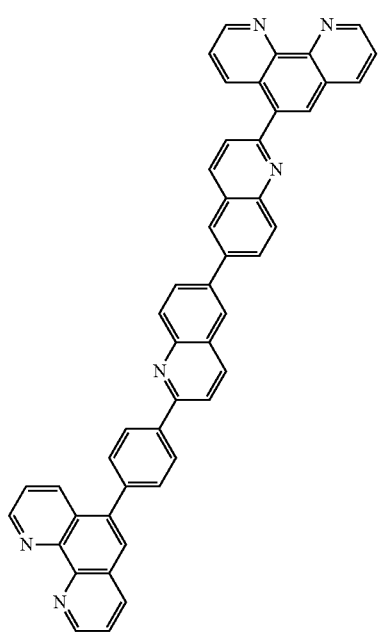
233
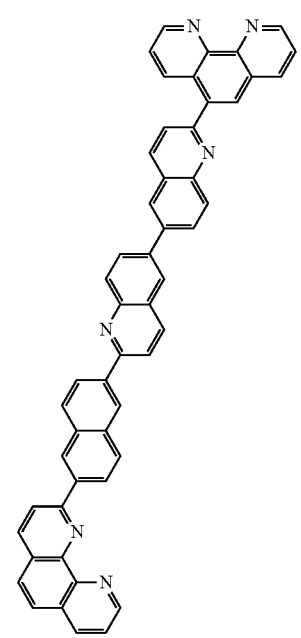
235

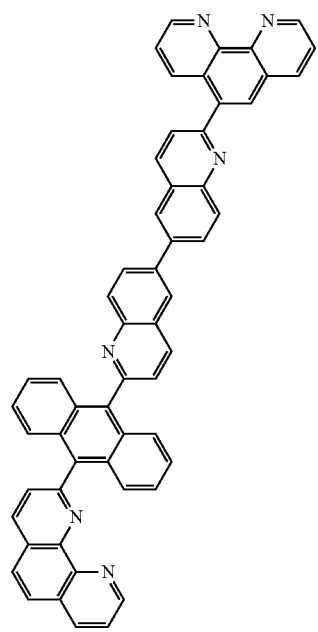
236
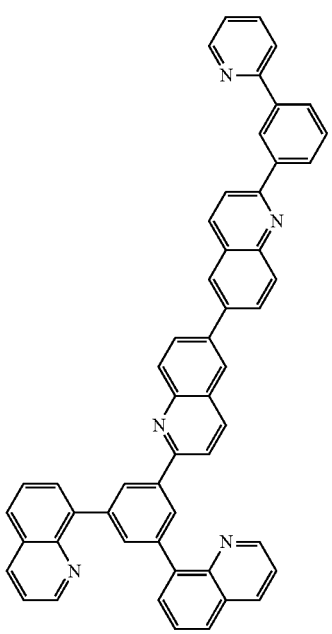
238
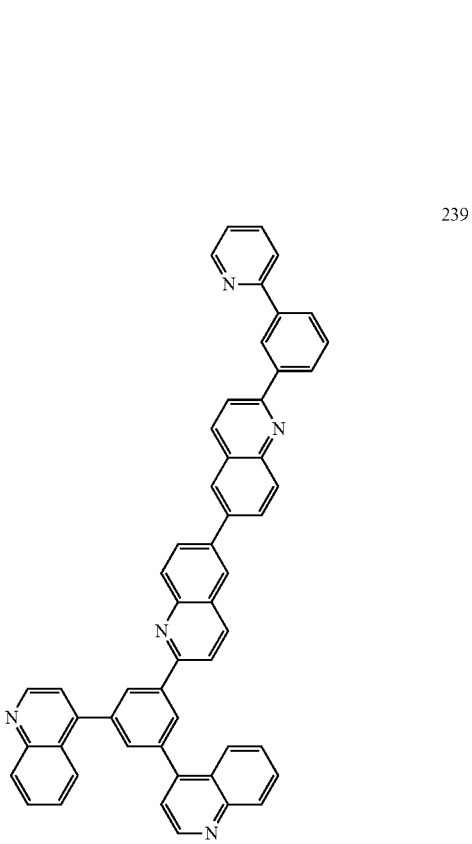
239
237

240
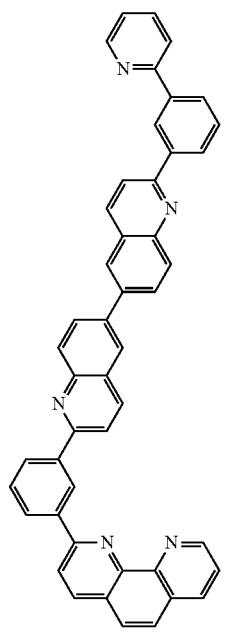
241
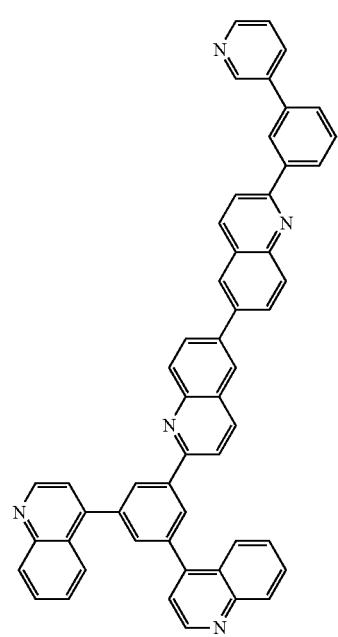
242
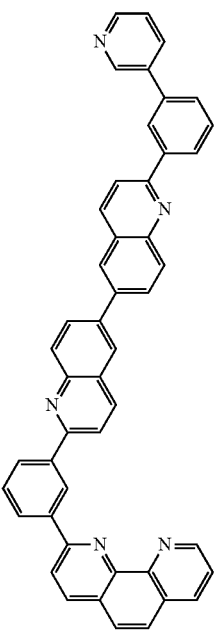
243
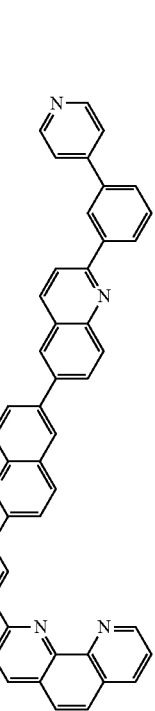

131
-continued
244
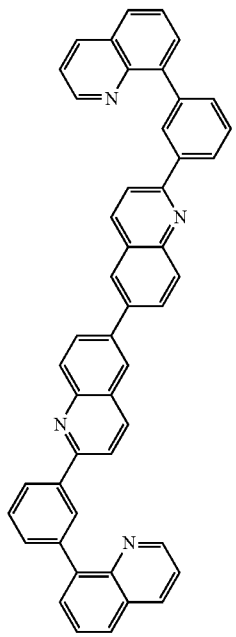
245
246
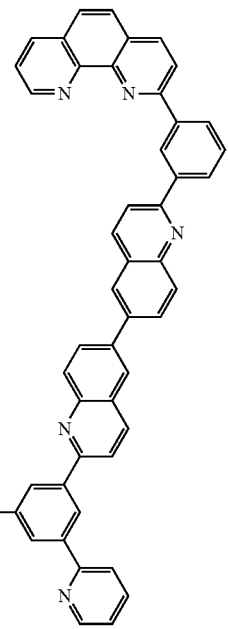
247

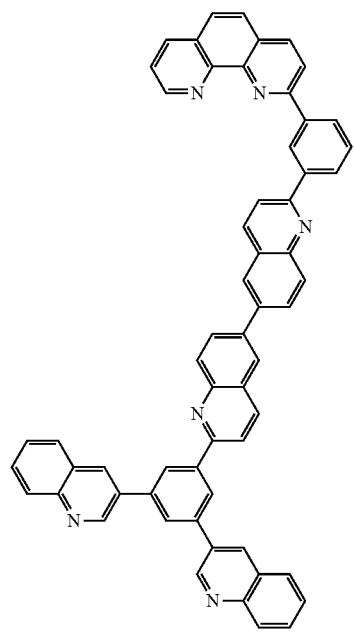
248
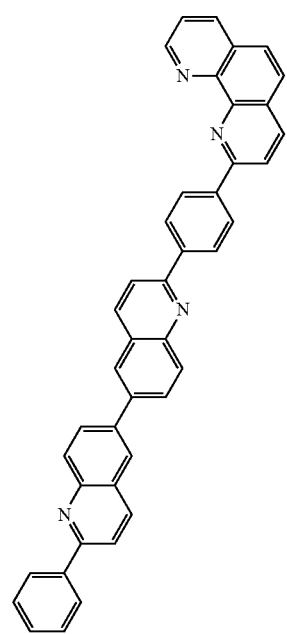
249
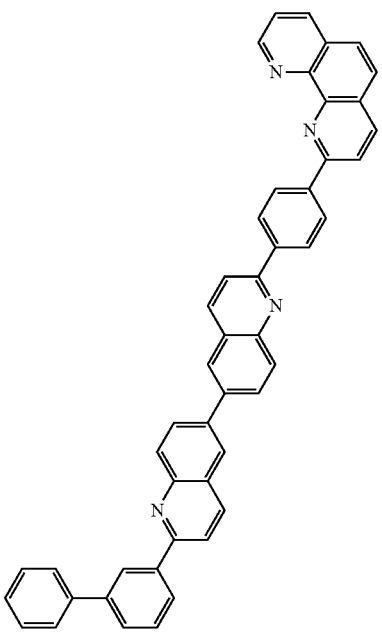
250
251

-continued
252
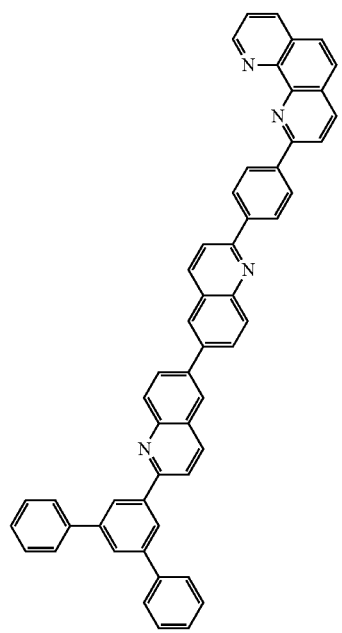
253
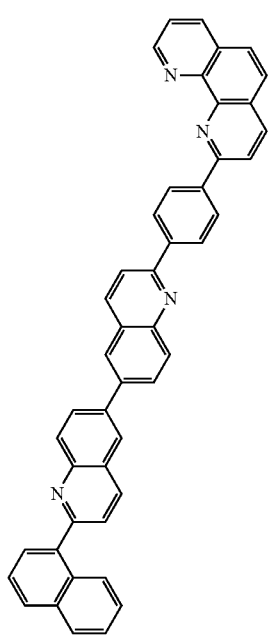
-continued
254
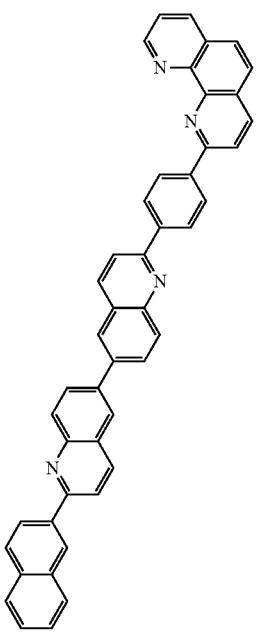
255
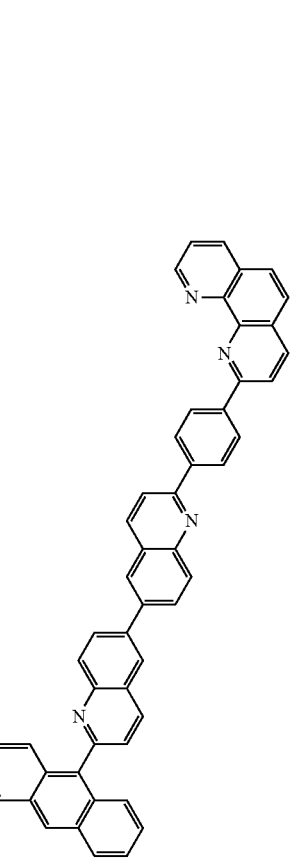

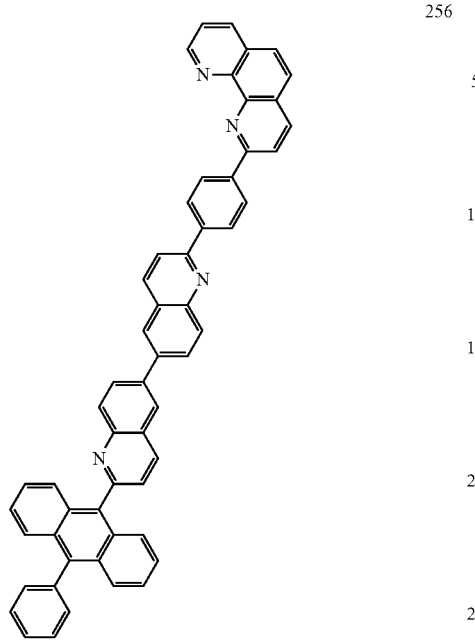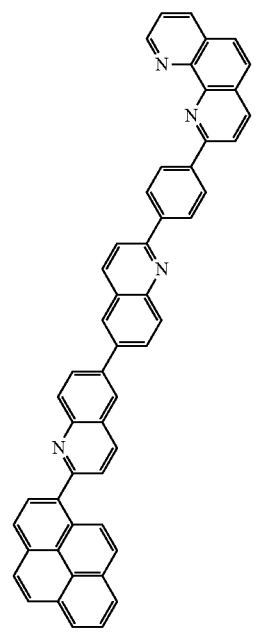

260
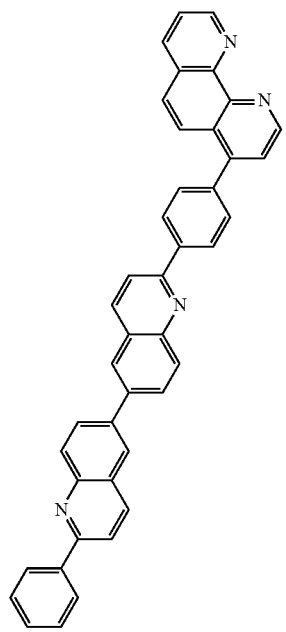
261
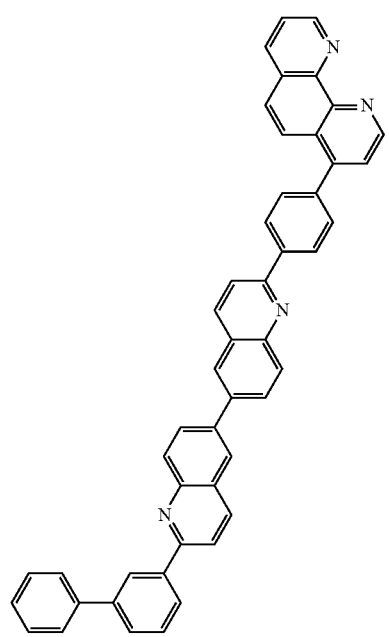
262
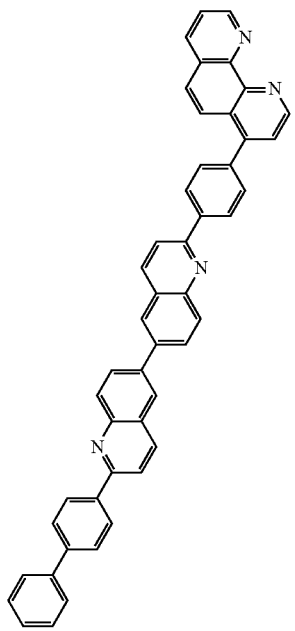
263
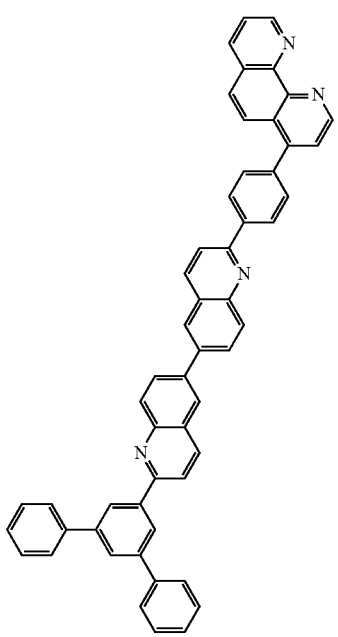

264
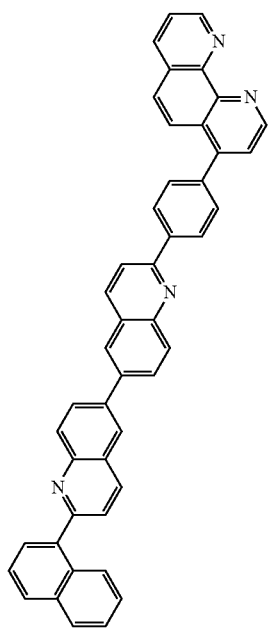
266
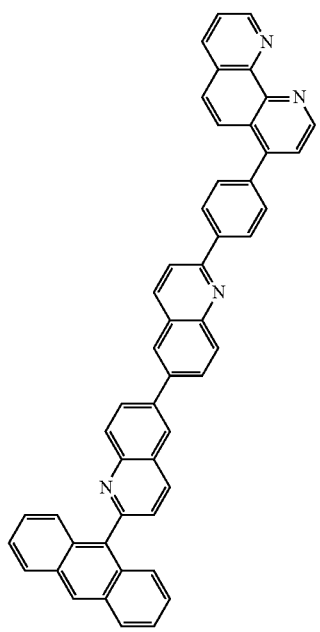
265
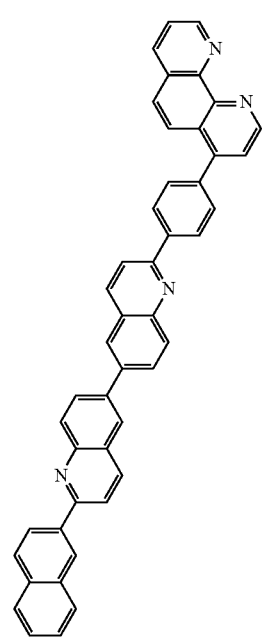
267
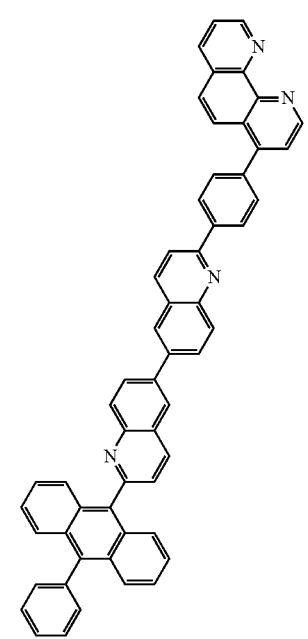

268
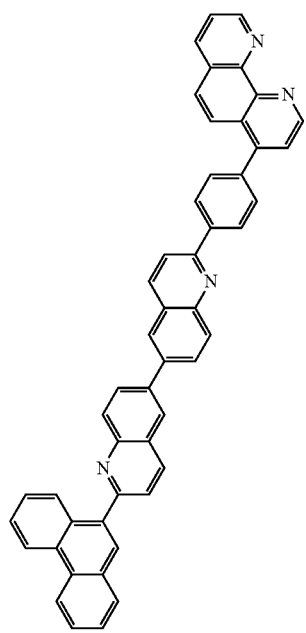
269
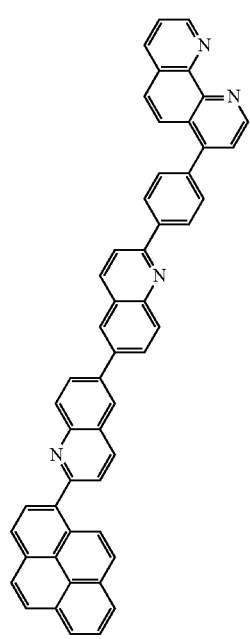
270
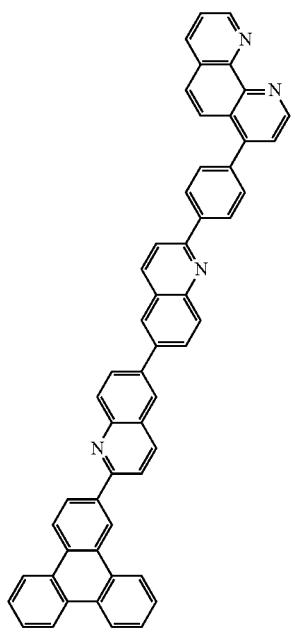
271
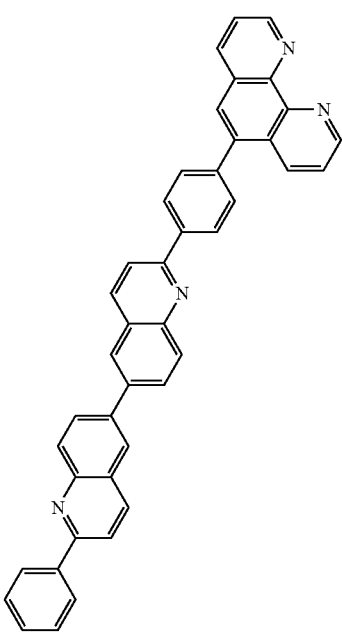

272
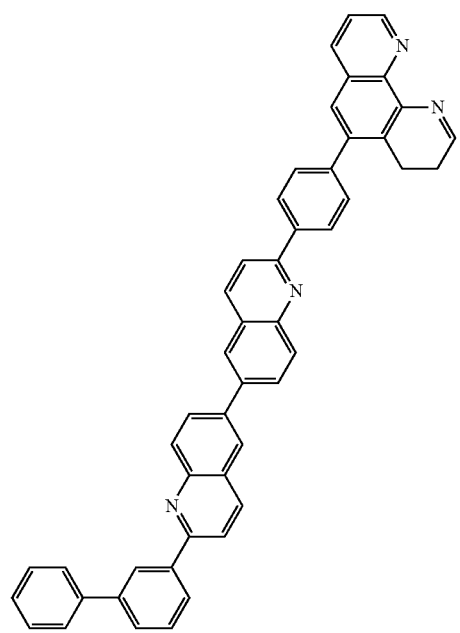
273
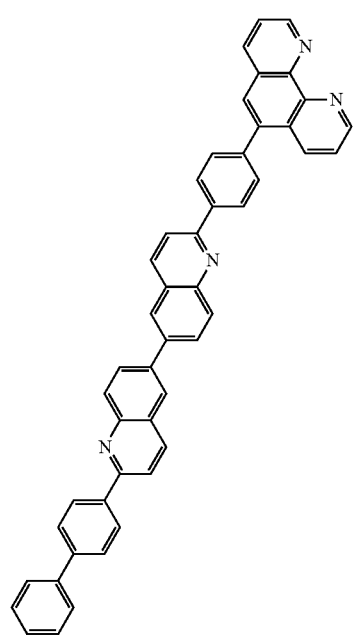
274
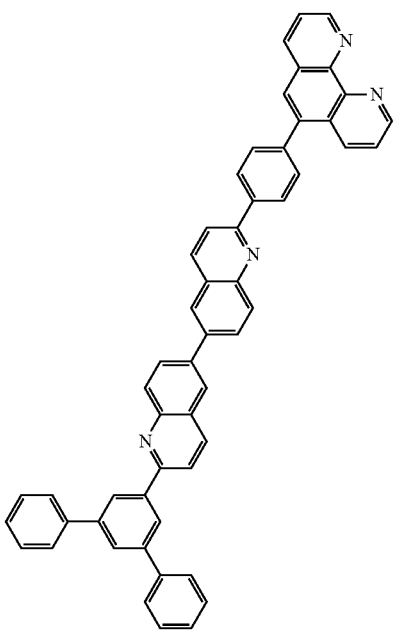
275
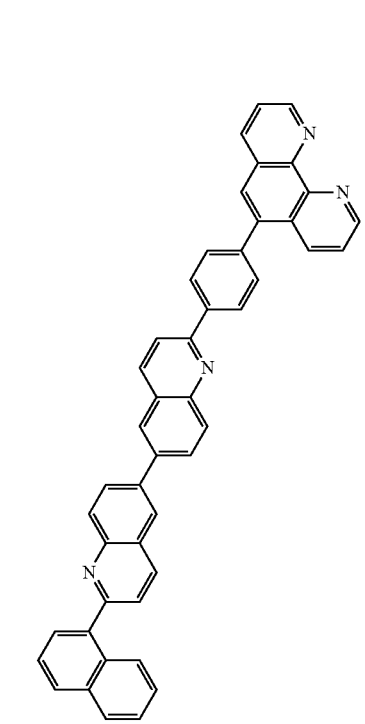

276
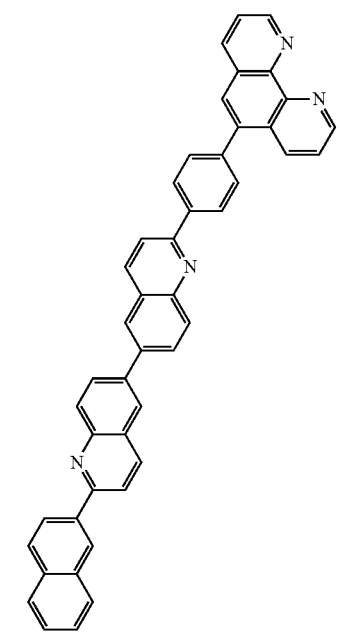
277
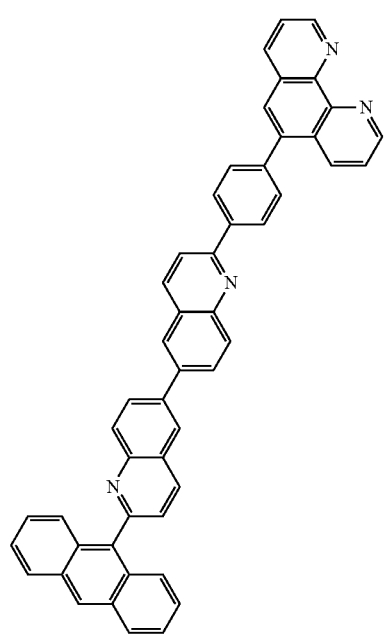
278
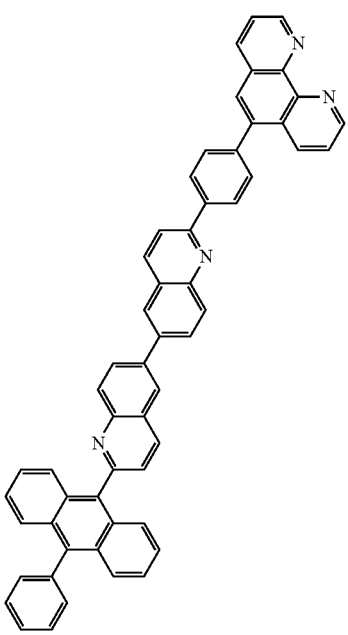
279
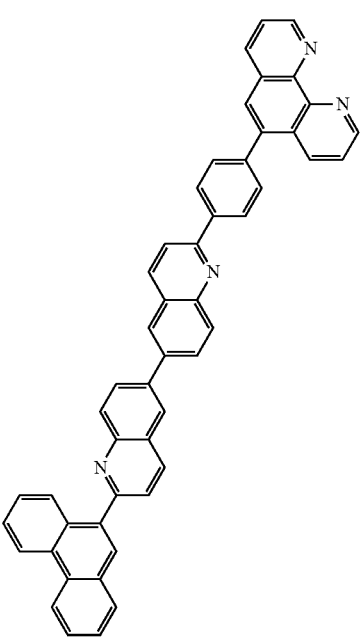

149
-continued
280
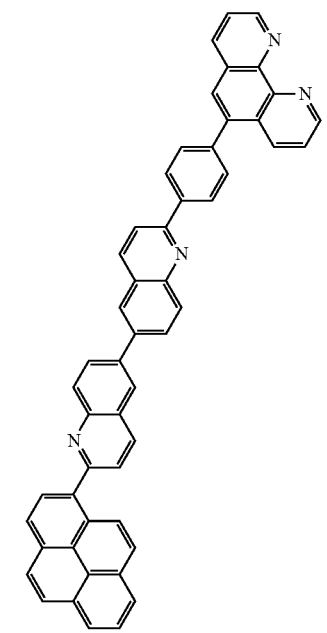
281
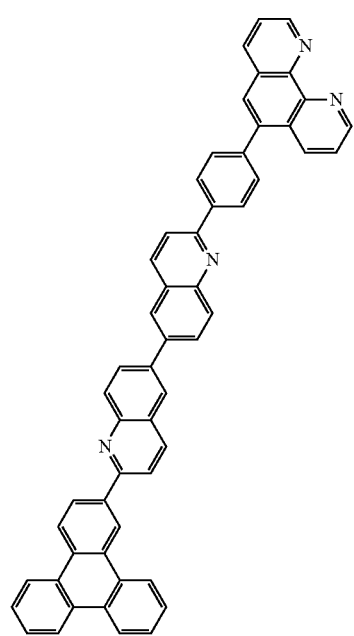
150
-continued
282
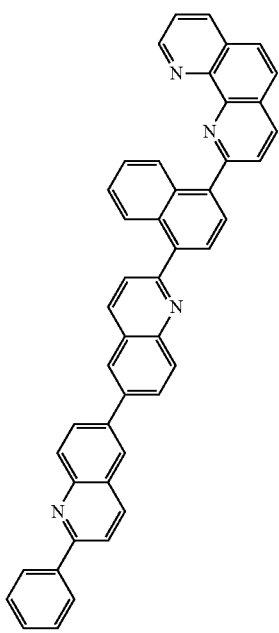
283
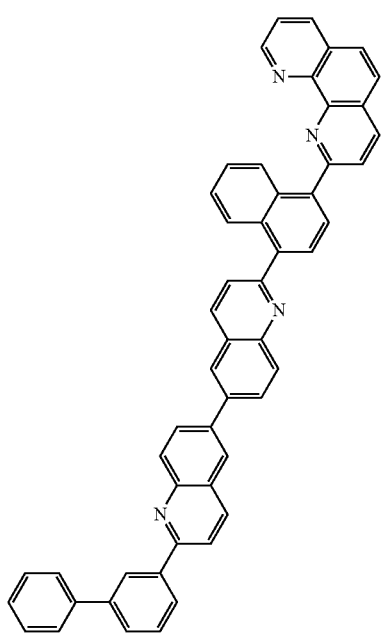

151
-continued
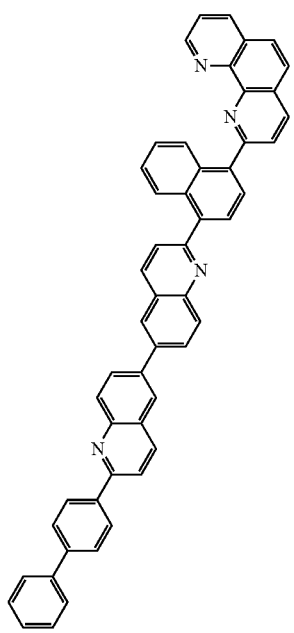
284
152
-continued
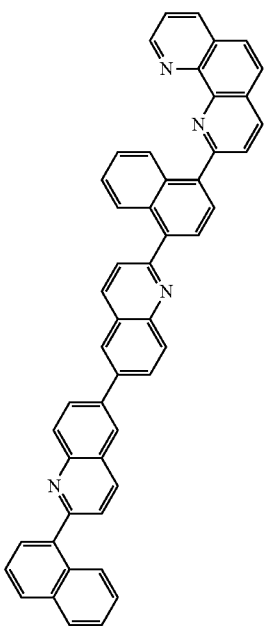
286
285
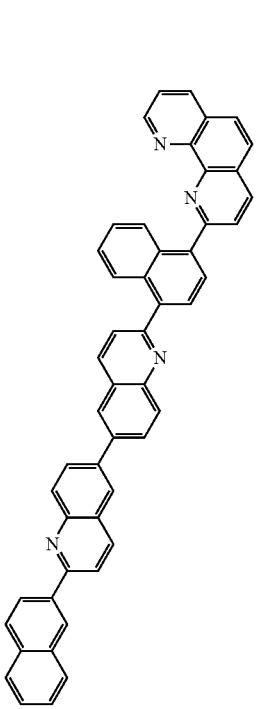
287

288
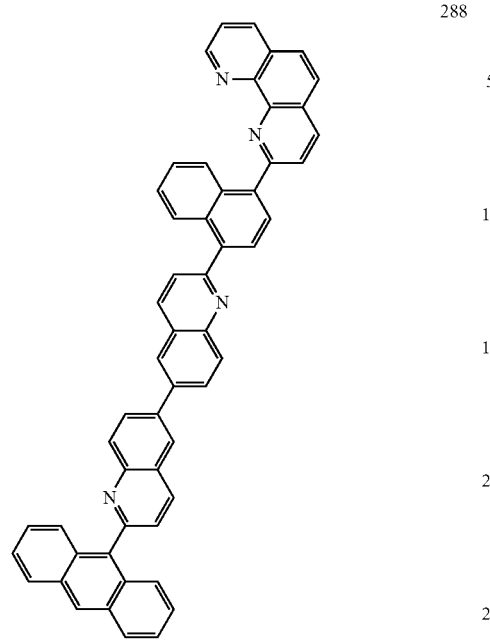
290
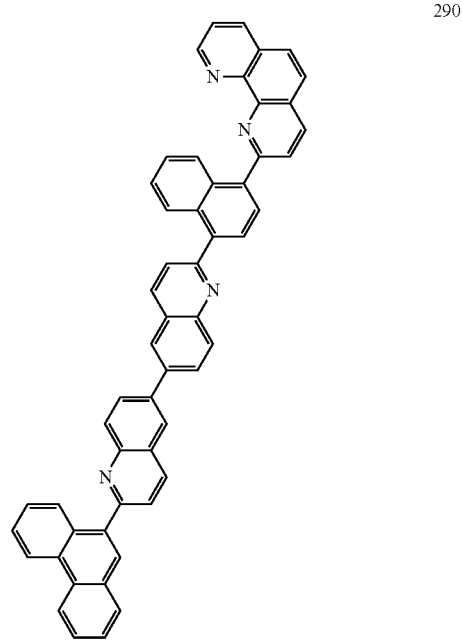
289
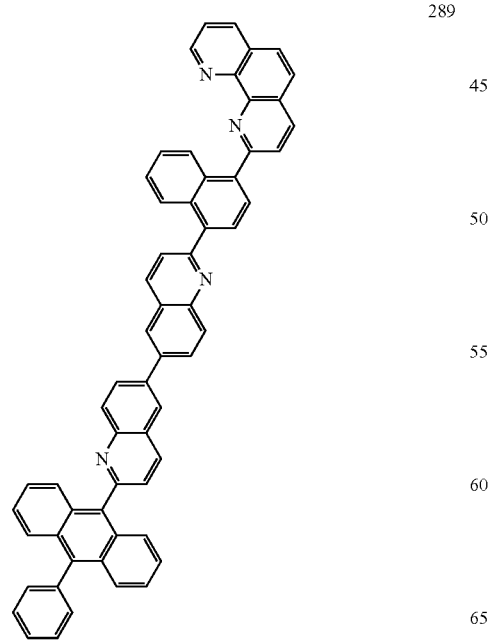
291
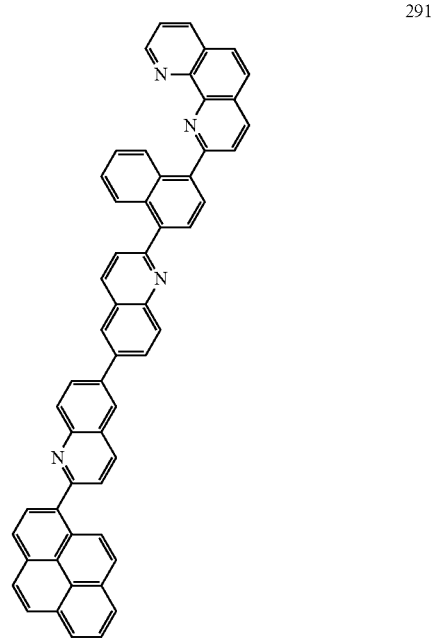

292
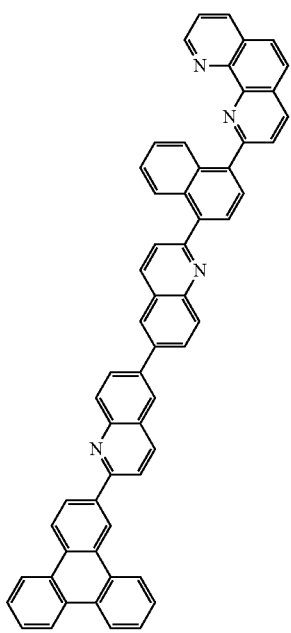
293
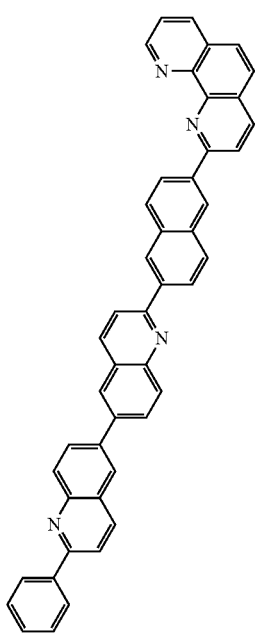
294
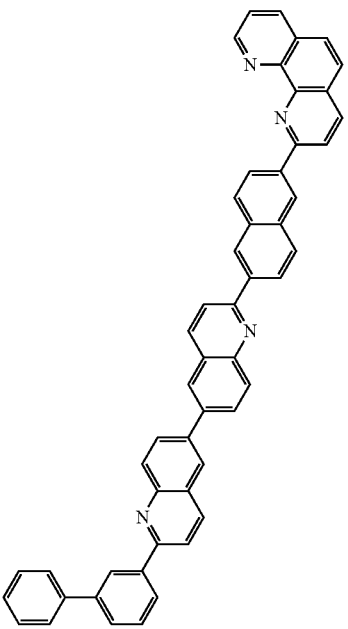
295
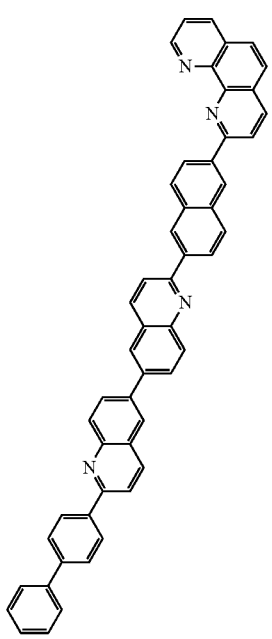

296
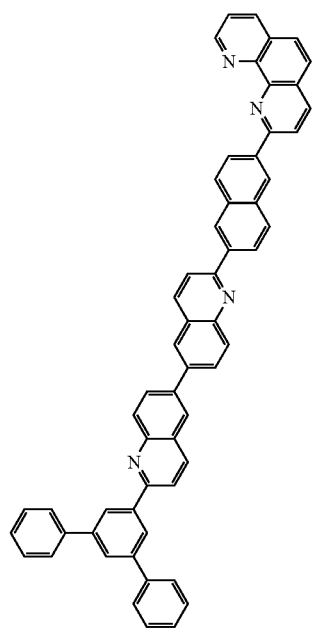
297
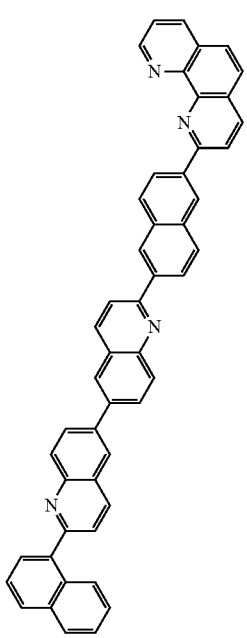
298
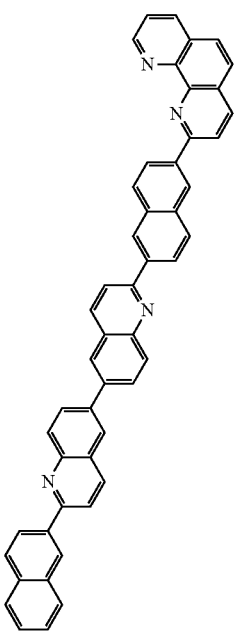
299
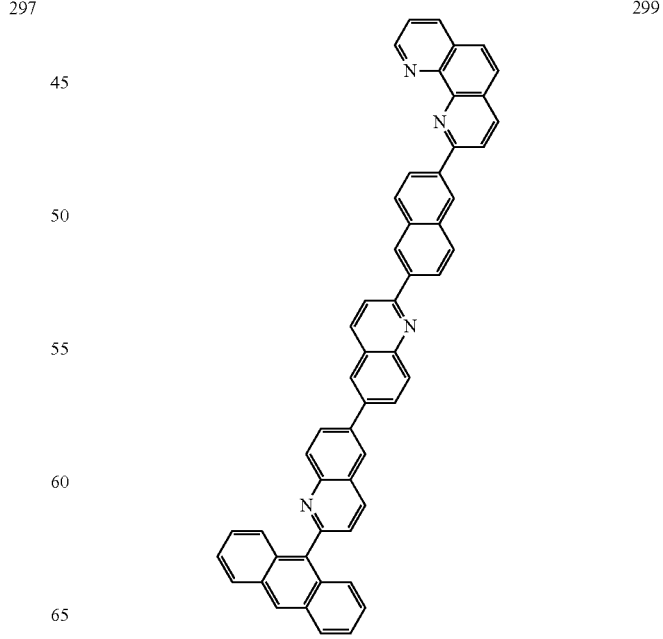

159
-continued
160
-continued
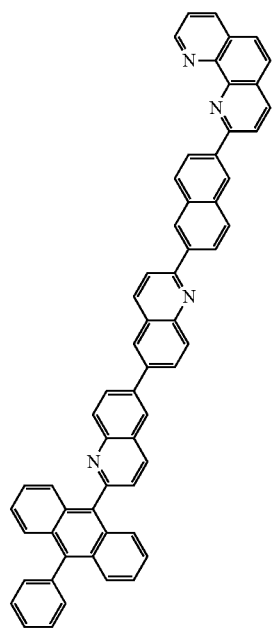
300
301
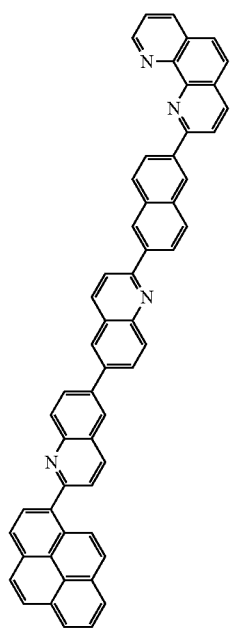
302
303

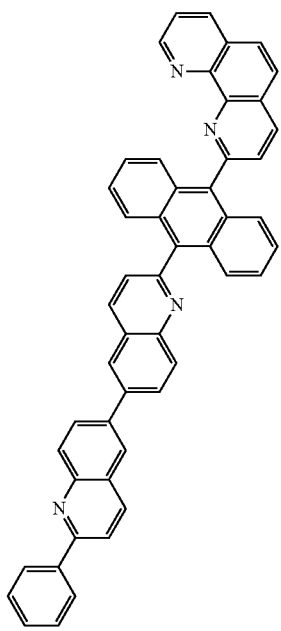
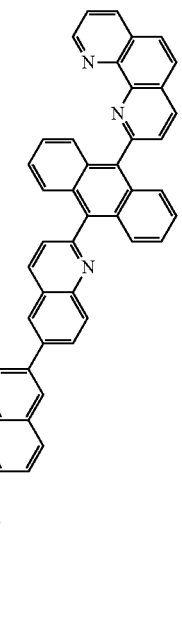

308
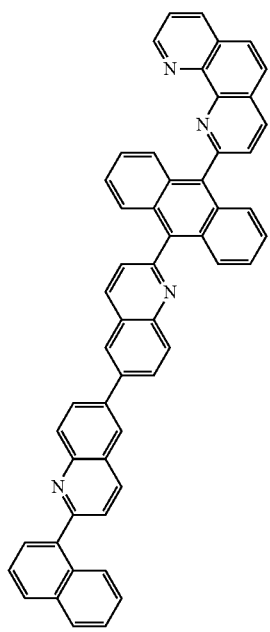
309
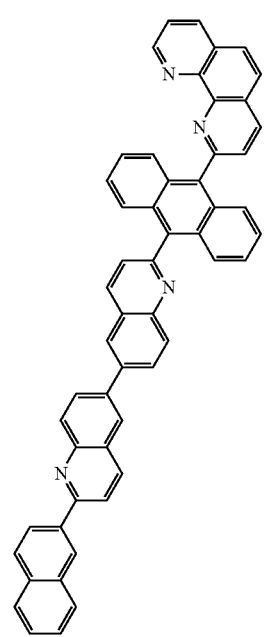
310
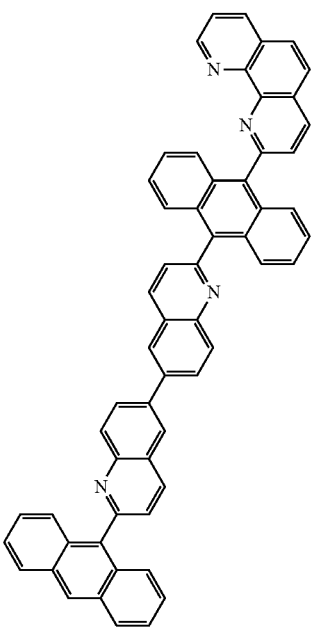
311
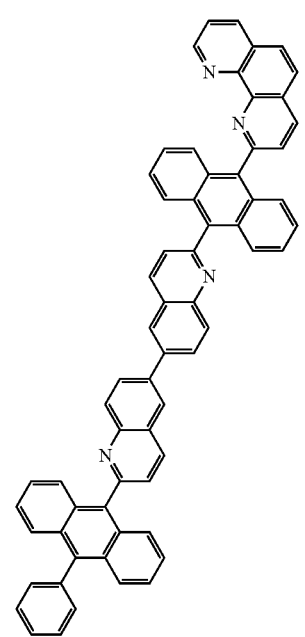

312 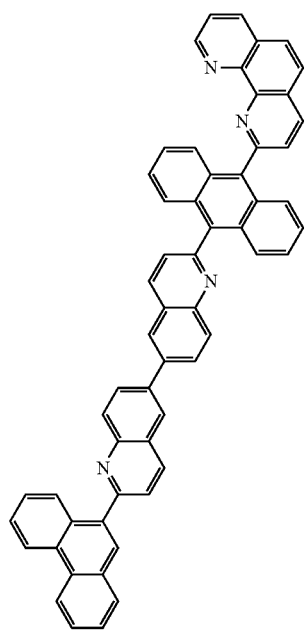
313 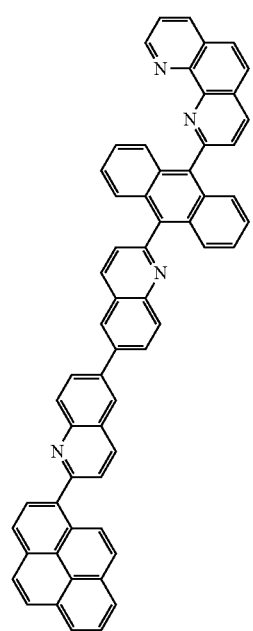
314 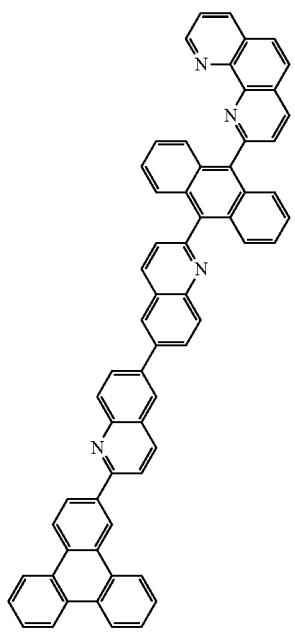
315 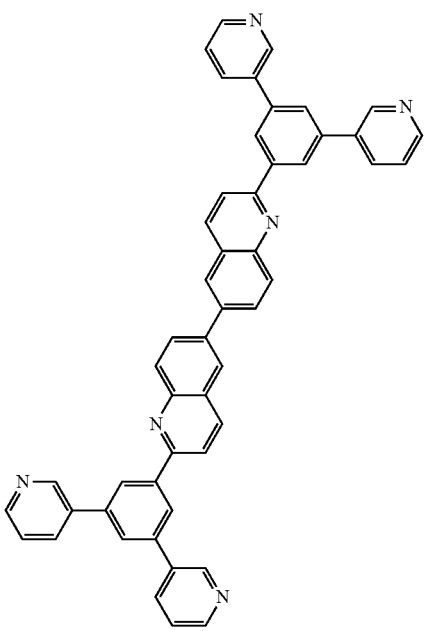

316
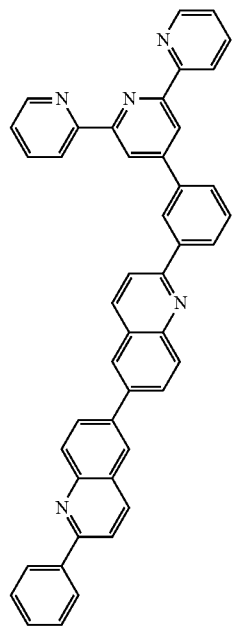
317
318
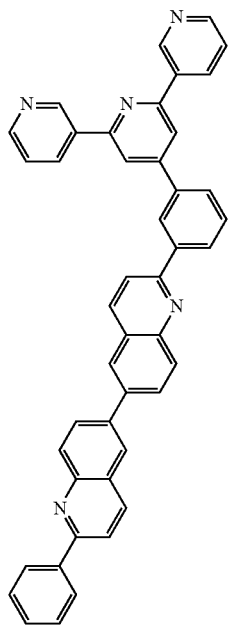
319

169
-continued
170
-continued
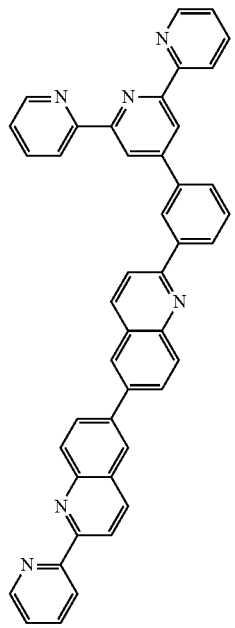
320
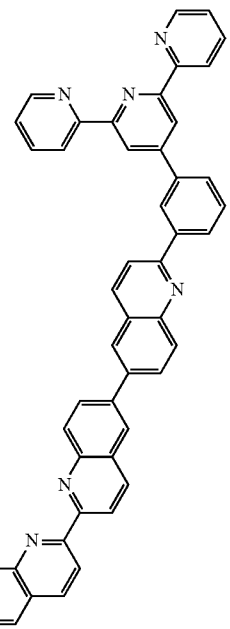
322
321
323

324

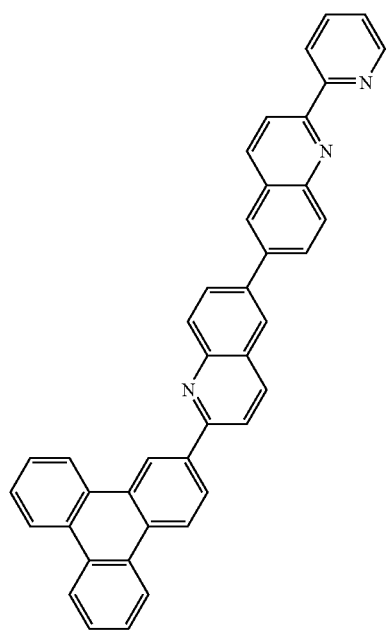

325

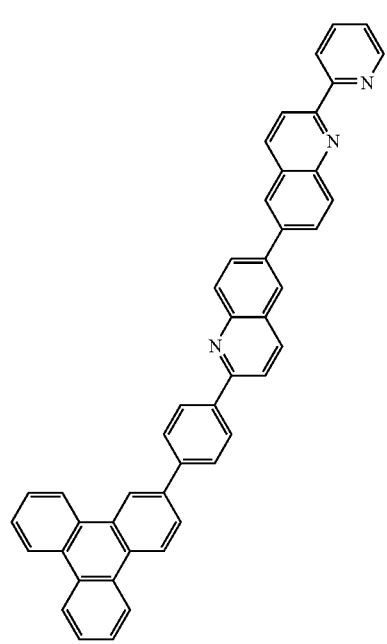

326

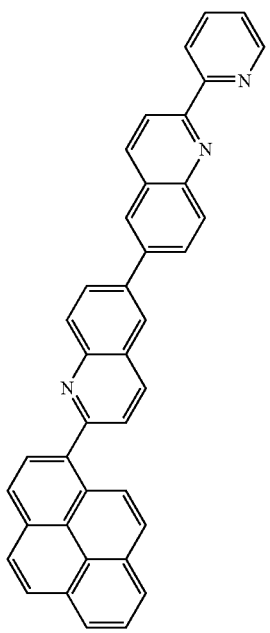

327

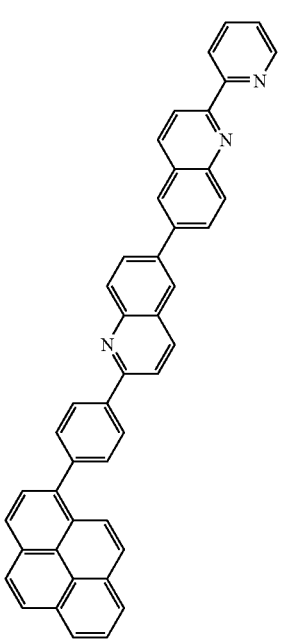

Further, it is possible to synthesize a compound having inherent characteristics of a substituent introduced by introducing various substituents into the structure of Chemical Formula 1. For example, a substituent usually used for a hole injection layer material, a material for transporting holes, a light emitting layer material, and an electron transporting layer material, which are used for manufacturing an organic light emitting device, may be introduced into the core structure to synthesize a material which satisfies conditions required for each organic material layer.

In addition, it is possible to finely adjust an energy band gap by introducing various substituents into the structure of Chemical Formula 1, and meanwhile, it is possible to improve characteristics at the interface between organic materials and diversify the use of material.

Meanwhile, the hetero-cyclic compound has a high glass transition temperature (Tg) and thus has excellent thermal stability. The increase in thermal stability becomes an important factor which provides driving stability to a device.

The hetero-cyclic compound according to an exemplary embodiment of the present application may be prepared by a multi-step chemical reaction. Some intermediate compounds are first prepared, and the compound of Chemical Formula 1 may be prepared from the intermediate compounds. More specifically, the hetero-cyclic compound according to an exemplary embodiment of the present application may be prepared based on the Preparation Examples to be described below.

Another exemplary embodiment of the present application provides an organic light emitting device comprising the hetero-cyclic compound represented by Chemical Formula 1.

The organic light emitting device according to an exemplary embodiment of the present application may be manufactured by typical manufacturing methods and materials of the organic light emitting device, except that the above-described hetero-cyclic compound is used to form an organic material layer having one or more layers.

The hetero-cyclic compound may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

Specifically, the organic light emitting device according to an exemplary embodiment of the present application comprises a positive electrode, a negative electrode, and an organic material layer having one or more layers disposed between the positive electrode and the negative electrode, in which one or more layers of the organic material layer comprise the hetero-cyclic compound represented by Chemical Formula 1.

FIGS. 1 to 3 exemplify the stacking sequence of the electrodes and the organic material layer of the organic light emitting device according to an exemplary embodiment of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited only to such a structure, and as in FIG. 2, an organic light emitting device in which a negative electrode, an organic material layer, and a positive electrode are sequentially stacked on a substrate may also be implemented.

FIG. 3 exemplifies a case where an organic material layer is a multilayer. An organic light emitting device according to FIG. 3 comprises a hole injection layer 301, a hole transporting layer 302, a light emitting layer 303, a hole blocking layer 304, an electron transporting layer 305, and an electron injection layer 306. However, the scope of the present application is not limited by the stacking structure as described above, and if necessary, the other layers except for the light emitting layer may be omitted, and another necessary functional layer may be further added.

The organic light emitting device according to the present specification may be manufactured by the materials and methods known in the art, except that one or more layers of the organic material layer comprise the hetero-cyclic compound represented by Chemical Formula 1.

The hetero-cyclic compound represented by Chemical Formula 1 may alone constitute one or more layers of the organic material layer of the organic light emitting device.

However, the hetero-cyclic compound represented by Chemical Formula 1 may be mixed with another material, if necessary, to constitute an organic material layer.

The hetero-cyclic compound represented by Chemical Formula 1 may be used as a material for an electron transporting layer, an electron transferring layer, a charge producing layer, a hole blocking layer, or a light emitting layer, and the like in an organic light emitting device. As an example, the hetero-cyclic compound represented by Chemical Formula 1 may be used as a material for an electron transferring layer, an electron transporting layer, or a charge producing layer of an organic light emitting device.

In addition, the hetero-cyclic compound represented by Chemical Formula 1 is used as a host of an electron transferring layer, an electron transporting layer, or a charge producing layer of an organic light emitting device, and the electron transferring layer, the electron transporting layer, or the charge producing layer may additionally comprise one or more n-type dopants selected from alkali metals and alkaline earth metals.

Furthermore, the hetero-cyclic compound represented by Chemical Formula 1 may be used as a material for a light emitting layer in an organic light emitting device. As an example, the hetero-cyclic compound represented by Chemical Formula 1 may be used as a material for a phosphorescent host of a light emitting layer in an organic light emitting device.

In the organic light emitting device according to an exemplary embodiment of the present application, materials other than the hetero-cyclic compound of Chemical Formula 1 will be exemplified below, but these materials are illustrative only and are not for limiting the scope of the present application, and may be replaced with materials publicly known in the art.

As a positive electrode material, materials having a relatively high work function may be used, and a transparent conductive oxide, a metal or a conductive polymer, and the like may be used. Specific examples of the positive electrode material comprise: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnOz_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As a material for the negative electrode, materials having a relatively low work function may be used, and a metal, a metal oxide, or a conductive polymer, and the like may be used. Specific examples of the negative electrode material comprise: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al; and the like, but are not limited thereto.

As a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, tris(4-carbazoyl-9-ylphenyl)amine (TCTA), 4,4',4"-tris[phenyl(m-tolyl)amino]triphenylamine (m-MTDATA), 1,3,5-tris[4-(3-methylphenylphenylamino)phenyl]benzene (m-MTDAPB), polyaniline/dodecylbenzenesulfonic acid or poly(3,4-ethylenedioxythiophene)/poly(4-styrenesulfonate), which is a soluble conductive polymer, polyaniline/camphor sulfonic acid or polyaniline/poly(4-styrene-sulfonate), and the like.

As a hole transport material, a pyrazoline derivative, an arylamine-based derivative, a stilbene derivative, a triphenyldiamine derivative, and the like may be used, and a low-molecular weight or polymer material may also be used.

As an electron transport material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

As an electron injection material, for example, LiF is representatively used in the art, but the present application is not limited thereto.

As a light emitting material, a red, green, or blue light emitting material may be used, and if necessary, two or more light emitting materials may be mixed and used. Further, as the light emitting material, a fluorescent material may also be used, but a phosphorescent material may also be used. As the light emitting material, it is also possible to use alone a material which emits light by combining holes and electrons each injected from a positive electrode and a negative electrode, but materials in which a host material and a dopant material are involved in light emission together may also be used.

The organic light emitting device according to an exemplary embodiment of the present application may be a top emission type, a bottom emission type, or a dual emission type according to the material to be used.

The hetero-cyclic compound according to an exemplary embodiment of the present application may act even in organic electronic devices including organic solar cells, organic photoconductors, organic transistors, and the like, based on the principle similar to those applied to organic light emitting devices.

MODE FOR INVENTION

Hereinafter, the present specification will be described in more detail through Examples, but these Examples are provided only for exemplifying the present application, and are not intended to limit the scope of the present application.

Examples

<Preparation Example 1> Preparation of Compound 6

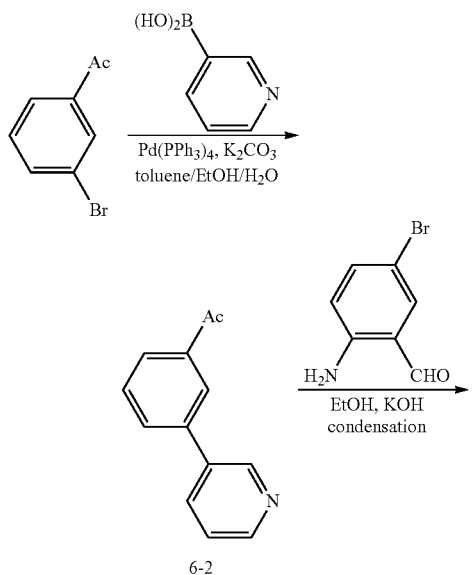

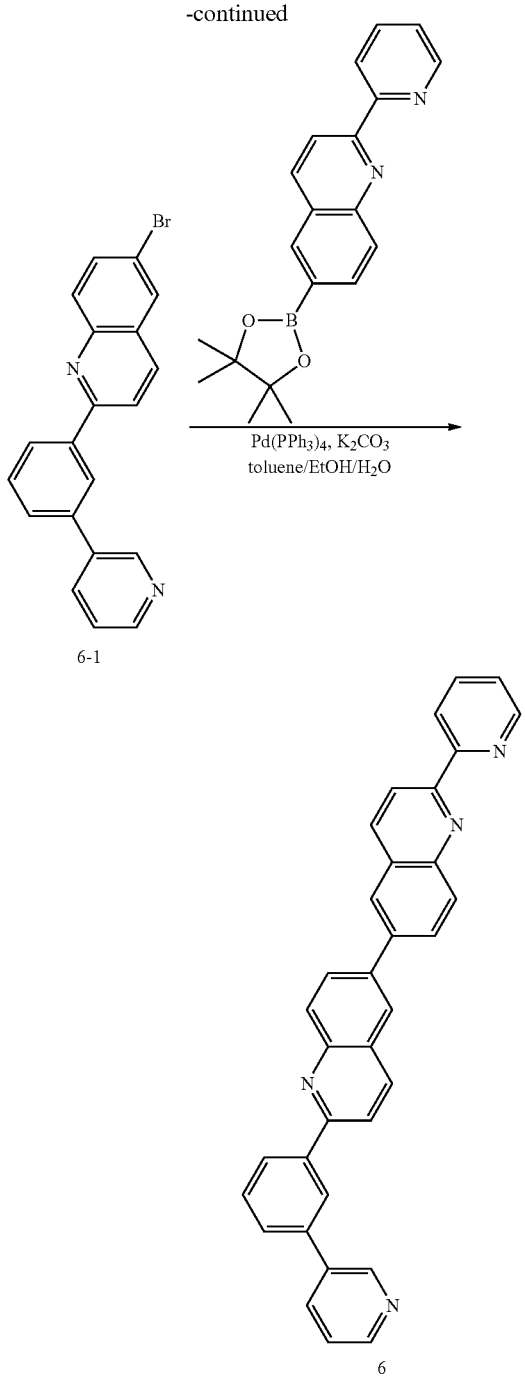

Preparation of Compound 6-2

A compound pyridin-3-ylboronic acid (12.4 g, 100 mmol) and 1-(3-bromophenyl)ethan-1-one (20 g, 100 mmol) were dissolved in 200 mL of toluene, and then Pd(PPh$_3$)$_4$ (3.4 g, 3 mmol) and K$_2$CO$_3$ (41 g, 300 mmol) were added thereto, and the resulting mixture was stirred for 10 minutes. EtOH (40 mL) and H$_2$O (40 mL) were additionally added dropwise to a reaction vessel, and then the resulting mixture was refluxed at high temperature. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using dichloromethane and hexane as an eluent to obtain Target Compound 6-2 (18 g, 91%).

Preparation of Compound 6-1

Compound 6-2 (18 g, 91.2 mmol) and 2-amino-5-bromobenzaldehyde (38 g, 91.2 mmol) were dissolved in EtOH (300 mL), and then KOH (91.2 mmol) was added to the resulting solution in a reaction vessel, and the resulting mixture was heated to 80° C. After the reaction was completed, the reaction product was cooled to normal temperature, and then an extraction was performed with distilled water and ethyl acetate. The extracted organic layer was dried over anhydrous $Na_2SO_4$, and then filtered. The solvent of the filtered organic layer was removed by using a rotary evaporator, and then the residue was purified with column chromatography using dichloromethane and hexane as an eluent to obtain Target Compound 6-1 (26 g, 80%).

Preparation of Compound 6

Compound 6-1 (8 g, 22.2 mmol) and 2-(pyridin-2-yl)-6-(4,4,5,5-tetramethyl-1,3,2-dioxaborolan-2-yl)quinoline (7.4 g, 22.2 mmol) were dissolved in toluene (50 mL), and then $Pd(PPh_3)_4$ (2.3 g, 2 mmol) and $K_2CO_3$ (8.3 g, 60 mmol) were added to the resulting solution, and the resulting mixture was stirred for 10 minutes. $H_2O$ (10 mL) and EtOH (6 mL) were additionally added dropwise to a reaction vessel, and then the resulting mixture was refluxed for 12 hours. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 6 (7 g, 65%).

<Preparation Example 2> Preparation of Compound 7

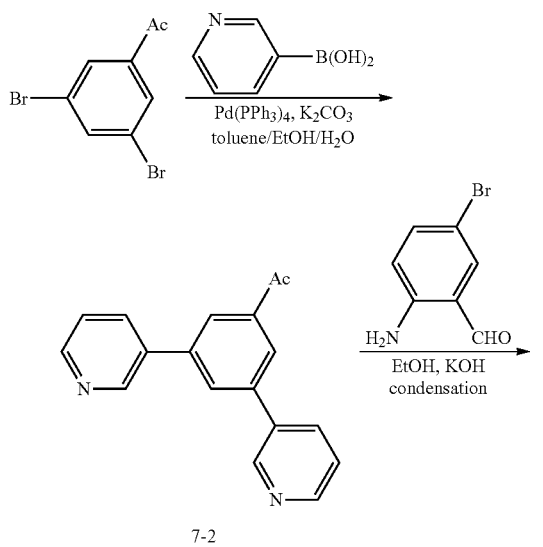

7-2

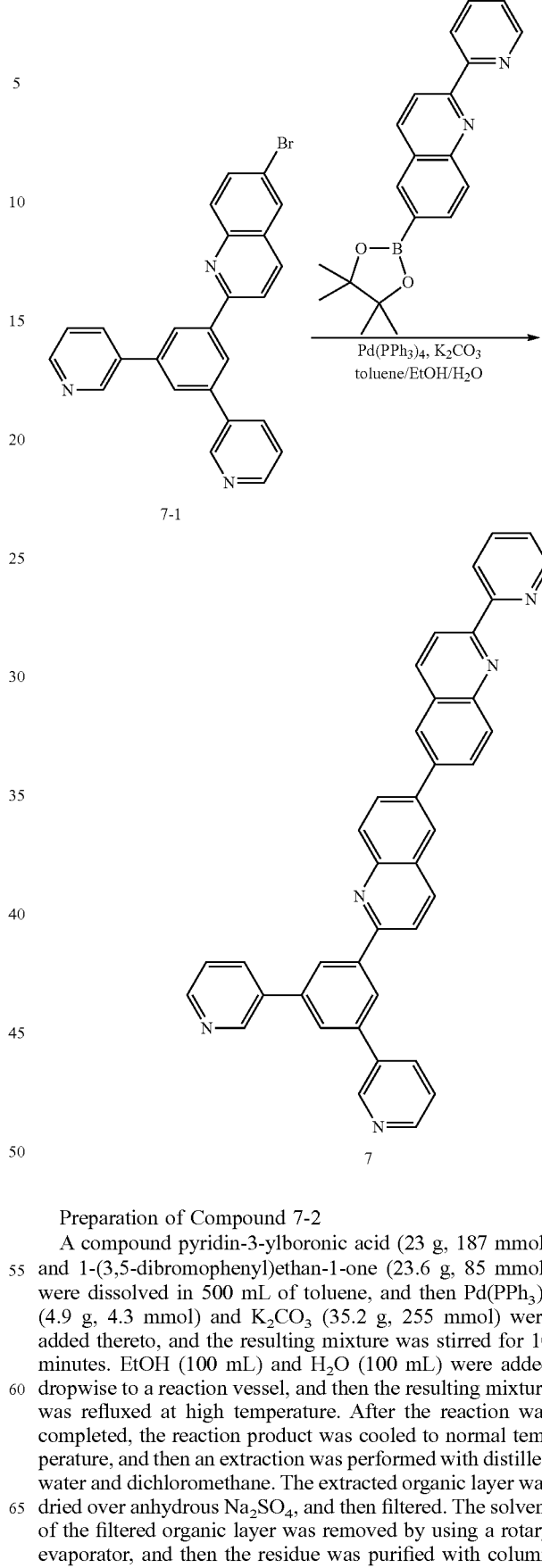

Preparation of Compound 7-2

A compound pyridin-3-ylboronic acid (23 g, 187 mmol) and 1-(3,5-dibromophenyl)ethan-1-one (23.6 g, 85 mmol) were dissolved in 500 mL of toluene, and then $Pd(PPh_3)_4$ (4.9 g, 4.3 mmol) and $K_2CO_3$ (35.2 g, 255 mmol) were added thereto, and the resulting mixture was stirred for 10 minutes. EtOH (100 mL) and $H_2O$ (100 mL) were added dropwise to a reaction vessel, and then the resulting mixture was refluxed at high temperature. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using dichloromethane and hexane as an eluent to obtain Target Compound 7-2 (16 g, 70%).

Preparation of Compound 7-1

Compound 7-2 (6.2 g, 22.6 mmol) and 2-amino-5-bromobenzaldehyde (4.52 g, 22.6 mmol) were dissolved in EtOH (150 mL), and then KOH (22.6 mmol) was added to the resulting solution, and the resulting mixture was heated to 80° C. After the reaction was completed, the reaction product was cooled to normal temperature, and then an extraction was performed with distilled water and ethyl acetate. The extracted organic layer was dried over anhydrous $Na_2SO_4$, and then filtered. The solvent of the filtered organic layer was removed by using a rotary evaporator, and then the residue was purified with column chromatography using dichloromethane and hexane as an eluent to obtain Target Compound 7-1 (9.6 g, 97%).

Preparation of Compound 7

Compound 7-1 (8.8 g, 20 mmol) and 2-(pyridin-2-yl)-6-(4,4,5,5-tetramethyl-1,3,2-dioxaborolan-2-yl)quinoline (6.5 g, 20 mmol) were dissolved in toluene (50 mL), and then $Pd(PPh_3)_4$ (2.3 g, 2 mmol) and $K_2CO_3$ (8.3 g, 60 mmol) were added to the resulting solution, and the resulting mixture was stirred for 10 minutes. And then, $H_2O$ (10 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 7 (6.8 g, 67%).

<Preparation Example 4> Preparation of Compound 11

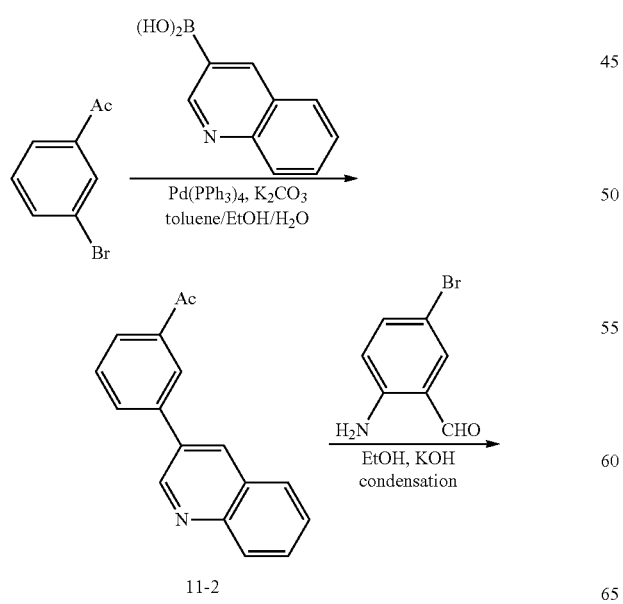

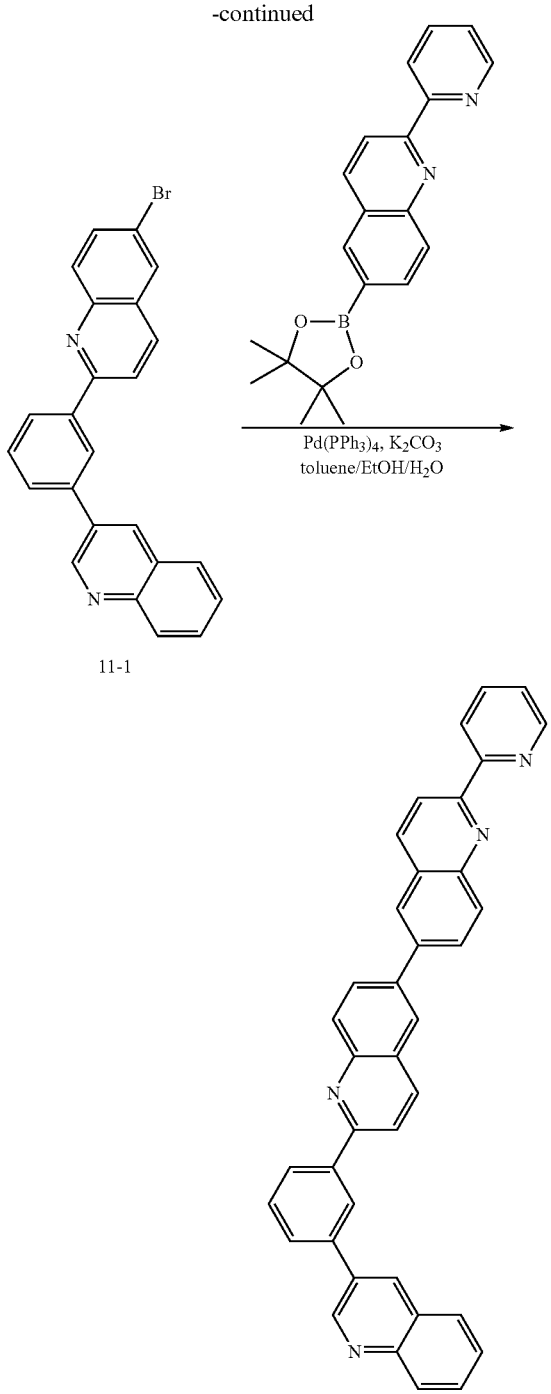

Preparation of Compound 11-2

A compound quinolin-3-ylboronic acid (26 g, 151 mmol) and 1-(3-bromophenyl)-ethan-1-one (30 g, 151 mmol) were dissolved in 300 mL of toluene, and then $Pd(PPh_3)_4$ (5.2 g, 4.5 mmol) and $K_2CO_3$ (63 g, 450 mmol) were added thereto, and the resulting mixture was stirred for 10 minutes. EtOH (60 mL) and $H_2O$ (60 mL) were additionally added dropwise to a reaction vessel, and then the resulting mixture was refluxed at high temperature. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using dichloromethane and hexane as an eluent to obtain Target Compound 11-2 (25 g, 68%).

Preparation of Compound 11-1

Compound 11-2 (25 g, 102.7 mmol) and 2-amino-5-bromobenzaldehyde (20.5 g, 102.7 mmol) were dissolved in EtOH (200 mL), and then KOH (102.7 mmol) was added to the resulting solution, and the resulting mixture was heated to 80° C. After the reaction was completed, the reaction product was cooled to normal temperature, and then an extraction was performed with distilled water and ethyl acetate. The organic layer was dried over anhydrous Na$_2$SO$_4$, and then filtered. The solvent of the filtered organic layer was removed by using a rotary evaporator, and the residue was purified with column chromatography using dichloromethane and hexane as an eluent to obtain Target Compound 11-1 (22 g, 52%).

Preparation of Compound 11

Compound 11-1 (6.8 g, 16.5 mmol) and 2-(pyridin-2-yl)-6-(4,4,5,5-tetramethyl-1,3,2-dioxaborolan-2-yl)quinoline (5.0 g, 12.9 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. H$_2$O (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed, and then the residue was purified with column chromatography using ethyl acetate and hexane as an eluent to obtain Target Compound 11 (7.1 g, 80%).

<Preparation Example 4> Preparation of Compound 13

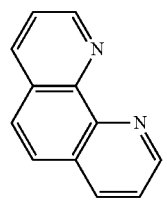

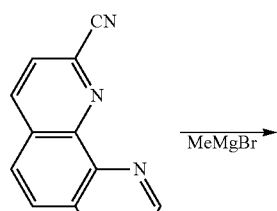

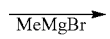

13-3

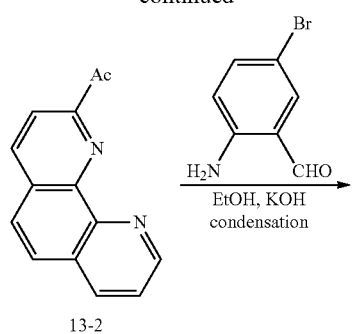

13-2

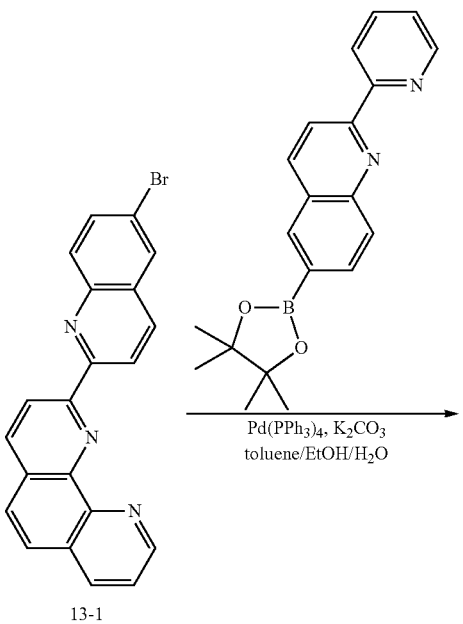

13-1

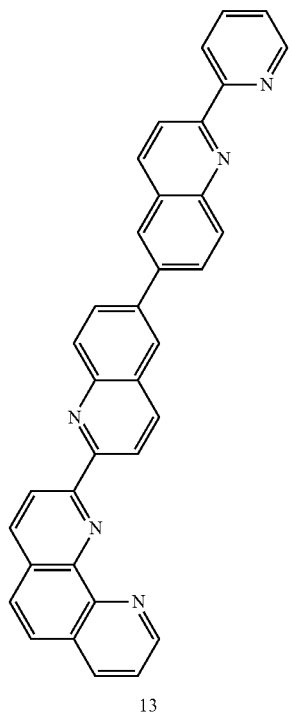 [SMILES: c1ccc(-c2ccc3cc(-c4ccc5nc(-c6ccc7ccc8cccnc8c7n6)ccc5c4)ccc3n2)nc1]

13

Preparation of Compound 13-3

A compound 1,10-phenanthroline (50 g, 250 mmol) was dissolved in AcOH (60 mL), and then 30% H$_2$O$_2$ (60 mL) was added thereto, and the resulting mixture was refluxed for 4 hours. After the reaction was completed, the reaction product was cooled to normal temperature, and then the pH was adjusted to 11 by using a saturated aqueous KOH solution. And then, an extraction was performed by using chloroform. The extracted organic layer was dried over anhydrous Na$_2$SO$_4$, and then filtered. The solvent of the filtered organic layer was removed by using a rotary evaporator. KCN (38 g) was added to 38 g of the thus obtained yellow solid, the resulting mixture was dissolved in water, and then benzoyl chloride (38 mL) was slowly added dropwise thereto. After the mixture was stirred at normal temperature for 4 hours, it was confirmed that the reaction was terminated, and then the resulting product was filtered with a paper filter. The filtered solute was purified with column chromatography using ethyl acetate and hexane as an eluent to obtain Target Compound 13-3 (28 g, 54%).

Preparation of Compound 13-2

Compound 13-3 (20 g, 97.5 mmol) was dissolved in THF (50 mL), and then 9.7 mL of MeMgBr(3M) was slowly added dropwise thereto at −78° C. It was confirmed that the reaction was terminated by warming the mixture to normal temperature, and an extraction was performed with an aqueous NH$_4$Cl solution and dichloromethane. After the organic layer was dried over anhydrous MgSO$_4$, the solvent was removed by using a rotary evaporator, and then the resulting product was purified with column chromatography using ethyl acetate and hexane as an eluent to obtain Target Compound 13-2 (10 g, 46%).

Preparation of Compound 13-1

After Compound 13-2 (10 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous Na$_2$SO$_4$, and then the solvent was removed by using a rotary evaporator. And then, the residue was purified with column chromatography using ethyl acetate and hexane as an eluent to obtain Target Compound 13-1 (14.6 g, 84%).

Preparation of Compound 13

Compound 13-1 (5.8 g, 15.0 mmol) and 2-(pyridin-2-yl)-6-(4,4,5,5-tetramethyl-1,3,2-dioxaborolan-2-yl)quinoline (5.0 g, 15.0 mmol) were dissolved in toluene (30 mL), and then Pd(PPh$_3$)$_4$ (1.7 g, 1.5 mmol) and K$_2$CO$_3$ (6.2 g, 45 mmol) were added to the resulting solution, and the resulting mixture was stirred for 10 minutes. And then, H$_2$O (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 13 (6.2 g, 81%).

<Preparation Example 5> Preparation of Compound 14

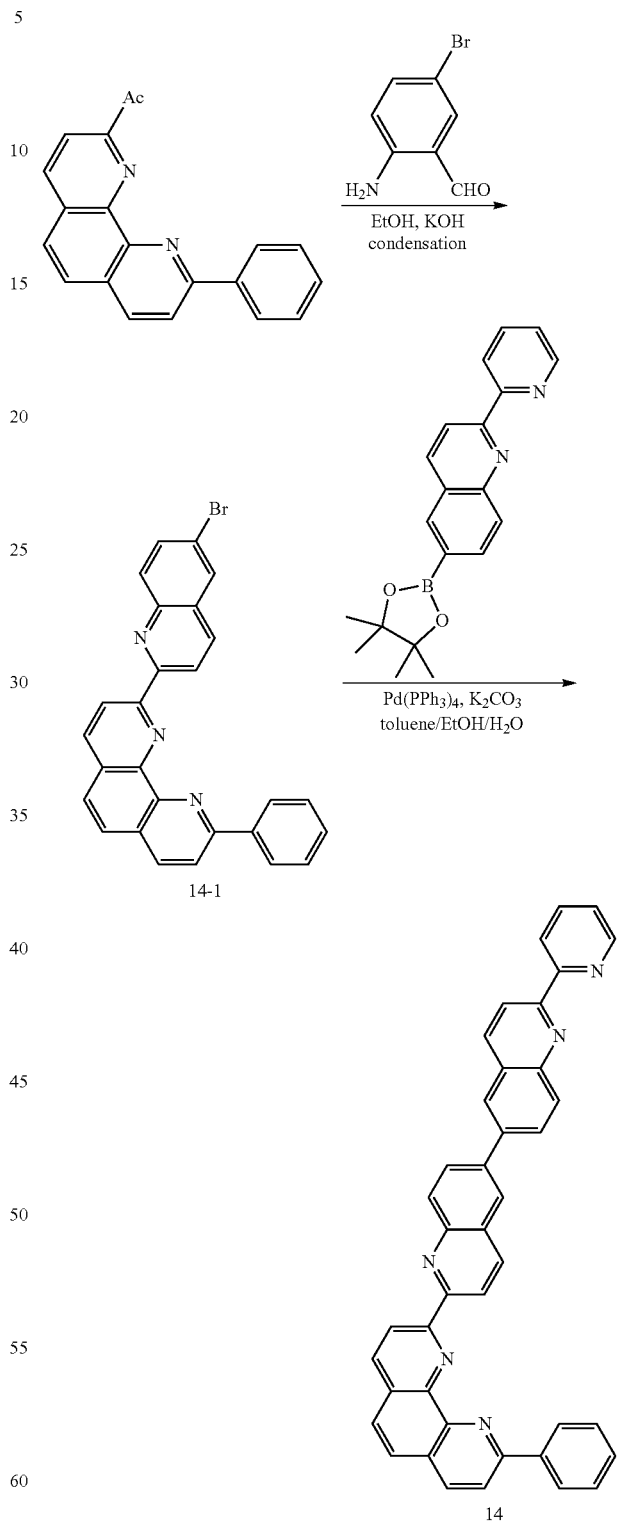

Preparation of Compound 14-1

After a compound 1-(9-phenyl-1,10-phenanthrolin-2-yl)ethan-1-one (13.4 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous Na$_2$SO$_4$, and then the solvent was removed by using a rotary evaporator. And then, the residue was purified with column chromatography using ethyl acetate and hexane as an eluent to obtain Target Compound 14-1 (18.5 g, 89%).

Preparation of Compound 14

Compound 14-1 (8.7 g, 15 mmol) and a compound 2-(pyridin-2-yl)-6-(4,4,5,5-tetramethyl-1,3,2-dioxaborolan-2-yl)quinoline (5.0 g, 15.0 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. And then, H$_2$O (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 14 (5.5 g, 62%).

<Preparation Example 6> Preparation of Compound 15

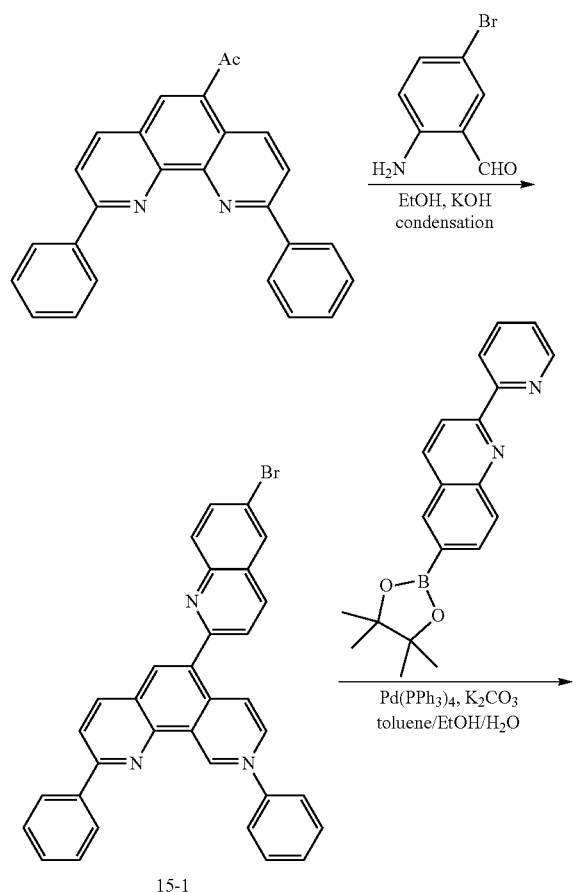

15-1

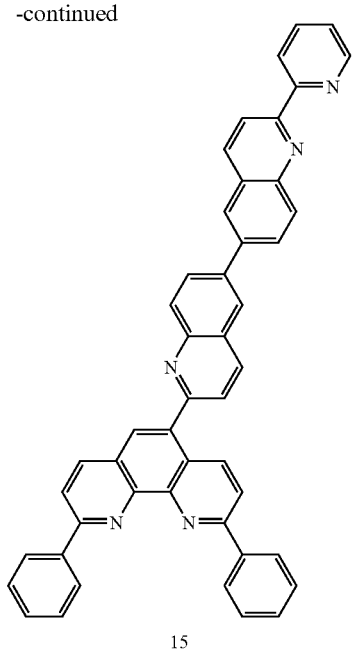

15

Preparation of Compound 15-1

After a compound 1-(2,9-diphenyl-1,10-phenanthrolin-5-yl)ethan-1-one (3.7 g, 10 mmol) and 2-amino-5-bromobenzaldehyde (2 g, 10 mmol) were dissolved in EtOH (200 mL), 3 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous Na$_2$SO$_4$, and then the solvent was removed by using a rotary evaporator. And then, the residue was purified with column chromatography using ethyl acetate and hexane as an eluent to obtain Target Compound 15-1 (5.2 g, 96%).

Preparation of Compound 15

Compound 15-1 (5.2 g, 9.6 mmol) and a compound 2-(pyridin-2-yl)-6-(4,4,5,5-tetramethyl-1,3,2-dioxaborolan-2-yl)quinoline (3.2 g, 9.6 mmol) were dissolved in toluene (25 mL), and then Pd(PPh$_3$)$_4$ (1.1 g, 0.96 mmol) and K$_2$CO$_3$ (3.9 g, 28.8 mmol) were added to the resulting solution, and the resulting mixture was stirred for 10 minutes. And then, H$_2$O (5 mL) and EtOH (5 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 15 (5.2 g, 81%).

<Preparation Example 7> Preparation of Compound 16

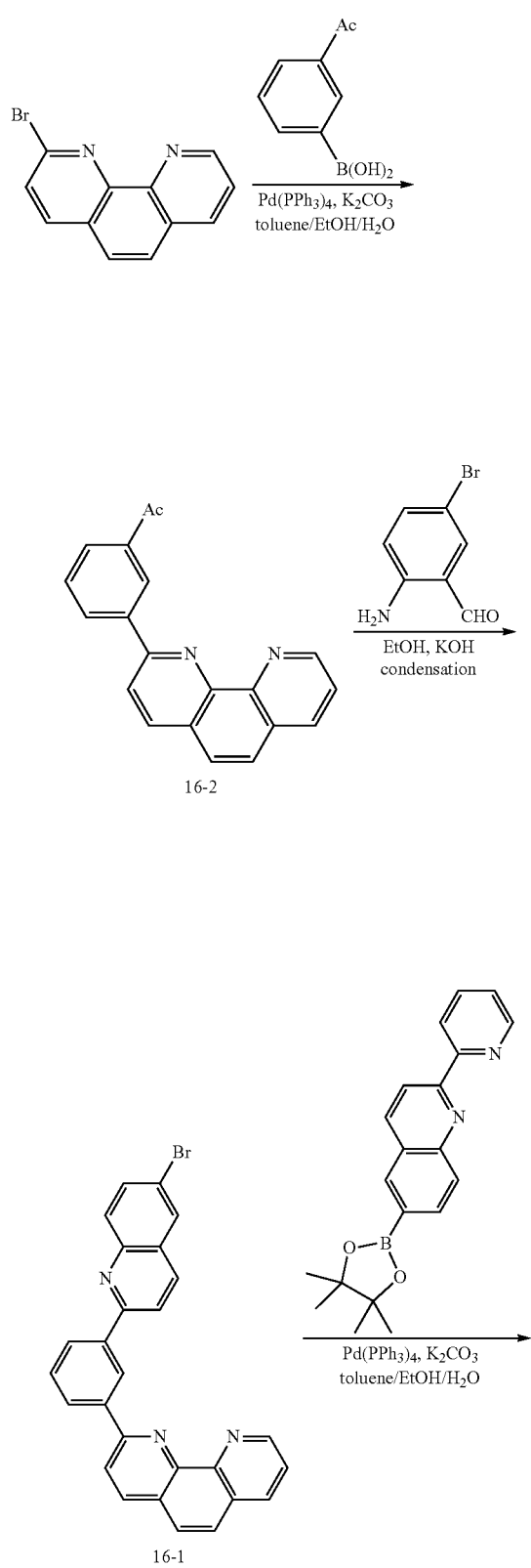

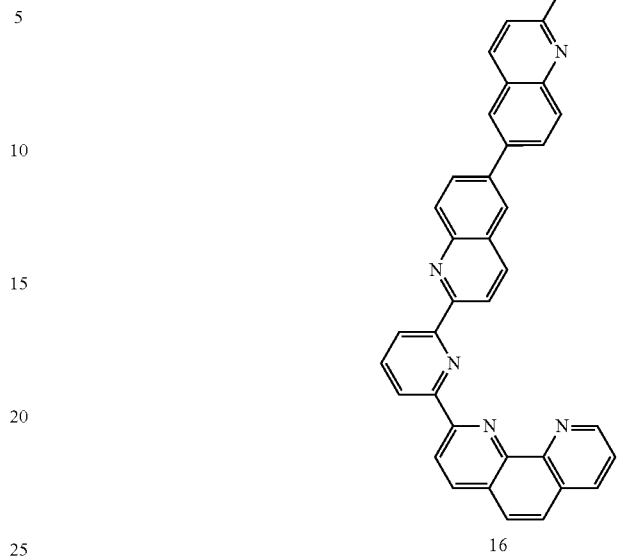

Preparation of Compound 16-2

A compound 2-bromo-1,10-phenanthroline (31.6 g, 121.9 mmol) and 1-(3-bromophenyl)ethan-1-one (20 g, 122 mmol) were dissolved in 200 mL of toluene, and then Pd(PPh$_3$)$_4$ (4.2 g, 3.65 mmol) and K$_2$CO$_3$ (50 g, 366 mmol) were added thereto, and the resulting mixture was stirred for 10 minutes. EtOH (40 mL) and H$_2$O (40 mL) were sequentially added dropwise to a reaction vessel, and then the resulting mixture was refluxed at high temperature. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using dichloromethane and hexane as an eluent to obtain Target Compound 16-2 (28 g, 78%).

Preparation of Compound 16-1

Compound 16-2 (10.8 g, 36.2 mmol) and 2-amino-5-bromobenzaldehyde (7.24 g, 36.2 mmol) were dissolved in EtOH (150 mL), and then KOH (43.4 mmol) was added to the resulting solution, and the resulting mixture was heated to 80° C. After the reaction was completed, the reaction product was cooled to normal temperature, and then an extraction was performed with distilled water and ethyl acetate. The extracted organic layer was dried over anhydrous Na$_2$SO$_4$, and then filtered. The solvent of the filtered reactant was removed by using a rotary evaporator, and then the residue was purified with column chromatography using dichloromethane and hexane as an eluent to obtain Target Compound 16-1 (15.2 g, 91%).

Preparation of Compound 16

Compound 16-1 (6.8 g, 14.8 mmol) and 2-(pyridin-2-yl)-6-(4,4,5,5-tetramethyl-1,3,2-dioxaborolan-2-yl)quinoline (5.0 g, 15.5 mmol) were dissolved in toluene (50 mL), and then Pd(PPh$_3$)$_4$ (1.4 g, 1.5 mmol) and K$_2$CO$_3$ (6.1 g, 38.7 mmol) were added to the resulting solution, and the resulting mixture was stirred for 10 minutes. H$_2$O (6 mL) and EtOH (6 mL) were sequentially added to a reaction vessel, and the resulting mixture was refluxed for 12 hours. After the reaction was completed, the reaction product was cooled to normal temperature, and then an extraction was performed with distilled water and dichloromethane. The extracted organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 16 (4.8 g, 55%).

<Preparation Example 8> Preparation of Compound 17

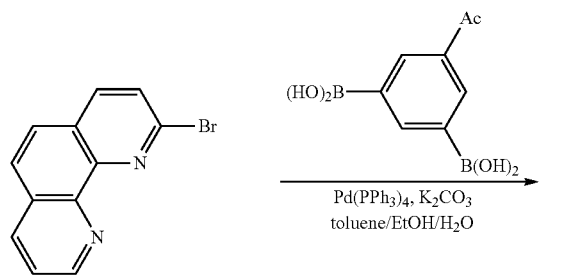

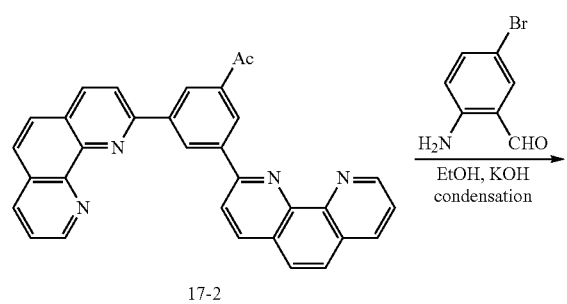

17-2

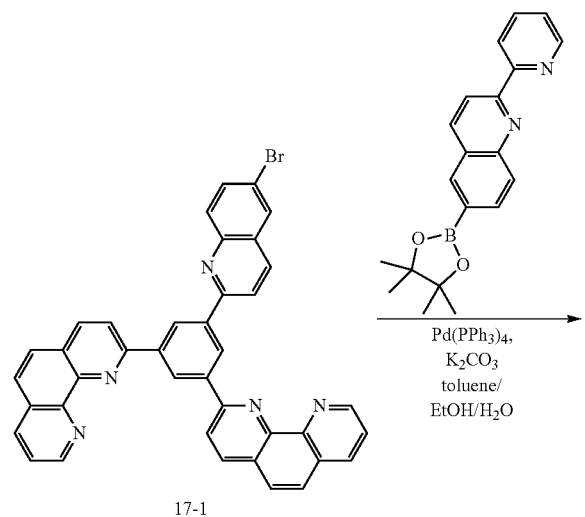

17-1

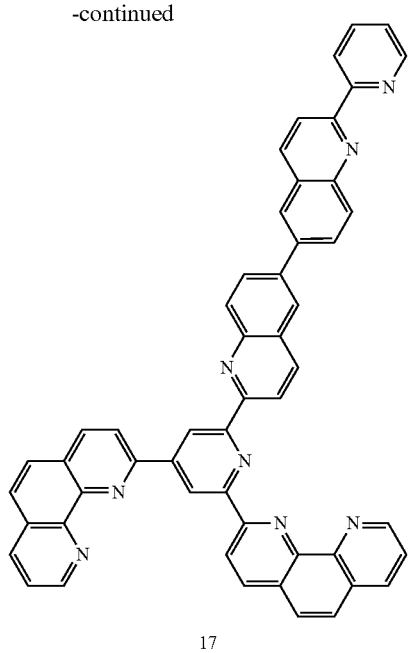

17

Preparation of Compound 17-2

A compound 2-bromo-1,10-phenanthroline (31.6 g, 122 mmol) and 1-(3-bromophenyl)ethan-1-one (10 g, 61 mmol) were dissolved in 140 mL of toluene, and then Pd(PPh₃)₄ (2.1 g, 1.82 mmol) and K₂CO₃ (50 g, 366 mmol) were added thereto, and the resulting mixture was stirred for 10 minutes. EtOH (25 mL) and H₂O (25 mL) were sequentially added dropwise to a reaction vessel, and then the resulting mixture was refluxed at high temperature. After the reaction was completed, the reaction product was cooled to normal temperature, and then an extraction was performed with distilled water and dichloromethane. The extracted organic layer was dried over anhydrous Na₂SO₄, and then filtered. The solvent of the filtered organic layer was removed by using a rotary evaporator, and then the residue was purified with column chromatography using dichloromethane and hexane as an eluent to obtain Target Compound 17-2 (24.4 g, 84%).

Preparation of Compound 17-1

Compound 17-2 (24.4 g, 51.2 mmol) and 2-amino-5-bromobenzaldehyde (10.2 g, 51.2 mmol) were dissolved in EtOH (250 mL), and then KOH (51.2 mmol) was added to the resulting solution, and the resulting mixture was heated to 80° C. After the reaction was completed, the reaction product was cooled to normal temperature, and then an extraction was performed with distilled water and ethyl acetate. The extracted organic layer was dried over anhydrous Na₂SO₄, and then filtered. The solvent of the filtered reactant was removed by using a rotary evaporator, and then the residue was purified with column chromatography using dichloromethane and hexane as an eluent to obtain Target Compound 17-1 (25.6 g, 78%).

Preparation of Compound 17

Compound 17-1 (8.0 g, 12.5 mmol) and 2-(pyridin-2-yl)-6-(4,4,5,5-tetramethyl-1,3,2-dioxaborolan-2-yl)quinoline (4.2 g, 12.5 mmol) were dissolved in toluene (30 mL), and then Pd(PPh₃)₄ (1.4 g, 1.3 mmol) and K₂CO₃ (5.8 g, 37.6 mmol) were added to the resulting solution, and the resulting mixture was stirred for 10 minutes. H₂O (6 mL) and EtOH (6 mL) were sequentially added to a reaction vessel, and the resulting mixture was refluxed for 12 hours. After the reaction was completed, the reaction product was cooled to normal temperature, and then an extraction was performed with distilled water and dichloromethane. The extracted organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 17 (4.7 g, 49%).

<Preparation Example 9> Preparation of Compound 18

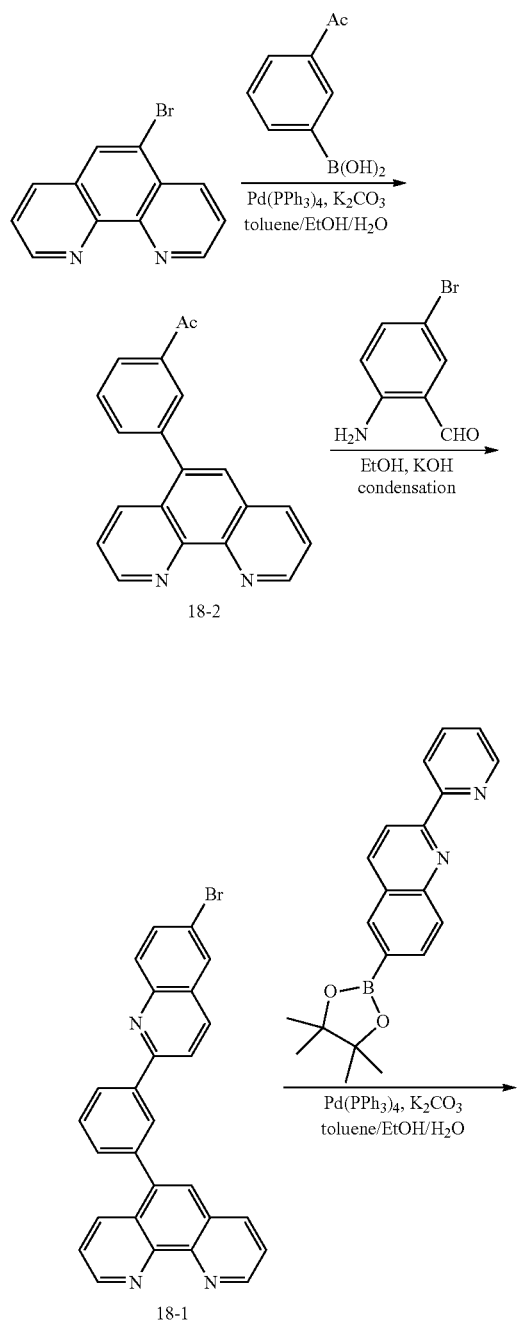

Preparation of Compound 18-2

A compound 5-bromo-1,10-phenanthroline (31.6 g, 122 mmol) and 1-(3-bromophenyl)ethan-1-one (20 g, 122 mmol) were dissolved in 250 mL of toluene, and then Pd(PPh₃)₄ (4.2 g, 3.65 mmol) and K₂CO₃ (50 g, 366 mmol) were added thereto, and the resulting mixture was stirred for 10 minutes. EtOH (50 mL) and H₂O (50 mL) were sequentially added dropwise to a reaction vessel, and then the resulting mixture was refluxed at high temperature. After the reaction was completed, the reaction product was cooled to normal temperature, and then an extraction was performed with distilled water and dichloromethane. The extracted organic layer was dried over anhydrous Na₂SO₄, and then filtered. The solvent of the filtered organic layer was removed by using a rotary evaporator, and then the residue was purified with column chromatography using dichloromethane and hexane as an eluent to obtain Target Compound 18-2 (28.7 g, 80%).

Preparation of Compound 18-1

Compound 18-2 (28.7 g, 97.6 mmol) and 2-amino-5-bromobenzaldehyde (19.5 g, 97.6 mmol) were dissolved in EtOH (300 mL), and then KOH (97.6 mmol) was added to the resulting solution, and the resulting mixture was heated to 80° C. After the reaction was completed, the reaction product was cooled to normal temperature, and then an extraction was performed with distilled water and ethyl acetate. The extracted organic layer was dried over anhydrous Na₂SO₄, and then filtered. The solvent of the filtered reactant was removed by using a rotary evaporator, and then the residue was purified with column chromatography using dichloromethane and hexane as an eluent to obtain Target Compound 18-1 (37.9 g, 84%).

Preparation of Compound 18

Compound 18-1 (6.9 g, 15 mmol) and 2-(pyridin-2-yl)-6-(4,4,5,5-tetramethyl-1,3,2-dioxaborolan-2-yl)quinoline (5.0 g, 15 mmol) were dissolved in toluene (30 mL), and then Pd(PPh₃)₄ (1.4 g, 1.5 mmol) and K₂CO₃ (6.1 g, 38.7 mmol) were added to the resulting solution, and the resulting mixture was stirred for 10 minutes. H₂O (6 mL) and EtOH (6 mL) were sequentially added to a reaction vessel, and the resulting mixture was refluxed for 12 hours. After the reaction was completed, the reaction product was cooled to normal temperature, and then an extraction was performed with distilled water and dichloromethane. The extracted organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 18 (7.6 g, 87%).

<Preparation Example 10> Preparation of Compound 25

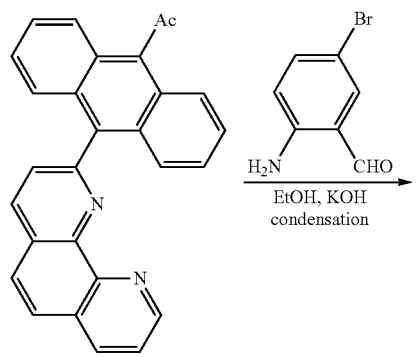

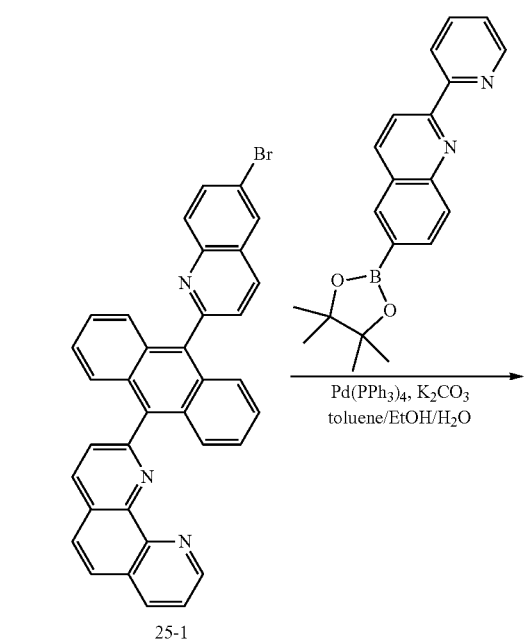

-continued

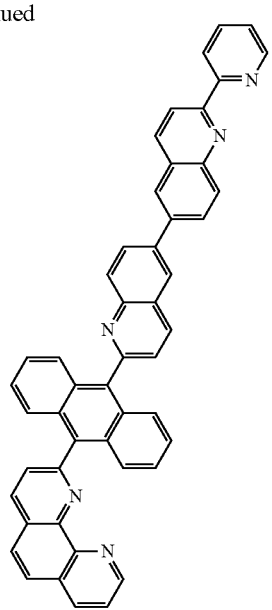

25

Preparation of Compound 25-1

After a compound 1-(10-(1,10-phenanthrolin-2-yl)anthracen-9-yl)ethan-1-one (17.9 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous Na₂SO₄, and then the solvent was removed by using a rotary evaporator. And then, the residue was purified with column chromatography using ethyl acetate and hexane as an eluent to obtain Target Compound 25-1 (19 g, 76%).

Preparation of Compound 25

Compound 25-1 (8.4 g, 15 mmol) and a compound 2-(pyridin-2-yl)-6-(4,4,5,5-tetramethyl-1,3,2-dioxaborolan-2-yl)quinoline (5.0 g, 15.0 mmol) were dissolved in toluene (30 mL), and then Pd(PPh₃)₄ (1.5 g, 1.3 mmol) and K₂CO₃ (5.3 g, 38.7 mmol) were added to the resulting solution, and the resulting mixture was stirred for 10 minutes. And then, H₂O (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 25 (8.2 g, 80%).

<Preparation Example 11> Preparation of Compound 40

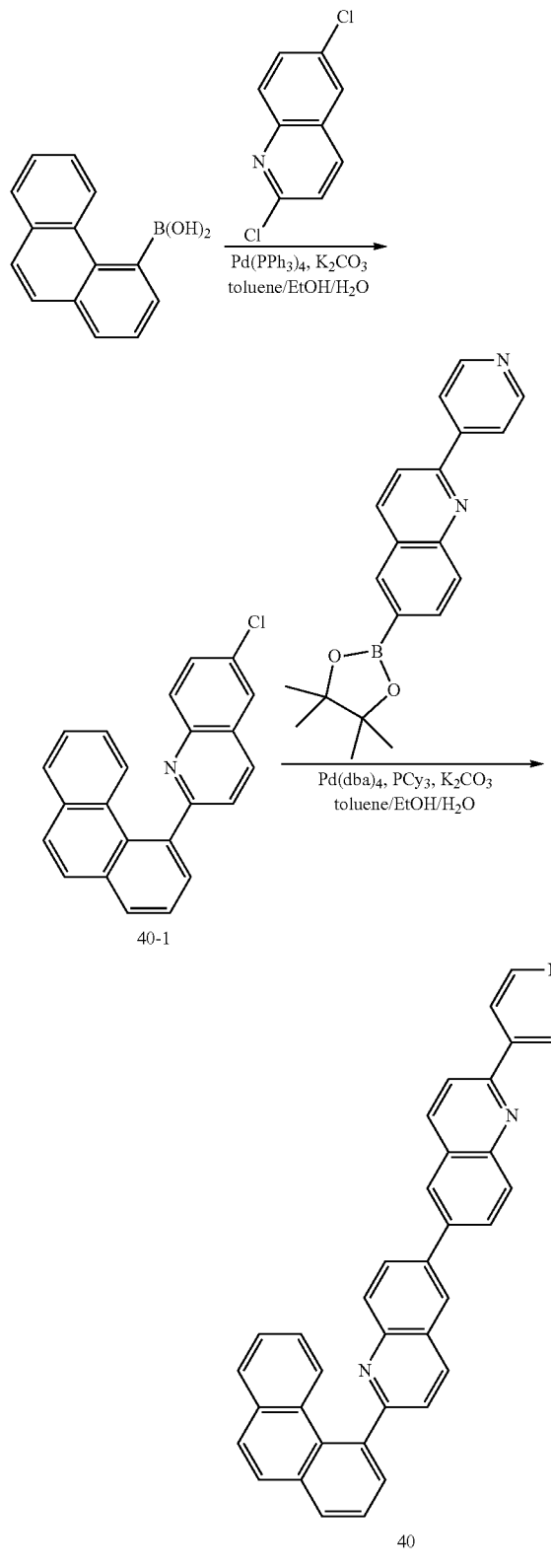

Preparation of Compound 40-1

A compound phenanthren-4-ylboronic acid (10 g, 45 mmol) and 2,6-dichloroquinoline (9.8 g, 49.5 mmol) were dissolved in toluene (100 mL), and then Pd(PPh$_3$)$_4$ (2.6 g, 2.3 mmol) and K$_2$CO$_3$ (18.6 g, 135 mmol) were added thereto, and the resulting mixture was stirred for 10 minutes. And then, H$_2$O (20 mL) and EtOH (20 mL) were added thereto, and then the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 40-1 (5.9 g, 39%).

Preparation of Compound 40

Compound 40-1 (5.9 g, 17.6 mmol) and 2-(pyridin-4-yl)-6-(4,4,5,5-tetramethyl-1,3,2-dioxaborolan-2-yl)quinoline (5.8 g, 17.6 mmol) were dissolved in toluene (40 mL), and then Pd(PPh$_3$)$_2$ (0.88 mmol), PCy$_3$ (0.88 mmol), and K$_2$CO$_3$ (7.3 g, 135 mmol) were added to the resulting solution, and the resulting mixture was stirred for 10 minutes. And then, H$_2$O (8 mL) and EtOH (8 mL) were added thereto, and then the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 40 (7.1 g, 79%).

<Preparation Example 12> Preparation of Compound 44

-continued

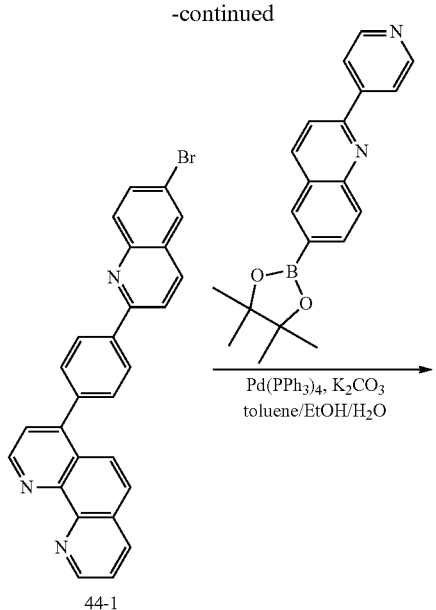

44-1

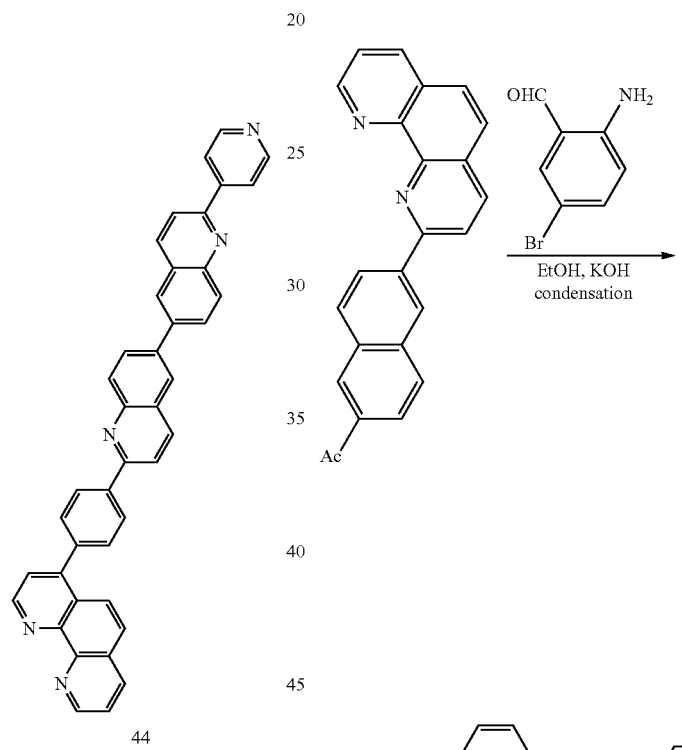

44

Preparation of Compound 44-1

After a compound 1-(4-(1,10-phenanthrolin-4-yl)phenyl)ethan-1-one (13.4 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous $Na_2SO_4$, and then the solvent was removed by using a rotary evaporator. And then, the residue was purified with column chromatography using ethyl acetate and hexane as an eluent to obtain Target Compound 44-1 (16.4 g, 79%).

Preparation of Compound 44

A compound 2-(pyridin-4-yl)-6-(4,4,5,5-tetramethyl-1,3,2-dioxaborolan-2-yl)quinoline (6.6 g, 20 mmol) and Compound 44-1 (9.2 g, 20 mmol) were dissolved in toluene (40 mL), and then $Pd(PPh_3)_4$ (2.3 g, 2 mmol) and $K_2CO_3$ (8.3 g, 60 mmol) were added to the resulting solution, and the resulting mixture was stirred for 10 minutes. And then, $H_2O$ (8 mL) and EtOH (8 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 44 (9.0 g, 77%).

<Preparation Example 13> Preparation of Compound 47

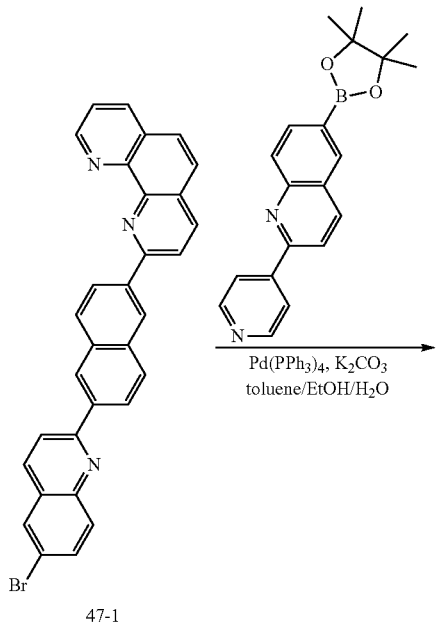

47-1

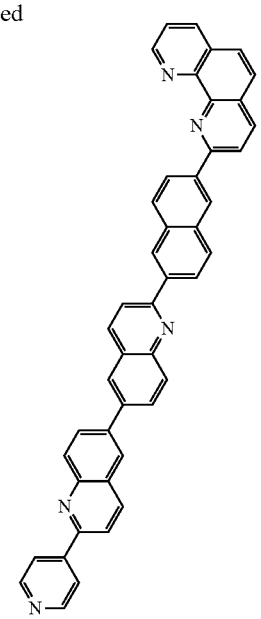

47

Preparation of Compound 47-1

After a compound 1-(6-(1,10-phenanthrolin-2-yl)naphthalen-2-yl)ethan-1-one (15.7 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous $Na_2SO_4$, and then the solvent was removed by using a rotary evaporator. And then, the residue was purified with column chromatography using ethyl acetate and hexane as an eluent to obtain Target Compound 47-1 (20 g, 88%).

Preparation of Compound 47

Compound 47-1 (7.7 g, 15 mmol) and a compound 2-(pyridin-4-yl)-6-(4,4,5,5-tetramethyl-1,3,2-dioxaborolan-2-yl)quinoline (5.0 g, 15.0 mmol) were dissolved in toluene (30 mL), and then $Pd(PPh_3)_4$ (1.5 g, 1.3 mmol) and $K_2CO_3$ (5.3 g, 38.7 mmol) were added to the resulting solution, and the resulting mixture was stirred for 10 minutes. And then, $H_2O$ (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 47 (7.5 g, 79%).

<Preparation Example 14> Preparation of Compound 52

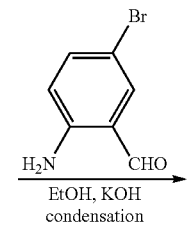

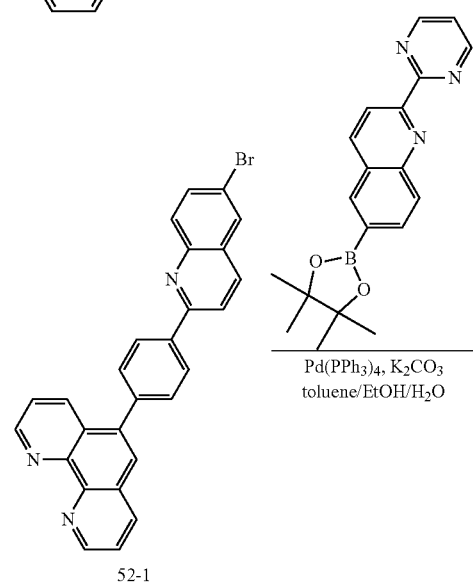

Preparation of Compound 52-1

After a compound 1-(4-(1,10-phenanthrolin-5-yl)phenyl)ethan-1-one (13.4 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous $Na_2SO_4$, and then the solvent was removed by using a rotary evaporator. And then, the residue was purified with column chromatography using ethyl acetate and hexane as an eluent to obtain Target Compound 52-1 (16.8 g, 81%).

Preparation of Compound 52

A compound 2-(pyridin-2-yl)-6-(4,4,5,5-tetramethyl-1,3,2-dioxaborolan-2-yl)quinoline (4.8 g, 14.4 mmol) and Compound 52-1 (6.6 g, 14.4 mmol) were dissolved in toluene (30 mL), and then $Pd(PPh_3)_4$ (1.5 g, 1.3 mmol) and $K_2CO_3$ (5.3 g, 38.7 mmol) were added to the resulting solution, and the resulting mixture was stirred for 10 minutes. And then, $H_2O$ (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 52 (6.5 g, 77%).

<Preparation Example 15> Preparation of Compound 68

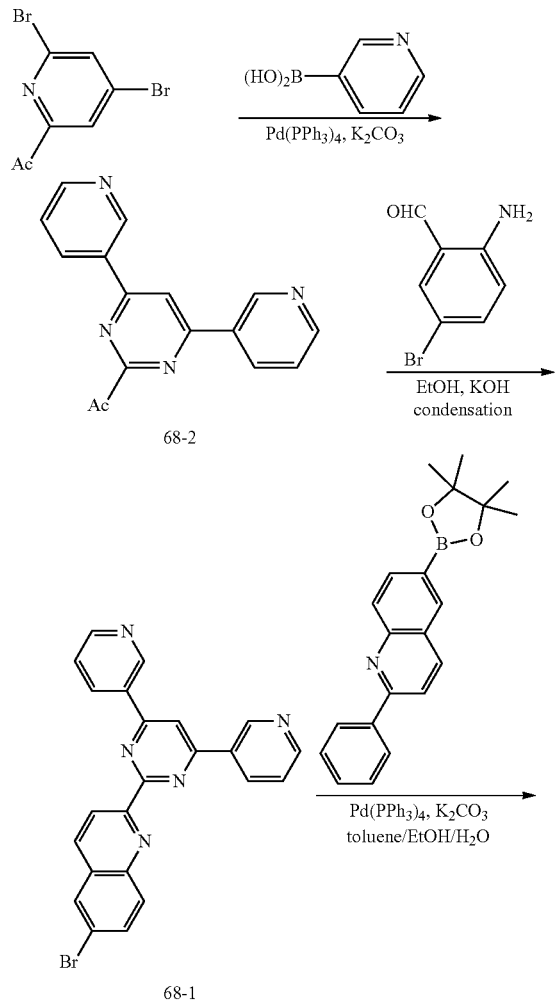

68-2

68-1

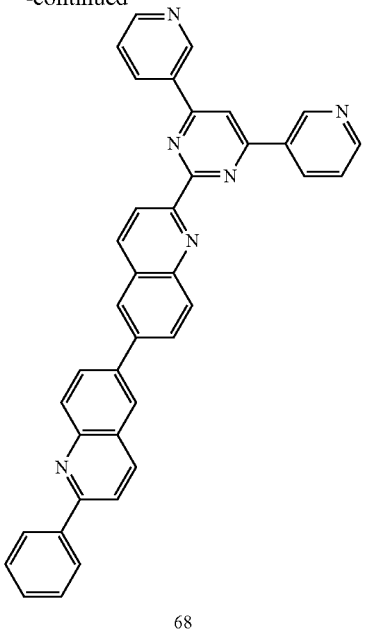

68

Preparation of Compound 68-2

A compound pyridin-3-ylboronic acid (5.3 g, 42.8 mmol) and 1-(4,6-dibromopyridin-2-yl)ethan-1-one (10 g, 35.7 mmol) were dissolved in 50 mL of toluene, and then $Pd(PPh_3)_4$ (1.1 g, 1.0 mmol) and $K_2CO_3$ (14.8 g, 107 mmol) were added thereto, and the resulting mixture was stirred for 10 minutes. And then, EtOH (10 mL) and $H_2O$ (10 mL) were added dropwise thereto, and then the resulting mixture was refluxed at high temperature. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using dichloromethane and hexane as an eluent to obtain Target Compound 68-2 (7.8 g, 80%).

Preparation of Compound 68-1

Compound 68-2 (7.8 g, 28.6 mmol) and 2-amino-5-bromobenzaldehyde (5.72 g, 28.6 mmol) were dissolved in EtOH (150 mL), and then KOH (28.6 mmol) was added to the resulting solution, and the resulting mixture was heated to 80° C. After the reaction was completed, the reaction product was cooled to normal temperature, and then an extraction was performed with distilled water and ethyl acetate. The extracted organic layer was dried over anhydrous $Na_2SO_4$, and then filtered. The solvent of the filtered organic layer was removed by using a rotary evaporator, and then the residue was purified with column chromatography using dichloromethane and hexane as an eluent to obtain Target Compound 68-1 (11.3 g, 90%).

Preparation of Compound 68

Compound 68-1 (10 g, 22.7 mmol) and 2-phenyl-6-(4,4,5,5-tertmethyl-1,3,2-dioxaborolan-2-yl)quinoline (9.0 g, 27.2 mmol) were dissolved in toluene (50 mL), and then $Pd(PPh_3)_4$ (0.8 g, 0.7 mmol) and $K_2CO_3$ (9.4 g, 68 mmol) were added to the resulting solution, and the resulting mixture was stirred for 10 minutes. And then, $H_2O$ (10 mL) and EtOH (10 mL) were added thereto, and then the resulting mixture was refluxed for 12 hours. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 68 (6.8 g, 67%).

<Preparation Example 16> Preparation of Compound 91

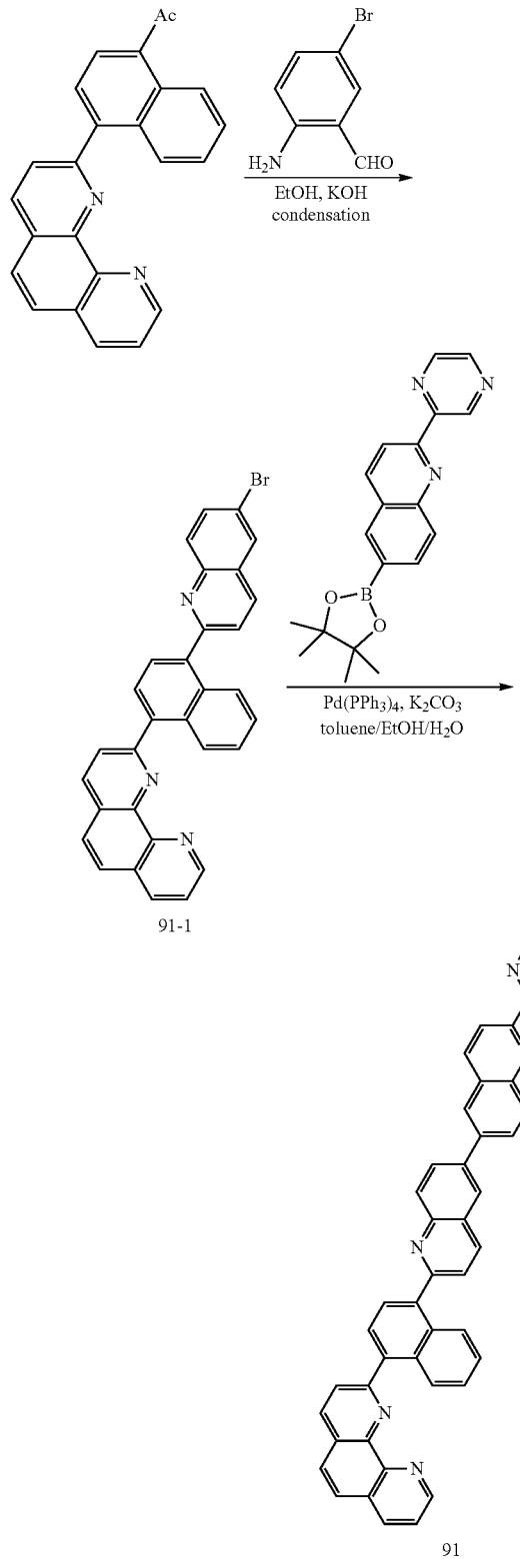

Preparation of Compound 91-1

After a compound 1-(4-(1,10-phenanthrolin-2-yl)naphthalen-1-yl)ethan-1-one (15.7 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous $Na_2SO_4$, and then the solvent was removed by using a rotary evaporator. And then, the residue was purified with column chromatography using ethyl acetate and hexane as an eluent to obtain Target Compound 91-1 (21.8 g, 95%).

Preparation of Compound 91

A compound 2-(pyrazin-2-yl)-6-(4,4,5,5-tetramethyl-1,3,2-dioxaborolan-2-yl)quinoline (5.0 g, 15 mmol) and Compound 91-1 (7.7 g, 15 mmol) were dissolved in toluene (30 mL), and then $Pd(PPh_3)_4$ (1.5 g, 1.3 mmol) and $K_2CO_3$ (5.3 g, 38.7 mmol) were added to the resulting solution, and the resulting mixture was stirred for 10 minutes. And then, $H_2O$ (6 mL) and EtOH (6 mL) were added thereto, and then the resulting mixture was refluxed for 10 hours. After the reaction was completed, the reaction product was cooled to normal temperature, and then an extraction was performed with distilled water and dichloromethane. The organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 91 (7.1 g, 74%).

<Preparation Example 17> Preparation of Compound 111

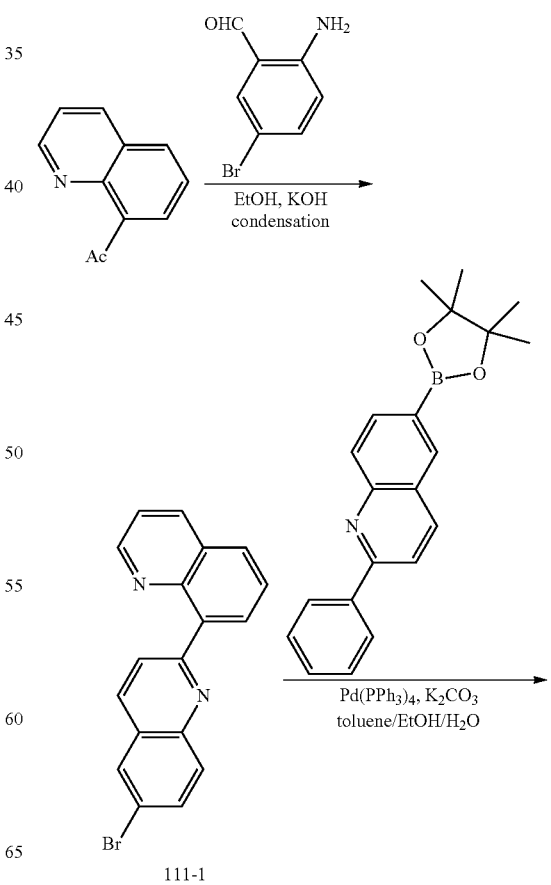

-continued

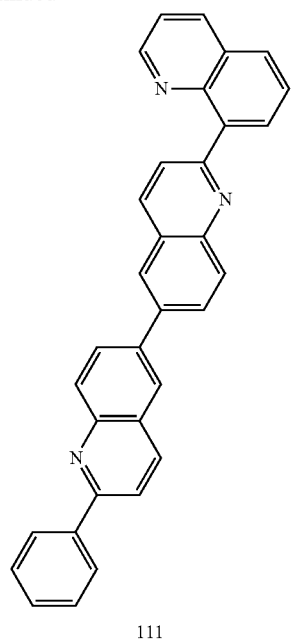

111

Preparation of Compound 111-1

A compound 1-(quinolin-8-yl)ethan-1-one (10 g, 58.5 mmol) and 2-amino-5-bromobenzaldehyde (11.7 g, 58.5 mmol) were dissolved in EtOH (150 mL), and then KOH (58.5 mmol) was added to the resulting solution, and the resulting mixture was heated to 80° C. After the reaction was completed, the reaction product was cooled to normal temperature, and then an extraction was performed with distilled water and ethyl acetate. The extracted organic layer was dried over anhydrous $Na_2SO_4$, and then filtered. The solvent of the filtered organic layer was removed by using a rotary evaporator, and then the residue was purified with column chromatography using dichloromethane and hexane as an eluent to obtain Target Compound 111-1 (16 g, 83%).

Preparation of Compound 111

Compound 111-1 (8 g, 23.9 mmol) and 2-phenyl-6-(4,4,5,5-tertmethyl-1,3,2-dioxaborolan-2-yl)quinoline (9.5 g, 28.7 mmol) were dissolved in toluene (50 mL), and then $Pd(PPh_3)_4$ (0.8 g, 0.7 mmol) and $K_2CO_3$ (9.9 g, 71.7 mmol) were added to the resulting solution, and the resulting mixture was stirred for 10 minutes. And then, $H_2O$ (10 mL) and EtOH (10 mL) were added thereto, and then the resulting mixture was refluxed for 12 hours. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 111 (8.5 g, 78%).

<Preparation Example 18> Preparation of Compound 175

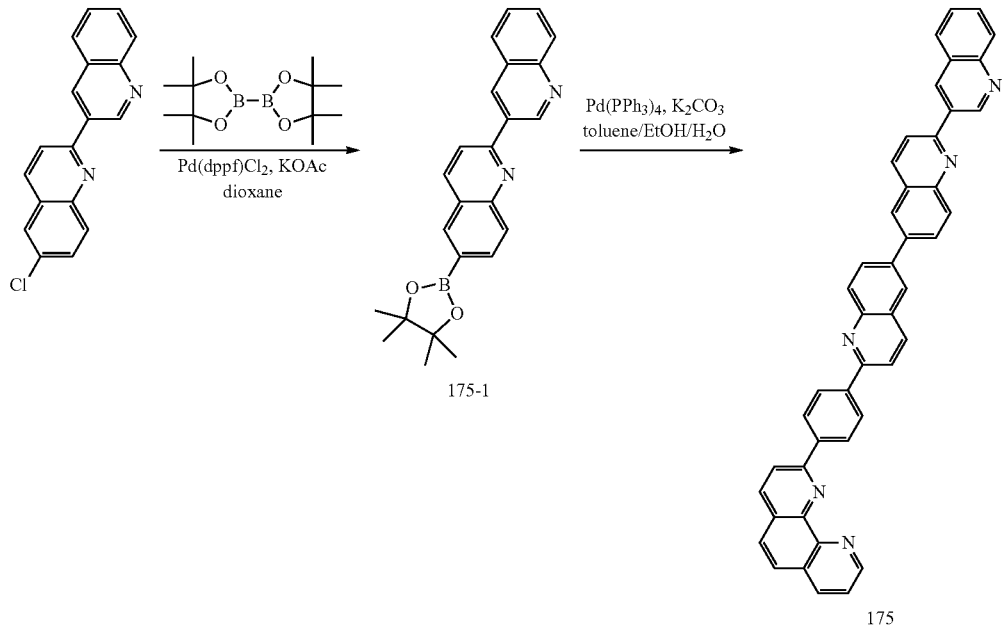

-continued

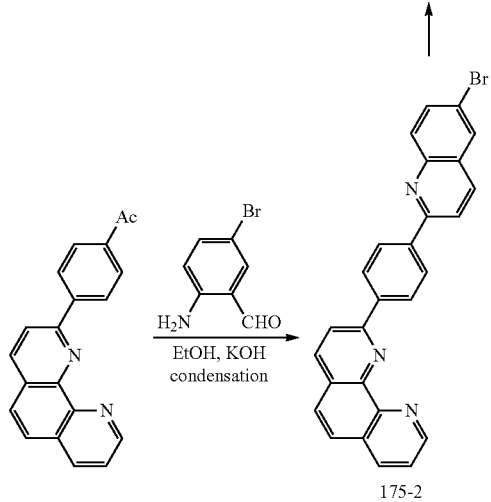

175-2

Preparation of Compound 175-1

A compound 6-chloro-2,3'-biquinoline (5.5 g, 18.9 mmol), 4,4,4',4',5,5,5',5'-octamethyl-2,2'-bi(1,3,2-dioxaborolane) (6.7 g, 26.5 mmol), Pd(dppf)$_2$Cl$_2$ (1.5 g, 2.1 mmol), and KOAc (5.6 g, 56.7 mmol) were put into a reaction vessel, dioxane (0.3 M) was added thereto, and then the resulting mixture was refluxed for 12 hours. After the reaction was completed, the reaction product was cooled to normal temperature, and then an extraction was performed with distilled water and ethyl acetate. After the extracted organic layer was dried over anhydrous Na$_2$SO$_4$, the solvent was removed by using a rotary evaporator, and then the residue was purified with column chromatography using dichloromethane and hexane as an eluent to obtain Target Compound 175-1 (5.5 g, 76%).

Preparation of Compound 175-2

After a compound 1-(4-(1,10-phenanthrolin-2-yl)phenyl)ethan-1-one (13.4 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous Na$_2$SO$_4$, and then the solvent was removed by using a rotary evaporator. And then, the residue was purified with column chromatography using ethyl acetate and hexane as an eluent to obtain Target Compound 175-2 (17 g, 82%).

Preparation of Compound 175

Compound 175-1 (5.5 g, 14.4 mmol) and Compound 175-2 (6.6 g, 14.4 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. And then, H$_2$O (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 175 (7.3 g, 74%).

<Preparation Example 19> Preparation of Compound 179

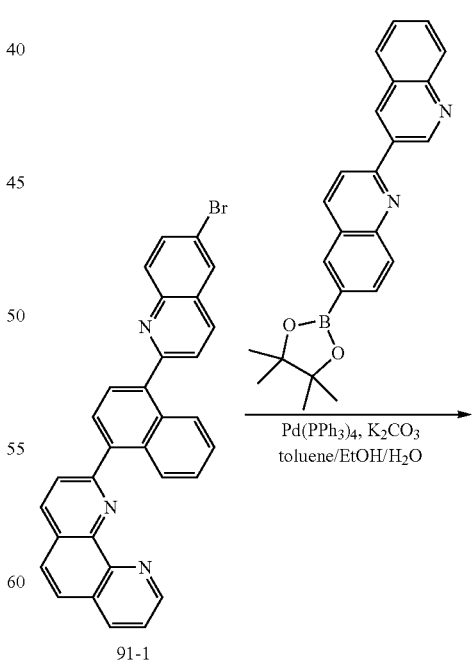

91-1

209

-continued

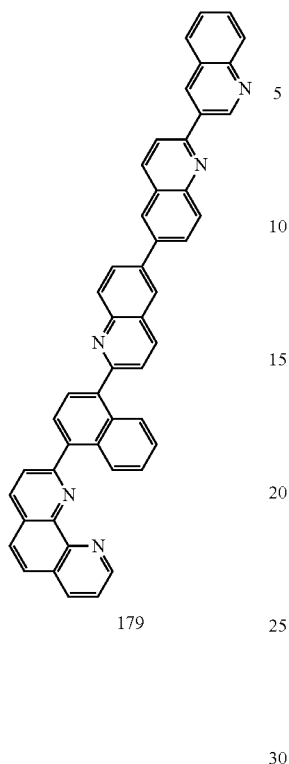

179

Preparation of Compound 179

Compound 91-1 (7.7 g, 15.0 mmol) and a compound 6-(4,4,5,5-tetramethyl-1,3,2-dioxaborolan-2-yl)-2,3'-biquinoline (5.7 g, 15 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. And then, H$_2$O (6 mL) and EtOH (6 mL) were added thereto, and then the resulting mixture was refluxed for 10 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 179 (8.4 g, 82%).

<Preparation Example 20> Preparation of Compound 195

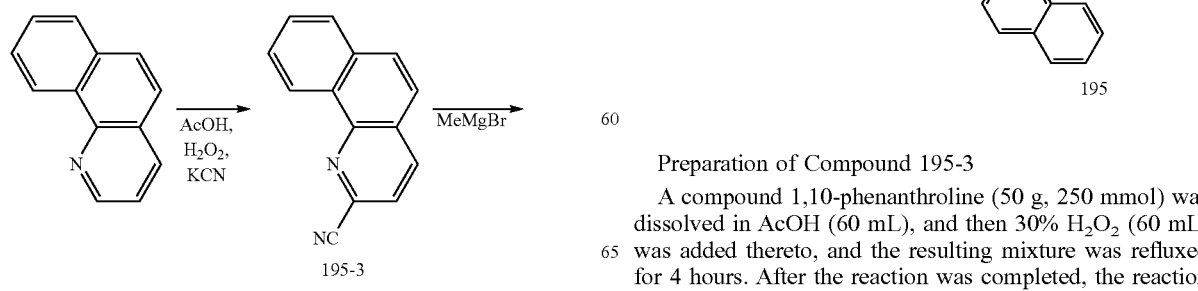

210

-continued

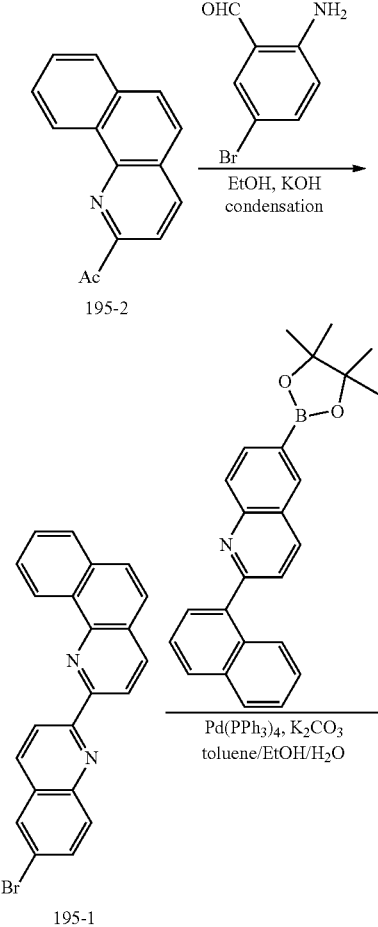

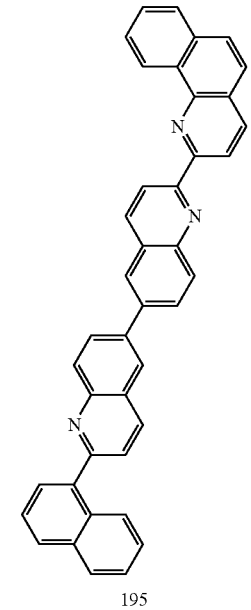

195

Preparation of Compound 195-3

A compound 1,10-phenanthroline (50 g, 250 mmol) was dissolved in AcOH (60 mL), and then 30% H$_2$O$_2$ (60 mL) was added thereto, and the resulting mixture was refluxed for 4 hours. After the reaction was completed, the reaction product was cooled to normal temperature, and then the pH was adjusted to 11 by using a saturated aqueous KOH solution. And then, an extraction was performed by using chloroform. The extracted organic layer was dried over anhydrous $Na_2SO_4$, and then filtered. The solvent of the filtered organic layer was removed by using a rotary evaporator. KCN (38 g) was added to 38 g of the thus obtained yellow solid, the resulting mixture was dissolved in water, and then benzoyl chloride (38 mL) was slowly added dropwise thereto. After the mixture was stirred at normal temperature for 4 hours, it was confirmed that the reaction was terminated, and then the resulting product was filtered with a paper filter. The filtered solute was purified with column chromatography using ethyl acetate and hexane as an eluent to obtain Target Compound 195-3 (28 g, 54%).

Preparation of Compound 195-2

Compound 195-3 (20 g, 97.5 mmol) was dissolved in THF (50 mL), and then 9.7 mL of MeMgBr(3M) was slowly added dropwise thereto at −78° C. It was confirmed that the reaction was terminated by warming the mixture to normal temperature, and an extraction was performed with an aqueous $NH_4Cl$ solution and dichloromethane. After the organic layer was dried over anhydrous $MgSO_4$, the solvent was removed by using a rotary evaporator, and then the resulting product was purified with column chromatography using ethyl acetate and hexane as an eluent to obtain Target Compound 195-2 (10 g, 46%).

Preparation of Compound 195-1

After Compound 195-2 (10 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous $Na_2SO_4$, and then the solvent was removed by using a rotary evaporator. And then, the residue was purified with column chromatography using ethyl acetate and hexane as an eluent to obtain Target Compound 195-1 (14.6 g, 84%).

Preparation of Compound 195

Compound 195-1 (5.8 g, 15.0 mmol) and 2-(pyridin-2-yl)-6-(4,4,5,5-tetramethyl-1,3,2-dioxaborolan-2-yl)quinoline (5.0 g, 15.0 mmol) were dissolved in toluene (30 mL), and then $Pd(PPh_3)_4$ (1.7 g, 1.5 mmol) and $K_2CO_3$ (6.2 g, 45 mmol) were added to the resulting solution, and the resulting mixture was stirred for 10 minutes. And then, $H_2O$ (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 195 (6.7 g, 80%).

<Preparation Example 21> Preparation of Compound 196

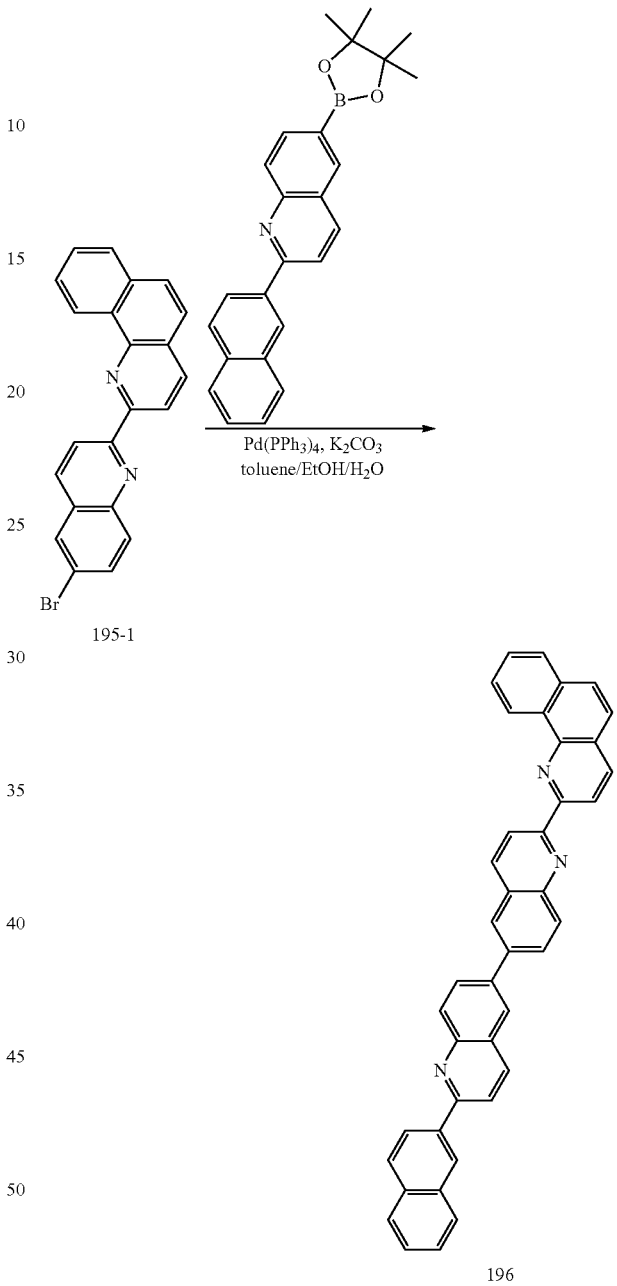

Preparation of Compound 196

Compound 195-1 (5.8 g, 15.0 mmol) and 2-naphthyl-6-(4,4,5,5-tetramethyl-1,3,2-dioxaborolan-2-yl)quinoline (5.7 g, 15.0 mmol) were dissolved in toluene (30 mL), and then $Pd(PPh_3)_4$ (1.7 g, 1.5 mmol) and $K_2CO_3$ (6.2 g, 45 mmol) were added to the resulting solution, and the resulting mixture was stirred for 10 minutes. And then, $H_2O$ (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 196 (7.0 g, 83%).

<Preparation Example 22> Preparation of Compound 198

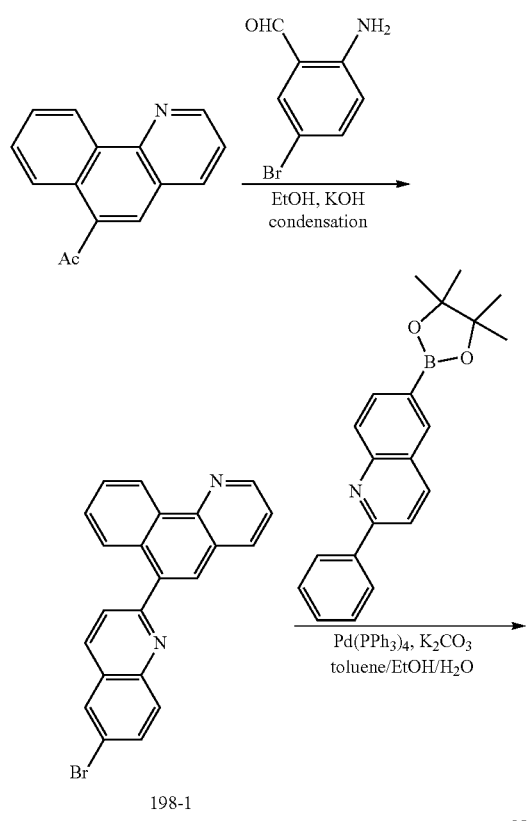

Preparation of Compound 198-1

After a compound 1-(benzo[h]quinolin-6-yl)ethan-1-one (9.9 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous Na$_2$SO$_4$, and then the solvent was removed by using a rotary evaporator. And then, the residue was purified with column chromatography using ethyl acetate and hexane as an eluent to obtain Target Compound 198-1 (15.9 g, 92%).

Preparation of Compound 198

Compound 198-1 (5.8 g, 15.0 mmol) and 2-phenyl-6-(4,4,5,5-tetramethyl-1,3,2-dioxaborolan-2-yl)quinoline (5.0 g, 15.0 mmol) were dissolved in toluene (30 mL), and then Pd(PPh$_3$)$_4$ (1.7 g, 1.5 mmol) and K$_2$CO$_3$ (6.2 g, 45 mmol) were added to the resulting solution, and the resulting mixture was stirred for 10 minutes. And then, H$_2$O (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 198 (5.8 g, 76%).

<Preparation Example 23> Preparation of Compound 206

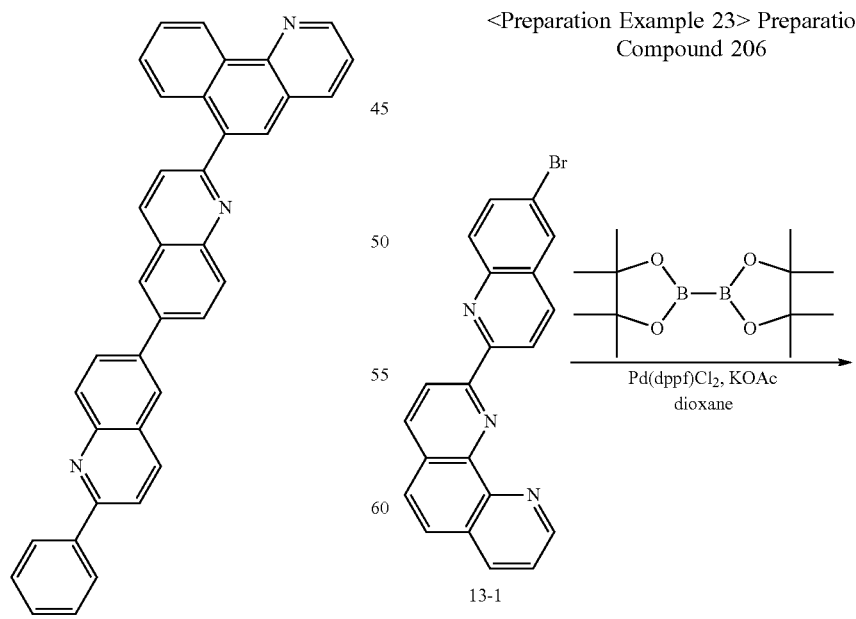

-continued

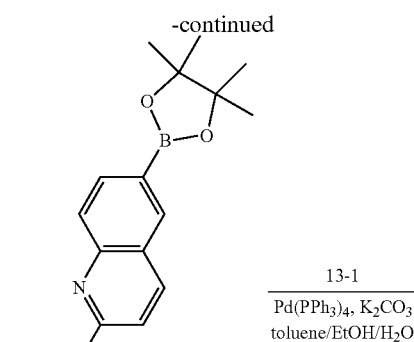

206-1

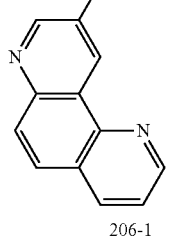

206

Preparation of Compound 206-1

Compound 13-1 (14.6 g, 37.8 mmol), 4,4,4',4',5,5,5',5'-octamethyl-2,2'-bi(1,3,2-dioxaborolane) (13.3 g, 52.9 mmol), Pd(dppf)₂Cl₂ (3 g, 4.2 mmol), and KOAc (11.1 g, 113.4 mmol) were put into a reaction vessel, dioxane (0.3 M) was added thereto, and then the resulting mixture was refluxed for 12 hours. After the reaction was completed, the reaction product was cooled to normal temperature, and then an extraction was performed with distilled water and ethyl acetate. After the extracted organic layer was dried over anhydrous Na₂SO₄, the solvent was removed by using a rotary evaporator, and then the residue was purified with column chromatography using dichloromethane and hexane as an eluent to obtain Target Compound 206-1 (9.8 g, 60%).

Preparation of Compound 206

Compound 206-1 (6.1 g, 14.2 mmol) and Compound 13-1 (5.0 g, 12.9 mmol) were dissolved in toluene (30 mL), and then Pd(PPh₃)₄ (1.5 g, 1.3 mmol) and K₂CO₃ (5.3 g, 38.7 mmol) were added to the resulting solution, and the resulting mixture was stirred for 10 minutes. And then, H₂O (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 206 (7 g, 80%).

<Preparation Example 24> Preparation of Compound 215

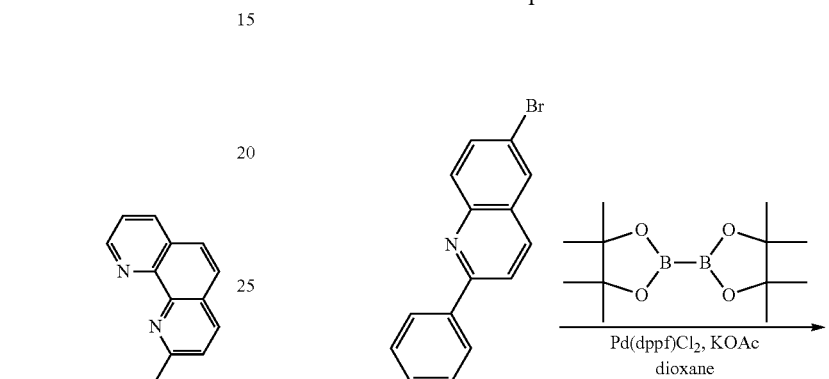

52-1

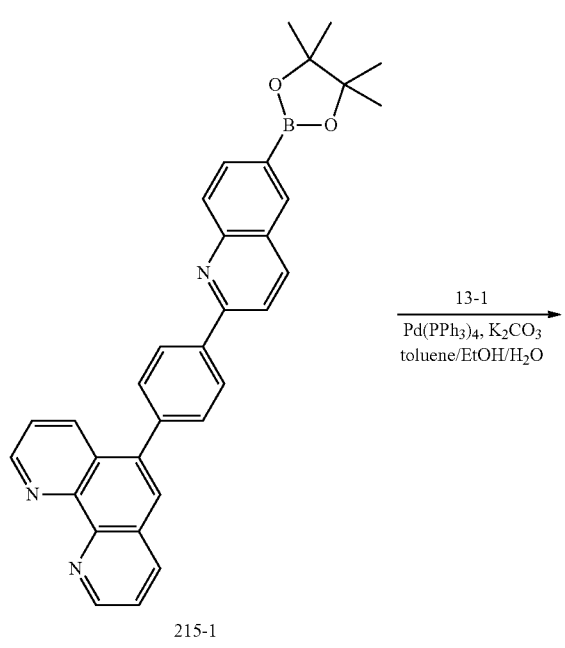

215-1

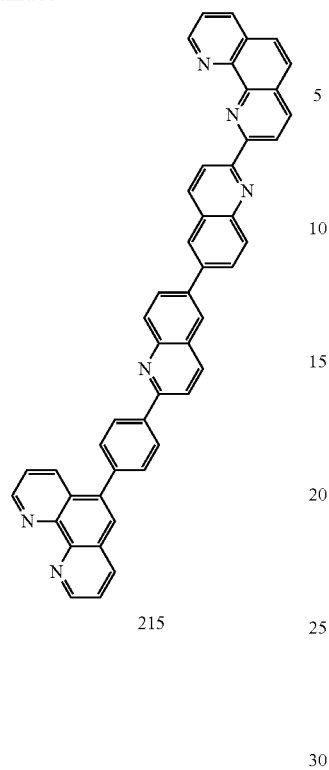

215

<Preparation Example 25> Preparation of Compound 220

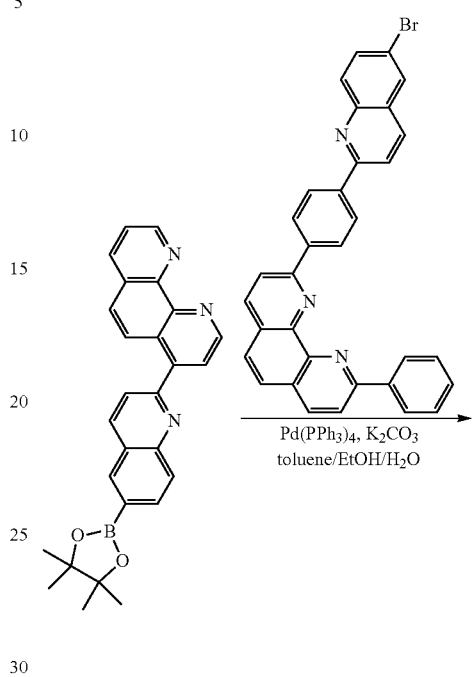

Preparation of Compound 215-1

Compound 52-1 (19.5 g, 42.3 mmol), 4,4,4',4',5,5,5',5'-octamethyl-2,2'-bi(1,3,2-dioxaborolane) (12.9 g, 50.8 mmol), Pd(dppf)$_2$Cl$_2$ (3 g, 4.2 mmol), and KOAc (12.4 g, 126.9 mmol) were put into a reaction vessel, dioxane (0.3 M) was added thereto, and then the resulting mixture was refluxed for 12 hours. After the reaction was completed, the reaction product was cooled to normal temperature, and then an extraction was performed with distilled water and ethyl acetate. After the extracted organic layer was dried over anhydrous Na$_2$SO$_4$, the solvent was removed by using a rotary evaporator, and then the residue was purified with column chromatography using dichloromethane and hexane as an eluent to obtain Target Compound 215-1 (18.6 g, 72%).

Preparation of Compound 215

Compound 215-1 (7.2 g, 14.2 mmol) and Compound 13-1 (5.0 g, 12.9 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. And then, H$_2$O (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 215 (6.4 g, 66%).

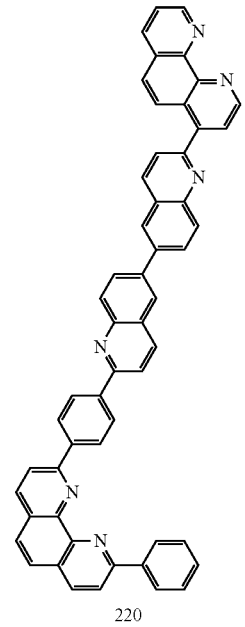

220

Preparation of Compound 220

A compound 4-(6-(4,4,5,5-tetramethyl-1,3,2-dioxaborolan-2-yl)quinolin-2-yl)-1,10-phenanthroline (6.0 g, 13.8 mmol) and a compound 2-(4-(6-bromoquinolin-2-yl)phenyl)-9-phenyl-1,10-phenanthroline (7.5 g, 13.8 mmol) were dissolved in toluene (30 mL), and then Pd(PPh$_3$)$_4$ (1.6 g, 1.4 mmol) and K$_2$CO$_3$ (5.7 g, 41.4 mmol) were added to the resulting solution, and the resulting mixture was stirred for 10 minutes. And then, H$_2$O (6 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 220 (8.6 g, 82%).
<Preparation Example 26> Preparation of Compound 241
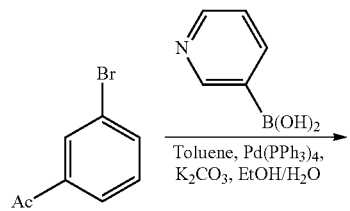
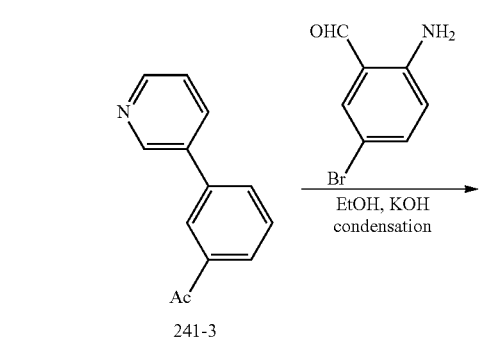
241-3
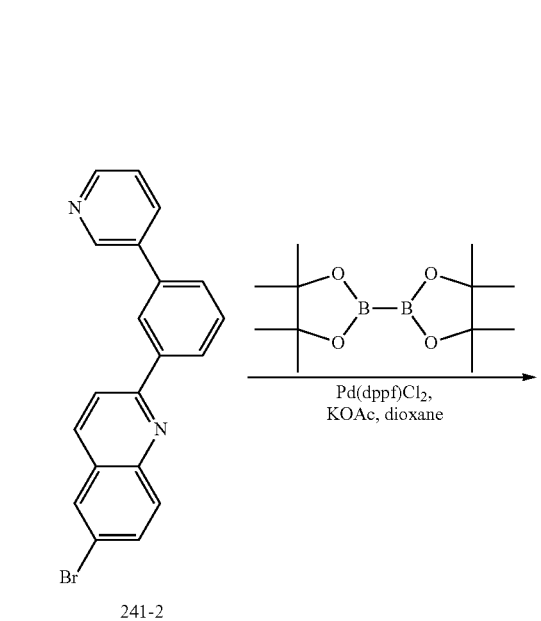
241-2
-continued
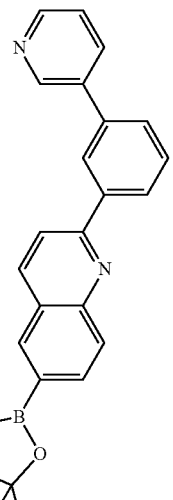
241-1
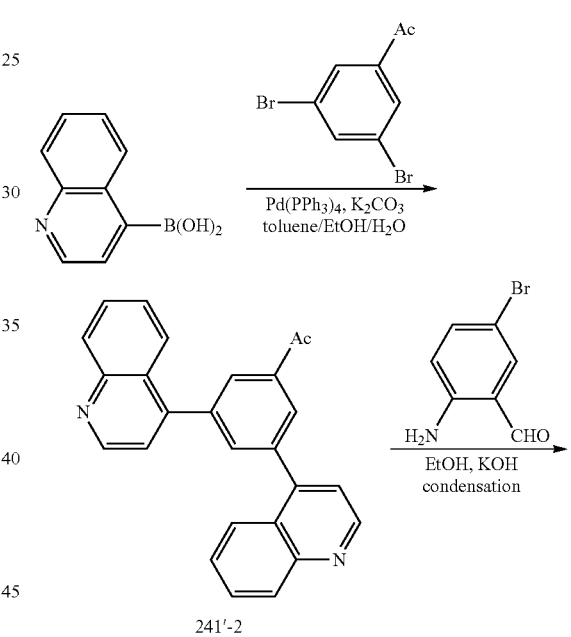
241'-2
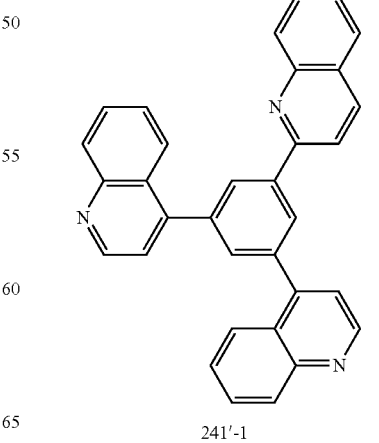
241'-1

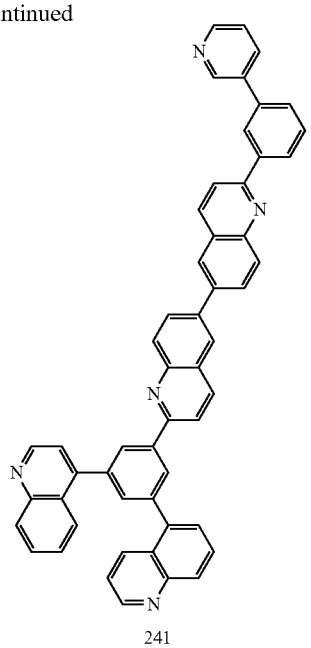

241

Preparation of Compound 241-3

A compound 1-(3-bromophenyl)ethan-1-one (20 g, 100 mmol) and pyridin-3-ylboronic acid (12.3 g, 100 mmol) were dissolved in toluene (100 mL), and then Pd(PPh$_3$)$_4$ (5.7 g, 5 mmol) and K$_2$CO$_3$ (41.5 g, 300 mmol) were added thereto, and the resulting mixture was stirred for 10 minutes. And then, EtOH (20 mL) and H$_2$O (20 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 241-3 (16.8 g, 85%).

Preparation of Compound 241-2

Compound 241-3 (16.8 g, 85 mmol) and 2-amino-5-bromobenzaldehyde (17 g, 85 mmol) were dissolved in EtOH (300 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 241-2 (27.6 g, 90%).

Preparation of Compound 241-1

Compound 241-2 (27.6 g, 76 mmol), 4,4,4',4',5,5,5',5'-octamethyl-2,2'-bi(1,3,2-dioxaborolane) (23.1 g, 91 mmol), Pd(dppf)$_2$Cl$_2$ (2.8 g, 3.8 mmol), and KOAc (22 g, 228 mmol) were put into a reaction vessel, dioxane (0.3 M) was added thereto, and then the resulting mixture was refluxed for 12 hours. After the reaction was completed, the reaction product was cooled to normal temperature, and then an extraction was performed with distilled water and ethyl acetate. After the organic layer was dried over anhydrous MgSO$_4$, the solvent was removed by a rotary evaporator, and then the resulting product was purified with column chromatography using dichloromethane and hexane as an eluent to obtain Target Compound 241-1 (19.2 g, 62%).

Preparation of Compound 241'-2

A compound quinolin-3-ylboronic acid (16.2 g, 94 mmol) and 1-(3,5-dibromophenyl)ethan-1-one (11.8 g, 43 mmol) were dissolved in 250 mL of toluene, and then Pd(PPh$_3$)$_4$ (2.5 g, 2.2 mmol) and K$_2$CO$_3$ (17.6 g, 123 mmol) were added thereto, and the resulting mixture was stirred for 10 minutes. EtOH (50 mL) and H$_2$O (50 mL) were added dropwise to a reaction vessel, and then the resulting mixture was refluxed at high temperature. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using dichloromethane and hexane as an eluent to obtain Target Compound 241'-2 (13 g, 81%).

Preparation of Compound 241'-1

Compound 241'-2 (8.4 g, 22.6 mmol) and 2-amino-5-bromobenzaldehyde (4.52 g, 22.6 mmol) were dissolved in EtOH (150 mL), and then KOH (22.6 mmol) was added to the resulting solution, and the resulting mixture was heated to 80° C. After the reaction was completed, the reaction product was cooled to normal temperature, and then an extraction was performed with distilled water and ethyl acetate. The extracted organic layer was dried over anhydrous Na$_2$SO$_4$, and then filtered. The solvent of the filtered organic layer was removed by using a rotary evaporator, and then the residue was purified with column chromatography using dichloromethane and hexane as an eluent to obtain Target Compound 241'-1 (11.2 g, 92%).

Preparation of Compound 241

Compound 241'-1 (10.8 g, 20 mmol) and Compound 241-1 (8.2 g, 20 mmol) were dissolved in toluene (50 mL), and then Pd(PPh$_3$)$_4$ (2.3 g, 2 mmol) and K$_2$CO$_3$ (8.3 g, 60 mmol) were added to the resulting solution, and the resulting mixture was stirred for 10 minutes. And then, H$_2$O (10 mL) and EtOH (6 mL) were added thereto, and then the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 241 (8.8 g, 69%).

<Preparation Example 27> Preparation of Compound 242

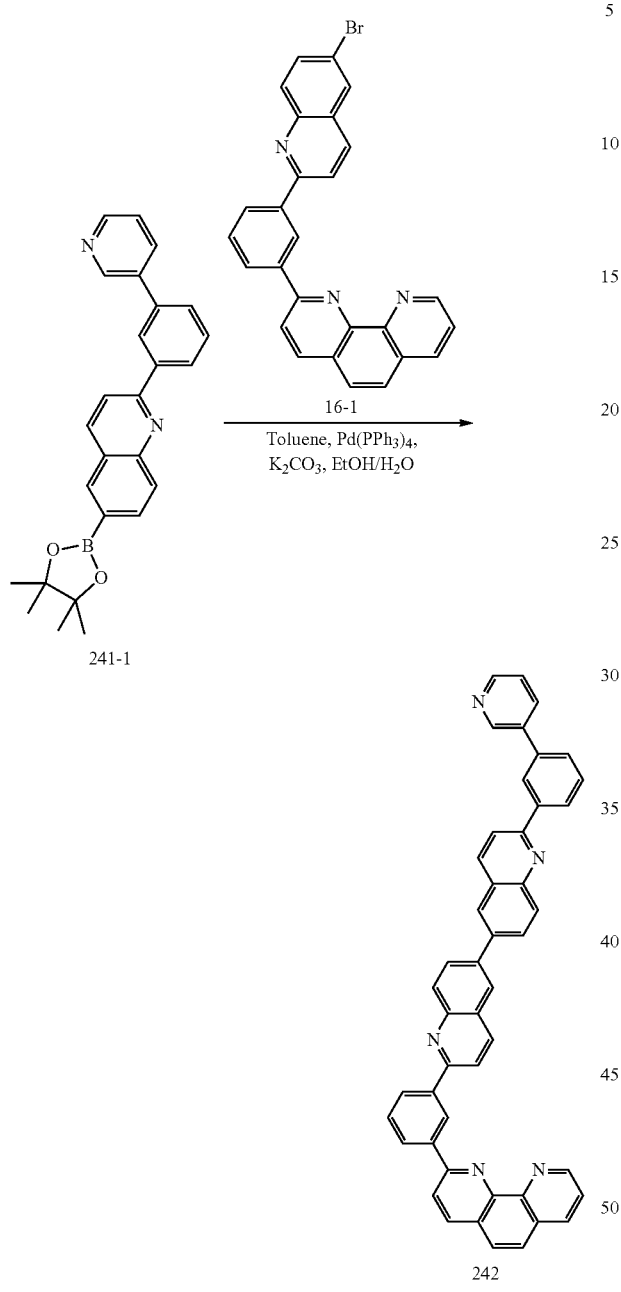

Preparation of Compound 242

Compound 241-1 (4.4 g, 10.8 mmol) and Compound 16-1 (4.5 g, 9.8 mmol) were dissolved in toluene (40 mL), and then Pd(PPh$_3$)$_4$ (0.6 g, 0.5 mmol) and K$_2$CO$_3$ (2.8 g, 29.4 mmol) were added to the resulting solution, and the resulting mixture was stirred for 10 minutes. And then, EtOH (8 mL) and H$_2$O (8 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 242 (3.9 g, 60%).

<Preparation Example 28> Preparation of Compound 245

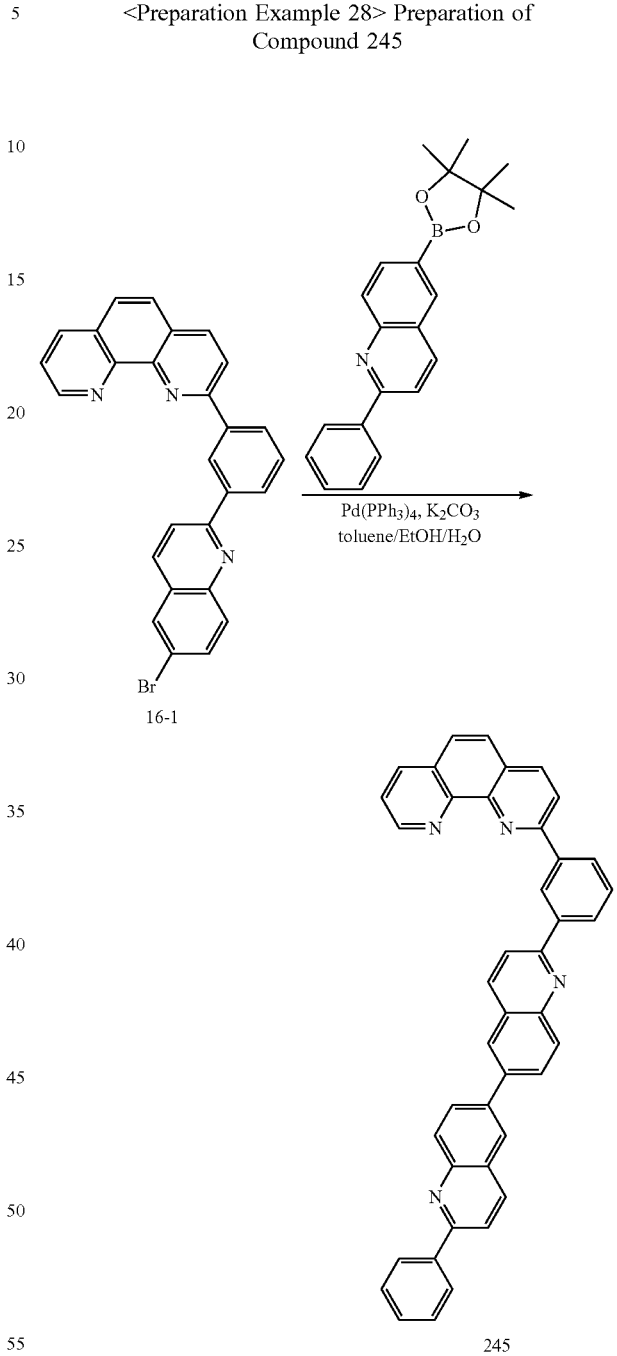

Preparation of Compound 245

Compound 16-1 (6.8 g, 14.8 mmol) and 2-phenyl-6-(4,4,5,5-tetramethyl-1,3,2-dioxaborolan-2-yl)quinoline (5.0 g, 15.5 mmol) were dissolved in toluene (50 mL), and then Pd(PPh$_3$)$_4$ (1.7 g, 1.5 mmol) and K$_2$CO$_3$ (6.1 g, 38.7 mmol) were added to the resulting solution, and the resulting mixture was stirred for 10 minutes. H$_2$O (6 mL) and EtOH (6 mL) were sequentially added to a reaction vessel, and the resulting mixture was refluxed for 12 hours. After the reaction was completed, the reaction product was cooled to normal temperature, and then an extraction was performed with distilled water and dichloromethane. The extracted organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 245 (6.0 g, 68%).

<Preparation Example 29> Preparation of Compound 247

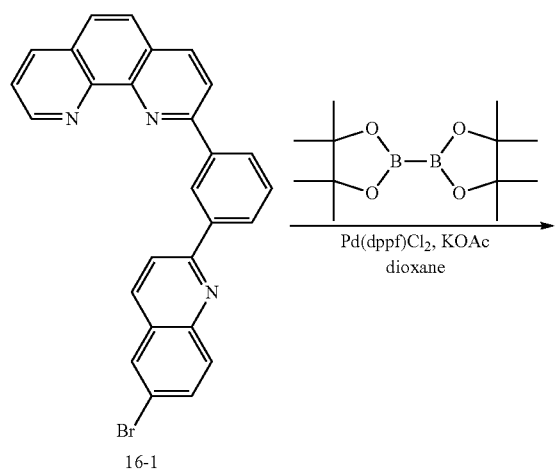

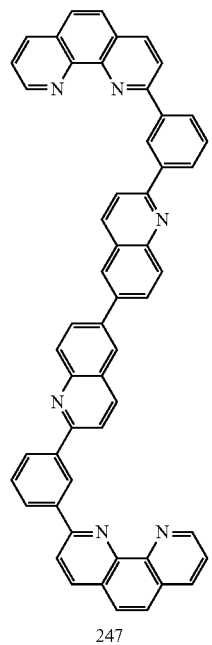

247

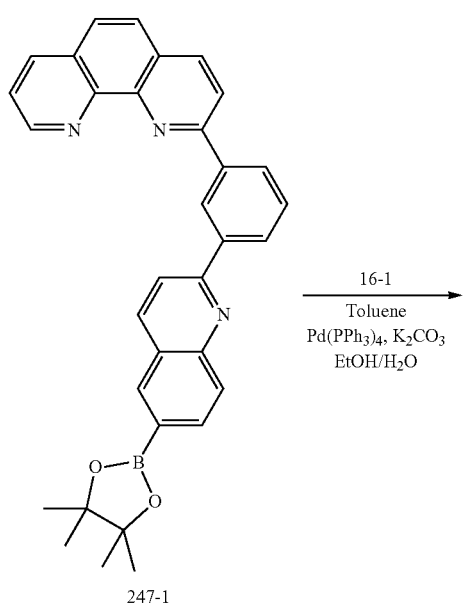

Preparation of Compound 247-1

Compound 16-1 (12.6 g, 27 mmol), 4,4,4',4',5,5,5',5'-octamethyl-2,2'-bi(1,3,2-dioxaborolane) (10 g, 37.8 mmol), Pd(dppf)₂Cl₂ (1.0 g, 1.4 mmol), and KOAc (7.9 g, 81 mmol) were put into a reaction vessel, dioxane (0.3 M) was added thereto, and then the resulting mixture was refluxed for 12 hours. After the reaction was completed, the reaction product was cooled to normal temperature, and then an extraction was performed with distilled water and ethyl acetate. The extracted organic layer was dried over anhydrous Na₂SO₄, and then filtered. The solvent of the filtered organic layer was removed by using a rotary evaporator, and then the residue was purified with column chromatography using dichloromethane and hexane as an eluent to obtain Target Compound 247-1 (8.5 g, 62%).

Preparation of Compound 247

Compound 247-1 (7.4 g, 14.7 mmol) and Compound 16-1 (5.7 g, 14.7 mmol) were dissolved in toluene (50 mL), and then Pd(PPh₃)₄ (1.6 g, 1.4 mmol) and K₂CO₃ (6.1 g, 44.3 mmol) were added to the resulting solution, and the resulting mixture was stirred for 10 minutes. And then, EtOH (10 mL) and H₂O (10 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 247 (6 g, 54%).

<Preparation Example 30> Preparation of Compound 255

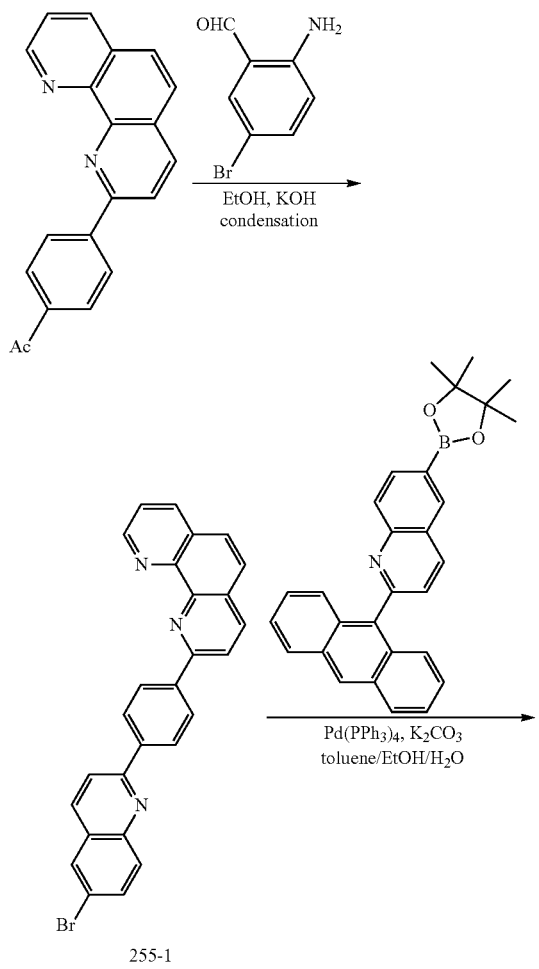

255-1

Preparation of Compound 255-1

After a compound 1-(4-(1,10-phenanthrolin-2-yl)phenyl)ethan-1-one (13.4 g, 45 mmol) and 2-amino-5-bromobenzaldehyde (9 g, 45 mmol) were dissolved in EtOH (200 mL), 5 mL of a saturated KOH solution was added dropwise to EtOH, and then the resulting mixture was refluxed for 4 hours. After the reaction was completed, the reaction product was cooled to normal temperature, and then an extraction was performed with distilled water and dichloromethane. The extracted organic layer was dried over anhydrous $Na_2SO_4$, and then the solvent was removed by using a rotary evaporator. And then, the residue was purified with column chromatography using ethyl acetate and hexane as an eluent to obtain Target Compound 255-1 (17 g, 82%).

Preparation of Compound 255

Compound 255-1 (6.9 g, 15.0 mmol) and 2-(anthracen-9-yl)-6-(4,4,5,5-tetramethyl-1,3,2-dioxaborolan-2-yl)quinoline (6.0 g, 15.0 mmol) were dissolved in toluene (30 mL), and then $Pd(PPh_3)_4$ (1.7 g, 1.5 mmol) and $K_2CO_3$ (6.2 g, 45 mmol) were added to the resulting solution, and the resulting mixture was stirred for 10 minutes. And then, $H_2O$ (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous $Na_2SO_4$, and then filtered. The solvent of the filtered organic layer was removed by using a rotary evaporator, and then the residue was purified with column chromatography using ethyl acetate and hexane as an eluent to obtain Target Compound 255 (7.4 g, 72%).

<Preparation Example 31> Preparation of Compound 269

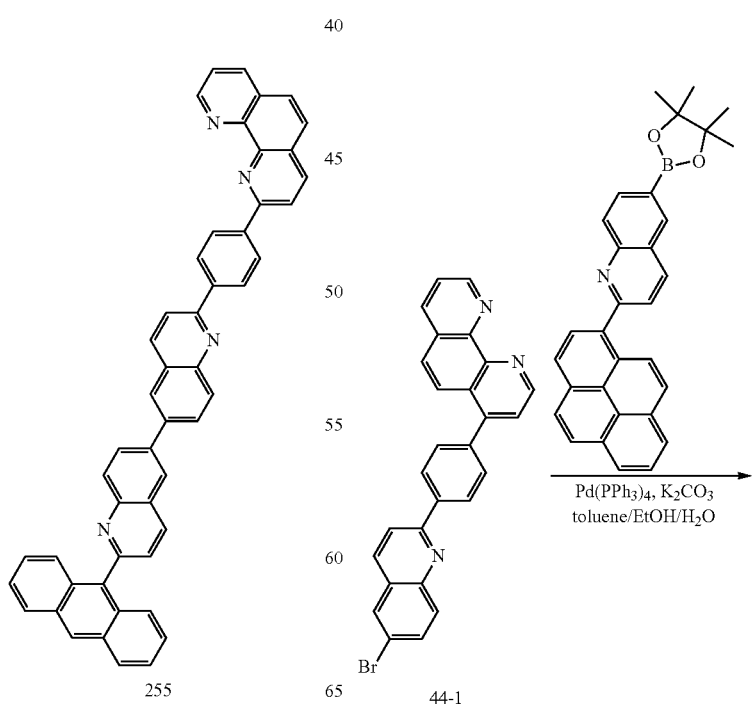

44-1

-continued

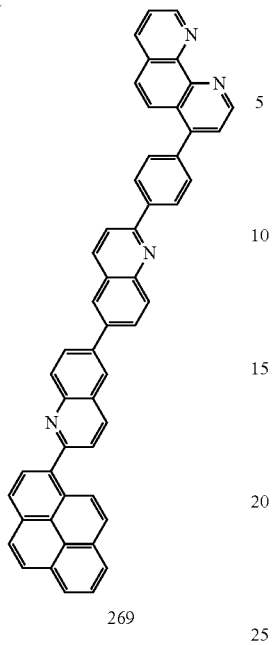

269

Preparation of Compound 269

Compound 44-1 (6.9 g, 15.0 mmol) and 2-(pyridin-2-yl)-6-(4,4,5,5-tetramethyl-1,3,2-dioxaborolan-2-yl)quinoline (6.8 g, 15.0 mmol) were dissolved in toluene (30 mL), and then Pd(PPh$_3$)$_4$ (1.7 g, 1.5 mmol) and K$_2$CO$_3$ (6.2 g, 45 mmol) were added to the resulting solution, and the resulting mixture was stirred for 10 minutes. And then, H$_2$O (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The extracted organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 269 (6.8 g, 64%).

<Preparation Example 32> Preparation of Compound 275

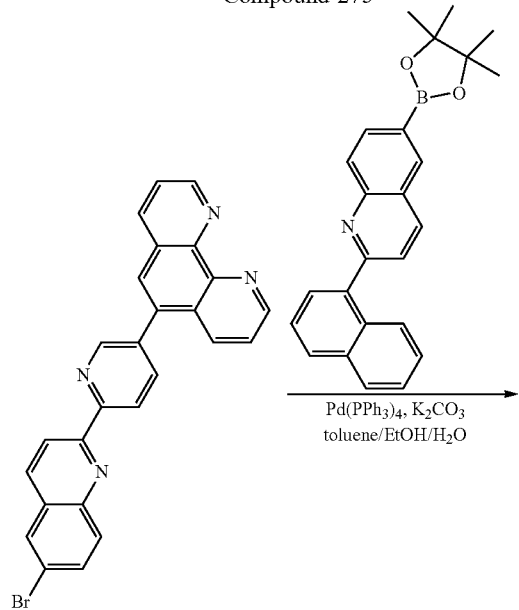

-continued

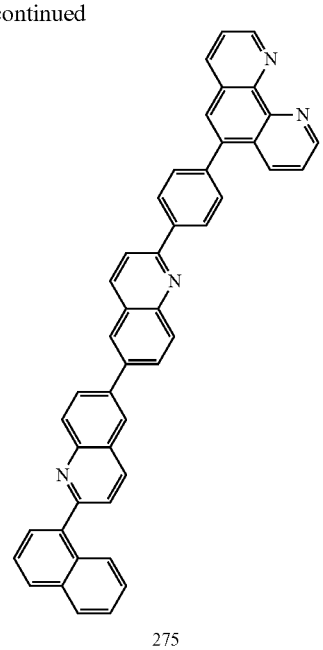

275

Preparation of Compound 275

Compound 52-1 (6.6 g, 14.4 mmol) and a compound 2-(naphthalen-1-yl)-6-(4,4,5,5-tetramethyl-1,3,2-dioxaborolan-2-yl)quinoline (5.5 g, 14.4 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. And then, H$_2$O (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 275 (7.7 g, 84%).

<Preparation Example 33> Preparation of Compound 284

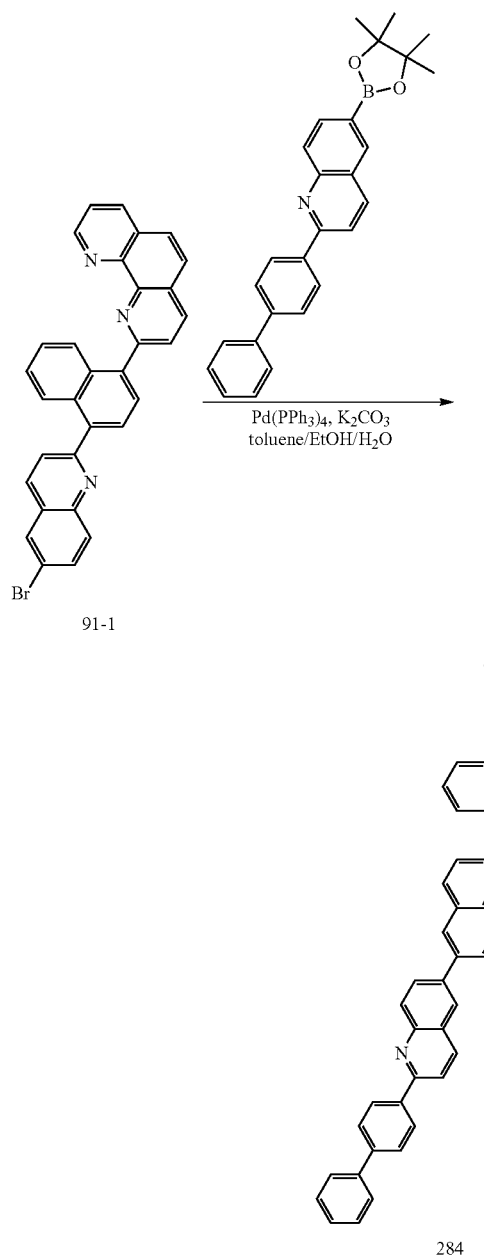

Preparation of Compound 284

Compound 91-1 (7.7 g, 15 mmol) and a compound 2-([1,1'-biphenyl]-4-yl)-6-(4,4,5,5-tetramethyl-1,3,2-dioxaborolan-2-yl)quinoline (12.1 g, 15.0 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. And then, H$_2$O (6 mL) and EtOH (6 mL) were added thereto, and the resulting mixture was refluxed for 18 hours. After the reaction was completed, the reaction product was cooled to normal temperature, and then an extraction was performed with distilled water and dichloromethane. The organic layer was dried over anhydrous Na$_2$SO$_4$, and then filtered. The solvent of the filtered organic layer was removed by using a rotary evaporator, and then the residue was purified with column chromatography using ethyl acetate and hexane as an eluent to obtain Target Compound 284 (7.0 g, 66%).

<Preparation Example 34> Preparation of Compound 301

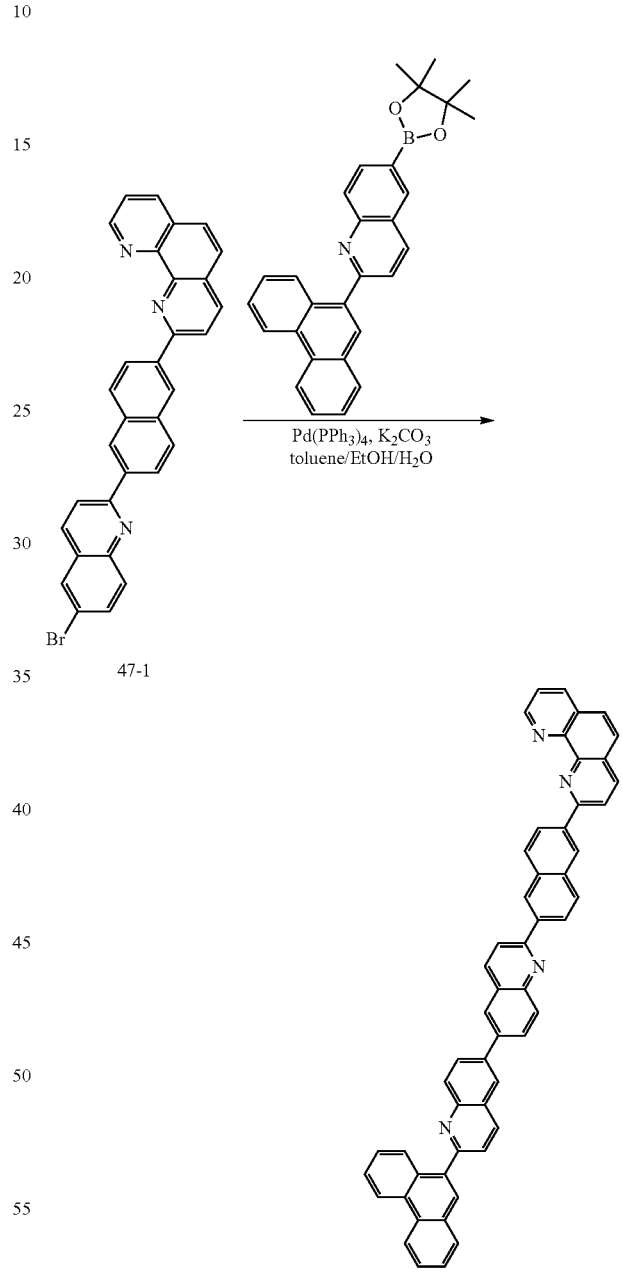

Preparation of Compound 301

Compound 47-1 (7.7 g, 15 mmol) and a compound 2-(phenanthren-9-yl)-6-(4,4,5,5-tetramethyl-1,3,2-dioxaborolan-2-yl)quinoline (6.5 g, 15.0 mmol) were dissolved in toluene (30 mL), and then Pd(PPh$_3$)$_4$ (1.5 g, 1.3 mmol) and K$_2$CO$_3$ (5.3 g, 38.7 mmol) were added to the resulting solution, and the resulting mixture was stirred for 10 minutes. And then, H₂O (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 301 (6.5 g, 59%).

<Preparation Example 35> Preparation of Compound 304

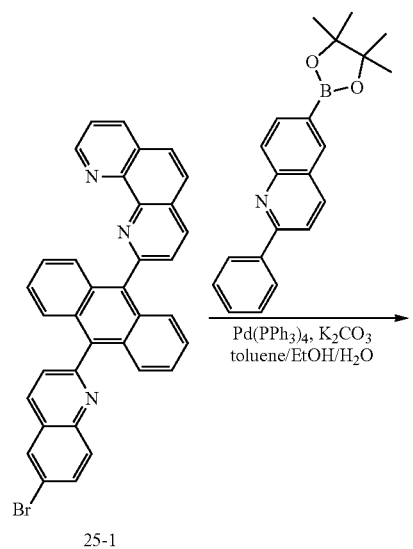

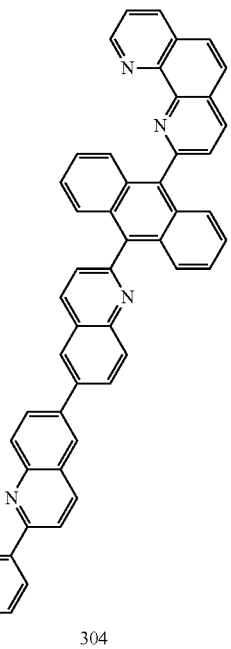

304

Preparation of Compound 304

Compound 25-1 (8.4 g, 15 mmol) and a compound 2-(pyridin-2-yl)-6-(4,4,5,5-tetramethyl-1,3,2-dioxaborolan-2-yl)quinoline (5.0 g, 15.0 mmol) were dissolved in toluene (30 mL), and then Pd(PPh₃)₄ (1.5 g, 1.3 mmol) and K₂CO₃ (5.3 g, 38.7 mmol) were added to the resulting solution, and the resulting mixture was stirred for 10 minutes. And then, H₂O (6 mL) and EtOH (6 mL) were added thereto, and the resulting mixture was refluxed for 12 hours. After the reaction was completed, the reaction product was cooled to normal temperature, and then an extraction was performed with distilled water and dichloromethane. The organic layer was dried over anhydrous Na₂SO₄, and then filtered. The solvent of the filtered organic layer was removed by using a rotary evaporator, and then the residue was purified with column chromatography using ethyl acetate and hexane as an eluent to obtain Target Compound 304 (7.4 g, 74%).

Compounds were prepared in the same manner as in the Preparation Examples, and the synthesis confirmation results thereof are shown in the following Tables 1 to 4.

TABLE 1

| Structure | 1H-NMR (δ, ppm) |
|---|---|
| Compound 7 | (CDCl₃, 400 MHz) δ = 9.08 (2H, s), 8.76~8.62 (5H, m), 8.46~8.33 (6H, m), 8.21~8.07 (7H, m), 7.95~7.84 (2H, d), 7.50~7.39 (3H, m) |
| Compound 13 | (CDCl₃, 400 MHz) δ = 9.32~9.28 (1H, m), 9.15 (1H, d), 8.79~8.75 (1H, m), 8.74~8.68 (1H, m), 8.64 (1H, d), 8.49~8.45 (1H, m), 8.41~8.17 (10H, m), 7.94~7.84 (3H, m), 7.70 (1H, dd), 7.42~7.37 (1H, m) |
| Compound 14 | (CDCl₃, 400 MHz) δ = 9.32~9.29 (1H, m), 9.13 (1H, d), 8.73~8.68 (1H, m), 8.62 (1H, d), 850~8.44 (1H, m), 8.40~8.17 (12H, m), 7.94~7.83 (3H, m), 7.71 (1H, dd), 7.56~7.48 (3H, m), 7.41~7.37 (1H, m) |
| Compound 16 | (CDCl₃, 400 MHz) δ = 9.28 (1H, dd), 9.12~9.11 (1H, m), 8.78~8.76 (1H, m), 8.71~8.68 (1H, m), 8.63 (1H, d), 8.56~8.52 (1H, m), 8.39~8.12 (13H, m), 7.93~7.72 (4H, m), 7.66 (1H, dd), 7.40~7.27 (1H, m) |
| Compound 17 | (CDCl₃, 400 MHz) δ = 9.48 (1H, dd), 9.31 (5H, m), 8.95~8.67 (9H, m), 8.45 (1H, d), 8.31 (2H, s), 8.02 (2H, m), 7.89 (3H, m), 7.77 (4H, m), 7.49 (3H, m), 7.23 (1H, dd) |
| Compound 18 | (CDCl3, 400 MHz) δ = 9.28 (1H, dd), 9.15 (1H, m), 9.02 (1H, d), 8.91 (2H, m), 8.74~8.60 (5H, m), 8.40 (2H, d), 8.38 (1H, d), 8.29 (1H, s), 8.25 (1H, s), 8.00 (4H, m), 8.92 (1H, m), 7.55~7.32 (4H, m), 7.24 (1H, dd) |

TABLE 1-continued

| Structure | 1H-NMR (δ, ppm) |
|---|---|
| Compound 25 | (CDCl$_3$, 400 MHz) δ = 9.28 (1H, dd), 9.03 (1H, d), 8.85 (2H, m), 8.84~8.62 (5H, m), 8.61 (4H, m), 8.35 (1H, s), 8.27 (1H, s), 8.24 (1H, d), 8.02 (3H, m), 7.87~7.65 (6H, m), 7.51 (2H, m), 7.32 (1H, dd) |
| Compound 40 | (CDCl$_3$, 400 MHz) δ = 9.42 (1H, dd), 9.15 (2H, d), 9.00 (1H, d), 8.83~8.62 (8H, m), 8.48 (1H, d), 8.30 (3H, m), 8.15~7.73 (6H, m), 7.56 (1H, d) |
| Compound 44 | (CDCl$_3$, 400 MHz) δ = 9.34 (1H, dd), 9.02~8.75 (5H, m), 8.52~8.25 (7H, m), 7.98 (1H, s), 7.84 (1H, s), 7.82~7.71 (4H, m), 7.56 (1H, dd), 7.48 (1H, d), 7.42 (1H, d), 7.25 (2H, d), 7.12 (1H, d) |
| Compound 47 | (CDCl$_3$, 400 MHz) δ = 9.25 (2H, s), 9.20 (1H, dd), 9.18 (2H, d), 8.89~8.62 (10H, m), 8.33~8.81 (5H, m), 8.19~8.09 (3H, m), 7.96 (2H, m), 7.73 (2H, m) |
| Compound 52 | (CDCl3, 400 MHz) δ = 9.37 (1H, dd), 9.25 (1H, d), 9.18 (3H, m), 8.72 (4H, m), 8.31 (1H, d), 8.22 (2H, d), 8.04~7.88 (2H, m), 7.94 (1H, m), 7.85 (2H, d), 7.64~7.42 (7H, m) |
| Compound 68 | (CDCl$_3$, 400 MHz) δ = 8.74 (1H, d), 8.69~8.29 (9H, m), 8.14~8.06 (4H, m), 7.96~7.91 (2H, m), 7.72~7.59 (3H, m), 7.56~7.48 (3H, m), 7.28 (1H, d) |
| Compound 91 | (CDCl$_3$, 400 MHz) δ = 9.25 (2H, m), 9.11 (2H, d), 9.01 (1H, d), 8.73 (2H, m), 8.44 (1H, d), 8.40 (1H, d), 8.30 (1H, m), 8.21 (3H, m), 8.05 (1H, d), 8.02 (4H, m), 7.99 (1H, d), 7.97~7.85 (4H, m), 7.67 (1H, dd), 7.63 (1H, m), 7.51 (1H, m) |
| Compound 111 | (CDCl$_3$, 400 MHz) δ = 9.02~8.98 (2H, m), 8.72 (2H, s), 8.66 (1H, s), 8.34~8.02 (7H, m), 7.94~7.87 (3H, m), 7.66~7.51 (4H, m), 7.40 (2H, s) |
| Compound 195 | (CDCl$_3$, 400 MHz) δ = 8.97 (1H, d,), 8.70 (1H, s), 8.51~8.25 (9H, m), 8.15~7.88 (9H, m), 7.72~7.52 (2H, m) 7.49~7.42 (2H, m), 7.36 (1H, s) |
| Compound 196 | (CDCl$_3$, 400 MHz) δ = 9.41 (1H, dd), 9.28 (1H, dd), 9.02 (1H, m), 8.72~8.65 (3H, m), 8.48~8.34 (3H, m), 8.21 (1H, d), 8.10 (2H, m), 8.08~7.91 (4H, m), 7.84 (1H, m), 7.77 (2H, m), 7.52~7.21 (9H, m) |
| Compound 198 | (CDCl$_3$, 400 MHz) δ = 9.01~8.88 (2H, m), 8.44~8.28 (7H, m), 8.11 (1H, d), 7.96 (2H, s), 7.86 (1H, m), 7.77 (2H, d), 7.58~7.33 (8H, m) |
| Compound 204 | (CDCl$_3$, 400 MHz) δ = 9.33~9.26 (1H, m), 9.14 (1H, d), 8.79~8.76 (1H, m), 8.73~8.69 (1H, m), 8.67 (1H, d), 8.48~8.45 (1H, m), 8.44~8.18 (10H, m), 7.94~7.84 (5H, m), 7.71 (1H, dd), 7.42~7.37 (2H, m) |
| Compound 206 | (CDCl$_3$, 400 MHz) δ = 8.84~8.78 (2H, m), 8.64~8.43 (6h, m), 8.38~8.29 (6H, m), 8.14 (2H, s), 8.07 (2H, s), 7.80~7.72 (4H, m), 7.59~7.56 (2H, m) |
| Compound 212 | (CDCl3, 400 MHz) δ = 9.38~9.25 (3H, m), 9.16 (1H, d), 8.79~8.75 (1H, m), 8.74~8.68 (3H, m), 8.64 (1H, d), 8.49~8.45 (1H, m), 8.41~8.17 (8H, m), 8.11 (2H, d), 7.94~7.84 (1H, m), 7.70 (1H, dd), 7.42~7.37 (1H, m), 7.36~7.32 (3H, m), 7.25 (2H, d) |
| Compound 241 | (CDCl$_3$, 400 MHz) δ = 9.28 (2H, m), 9.12 (1H, s), 8.83~8.27 (9H, m), 8.61 (2H, d), 8.44 (1H, s), 8.33 (2H, s), 8.18~8.01 (5H, m), 7.90~7.68 (7H, m), 7.45 (3H, m), 7.20 (1H, dd) |
| Compound 242 | (CDCl$_3$, 400 MHz) δ = 9.28 (1H, s), 8.92~8.80 (6H, m), 8.69~8.66 (2H, m), 8.59~8.45 (6H, m), 8.33~8.21 (5H, m), 7.83~7.73 (3H, m), 7.48~7.41 (2H, m), 7.36~7.31 (4H, m) |
| Compound 245 | (CDCl$_3$, 400 MHz) δ = 9.28 (1H, dd), 8.71~8.68 (1H, m), 8.63 (1H, d), 8.56~8.5 (3H, m), 8.39~8.12 (13H, m), 7.93~7.72 (3H, m), 7.66 (1H, dd), 7.58 (2H, m), 7.49 (1H, m) |
| Compound 247 | (CDCl$_3$, 400 MHz) δ = 8.84~8.77 (2H,), 8.72~8.64 (6H, m), 8.56~8.53 (2H, m), 8.20~8.08 (6H, m), 8.01~7.96 (2H, m), 7.90~7.84 (2H, m), 7.80~7.62 (4H, m), 7.54~7.49 (2H, m), 7.37~7.31 (2H, m), 7.29~7.25 (4H, m) |
| Compound 255 | (CDCl$_3$, 400 MHz) δ = 9.25 (1H, dd), 9.15~9.11 (1H, m), 8.78~8.73 (1H, m), 8.71~8.68 (1H, m), 8.63 (1H, d), 8.58 (1H, s), 8.56~8.52 (1H, m), 8.50 (2H, d), 8.39~8.12 (10H, m), 8.03 (2H, d), 7.93~7.72 (2H, m), 7.80 (2H, d), 7.57~7.53 (4H, m), 7.40~7.27 (1H, m) |
| Compound 275 | (CDCl3, 400 MHz) δ = 9.41 (1H, dd), 9.28 (1H, dd), 9.02 (1H, m), 8.72~8.65 (3H, m), 8.48~8.34 (3H, m), 8.21 (1H, d), 8.10 (2H, m), 8.08~7.91 (4H, m), 7.84 (1H, m), 7.77 (2H, m), 7.52~7.21 (9H, m) |
| Compound 284 | (CDCl$_3$, 400 MHz) δ = 9.22 (1H, dd), 9.02 (1H, d), 8.75 (2H, m), 8.47 (1H, d), 8.41 (1H, d), 8.37 (2H, d), 8.31 (1H, m), 8.21 (3H, m), 8.06 (1H, d), 8.02 (4H, m), 7.98 (1H, d), 7.95~7.86 (4H, m), 7.82 (2H, d), 7.73 (2H, d), 7.66 (1H, dd), 7.62 (1H, m), 7.52 (3H, m), 7.43 (1H, m) |
| Compound 304 | (CDCl$_3$, 400 MHz) δ = 9.24 (1H, dd), 8.88~8.64 (8H, m), 8.58 (4H, m), 8.31 (1H, s), 8.29 (1H, s), 8.05 (1H, d), 7.98 (2H, d), 7.8~7.63 (10H, m), 7.52 (2H, m) |

TABLE 2

| Compound | HOMO (eV) | Band gap (eV) | LUMO (eV) | Compound | HOMO (eV) | Band gap (eV) | LUMO (eV) |
|---|---|---|---|---|---|---|---|
| Compound 6 | −6.24 | 3.29 | −2.95 | Compound 7 | −6.18 | 3.28 | −2.9 |
| Compound 11 | −6.04 | 3.28 | −2.76 | Compound 13 | −6.34 | 3.21 | −3.13 |
| Compound 14 | −6.33 | 3.13 | −3.20 | Compound 15 | −6.26 | 3.04 | −3.22 |
| Compound 16 | −6.31 | 3.28 | −3.03 | Compound 17 | −6.25 | 3.28 | −2.97 |
| Compound 18 | −6.48 | 3.36 | −3.12 | Compound 25 | −5.70 | 2.66 | −3.04 |
| Compound 40 | −6.38 | 3.16 | −3.22 | Compound 44 | −6.59 | 3.25 | −3.34 |
| Compound 47 | −6.10 | 2.82 | −3.28 | Compound 52 | −6.43 | 3.19 | −3.24 |
| Compound 68 | −6.46 | 3.19 | −3.27 | Compound 91 | −6.11 | 2.87 | −3.24 |
| Compound 111 | −6.27 | 3.25 | −3.02 | Compound 175 | −6.25 | 3.02 | −3.23 |
| Compound 179 | −6.11 | 2.92 | −3.19 | Compound 195 | −6.26 | 3.18 | −3.08 |
| Compound 196 | −6.25 | 3.08 | −3.17 | Compound 198 | −6.34 | 3.25 | −3.09 |
| Compound 206 | −6.30 | 3.17 | −3.13 | Compound 215 | −6.03 | 2.89 | −3.14 |
| Compound 220 | −6.29 | 3.05 | −3.24 | Compound 241 | −6.50 | 3.28 | −3.22 |
| Compound 242 | −6.13 | 3.05 | −3.08 | Compound 245 | −6.26 | 3.30 | −2.96 |
| Compound 247 | −6.13 | 3.05 | −3.08 | Compound 255 | −5.81 | 2.68 | −3.13 |
| Compound 269 | −5.91 | 2.72 | −3.19 | Compound 275 | −6.31 | 3.18 | −3.13 |
| Compound 284 | −6.06 | 3.02 | −3.04 | Compound 301 | −6.04 | 2.89 | −3.15 |
| Compound 304 | −5.71 | 2.74 | −2.97 | NPB | −5.10 | 3.52 | −1.58 |

TABLE 3

| Compound | FD-MASS | Compound | FD-MASS | Compound | FD-MASS |
|---|---|---|---|---|---|
| Compound 6 | 486.18 | Compound 7 | 563.21 | Compound 11 | 536.20 |
| Compound 13 | 511.18 | Compound 14 | 587.21 | Compound 15 | 663.24 |
| Compound 16 | 587.21 | Compound 17 | 765.26 | Compound 18 | 587.21 |
| Compound 25 | 687.24 | Compound 40 | 509.19 | Compound 44 | 587.21 |
| Compound 47 | 637.23 | Compound 52 | 588.21 | Compound 68 | 564.21 |
| Compound 91 | 638.22 | Compound 111 | 459.17 | Compound 175 | 637.23 |
| Compound 179 | 687.24 | Compound 195 | 559.20 | Compound 196 | 559.20 |
| Compound 198 | 509.19 | Compound 206 | 612.21 | Compound 212 | 738.25 |
| Compound 220 | 764.27 | Compound 241 | 739.27 | Compound 242 | 663.24 |
| Compound 245 | 586.22 | Compound 247 | 764.27 | Compound 255 | 686.25 |
| Compound 269 | 710.25 | Compound 275 | 636.23 | Compound 284 | 712.26 |
| Compound 301 | 736.26 | Compound 304 | 686.25 | | |

TABLE 4

| | Td | Tg | Tm |
|---|---|---|---|
| Compound 6 | 455° C. | ND | 250° C., 258° C. |
| Compound 7 | 489° C. | ND | 301° C. |
| Compound 11 | 483.13° C. | ND | 290° C. |
| Compound 13 | 469° C. | ND | 349° C. |
| Compound 16 | 495° C. | 122° C. | 290° C. |

Table 1 shows NMR values, and Table 2 shows HOMO, LUMO, and BAND GAP values according to the calculation results of molecules.

Experimental Example 1

1) Manufacture of Organic Light Emitting Device

A glass substrate thinly coated with ITO to have a thickness of 1,500 Å was ultrasonically washed with distilled water. When the washing with distilled water is finished, the glass substrate was ultrasonically washed with a solvent such as acetone, methanol, and isopropyl alcohol, was dried and then was subjected to UVO treatment for 5 minutes by using UV in a UV washing machine. Thereafter, the substrate was transferred to a plasma washing machine (PT), and then was subjected to plasma treatment in order to implement an ITO work function and remove a residual film in a vacuum state, and thus, was transferred to a thermal deposition equipment for organic deposition.

An organic material having a 2-stack white organic light device (WOLED) structure was formed on the ITO transparent electrode (positive electrode). For a first stack, a hole transporting layer was first formed by thermally vacuum depositing TAPC to have a thickness of 300 Å. The hole transporting layer was formed, and then a light emitting layer was thermally vacuum deposited thereon as follows. The light emitting layer was deposited to have a thickness of 300 Å by doping a host TCzl with a blue phosphorescent dopant FIrpic at a concentration of 8%. An electron transporting layer was formed to have a thickness of 400 Å by using TmPyPB, and then a charge producing layer was formed to have a thickness of 100 Å by doping the compound described in the following Table 5 with $Cs_2CO_3$ at a concentration of 20%.

For a second stack, a hole injection layer was first formed by thermally vacuum depositing $MoO_3$ to have a thickness of 50 Å. A hole transporting layer, which is a common layer, was formed to have a thickness of 100 Å by doping TAPC with $MoO_3$ at a concentration of 20%, and then depositing TAPC to have a thickness of 300 Å. A light emitting layer was deposited thereon to have a thickness of 300 Å by doping a host TCzl with a green phosphorescent dopant Ir(ppy)$_3$ at a concentration of 8%, and then an electron transporting layer was formed to have a thickness of 600 Å by using TmPyPB. Finally, lithium fluoride (LiF) was deposited to have a thickness of 10 Å on the electron transporting layer to form an electron injection layer, and then aluminum (Al) was deposited to have a thickness of 1,200 Å on the electron injection layer to form a negative electrode, thereby manufacturing an organic electroluminescence device.

Meanwhile, all the organic compounds required for manufacturing an OLED were subjected to vacuum sublimed purification under $10^{-6}$ to $10^{-8}$ torr for each material, and then used for the manufacture of OLED.

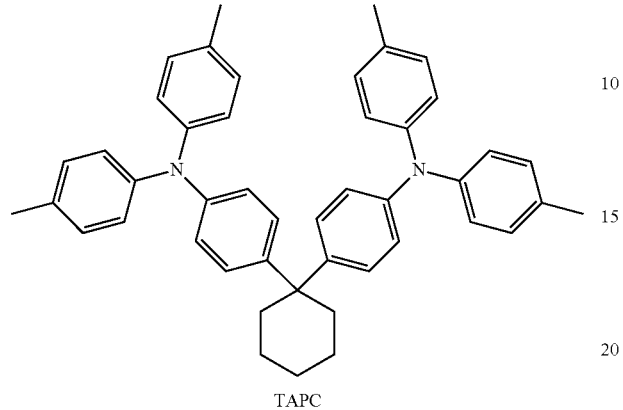

TAPC

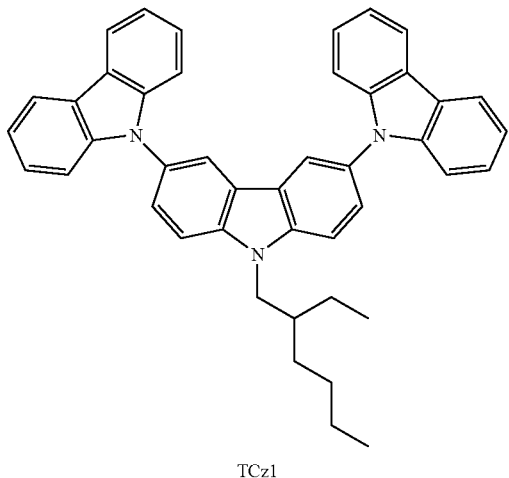

TCz1

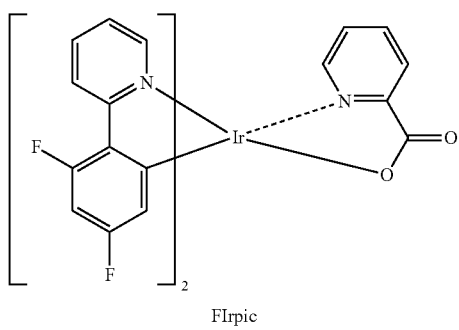

FIrpic

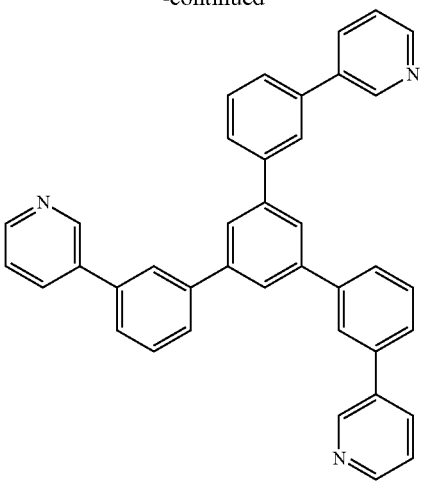

TmPyPb

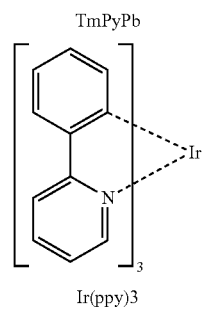

Ir(ppy)3

2) Driving Voltage and Light Emitting Efficiency of Organic Electroluminescence Device For the organic electroluminescence device manufactured as described above, the electroluminescent (EL) characteristics were measured using M7000 manufactured by McScience Inc., and the measurement results were used to measure $T_{95}$ through a service life measurement device (M6000) manufactured by McScience Inc., when the reference brightness was 3,500 cd/m². The results of measuring the driving voltage, light emitting efficiency, external quantum efficiency, and color coordinate (CIE) of the white organic electroluminescence device manufactured according to the present invention are shown as in Table 5.

TABLE 5

| | Compound | Driving voltage (V) | Light emitting efficiency (cd/A) | External quantum efficiency (%) | CIE (x, y) |
|---|---|---|---|---|---|
| Example 1 | 6 | 7.52 | 65.31 | 32.45 | (0.229, 0.481) |
| Example 2 | 7 | 7.41 | 64.86 | 31.92 | (0.220, 0.480) |
| Example 3 | 11 | 7.15 | 65.25 | 35.23 | (0.234, 0.483) |
| Example 4 | 13 | 8.08 | 61.92 | 30.18 | (0.226, 0.433) |
| Example 5 | 14 | 8.33 | 62.27 | 25.06 | (0.210, 0.424) |
| Example 6 | 15 | 7.52 | 68.80 | 32.24 | (0.209, 0.422) |
| Example 7 | 16 | 7.65 | 68.23 | 34.15 | (0.234, 0.463) |
| Example 8 | 17 | 7.66 | 67.14 | 30.06 | (0.208, 0.421) |

TABLE 5-continued

| | Compound | Driving voltage (V) | Light emitting efficiency (cd/A) | External quantum efficiency (%) | CIE (x, y) |
|---|---|---|---|---|---|
| Example 9 | 18 | 7.49 | 71.18 | 30.08 | (0.212, 0.420) |
| Example 10 | 25 | 7.53 | 67.13 | 33.02 | (0.207, 0.421) |
| Example 11 | 28 | 8.35 | 58.95 | 23.75 | (0.212, 0.390) |
| Example 12 | 40 | 7.44 | 64.18 | 27.06 | (0.212, 0.425) |
| Example 13 | 44 | 7.34 | 65.83 | 34.92 | (0.208, 0.420) |
| Example 14 | 47 | 7.56 | 62.05 | 26.04 | (0.215, 0.422) |
| Example 15 | 48 | 7.52 | 66.06 | 34.45 | (0.234, 0.478) |
| Example 16 | 52 | 8.11 | 60.37 | 27.38 | (0.208, 0.419) |
| Example 17 | 59 | 7.58 | 68.68 | 22.65 | (0.217, 0.463) |
| Example 18 | 72 | 7.64 | 64.52 | 32.54 | (0.210, 0.423) |
| Example 19 | 84 | 8.12 | 60.43 | 28.73 | (0.216, 0.483) |
| Example 20 | 89 | 7.93 | 58.25 | 22.31 | (0.201, 0.483) |
| Example 21 | 91 | 7.43 | 67.57 | 32.46 | (0.208, 0.418) |
| Example 22 | 175 | 7.58 | 65.28 | 32.98 | (0.210, 0.422) |
| Example 23 | 179 | 7.55 | 67.70 | 29.74 | (0.208, 0.419) |
| Example 24 | 196 | 7.88 | 64.86 | 26.95 | (0.208, 0.422) |
| Example 25 | 198 | 7.90 | 65.34 | 31.02 | (0.209, 0.420) |
| Example 26 | 215 | 7.72 | 67.13 | 32.08 | (0.213, 0.427) |
| Example 27 | 220 | 7.56 | 65.73 | 31.22 | (0.209, 0.420) |
| Example 28 | 241 | 6.94 | 68.16 | 33.04 | (0.208, 0.419) |
| Example 29 | 245 | 7.42 | 66.15 | 29.16 | (0.212, 0.420) |
| Example 30 | 255 | 8.35 | 62.93 | 25.72 | (0.209, 0.416) |
| Example 31 | 269 | 8.08 | 64.84 | 32.90 | (0.208, 0.420) |
| Example 32 | 275 | 7.58 | 67.30 | 32.81 | (0.208, 0.419) |
| Example 33 | 284 | 7.56 | 66.21 | 31.93 | (0.207, 0.414) |
| Example 34 | 301 | 7.63 | 66.12 | 31.14 | (0.206, 0.415) |
| Example 35 | 304 | 7.82 | 62.77 | 25.27 | (0.210, 0.424) |
| Comparative Example 1 | TmPyPB | 8.68 | 53.95 | 20.73 | (0.214, 0.443) |

As can be seen from the results in Table 5, the organic electroluminescence device using a charge producing layer material of the white organic electroluminescence device of the present invention has a low driving voltage and significantly improved light emitting efficiency as compared to Comparative Example 1.

Experimental Example 2

1) Manufacture of Organic Light Emitting Device

A glass substrate thinly coated with ITO to have a thickness of 1,500 Å was ultrasonically washed with distilled water. When the washing with distilled water is finished, the glass substrate was ultrasonically washed with a solvent such as acetone, methanol, and isopropyl alcohol, was dried and then was subjected to UVO treatment for 5 minutes by using UV in a UV washing machine. Thereafter, the substrate was transferred to a plasma washing machine (PT), and then was subjected to plasma treatment in order to implement an ITO work function and remove a residual film in a vacuum state, and thus, was transferred to a thermal deposition equipment for organic deposition. An organic material having a single stack structure was formed on the ITO transparent electrode (positive electrode). HAT-CN was deposited to have a thickness of 50 Å as a hole injection layer, NPD, which is a hole transporting layer, was doped with DNTPD at a concentration within 10% and deposited to have a thickness of 1,500 Å and formed, and TCTA was continuously deposited to have a thickness of 200 Å. Subsequently, a light emitting layer including an ADN host and a t-Bu-perylene dopant was formed to have a thickness of 250 Å. Subsequently, Alq$_3$, which is an electron transporting layer, was film-formed to have a thickness of 250 Å, the compound described in the following Table 6 was doped with lithium, which is an alkali metal, to film-form an N-type charge producing layer having a thickness of 100 Å, and Al as a negative electrode was film-formed to have a thickness of approximately 1,000 Å, thereby manufacturing an organic electroluminescence device.

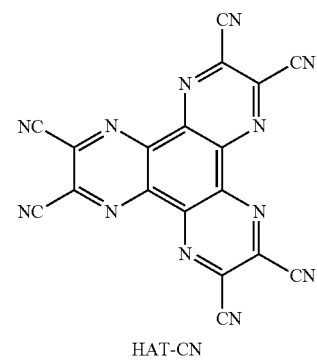

HAT-CN

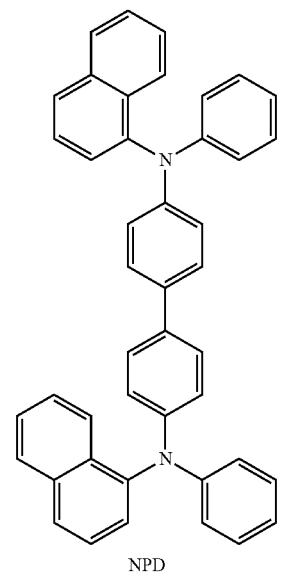

NPD

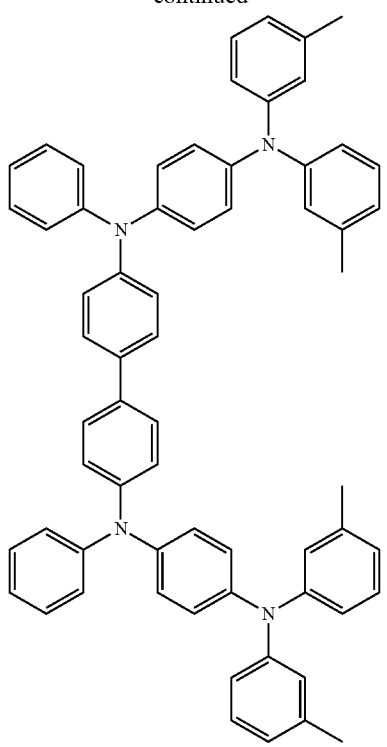
DNTPD
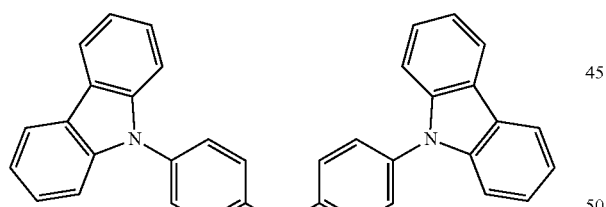
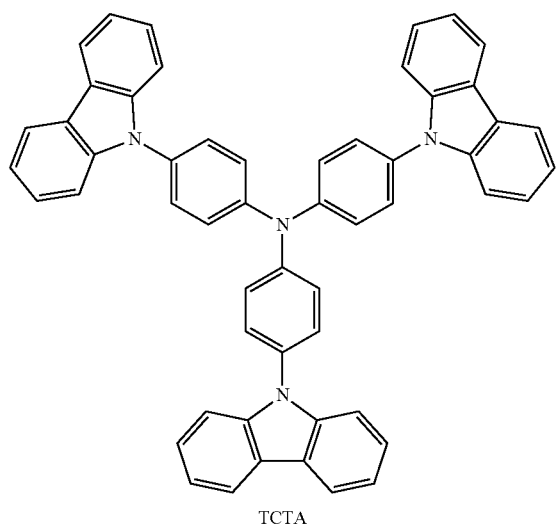
TCTA
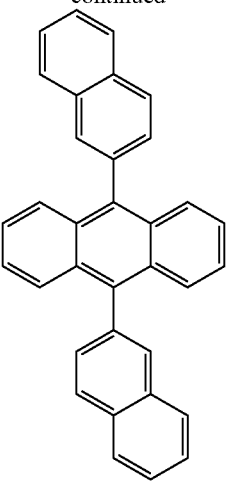
ADN
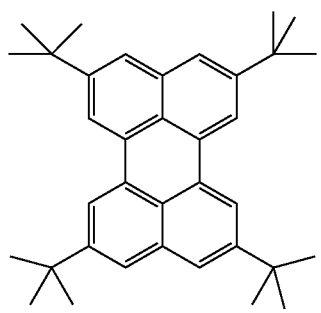
t-Bu-Perylene
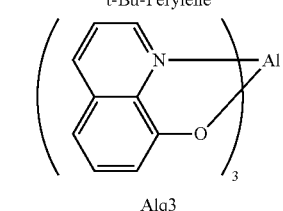
Alq3
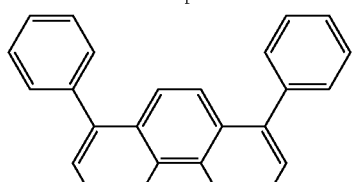
Bphen
TABLE 6
|  | Compound | Driving voltage (V) | Light emitting efficiency (cd/A) | External quantum efficiency (%) | CIE (x, y) |
| --- | --- | --- | --- | --- | --- |
| Example 1 | 6 | 5.48 | 6.53 | 8.11 | (0.134 0.107) |
| Example 2 | 7 | 5.38 | 6.49 | 7.98 | (0.134 0.100) |
| Example 3 | 11 | 5.10 | 6.53 | 8.81 | (0.134 0.106) |
| Example 4 | 13 | 5.92 | 6.19 | 7.55 | (0.134 0.101) |
| Example 5 | 14 | 6.19 | 6.23 | 6.27 | (0.134 0.110) |

TABLE 6-continued

| | Compound | Driving voltage (V) | Light emitting efficiency (cd/A) | External quantum efficiency (%) | CIE (x, y) |
|---|---|---|---|---|---|
| Example 6 | 15 | 5.33 | 6.88 | 8.06 | (0.134 0.099) |
| Example 7 | 16 | 5.47 | 6.82 | 8.54 | (0.134 0.099) |
| Example 8 | 17 | 5.51 | 6.71 | 7.52 | (0.134 0.100) |
| Example 9 | 18 | 5.35 | 7.12 | 7.52 | (0.134 0.100) |
| Example 10 | 25 | 5.41 | 6.71 | 8.26 | (0.134 0.104) |
| Example 11 | 28 | 6.23 | 5.90 | 5.94 | (0.134 0.111) |
| Example 12 | 40 | 5.38 | 6.42 | 6.77 | (0.134 0.106) |
| Example 13 | 44 | 5.17 | 6.58 | 8.73 | (0.134 0.105) |
| Example 14 | 47 | 5.30 | 6.21 | 6.51 | (0.134 0.108) |
| Example 15 | 48 | 5.48 | 6.61 | 8.61 | (0.134 0.105) |
| Example 16 | 52 | 6.05 | 6.04 | 6.85 | (0.134 0.110) |
| Example 17 | 59 | 5.39 | 6.87 | 5.66 | (0.134 0.110) |
| Example 18 | 72 | 5.49 | 6.45 | 8.14 | (0.134 0.099) |
| Example 19 | 84 | 6.00 | 6.04 | 7.18 | (0.134 0.101) |
| Example 20 | 89 | 5.86 | 5.83 | 5.58 | (0.134 0.110) |
| Example 21 | 91 | 5.26 | 6.76 | 8.12 | (0.134 0.099) |
| Example 22 | 175 | 5.39 | 6.53 | 8.25 | (0.134 0.099) |
| Example 23 | 179 | 5.46 | 6.77 | 7.44 | (0.134 0.100) |
| Example 24 | 196 | 5.62 | 6.49 | 6.74 | (0.134 0.106) |
| Example 25 | 198 | 5.85 | 6.53 | 7.76 | (0.134 0.100) |
| Example 26 | 215 | 5.58 | 6.71 | 8.02 | (0.134 0.099) |
| Example 27 | 220 | 5.24 | 6.57 | 7.81 | (0.134 0.100) |
| Example 28 | 241 | 4.58 | 6.82 | 8.26 | (0.134 0.099) |
| Example 29 | 245 | 5.17 | 6.62 | 7.29 | (0.134 0.100) |
| Example 30 | 255 | 6.22 | 6.29 | 6.43 | (0.134 0.109) |
| Example 31 | 269 | 5.92 | 6.48 | 8.23 | (0.134 0.100) |
| Example 32 | 275 | 5.45 | 6.73 | 8.20 | (0.134 0.099) |
| Example 33 | 284 | 5.36 | 6.62 | 7.98 | (0.134 0.100) |
| Example 34 | 301 | 5.68 | 6.61 | 7.79 | (0.134 0.100) |
| Example 35 | 304 | 5.79 | 6.28 | 6.32 | (0.134 0.109) |
| Comparative Example 2 | Bphen | 8.22 | 5.63 | 5.72 | (0.134 0.110) |

As can be seen from the results in Table 6, the organic electroluminescence device using a charge producing layer material of the white organic electroluminescence device of the present invention has a low driving voltage and significantly improved light emitting efficiency as compared to Comparative Example 2.

The invention claimed is:
1. A hetero-cyclic compound represented by the following Chemical Formula 1:

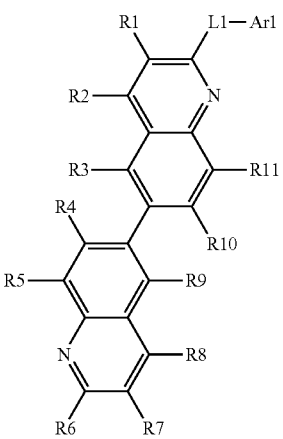

[Chemical Formula 1]

in Chemical Formula 1,
L1 is a direct bond; or a substituted or unsubstituted $C_6$ to $C_{60}$ arylene group,
Ar1 is a substituted pyridine group; a substituted pyrimidine group; a substituted triazine group; a substituted phenanthroline group; or is represented by any one of the following Chemical Formulae 2 to 5:

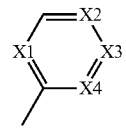

[Chemical Formula 2]

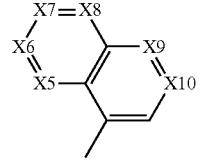

[Chemical Formula 3]

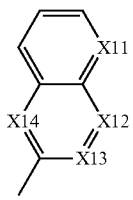

[Chemical Formula 4]

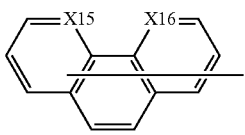

[Chemical Formula 5]

wherein in Chemical Formulae 2 to 5,
at least one of X1 to X4 is N, O, or S, and the others are CR12,
at least one of X5 to X10 is N, O, or S, and the others are CR13,
at least one of X11 to X14 is N, O, or S, and the others are CR14, at least one of X15 and X16 is N, O, or S, and the other is CR15, R12 to R15 are hydrogen, R1 to R5 and R7 to R11 are hydrogen, wherein R6 of Chemical Formula 1 is -(L2)m-(Z)n, L2 is a substituted or unsubstituted C6 to C60 arylene; or a substituted or unsubstituted C2 to C60 heteroarylene, Z is a substituted or unsubstituted phenyl group; a substituted or unsubstituted biphenyl group; a substituted or unsubstituted naphthyl group; a substituted or unsubstituted triphenylenyl group; a substituted or unsubstituted pyrenyl group; a substituted or unsubstituted anthracenyl group; a substituted or unsubstituted phenanthrenyl group; a substituted or unsubstituted pyridine group; a substituted or unsubstituted pyrimidine group; a substituted or unsubstituted triazine group; a substituted or unsubstituted benzoimidazole group; a substituted or unsubstituted quinoline group; or a substituted or unsubstituted phenanthrolinyl group, in chemical formula 2, wherein when one of X1 or X4 is N, the others are CR12 and L1 is a direct bond, Z is a substituted or unsubstituted phenyl group; a substituted or unsubstituted biphenyl group; a substituted or unsubstituted naphthyl group; a substituted or unsubstituted triphenylenyl group; a substituted or unsubstituted pyrenyl group; a substituted or unsubstituted anthracenyl group; a substituted or unsubstituted phenanthrenyl group; a substituted pyridine group; a substituted or unsubstituted pyrimidine group; a substituted or unsubstituted triazine group; a substituted or unsubstituted benzoimidazole group; a substituted or unsubstituted quinoline group; or a substituted or unsubstituted phenanthrolinyl group, m is an integer from 0 to 5, and n is an integer from 1 to 3.

2. The hetero-cyclic compound of claim 1, wherein Chemical Formula 1 is represented by any one of the following compounds:

1

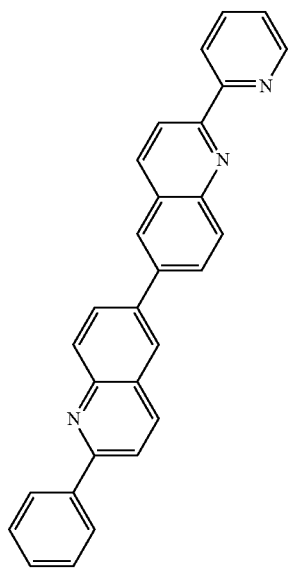

2

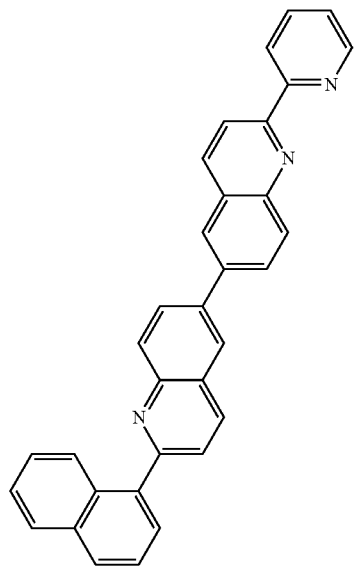

3

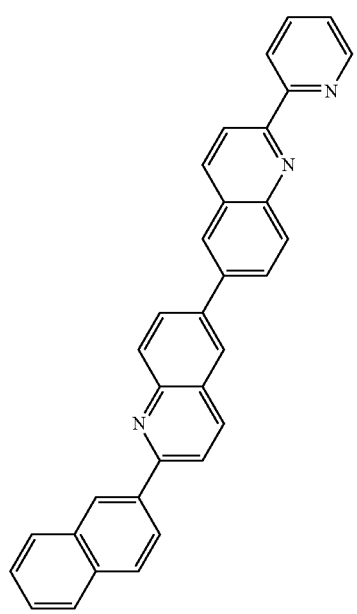

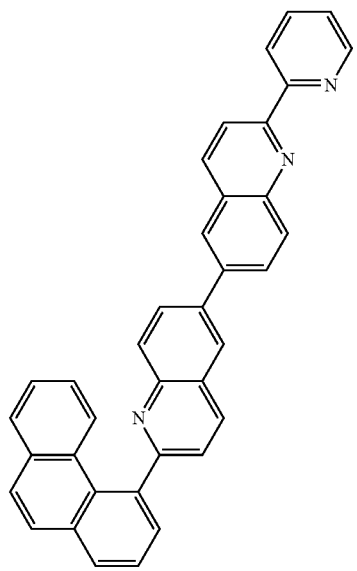
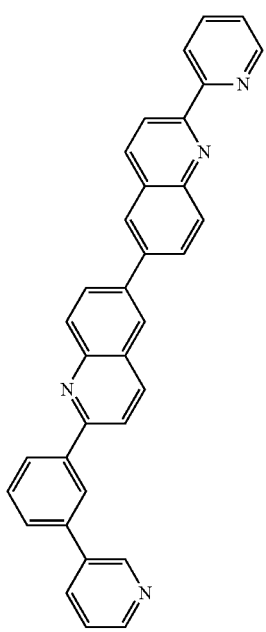
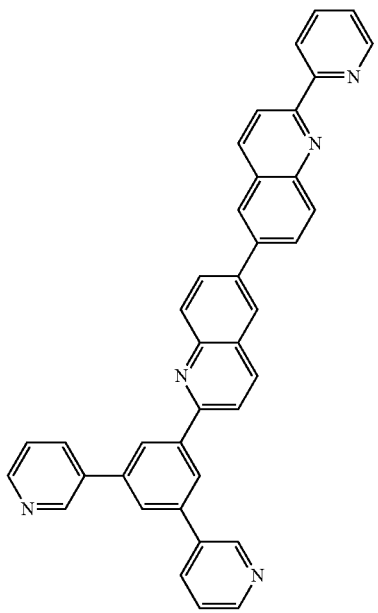
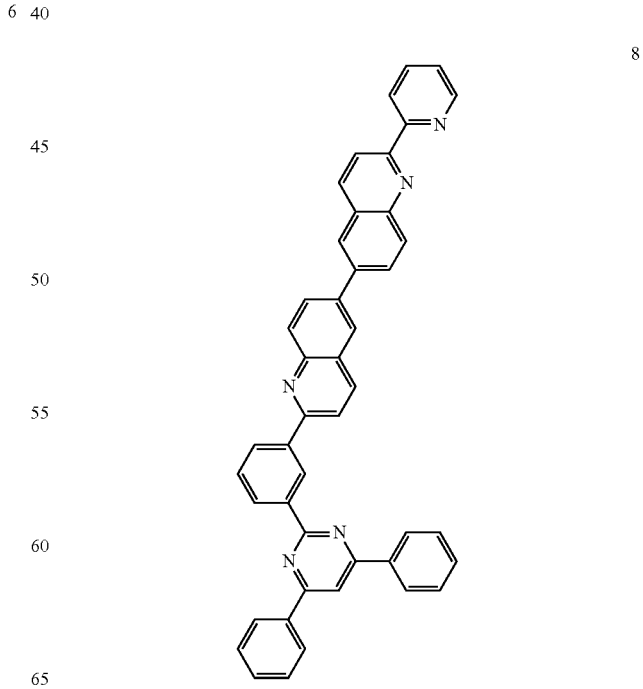

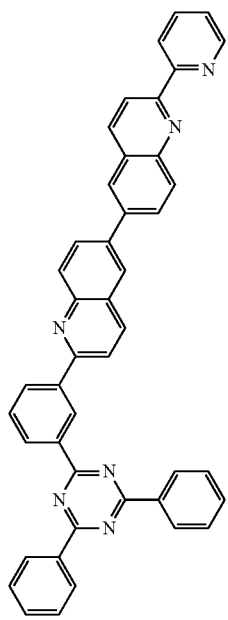
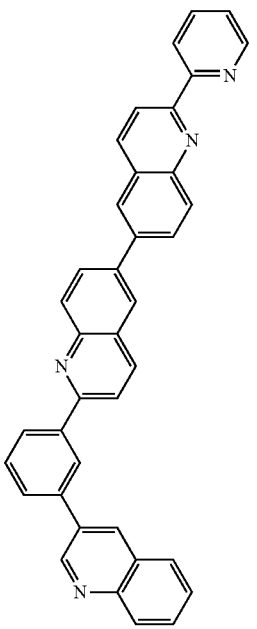
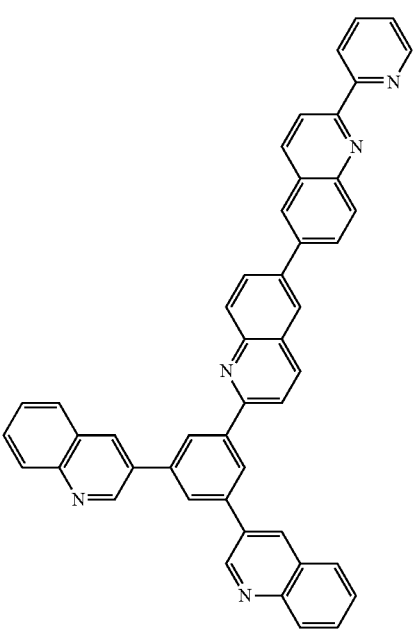

253
-continued
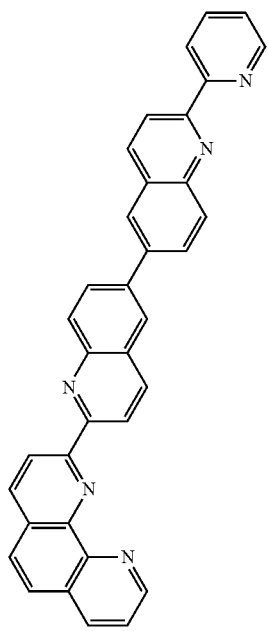
13
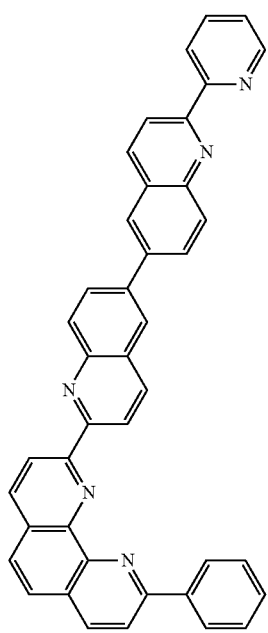
14
254
-continued
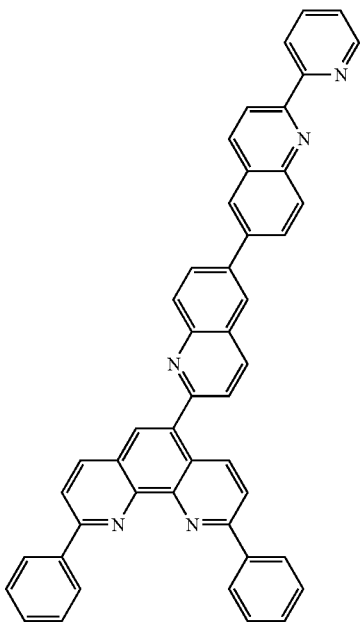
15
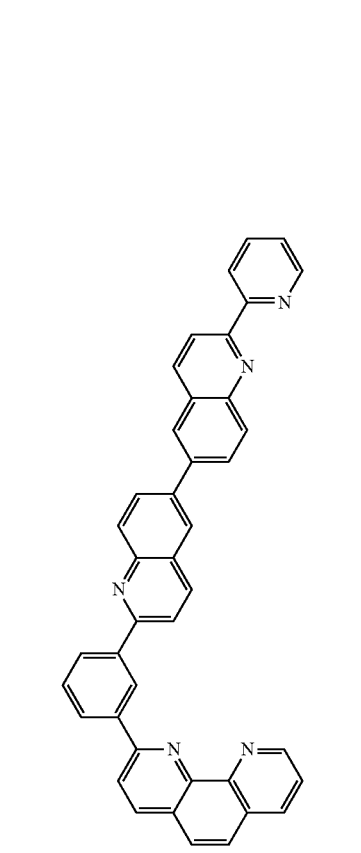
16

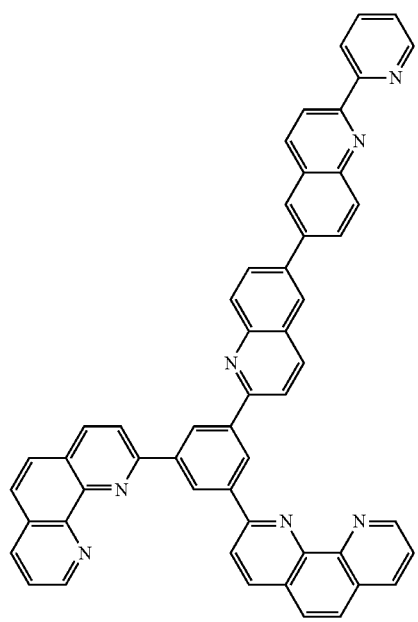
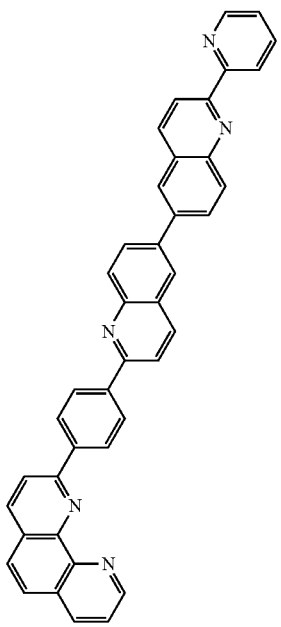

21
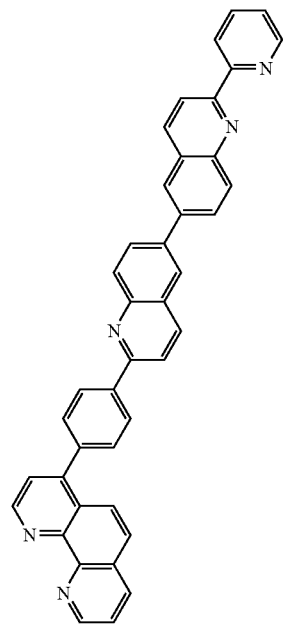
22
23
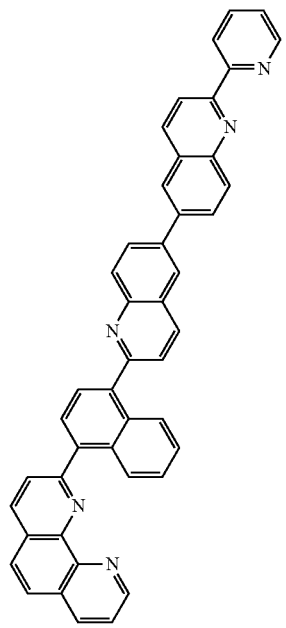
24

25
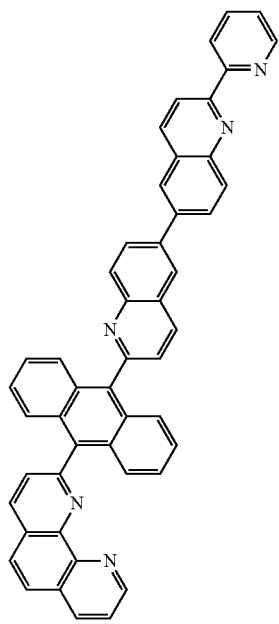
26
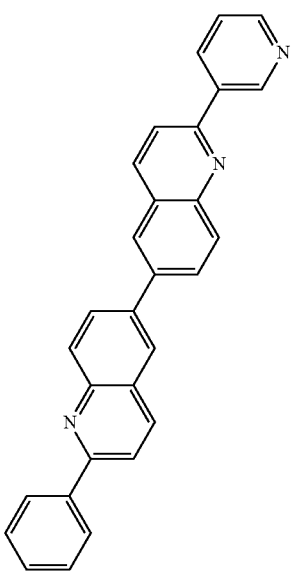
27
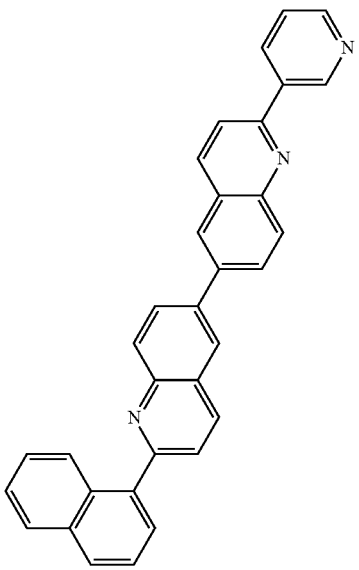
28
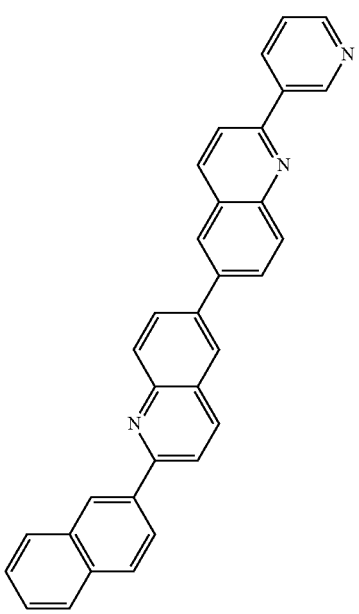

261
-continued
29
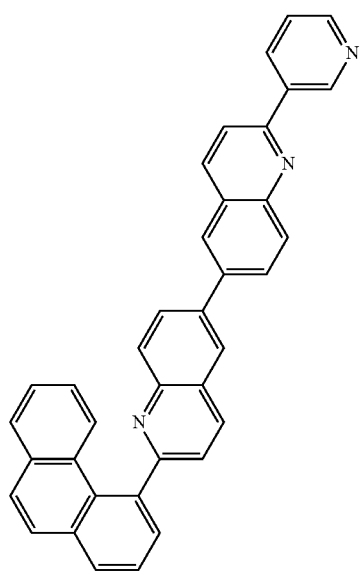
30
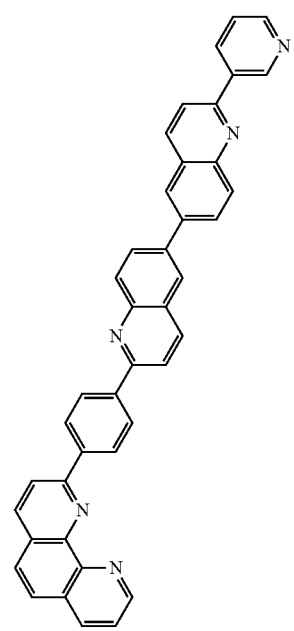
262
-continued
31
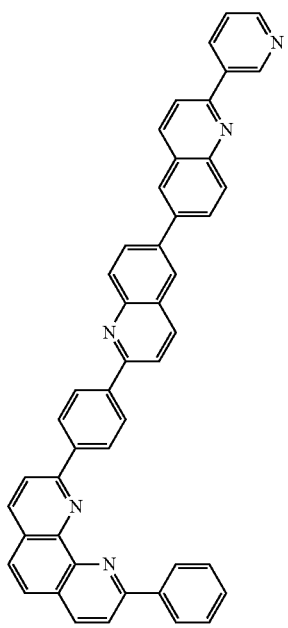
32
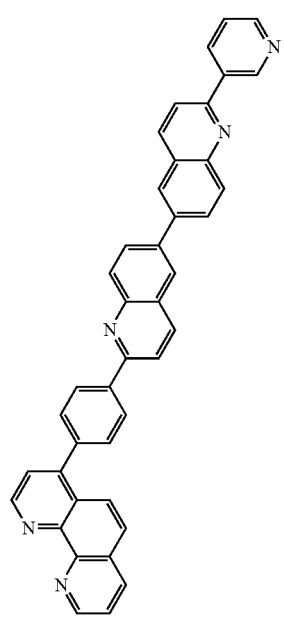

33
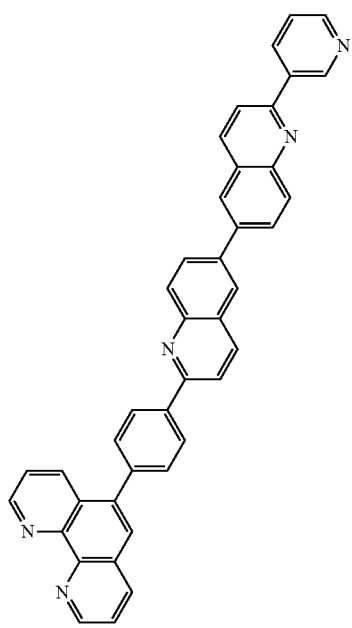
34
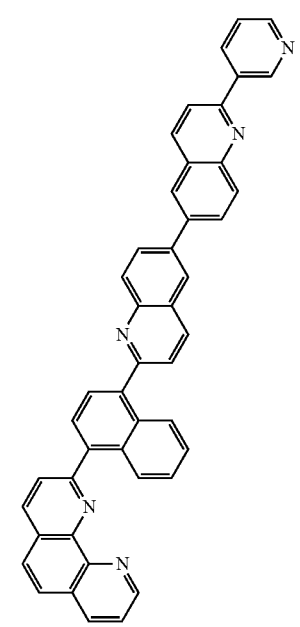
35
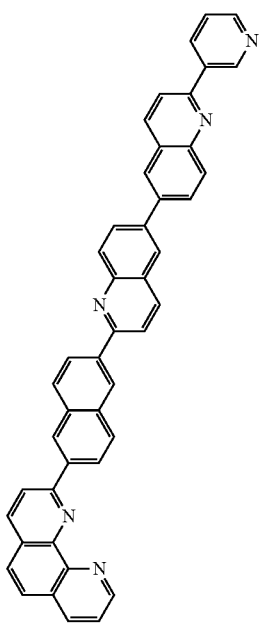
36
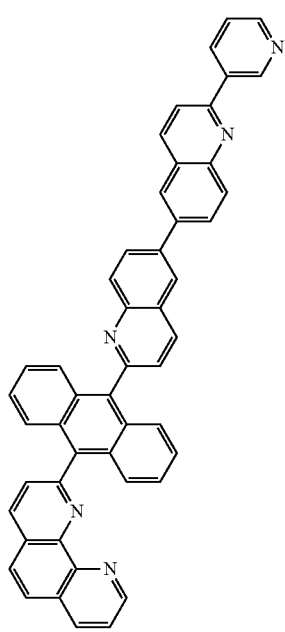

37
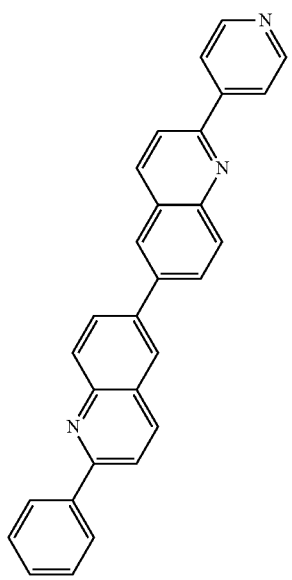
38
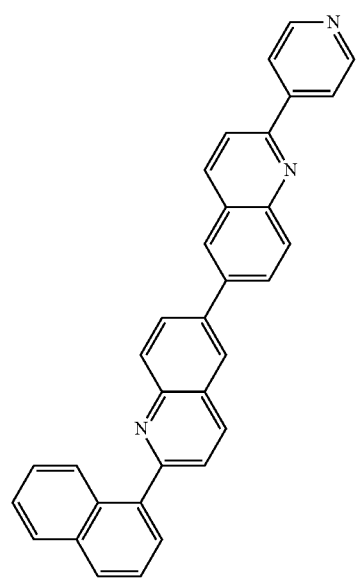
39
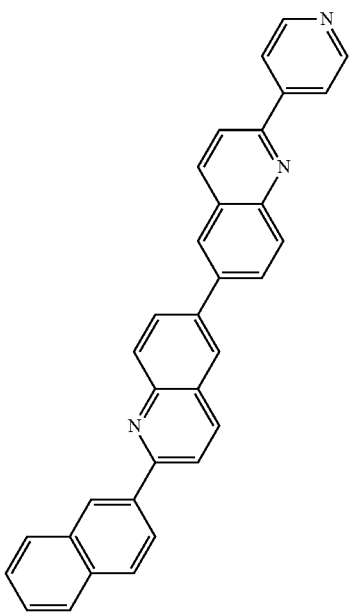
40
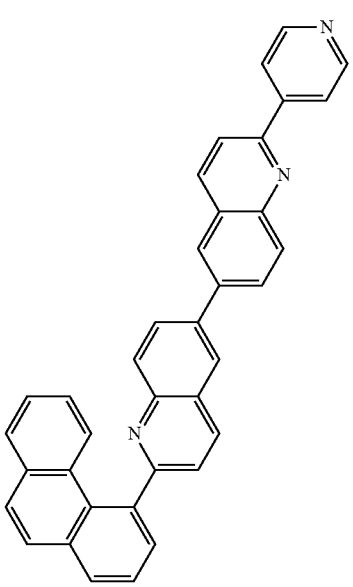

267
-continued
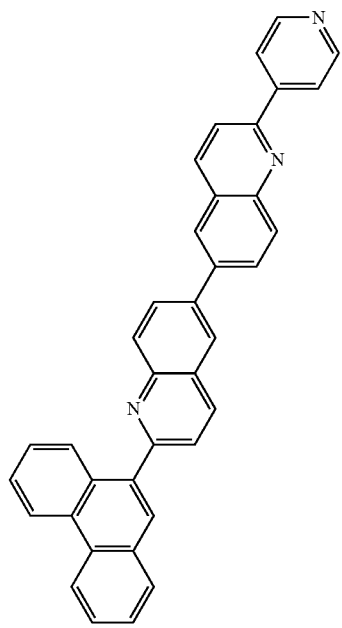
41
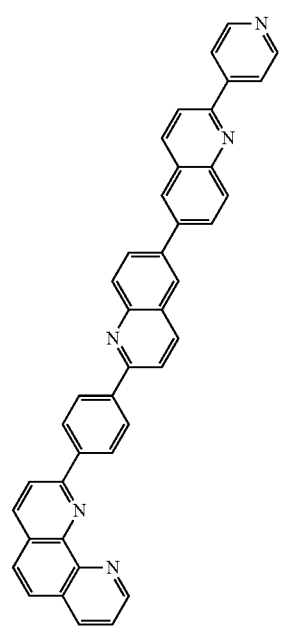
42
268
-continued
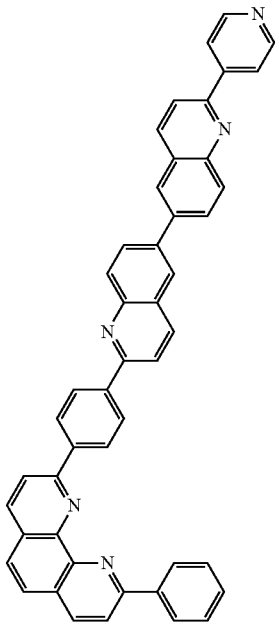
43
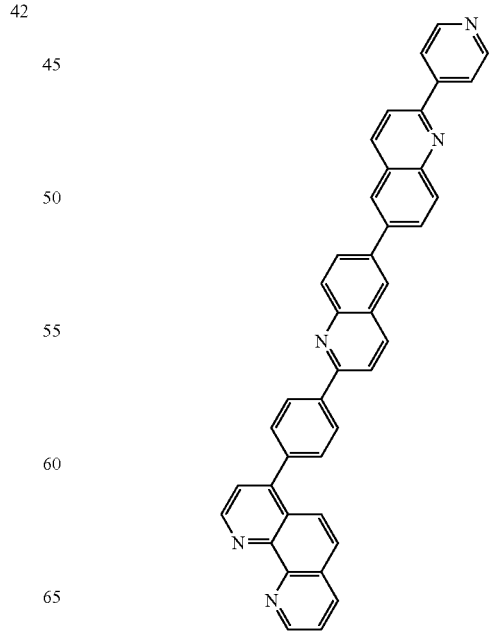
44

45
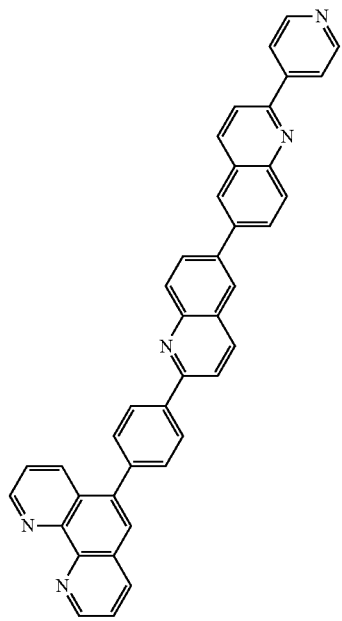
46
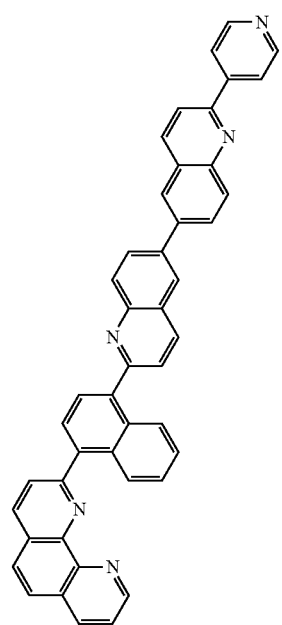
47
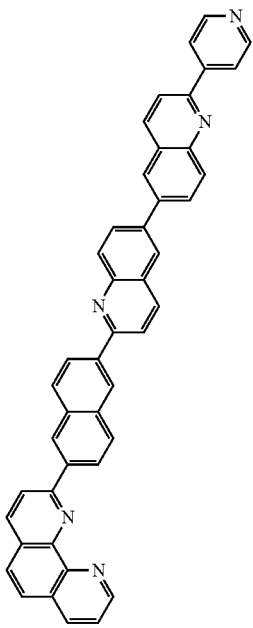
48
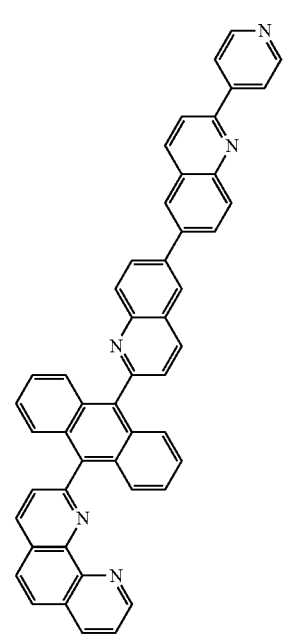

49
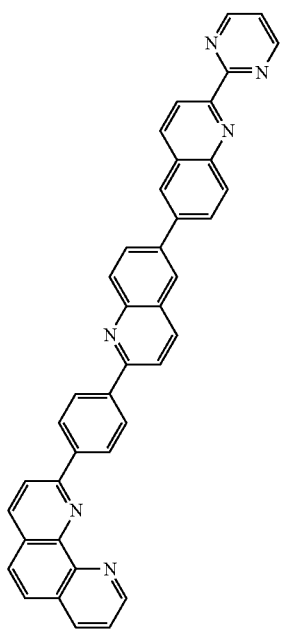
50
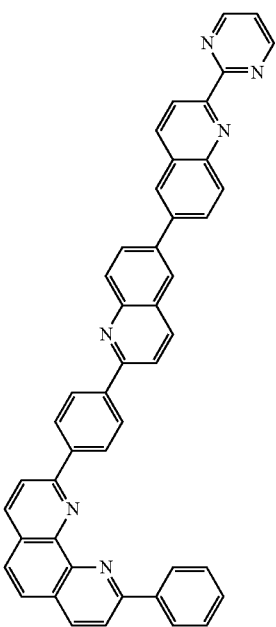
51
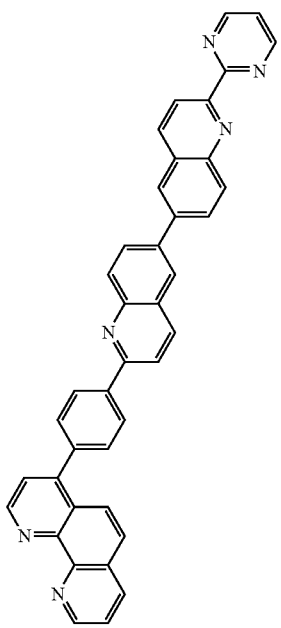
52
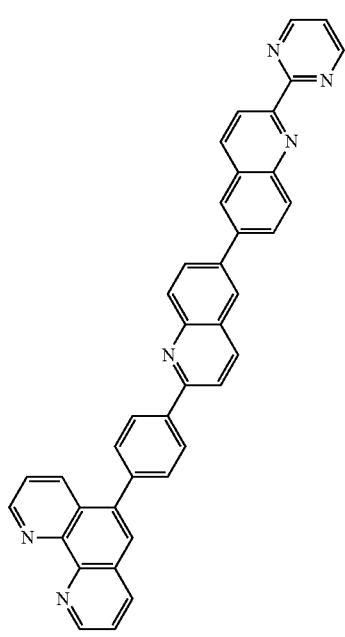

53
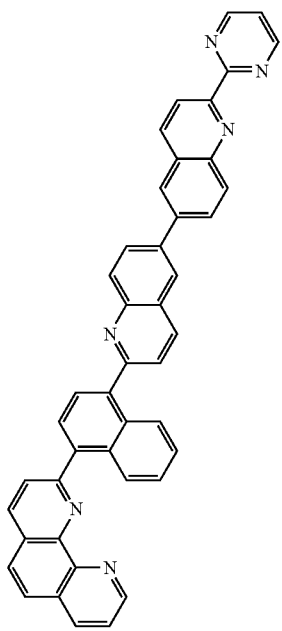
54
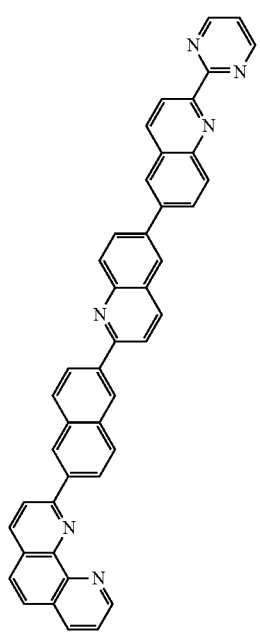
55
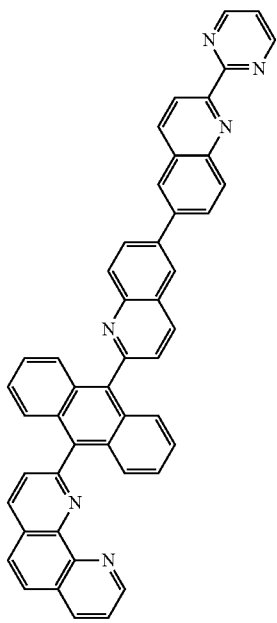
56
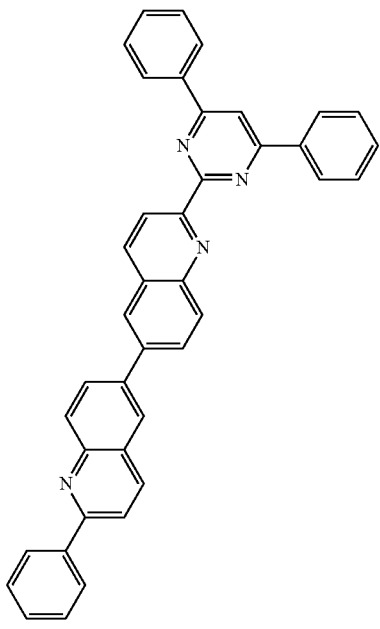

275
-continued
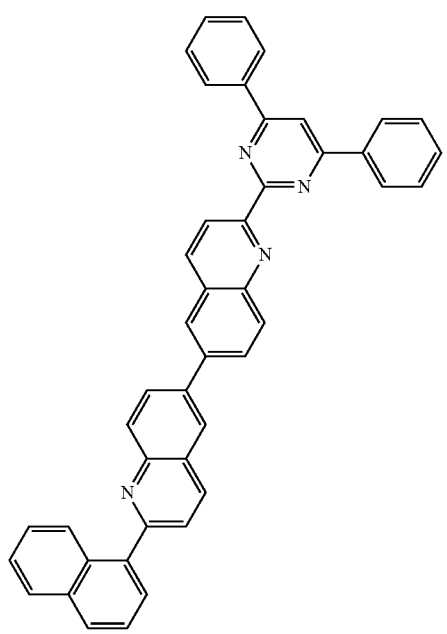
276
-continued
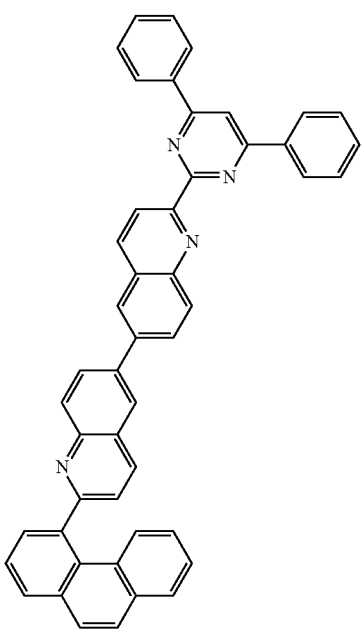

61
-continued
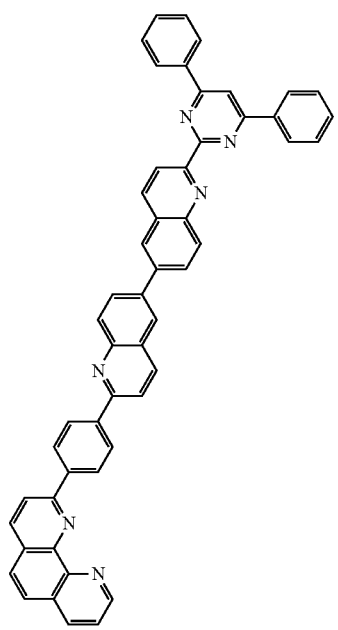
277
62
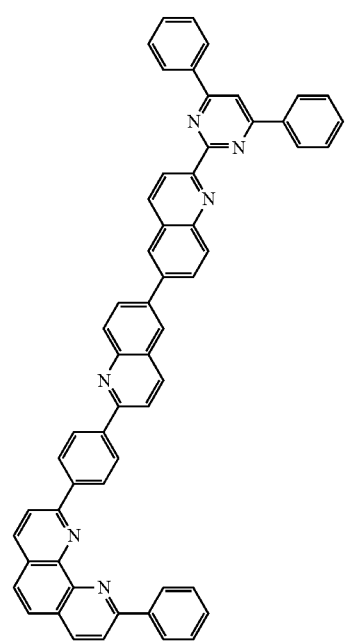
63
-continued
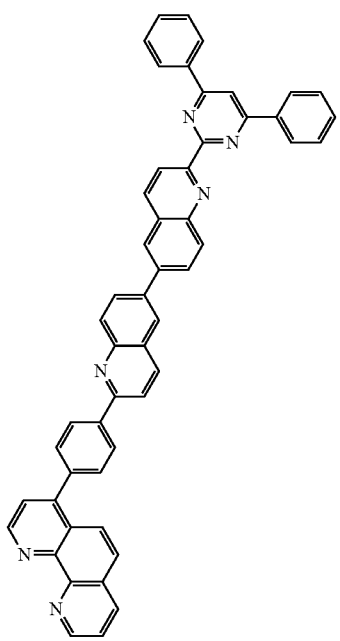
278
64
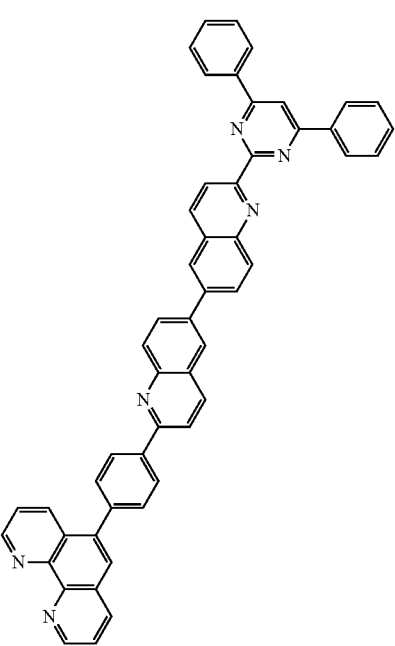

279
-continued
65
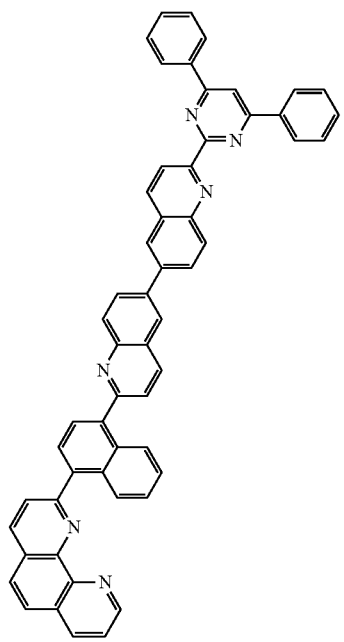
66
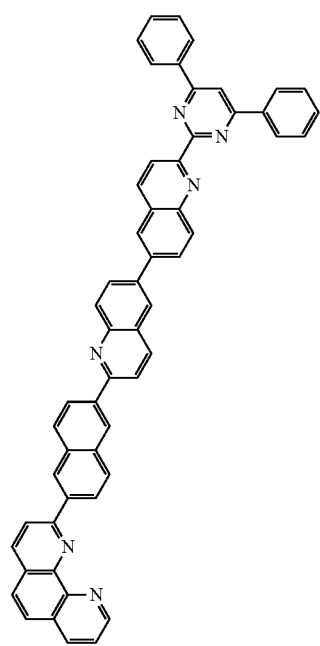
280
-continued
67
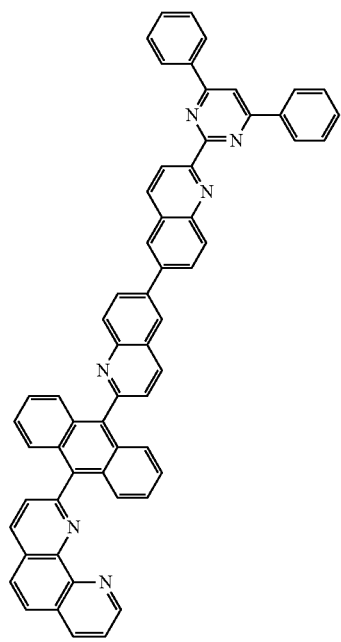
68
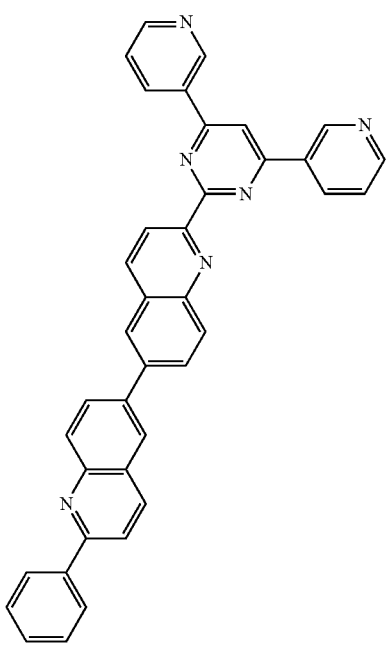

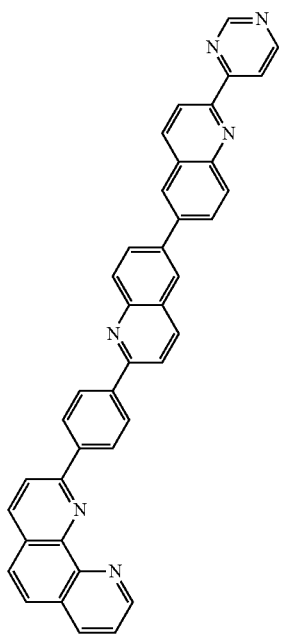
69
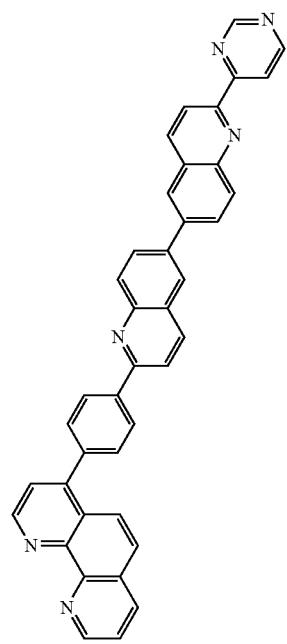
71
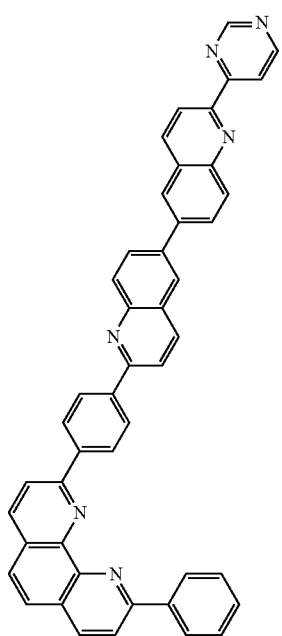
70
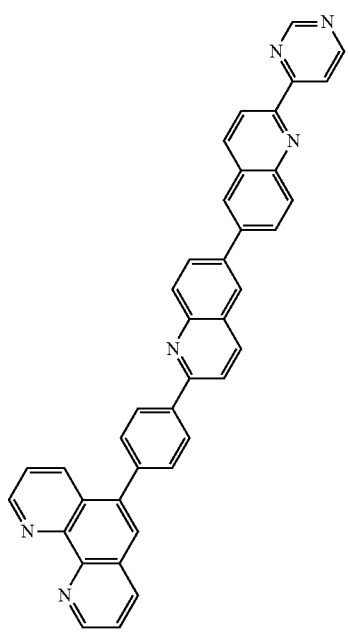
72

73
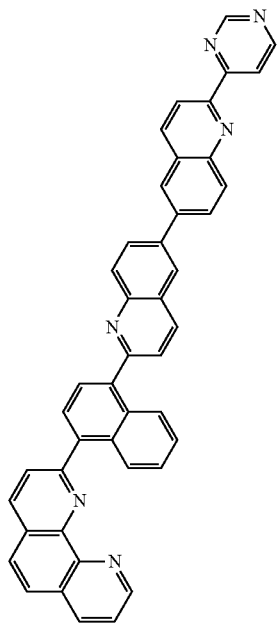
74
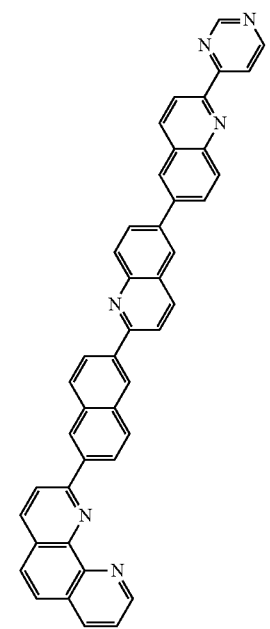
75
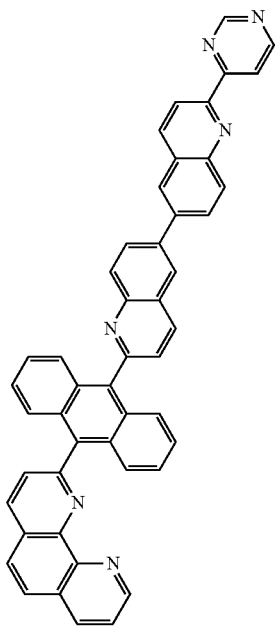
76
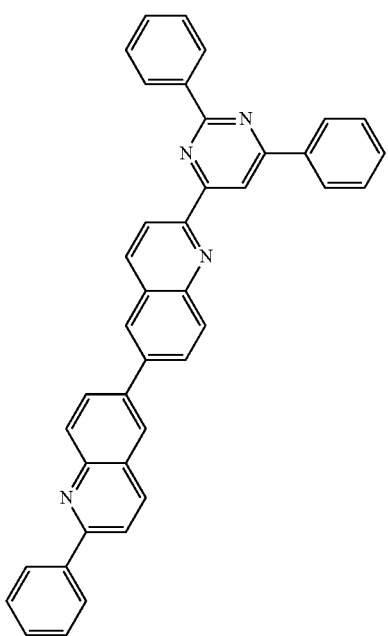

77
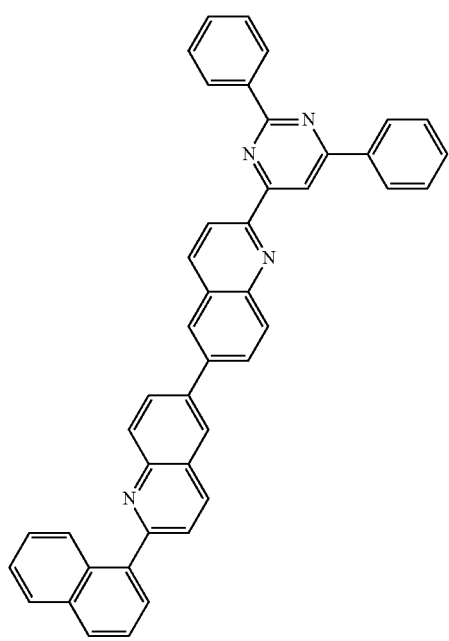
79
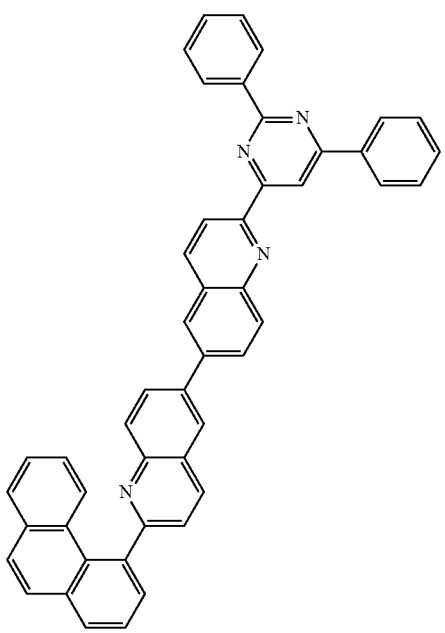
78
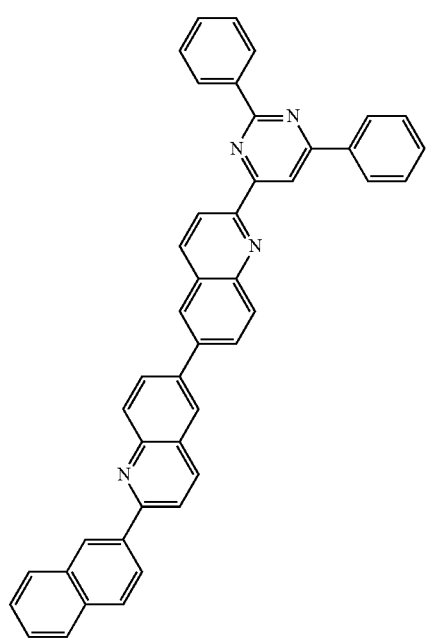
80
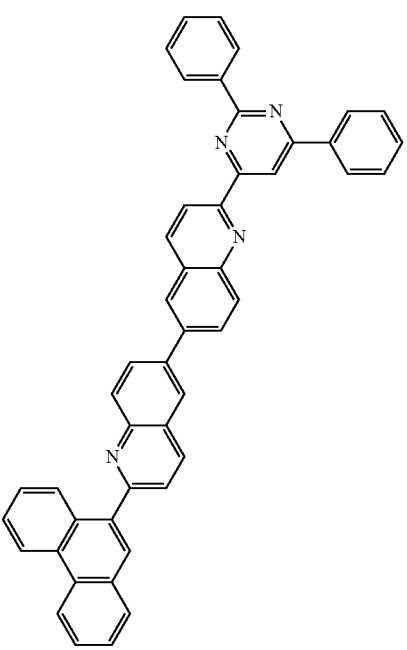

287
-continued
81
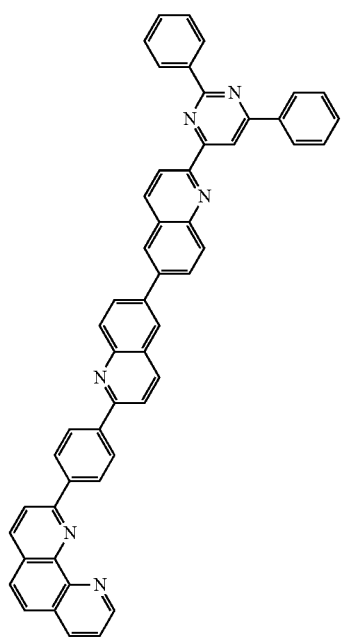
82
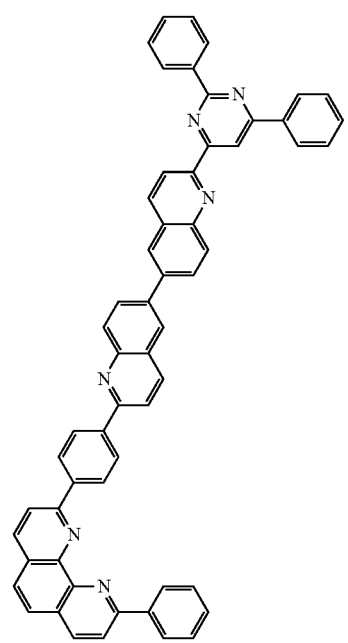
288
-continued
83
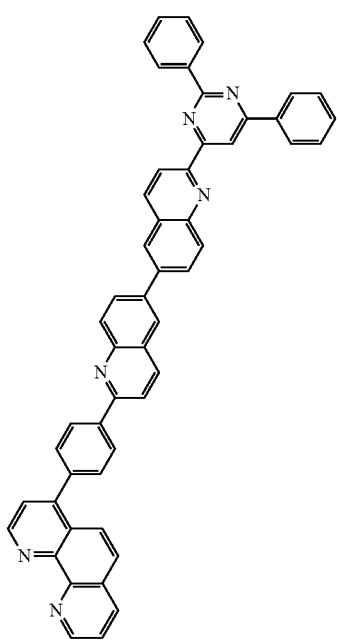
84
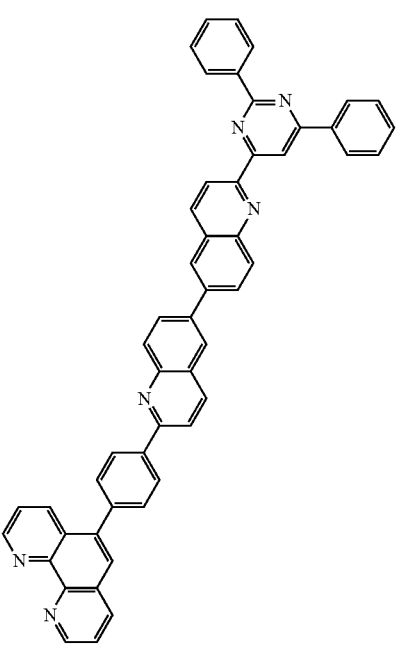

85
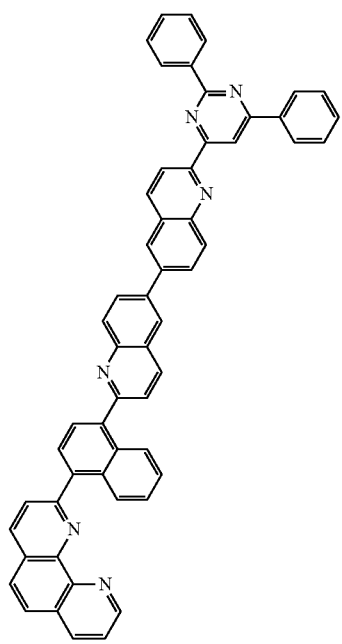
86
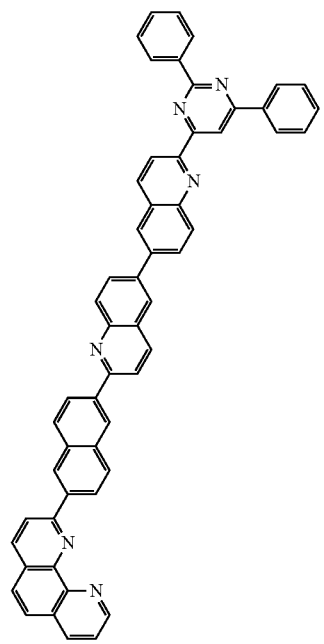
87
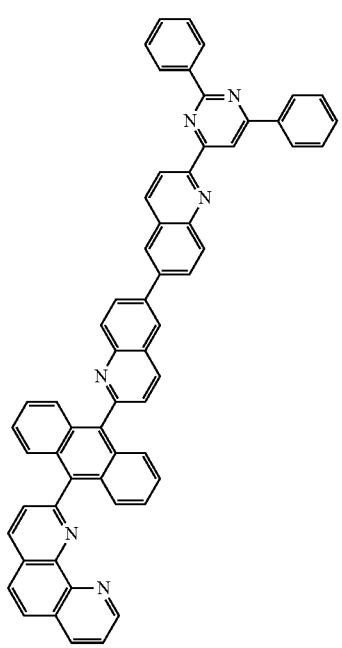
88

291
-continued
89
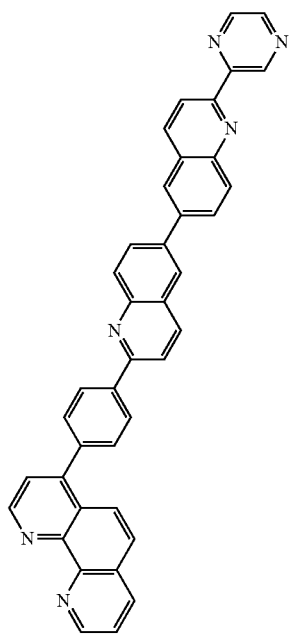
90
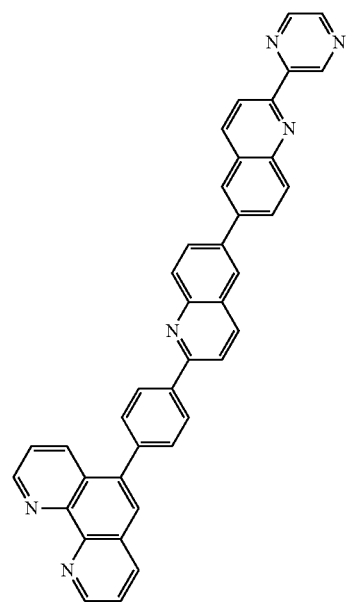
292
-continued
91
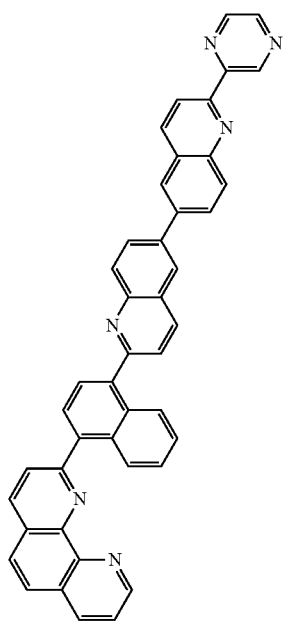
92
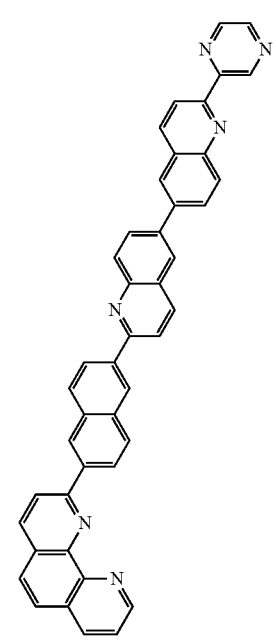

93
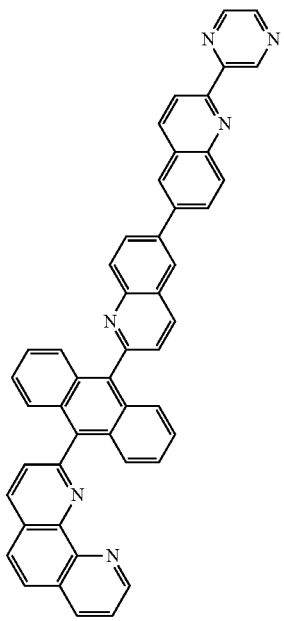
94
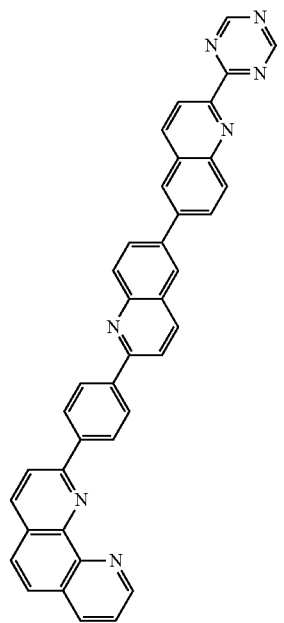
95
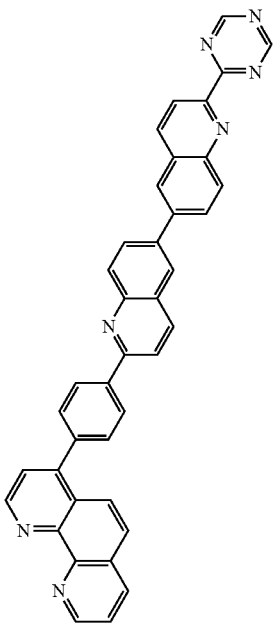
96
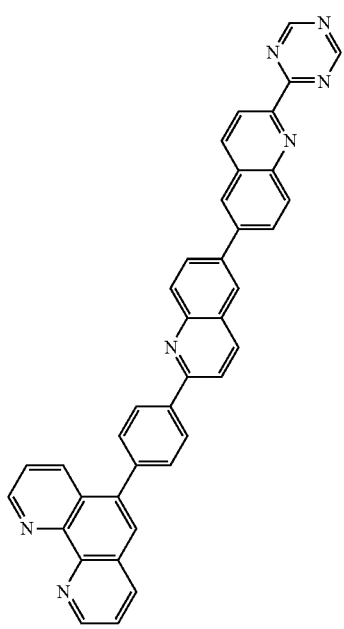

97
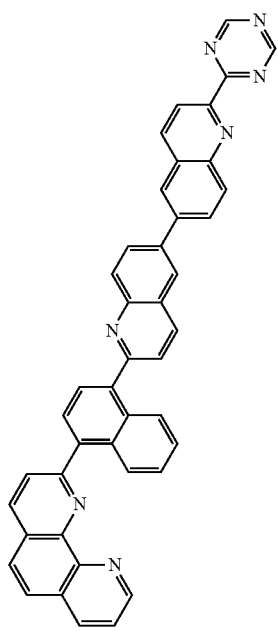
99
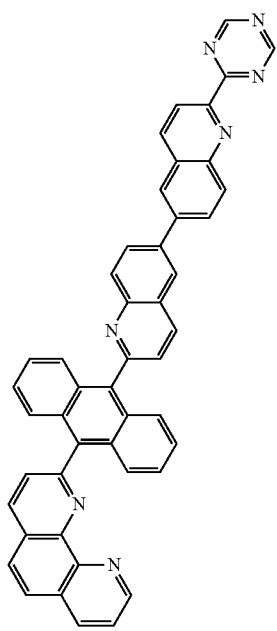
98
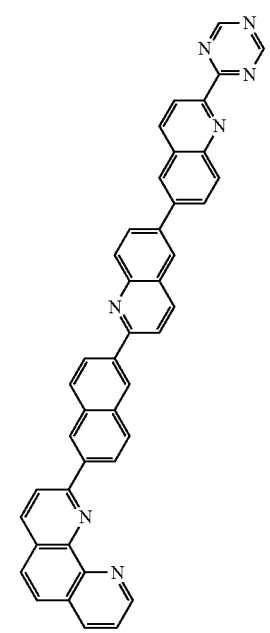
100
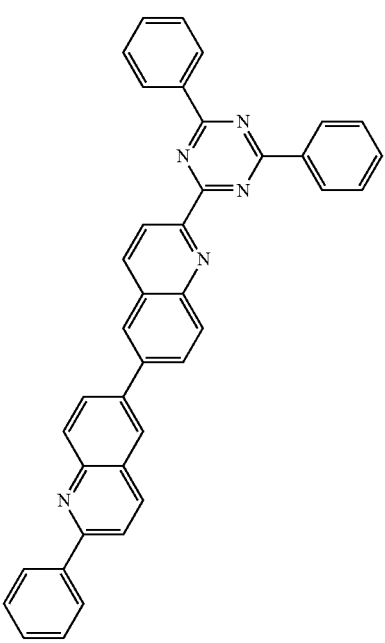

297
-continued
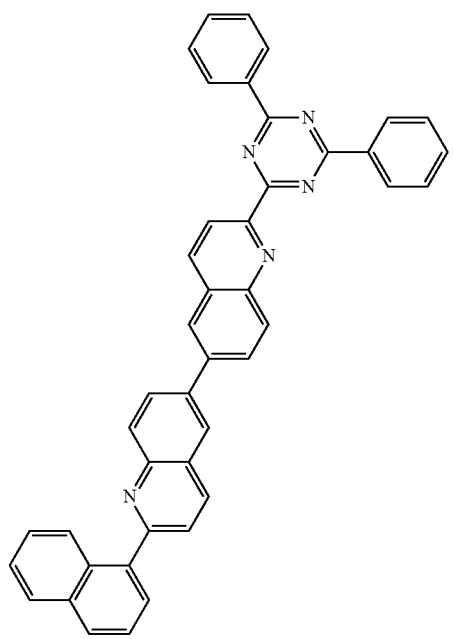
101
298
-continued
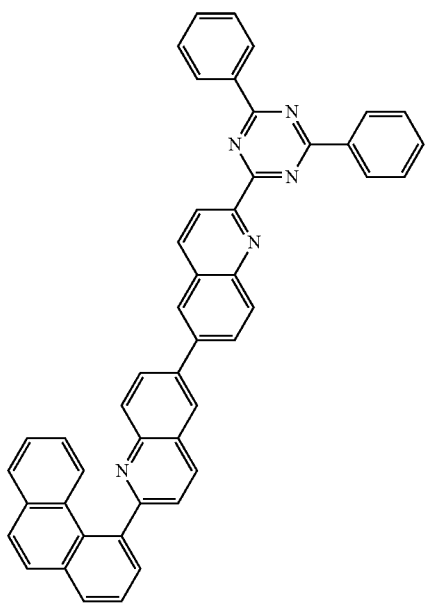
103
102
104

105
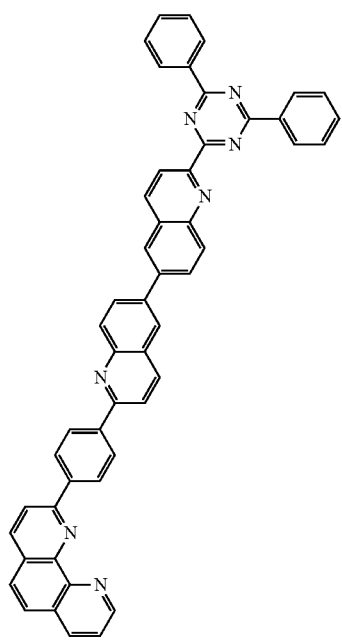
107
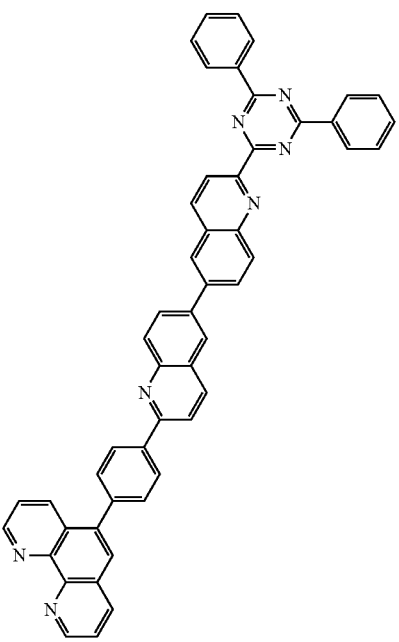
106
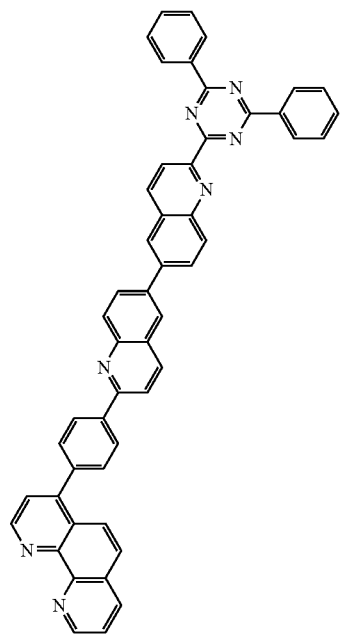
108
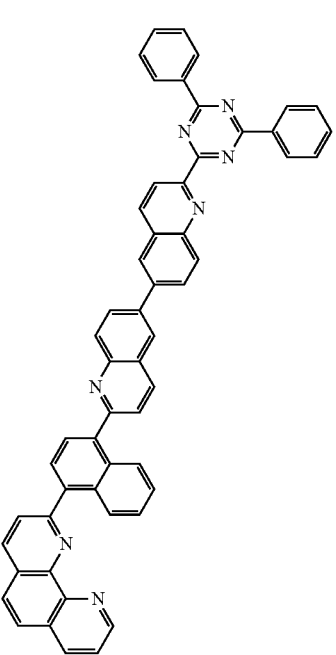

301
-continued
109
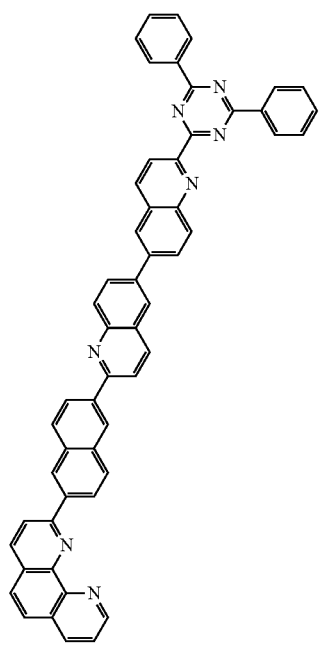
110
302
-continued
111
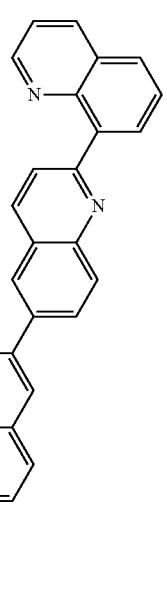
112

113
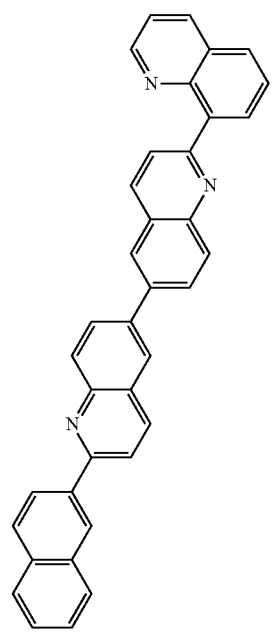
115
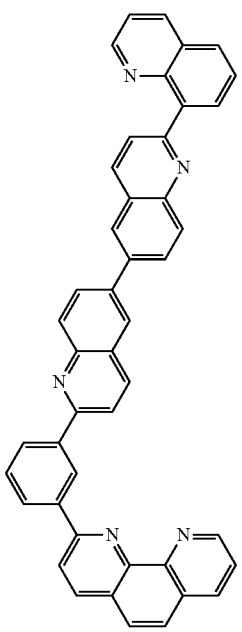
114
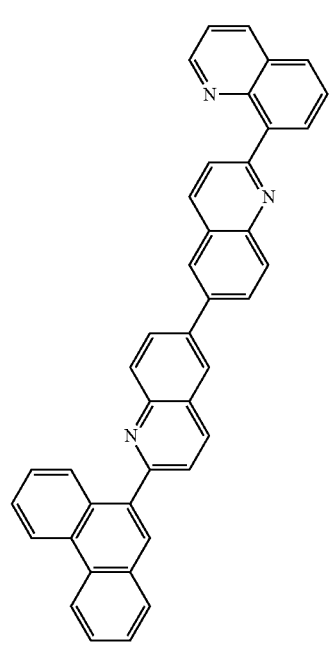
116

305
-continued
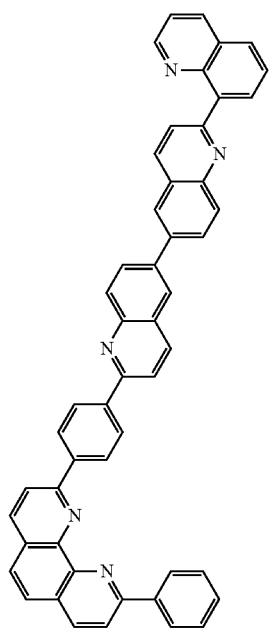
117
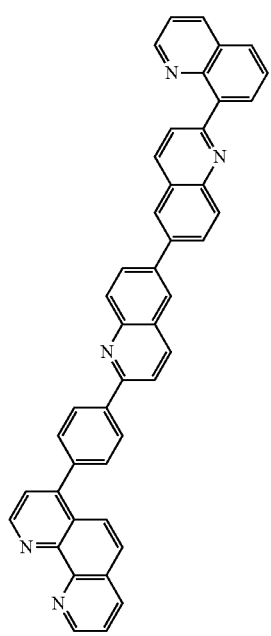
118
306
-continued
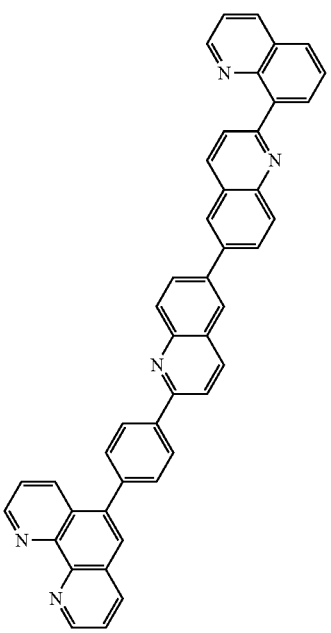
119
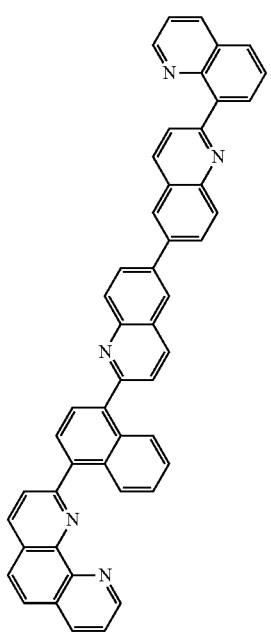
120

307
-continued
121
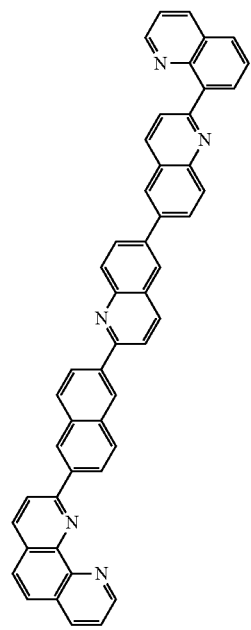
122
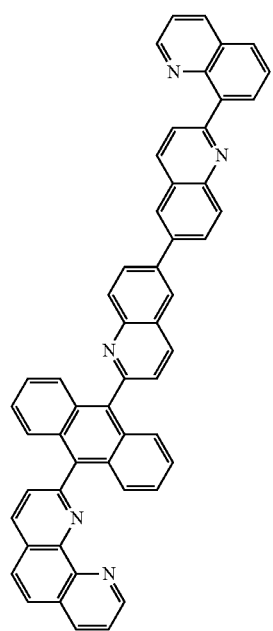
308
-continued
123
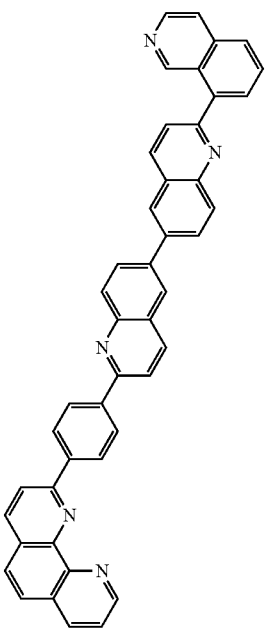
124
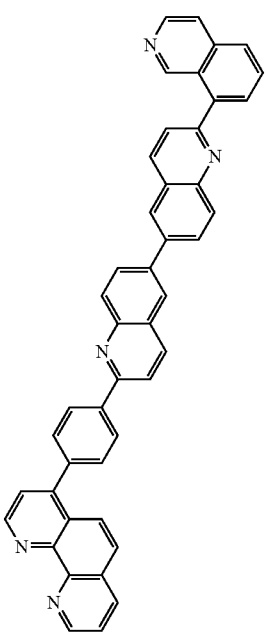

309
-continued
125
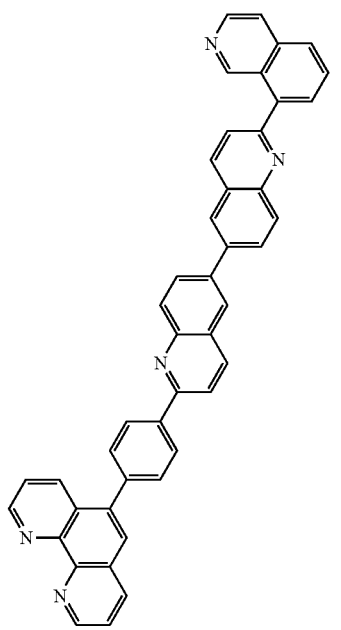
310
-continued
127
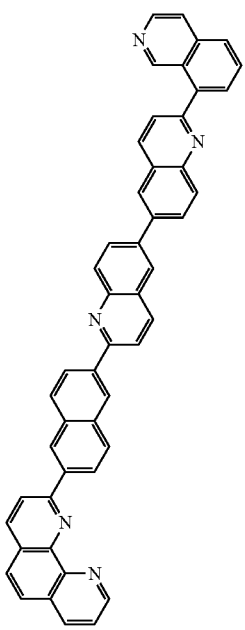
126
128
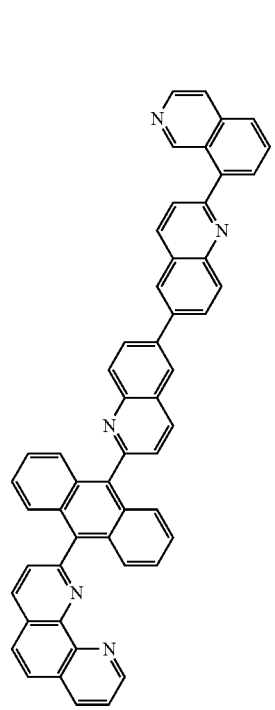

311
-continued
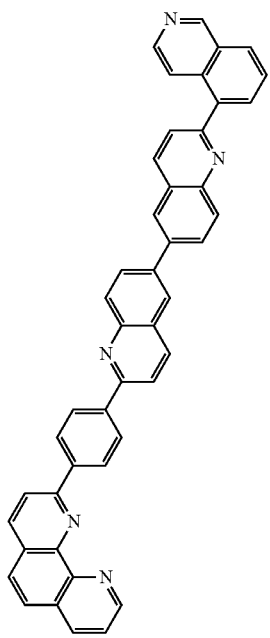
312
-continued
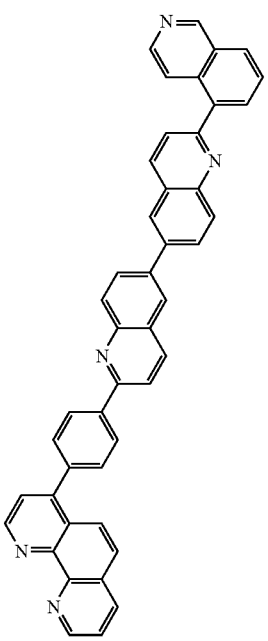
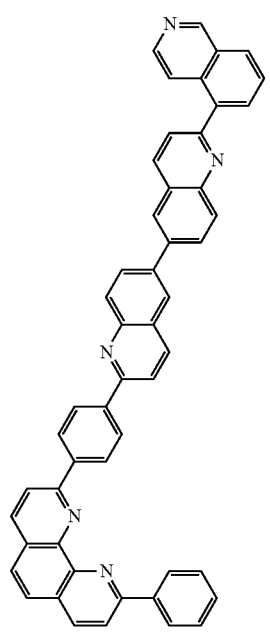
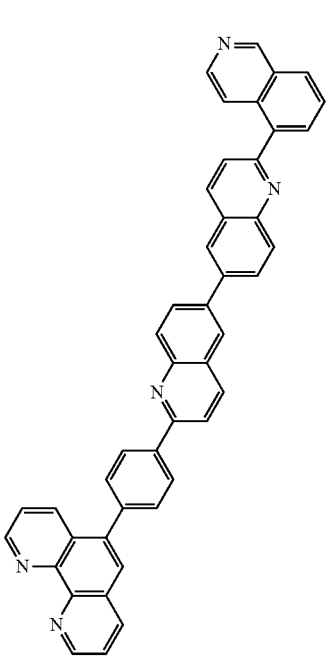

133
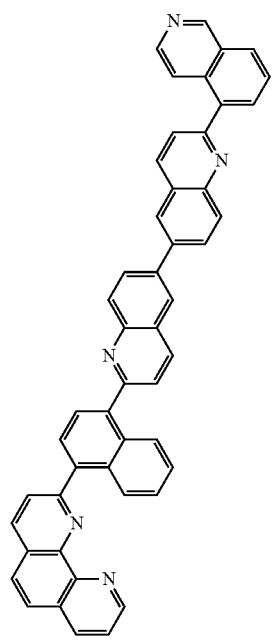
134
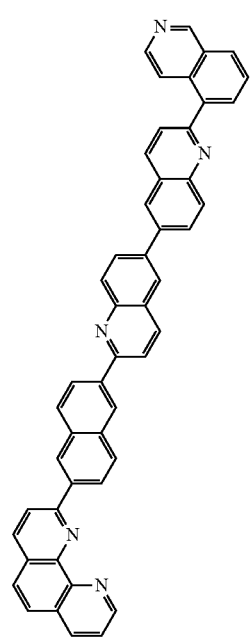
135
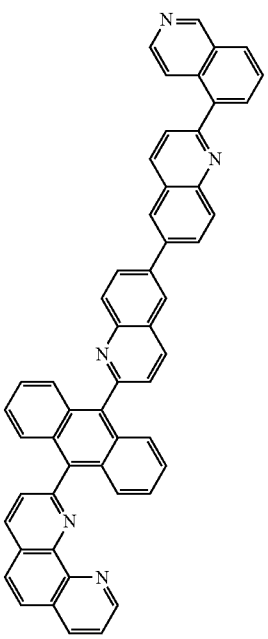
136
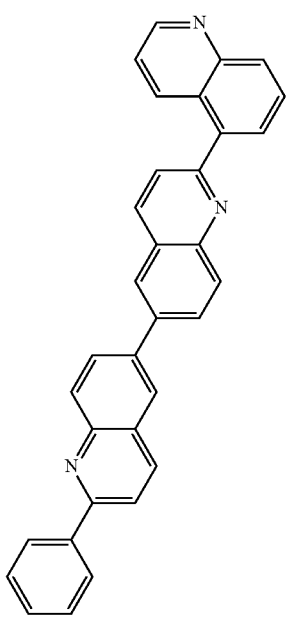

315
-continued
137
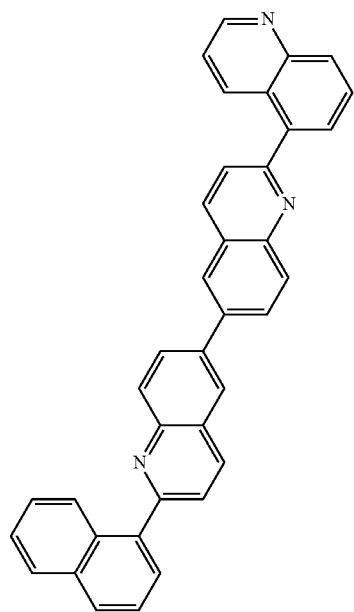
138
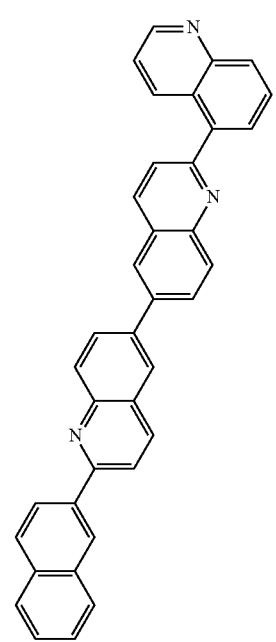
316
-continued
139
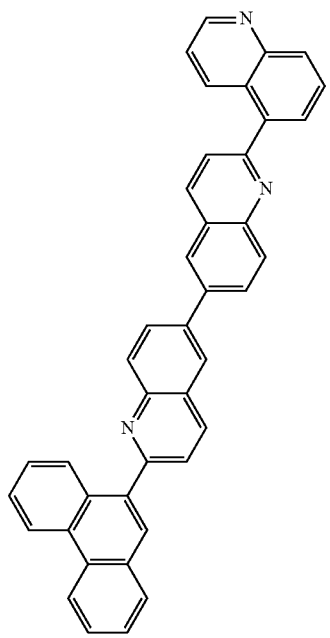
140
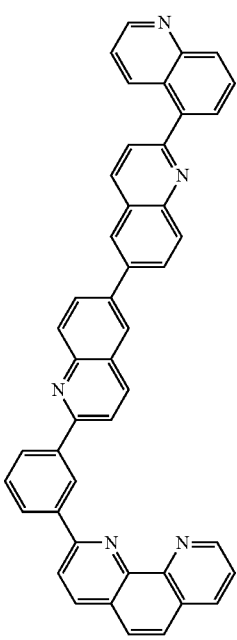

141
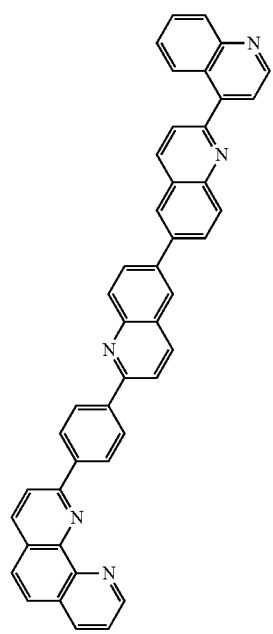
142
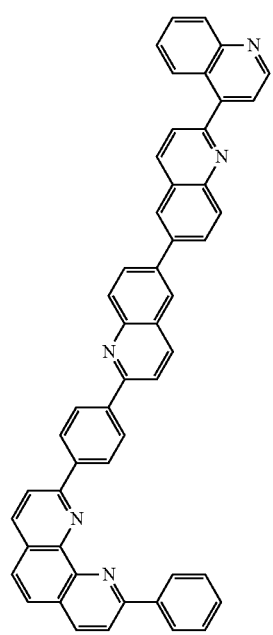
143
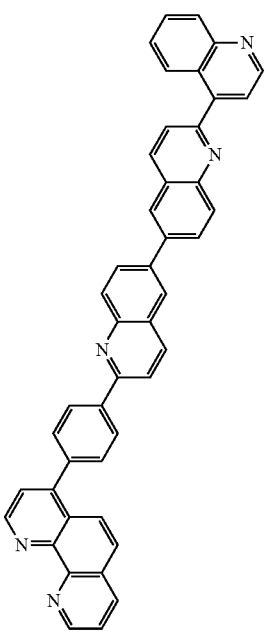
144
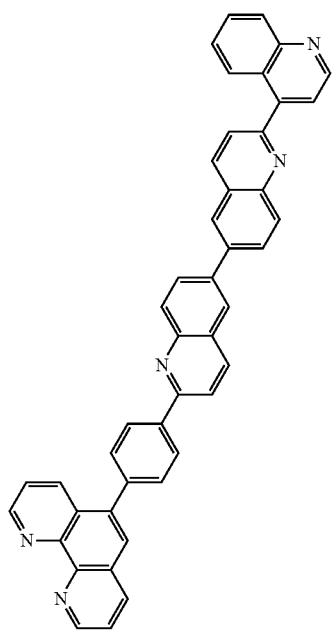

319
-continued
145
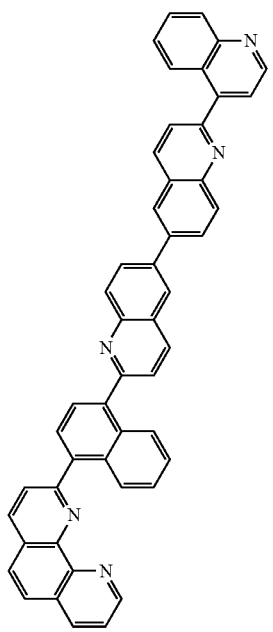
146
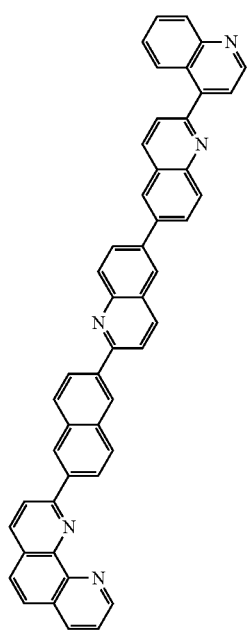
320
-continued
147
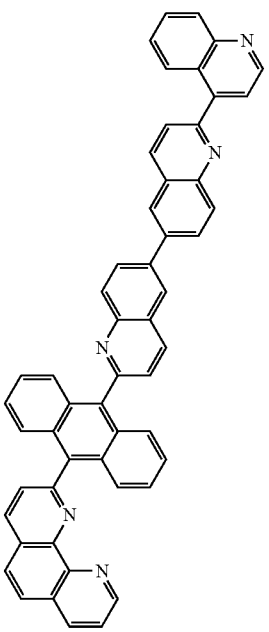
148
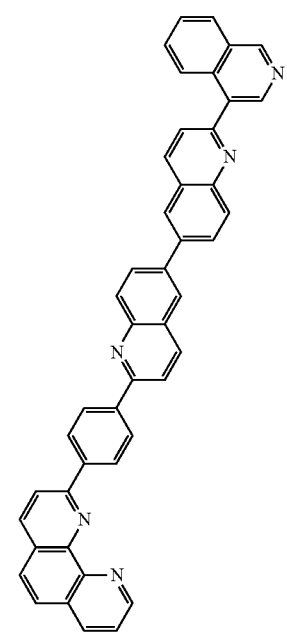

321
-continued
322
-continued
149
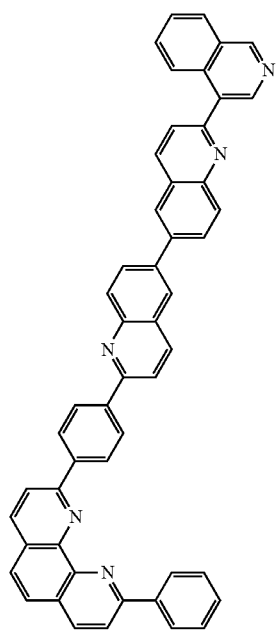
151
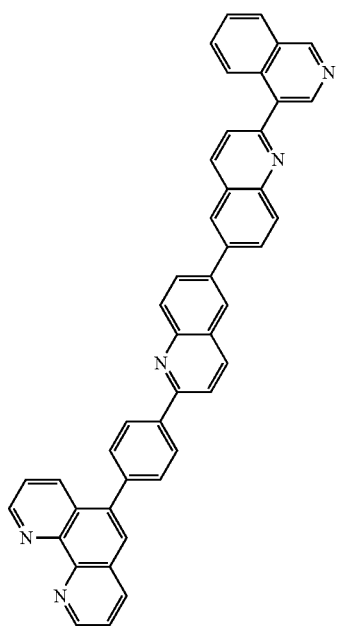
150
152
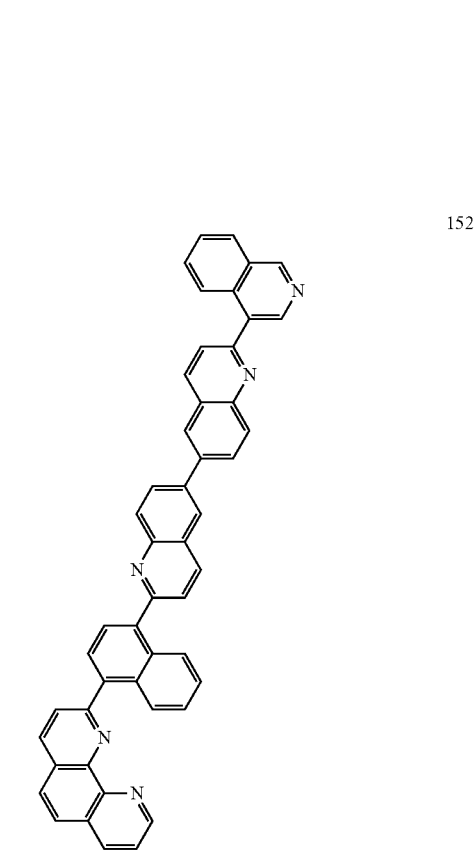

323
-continued
153
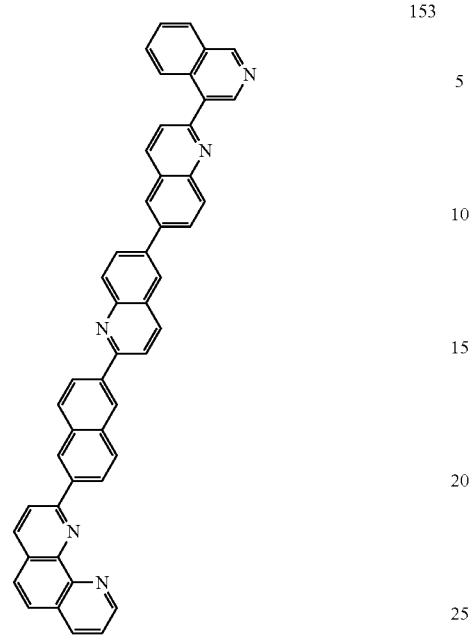
154
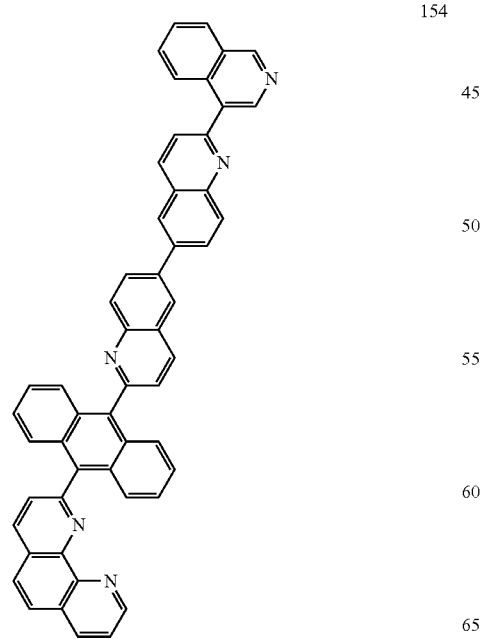
324
-continued
155
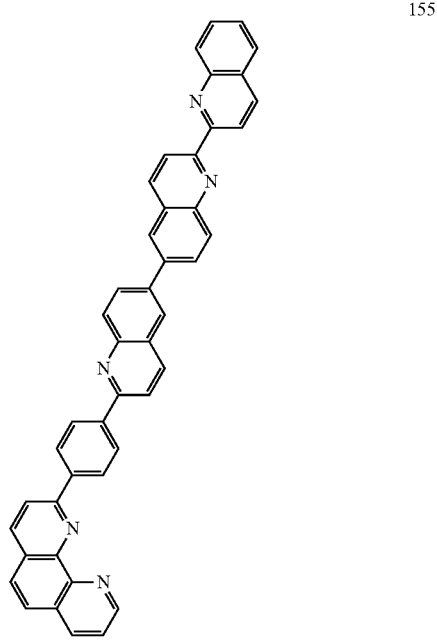
156

325
-continued
157
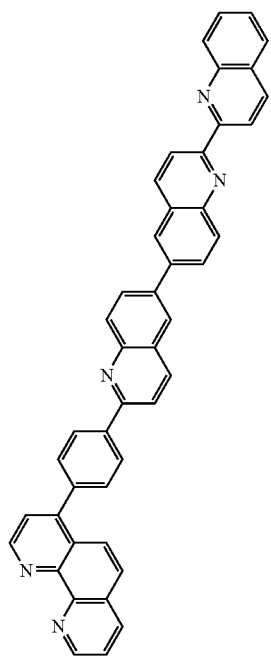
158
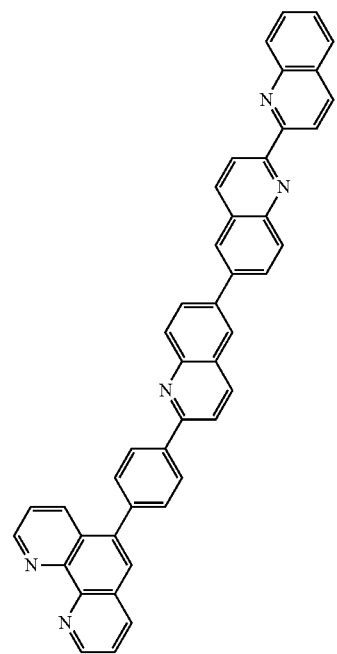
326
-continued
159
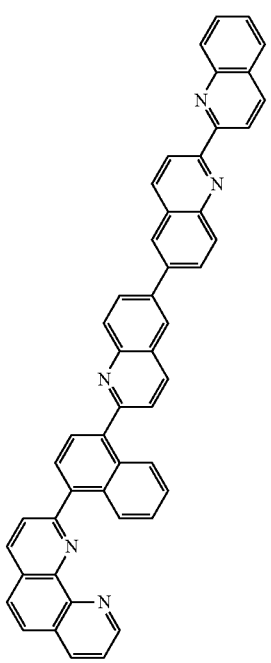
160
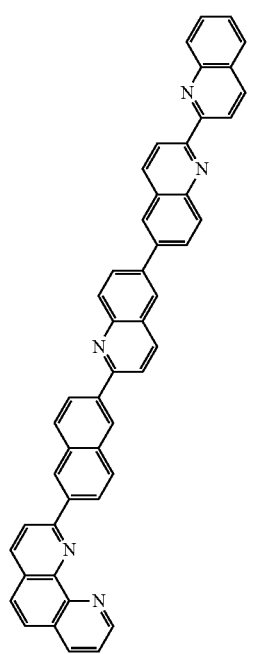

327
-continued
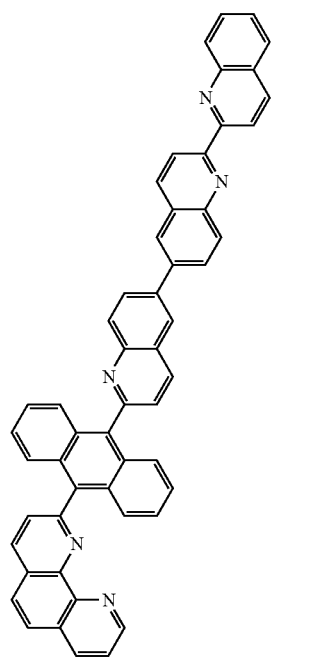
161
328
-continued
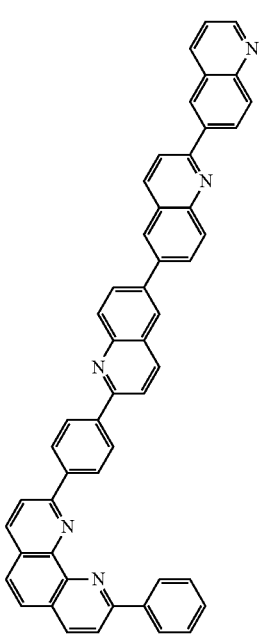
163
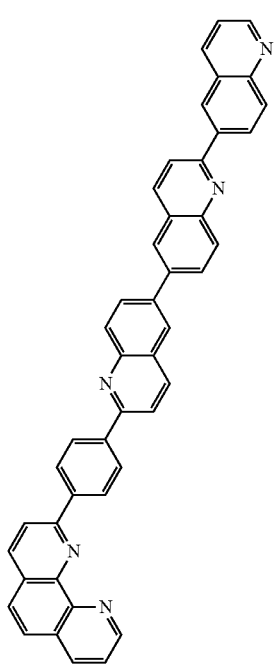
162
164

165
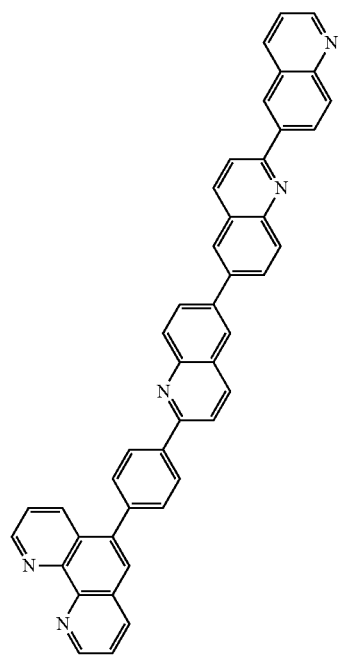
166
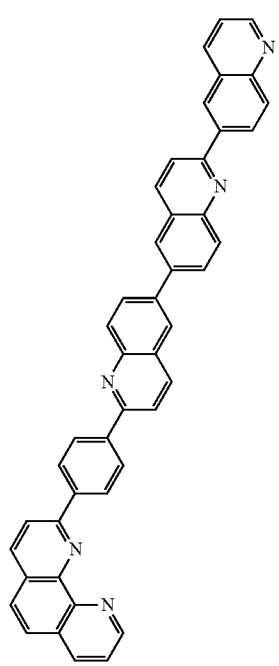
167
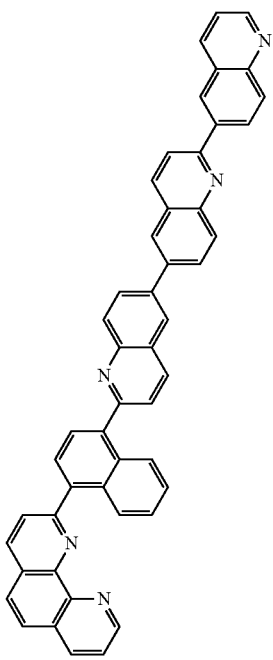
168
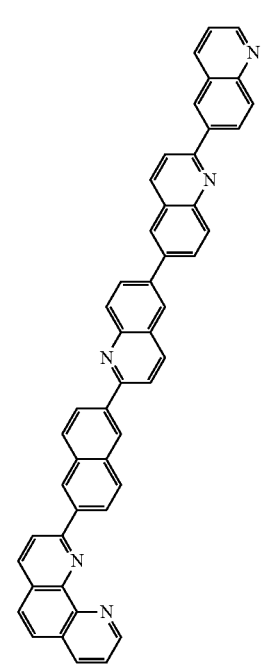

331
-continued
169
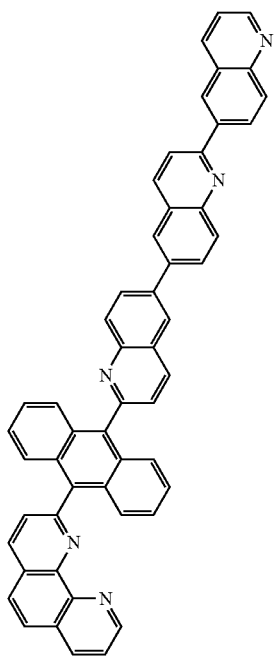
170
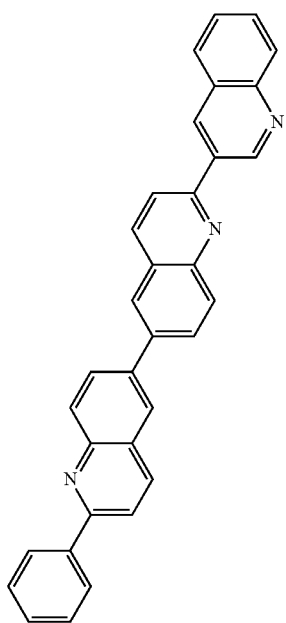
332
-continued
171
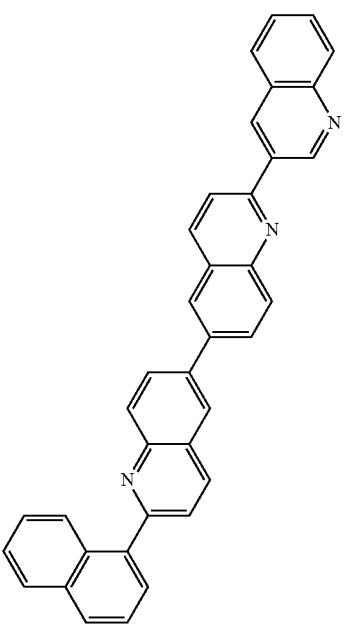
172
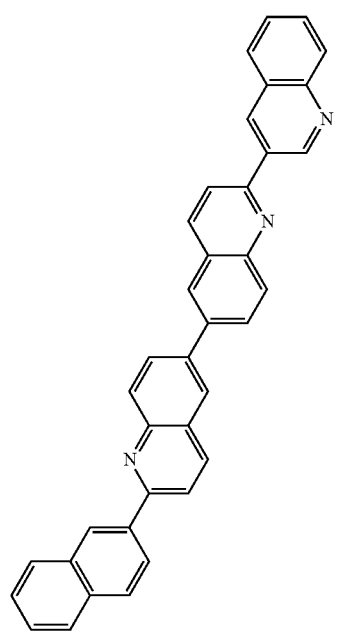

333
-continued
173
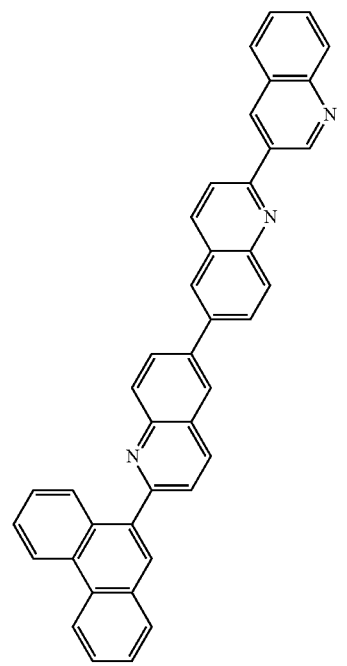
174
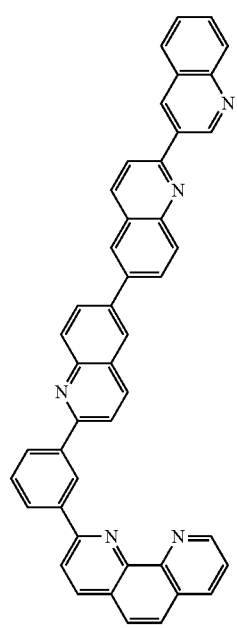
334
-continued
175
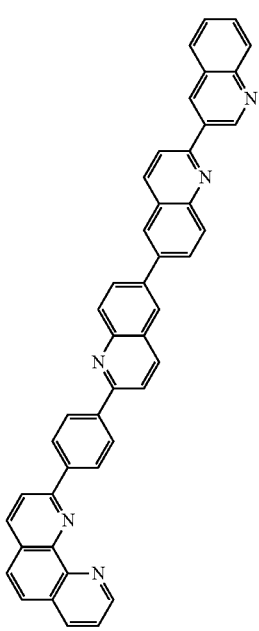
176
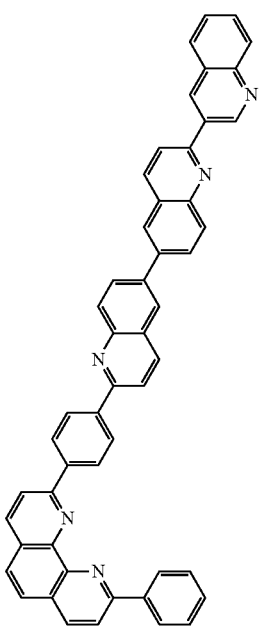

335 336
-continued -continued
177 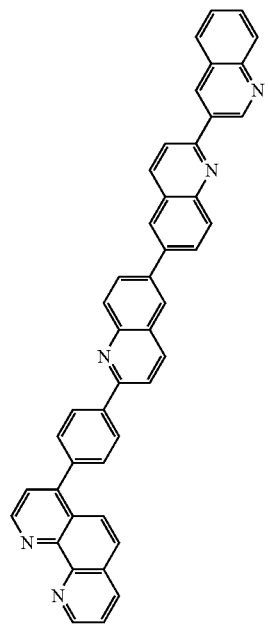 179 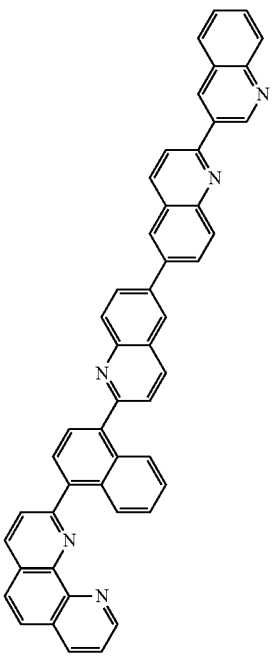
178 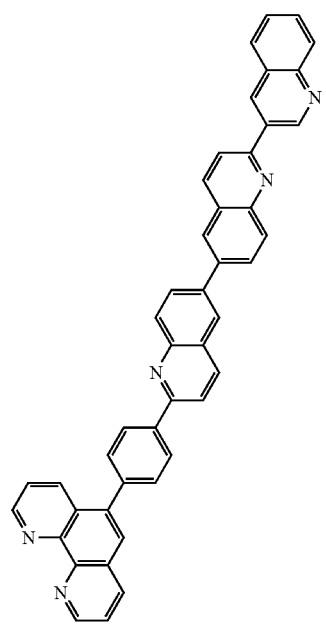 180

181
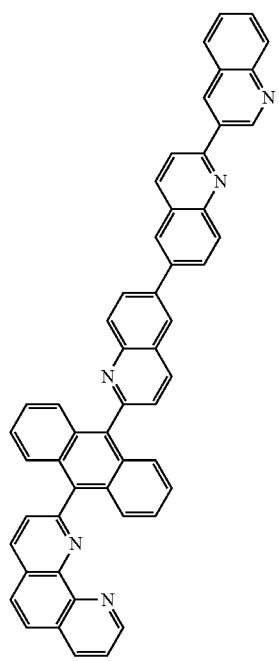
182
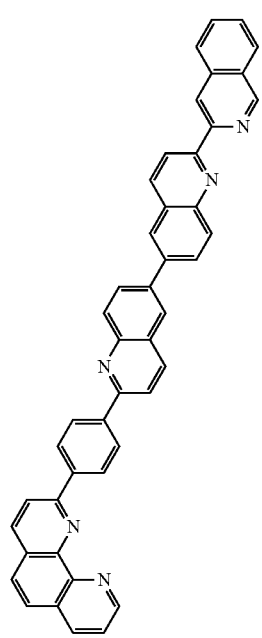
183
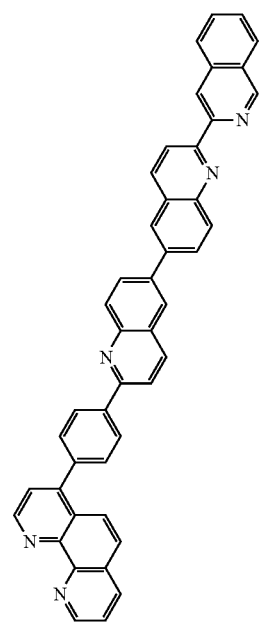
184
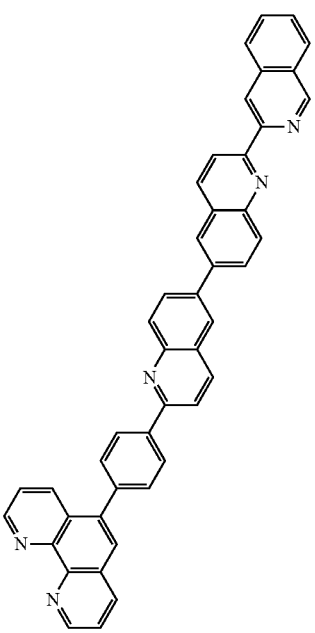

185
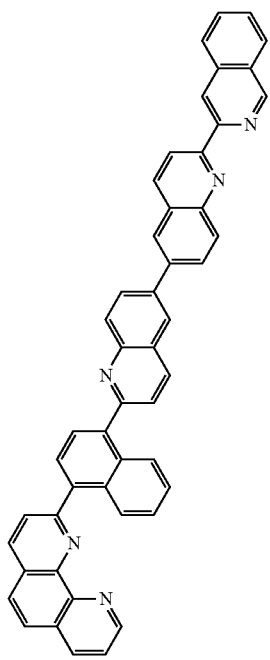
187
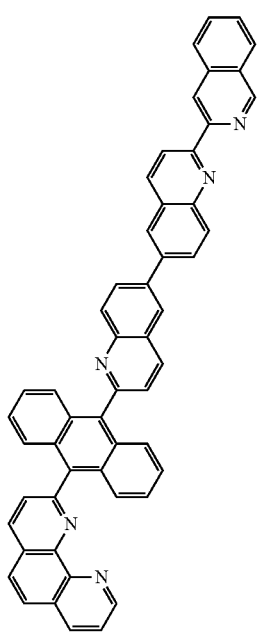
186
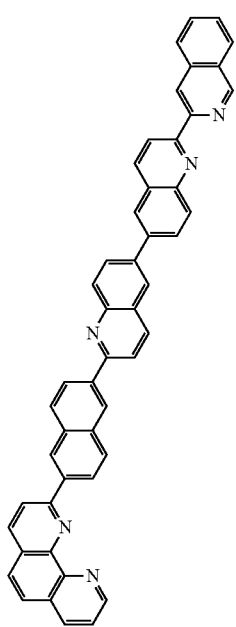
188
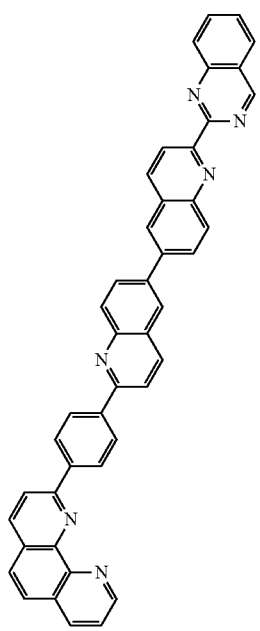

189
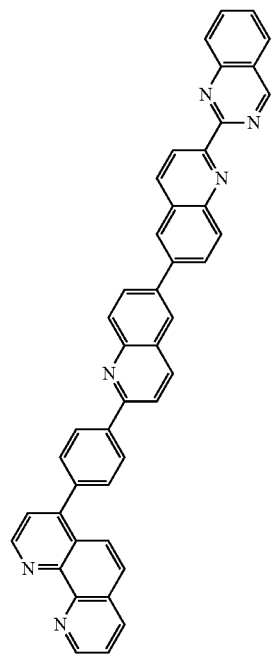
190
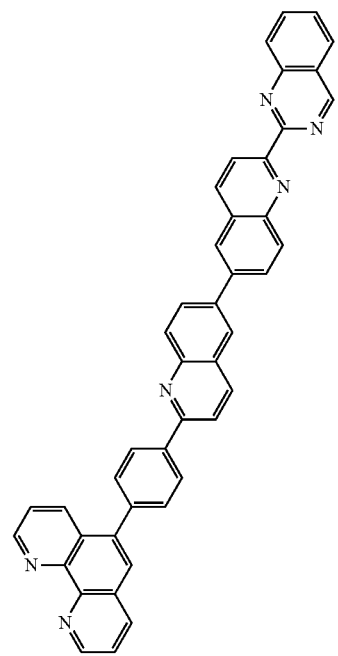
191
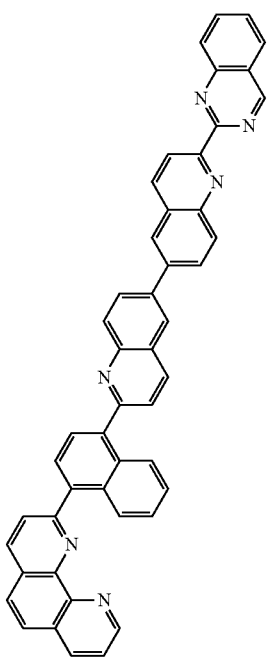
192
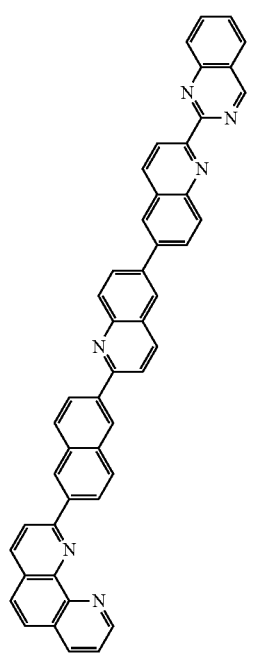

193
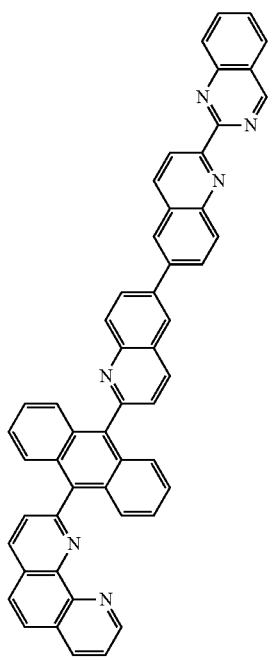
194
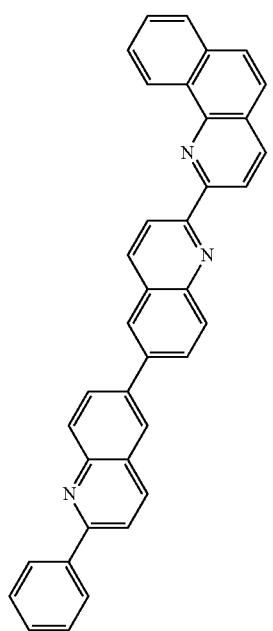
195
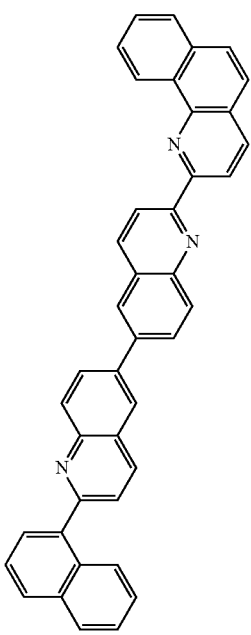
196
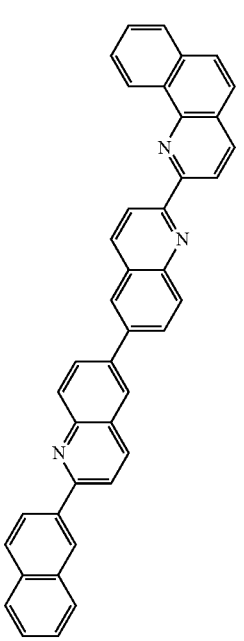

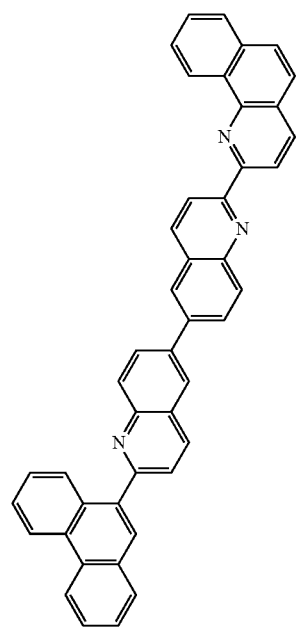
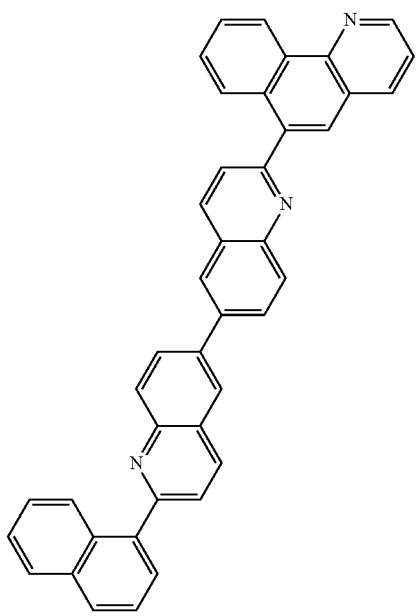

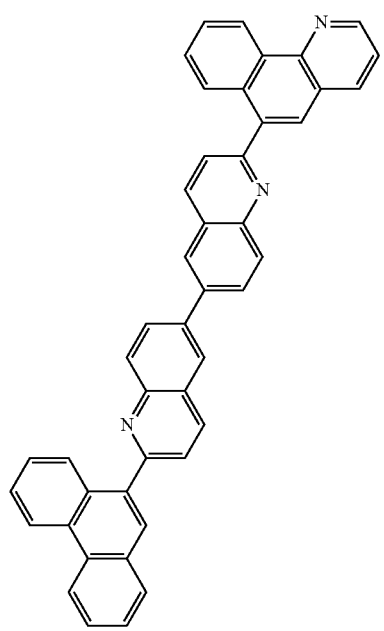
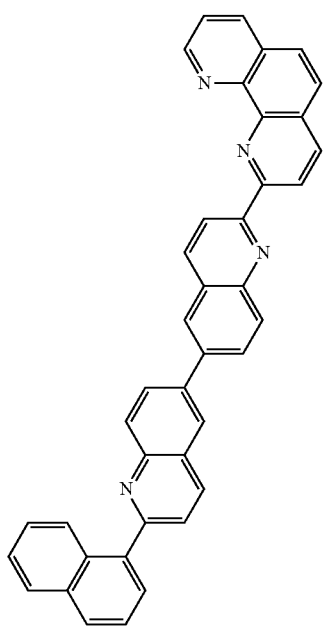
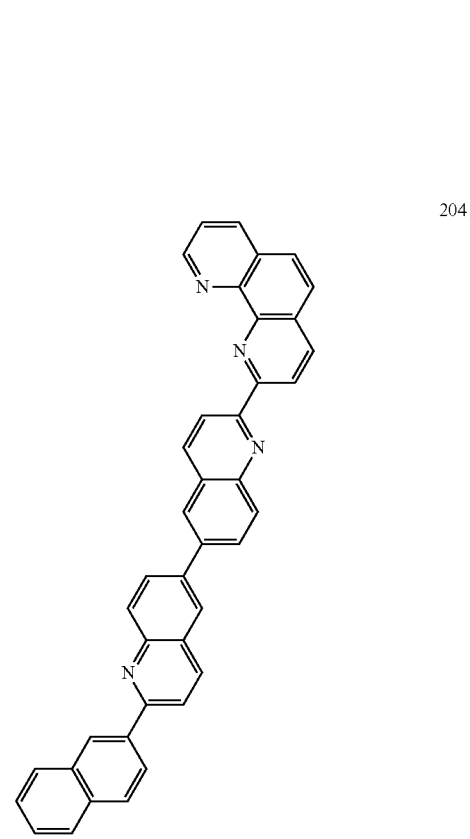

349
-continued
205
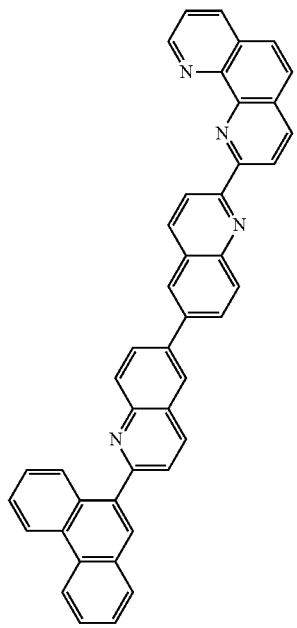
206
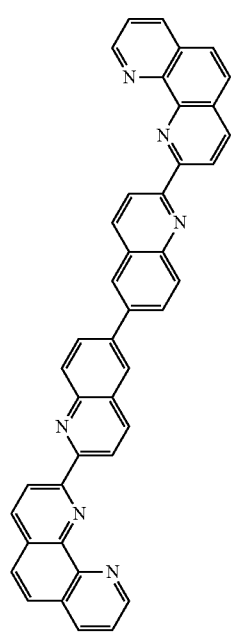
350
-continued
207
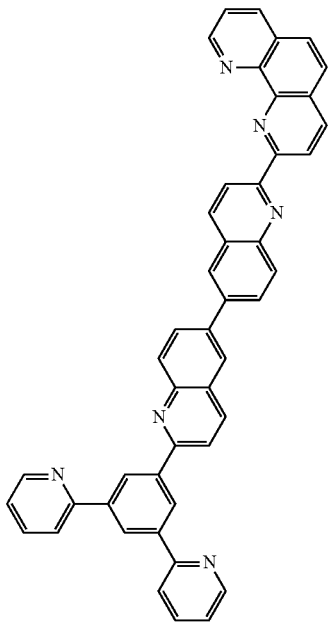
208
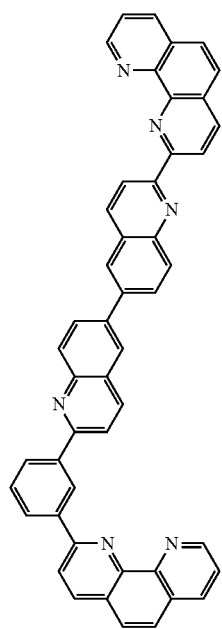

351
-continued
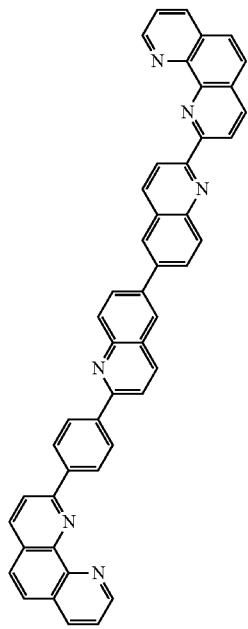
209
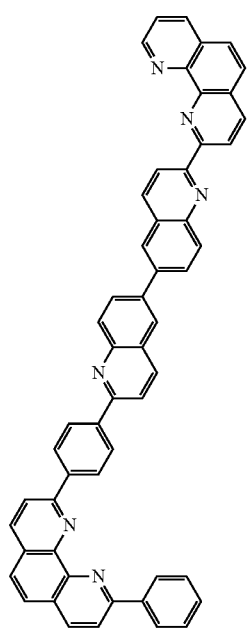
210
352
-continued
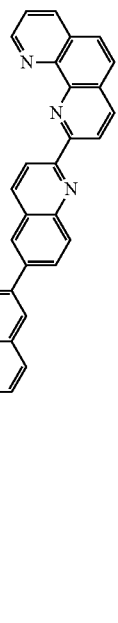
211
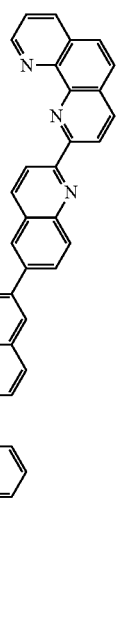
212

213
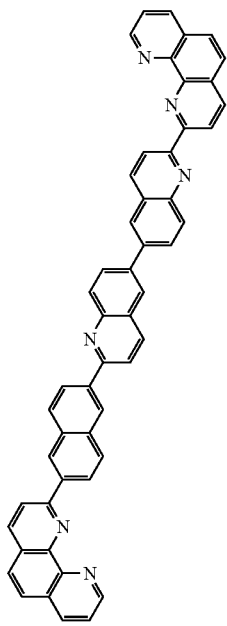
214
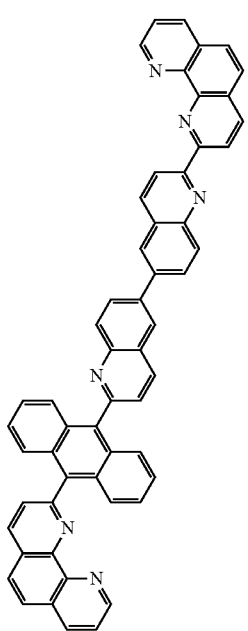
215
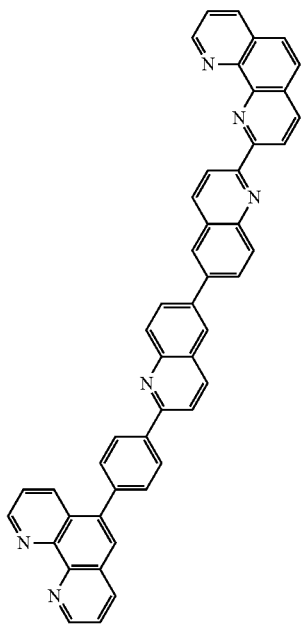
216
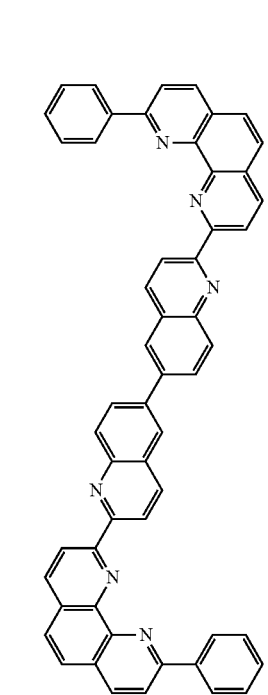

355
-continued
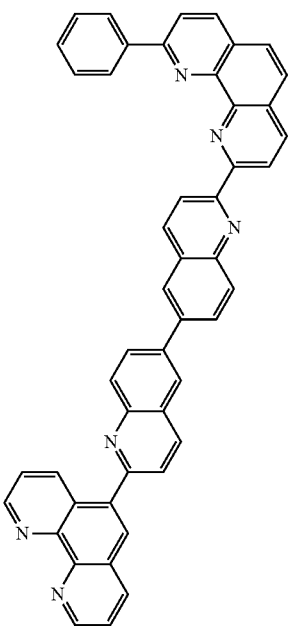
217
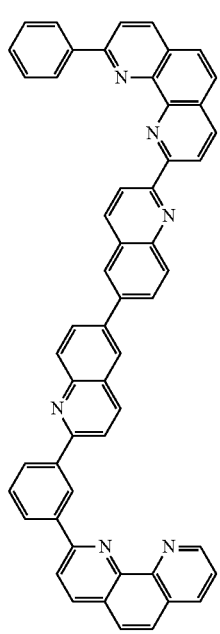
218
356
-continued
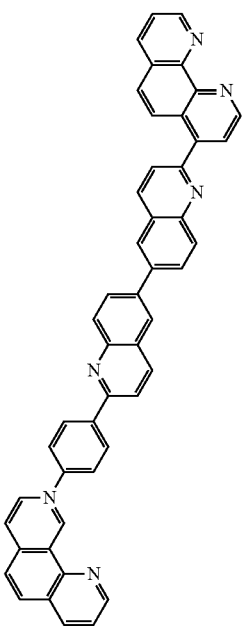
219
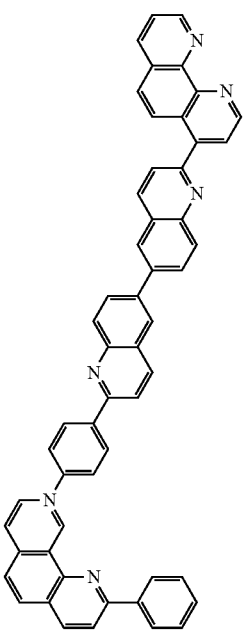
220

357
-continued
358
-continued
221
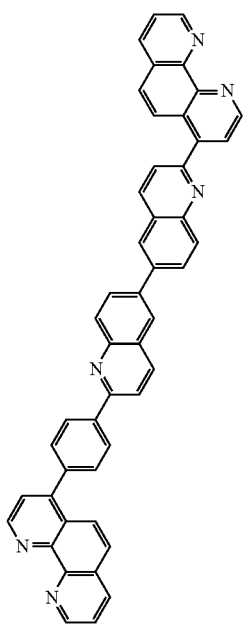
223
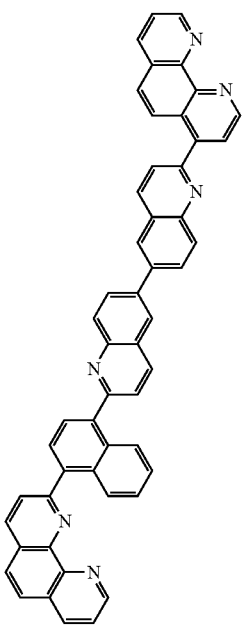
222
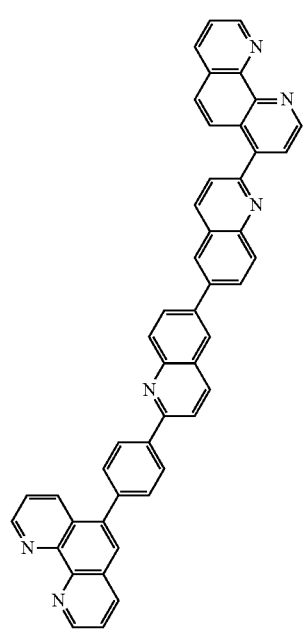
224
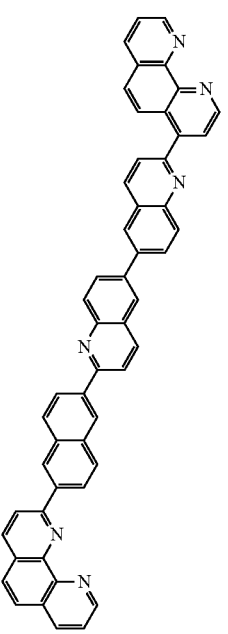

359
-continued
225
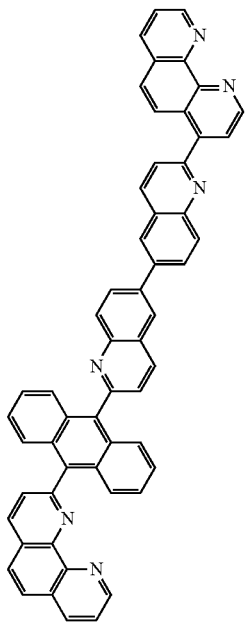
226
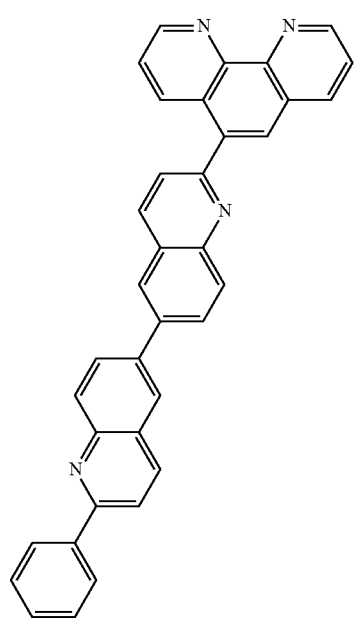
360
-continued
227
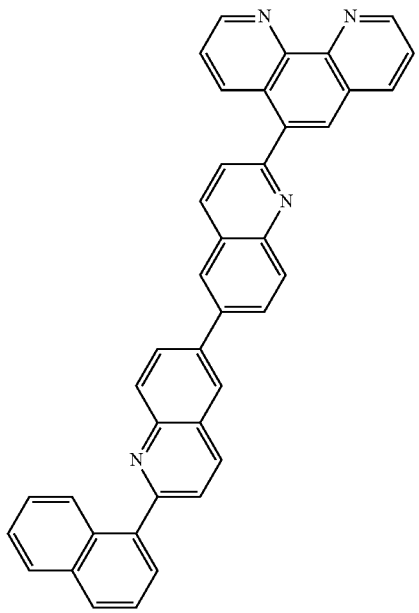
228
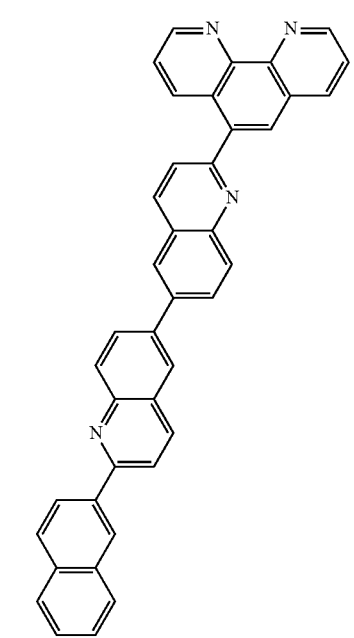

361
-continued
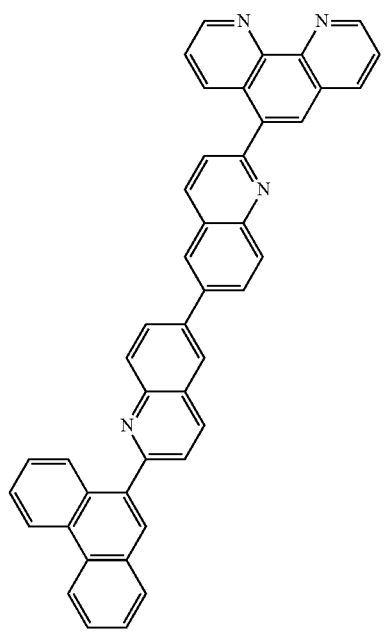
229
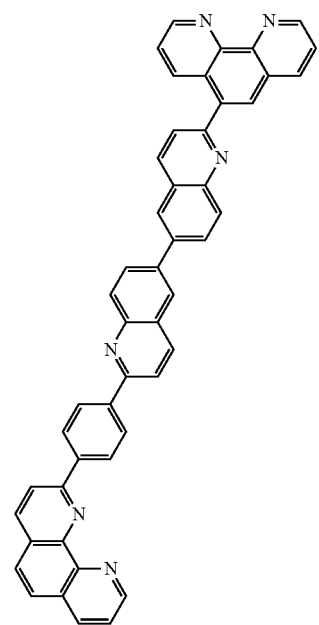
230
362
-continued
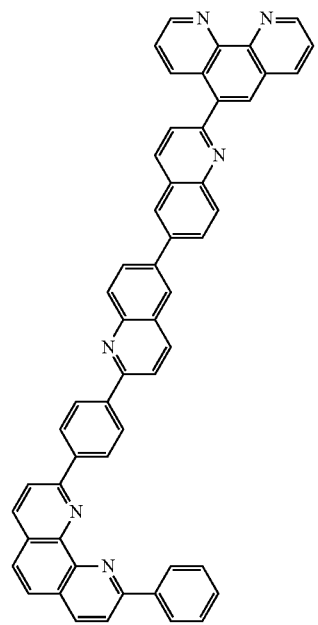
231
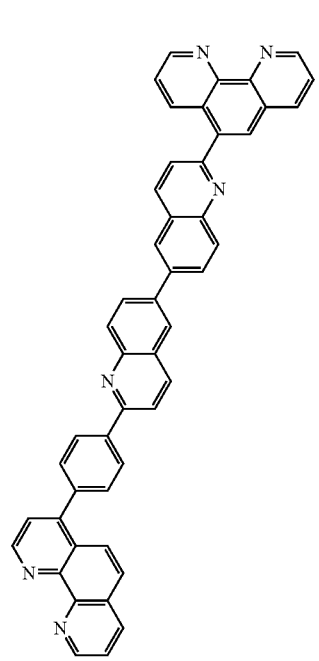
232

363
-continued
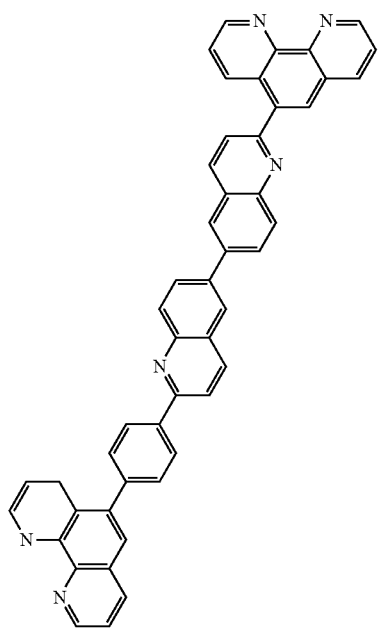
233
364
-continued
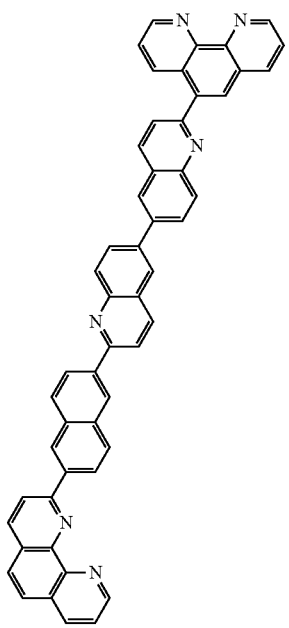
235
234
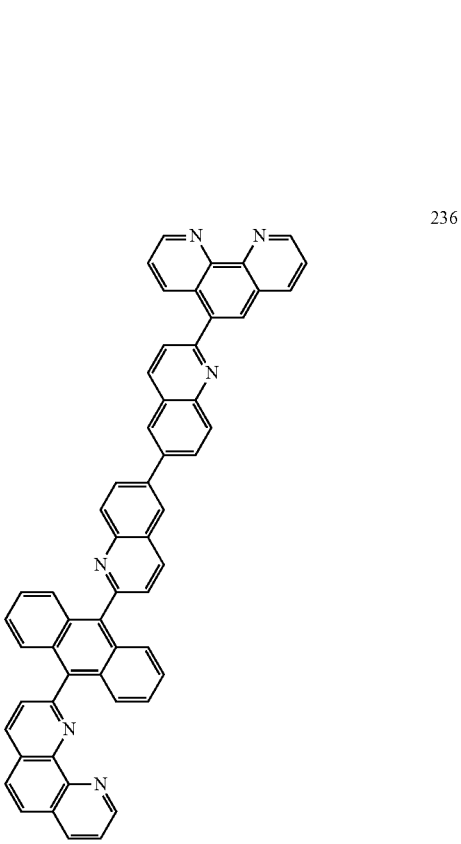
236

365
-continued
366
-continued
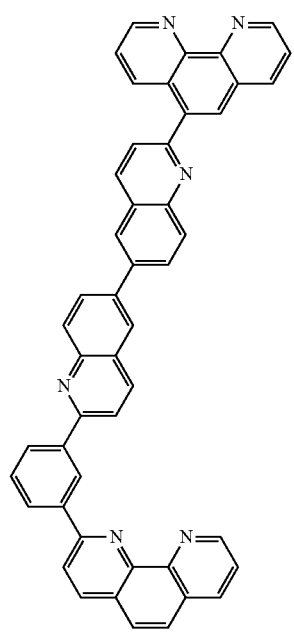
237
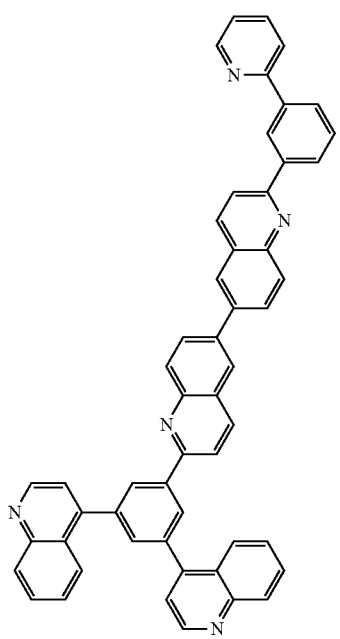
239
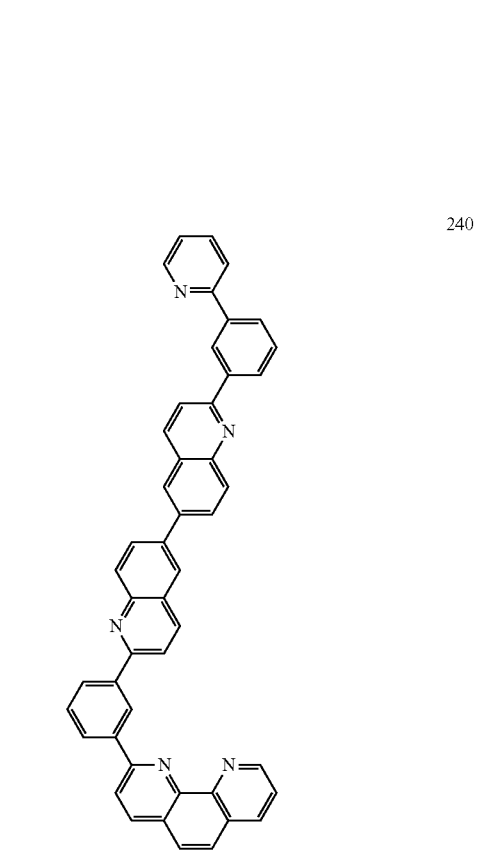
238 240

241
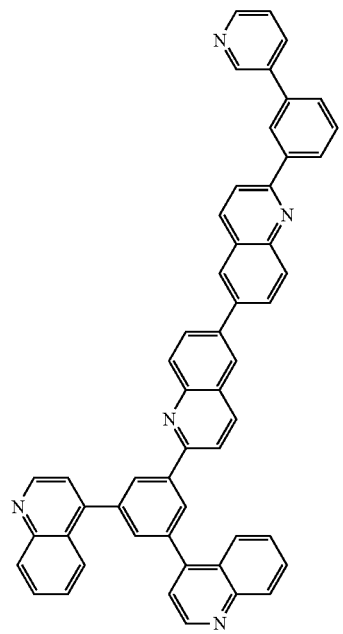
242
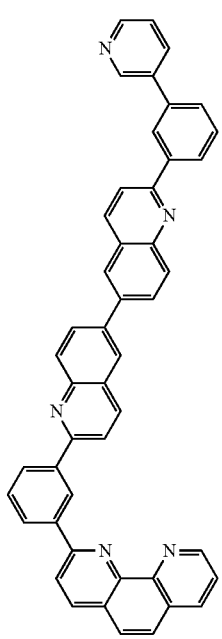
243
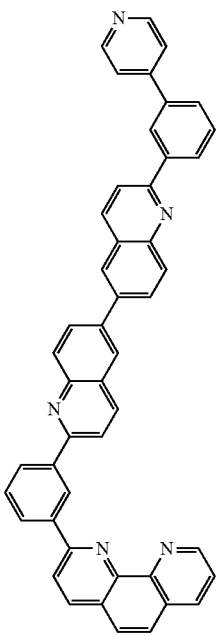
244
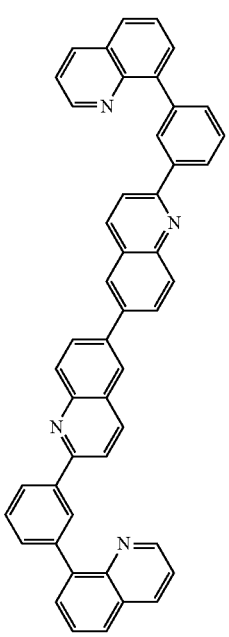

369
-continued
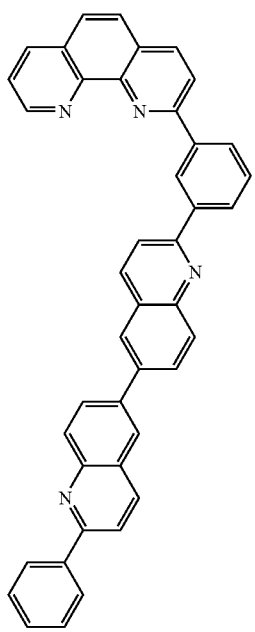
245
370
-continued
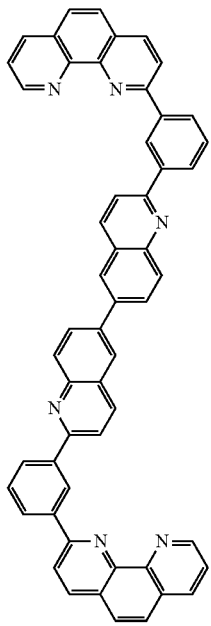
247
246
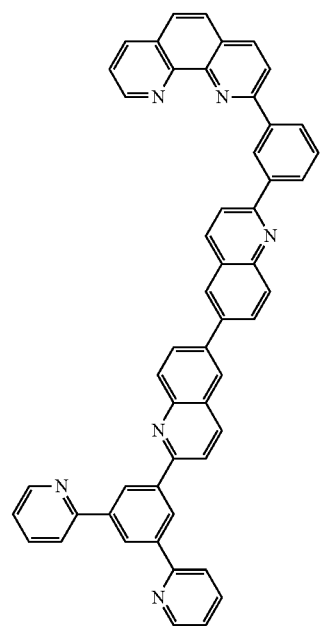
248
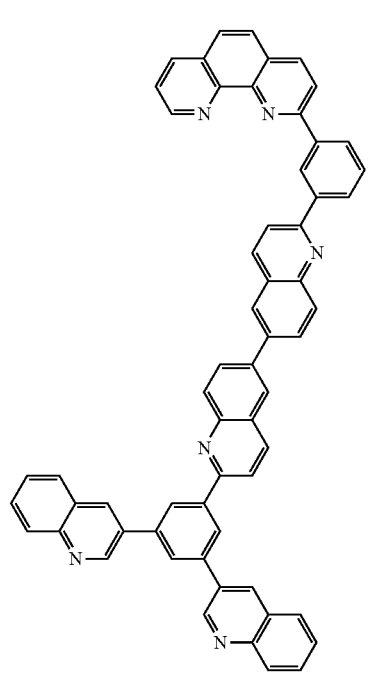

371
-continued
249
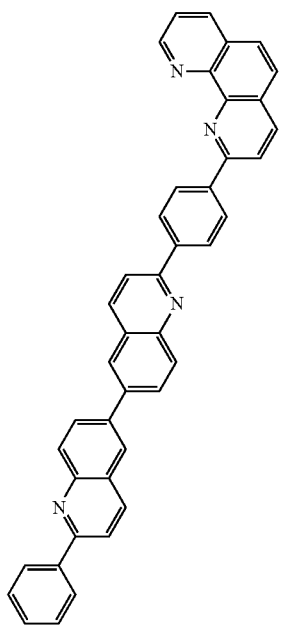
250
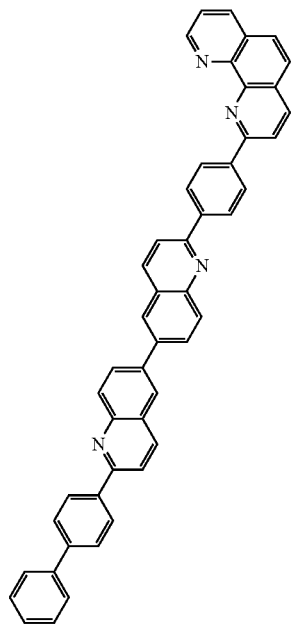
372
-continued
251
252
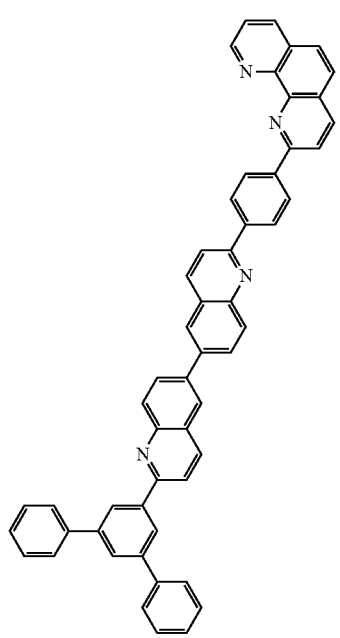

253
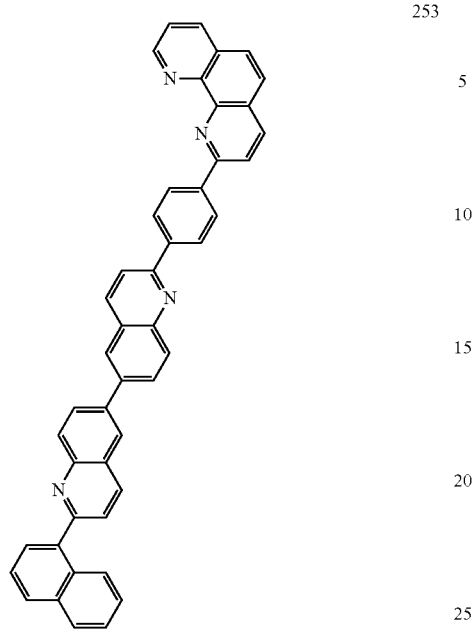
254
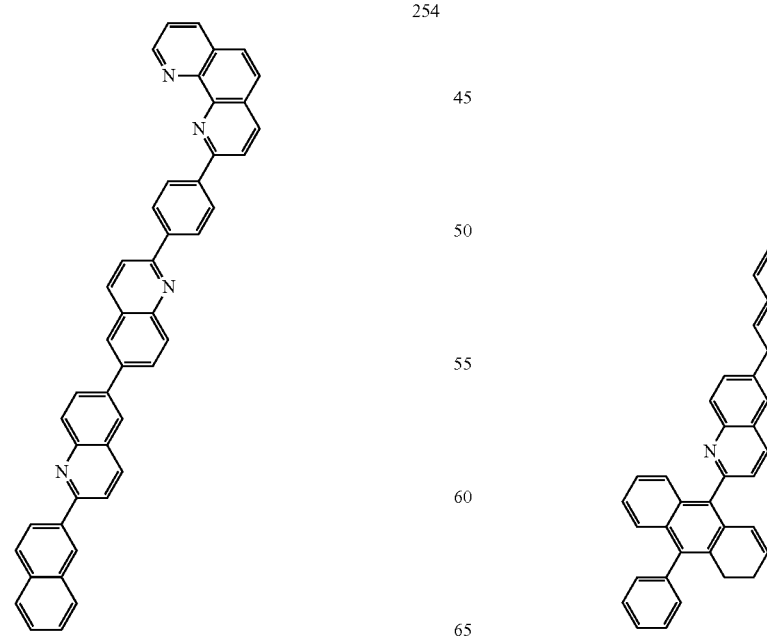
255
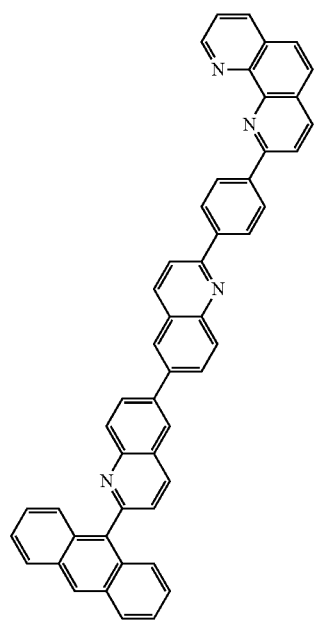
256

375
-continued
257
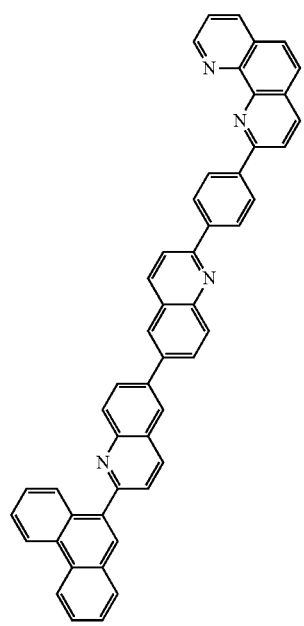
258
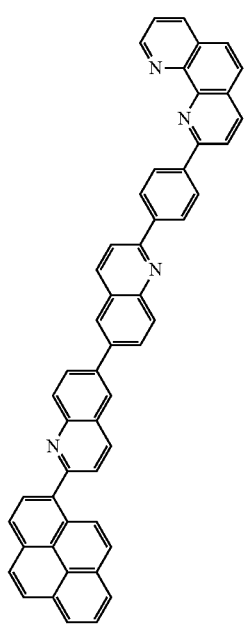
376
-continued
259
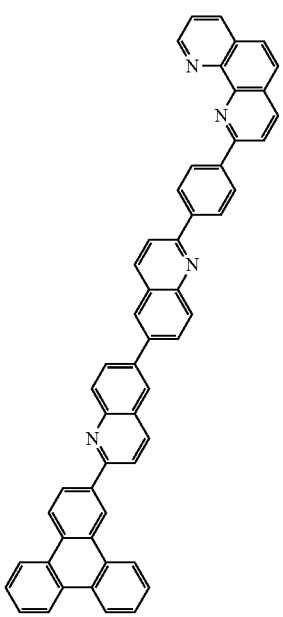
260
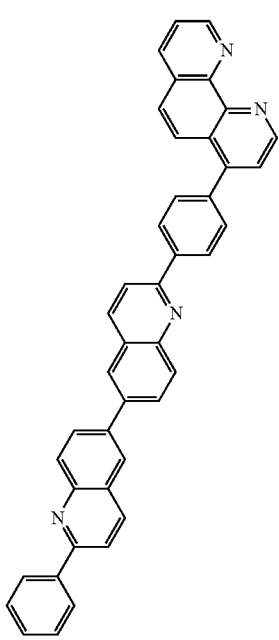

261 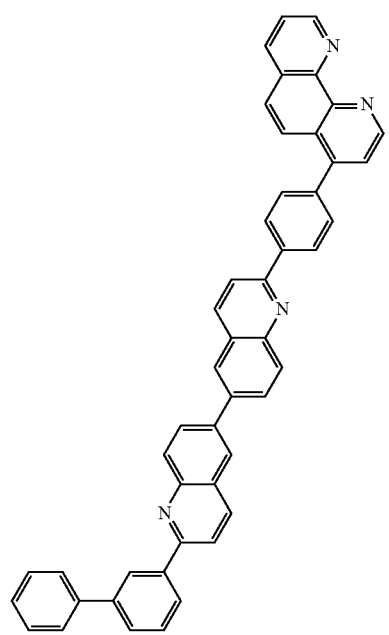
262 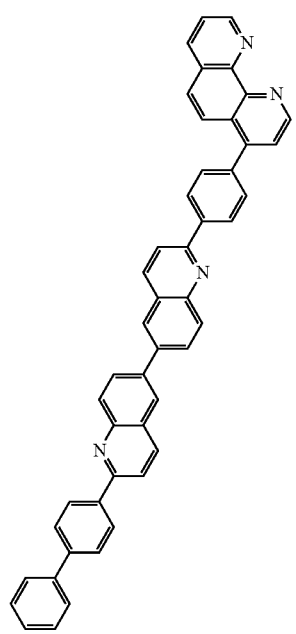
263 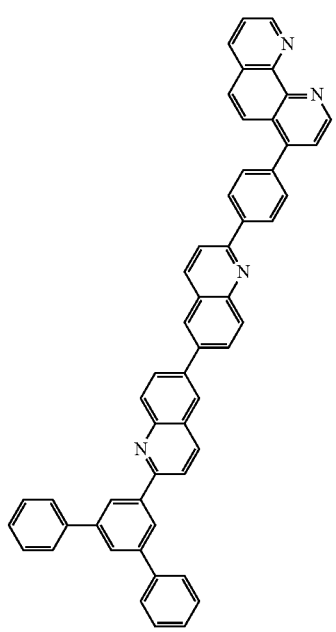
264 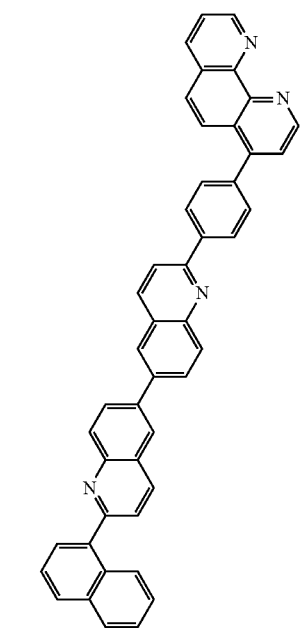

-continued
265
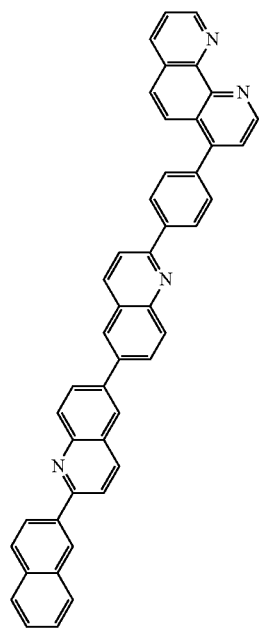
266
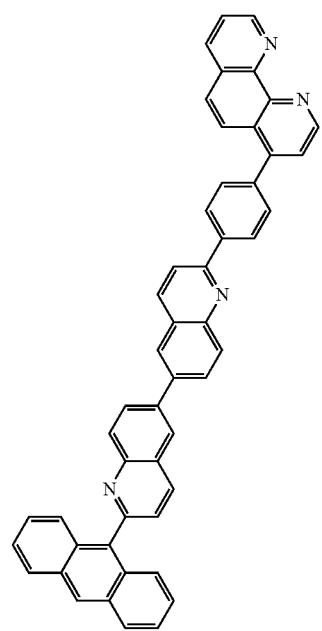
-continued
267
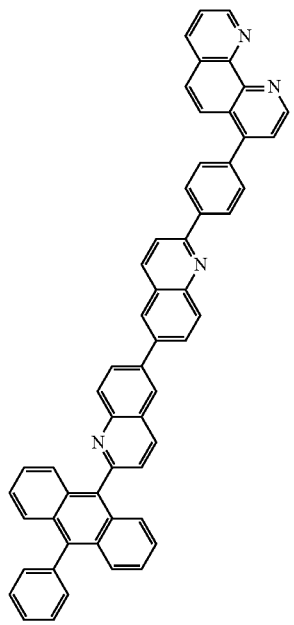
268
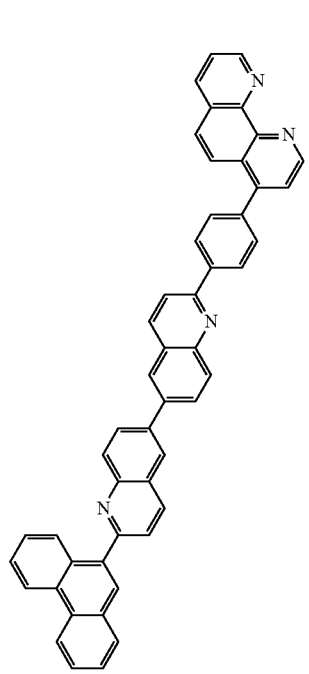

| 381 -continued | 382 -continued |
|---|---|
| 269 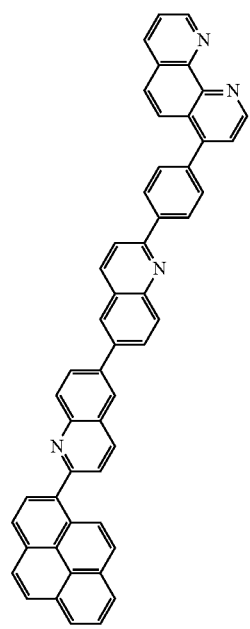 | 271 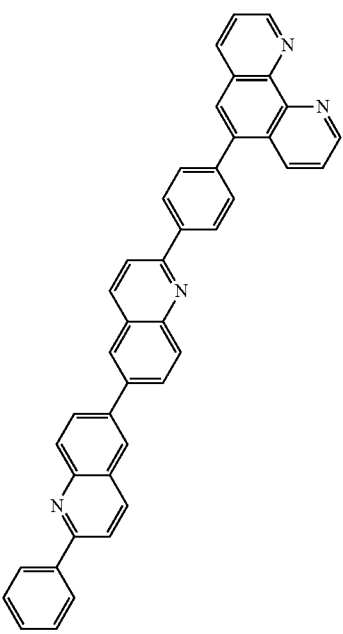 |
| 270 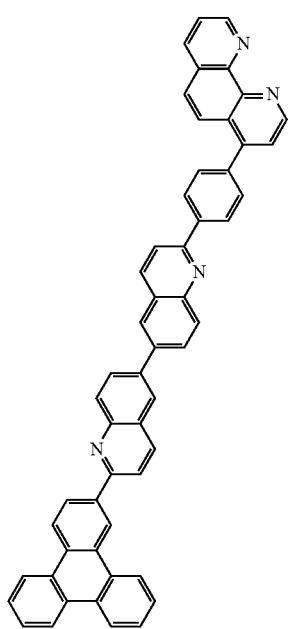 | 272 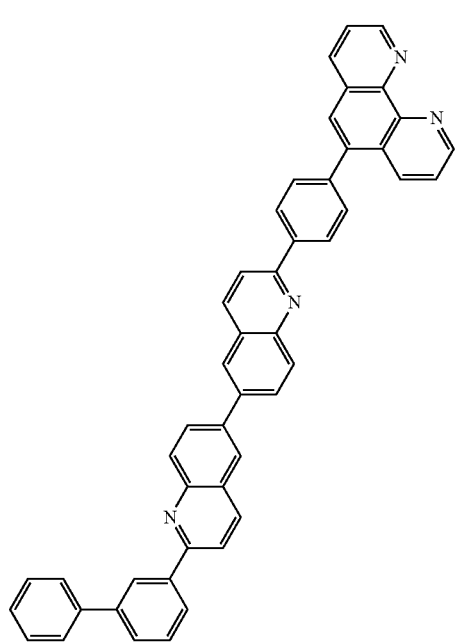 |

273
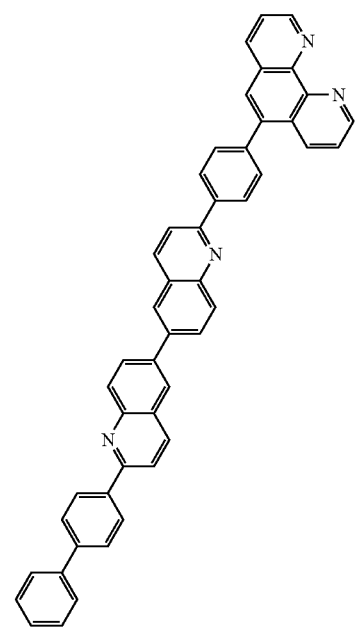
275
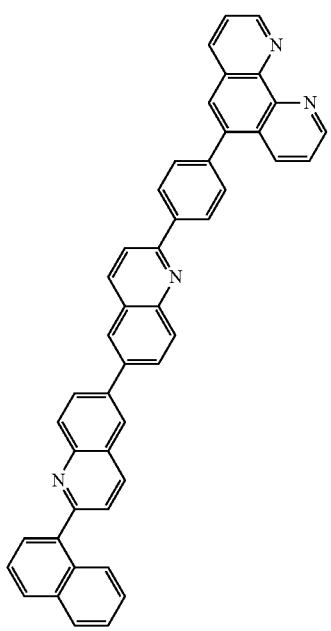
274
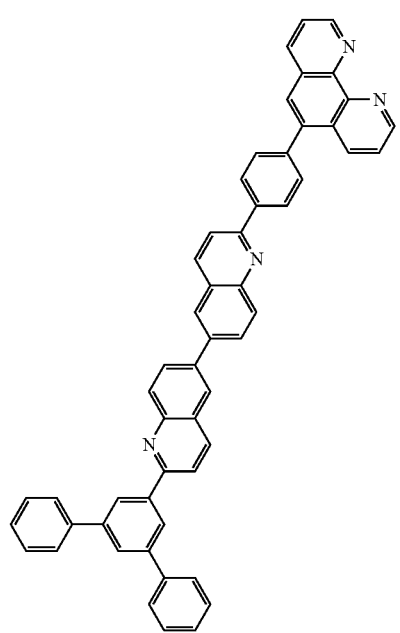
276

277
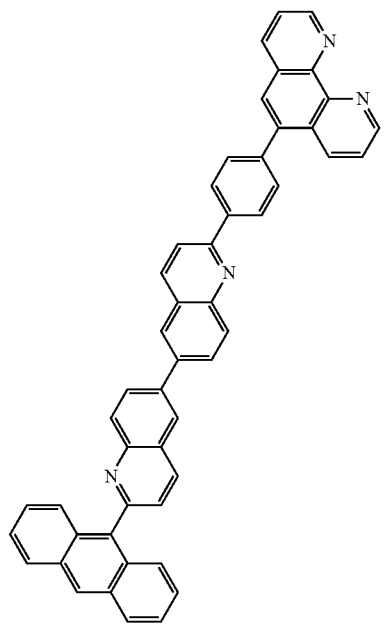
278
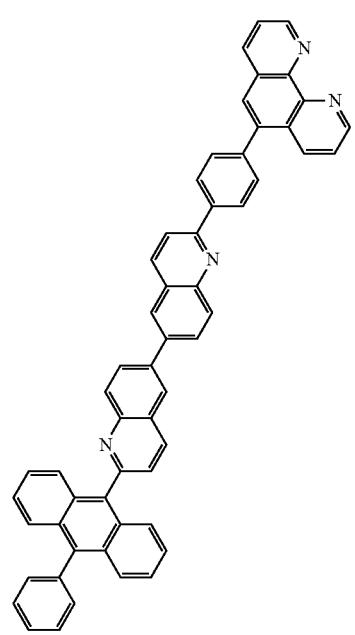
279
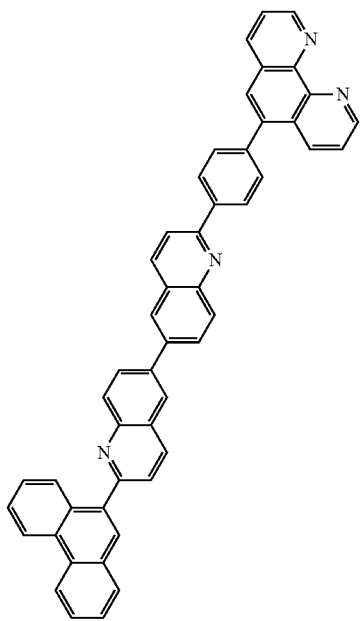
280
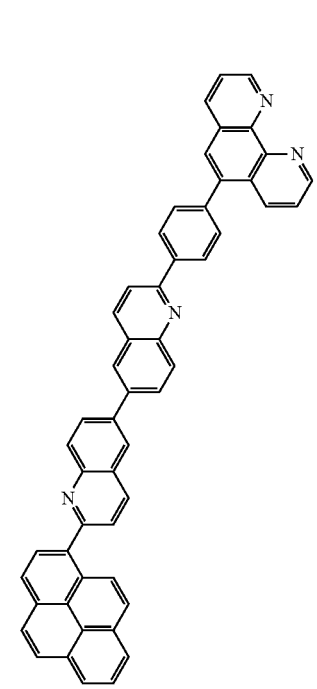

387
-continued
388
-continued
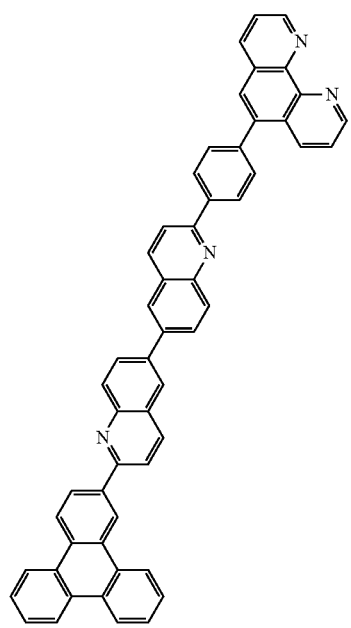
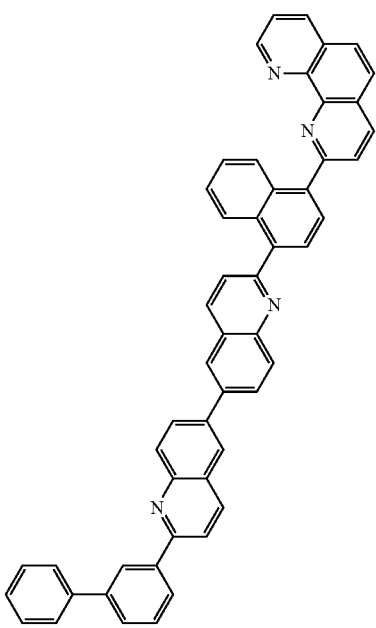

389
-continued
285
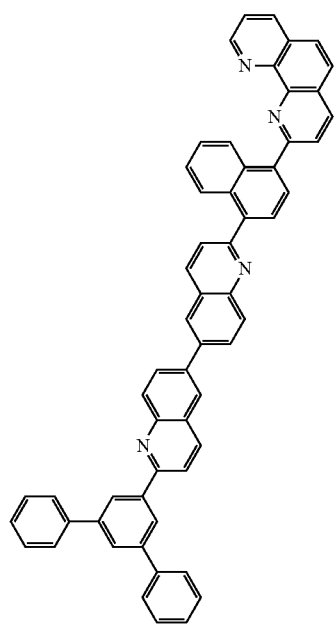
286
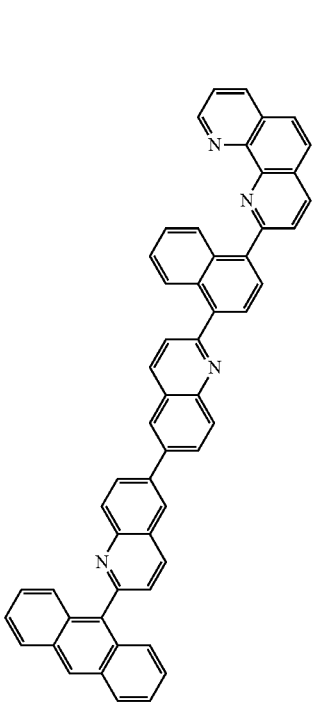
390
-continued
287
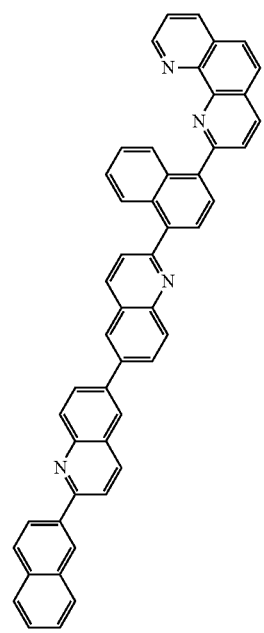
288

391
-continued
392
-continued
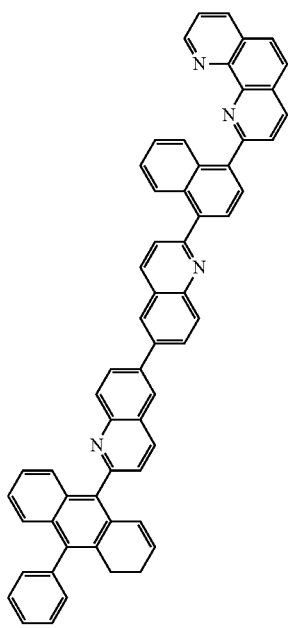
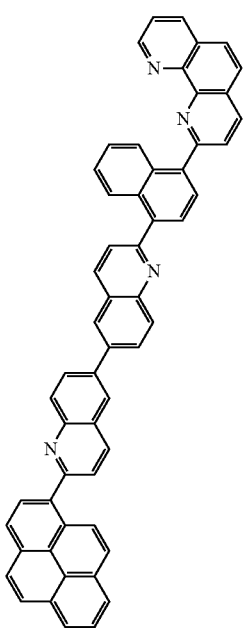

393
-continued
294
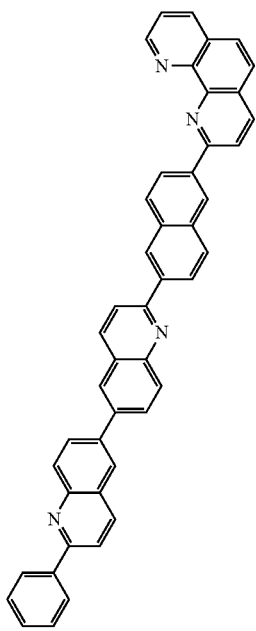
293
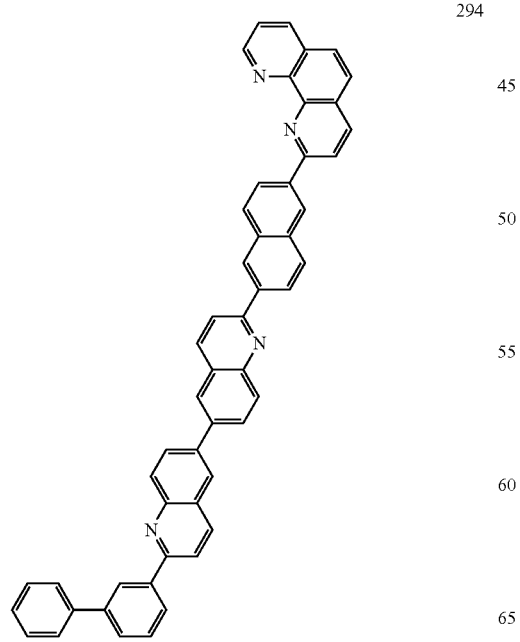
394
-continued
295
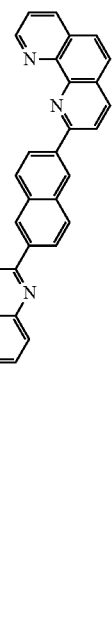
296
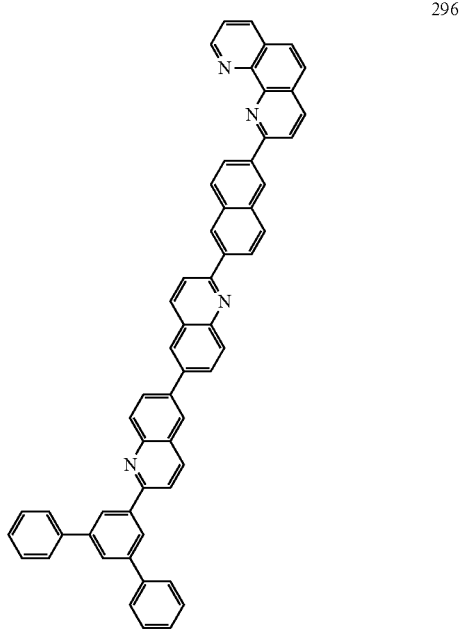

395
-continued
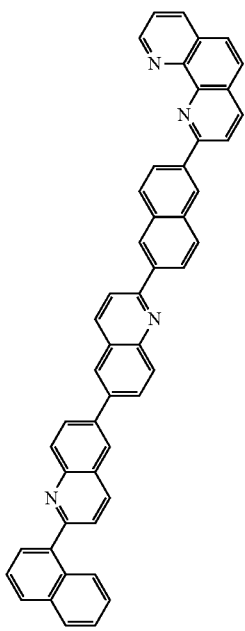
297
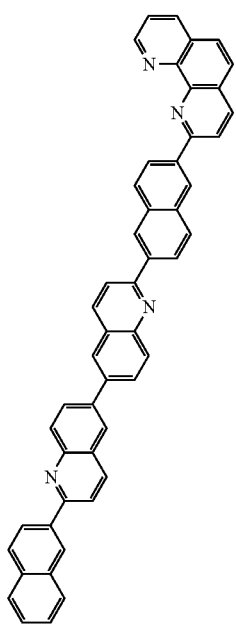
298
396
-continued
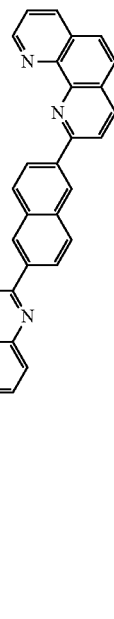
299
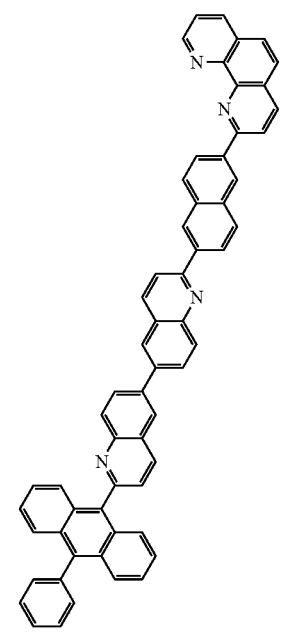
300

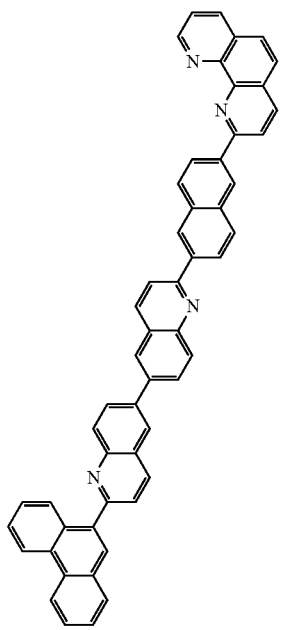
301
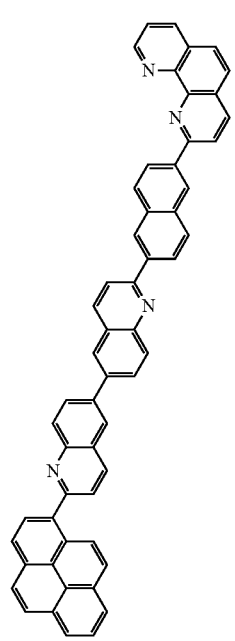
302
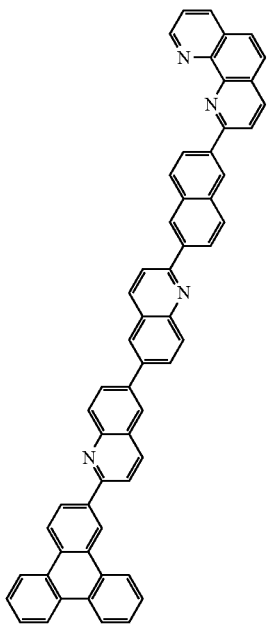
303
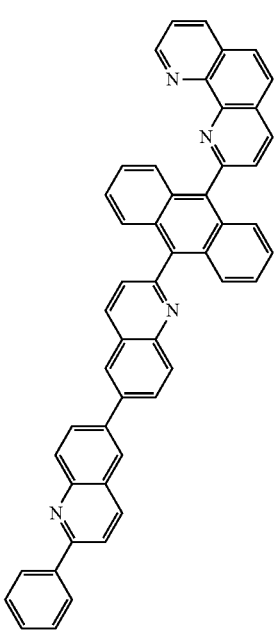
304

399
-continued
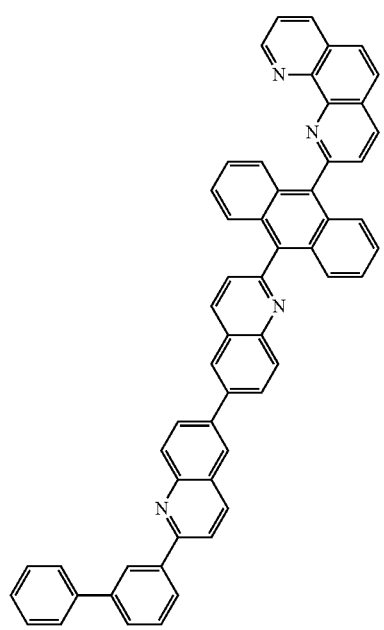
305
306
400
-continued
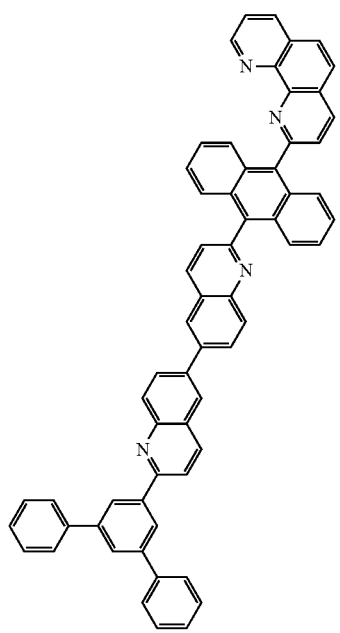
307
308

401
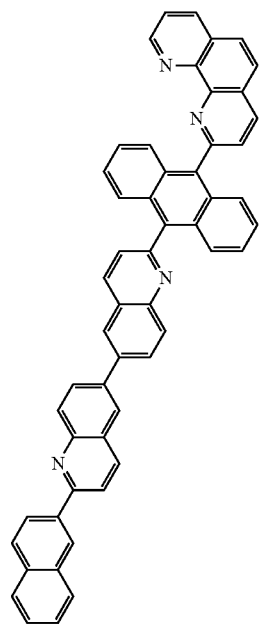
402
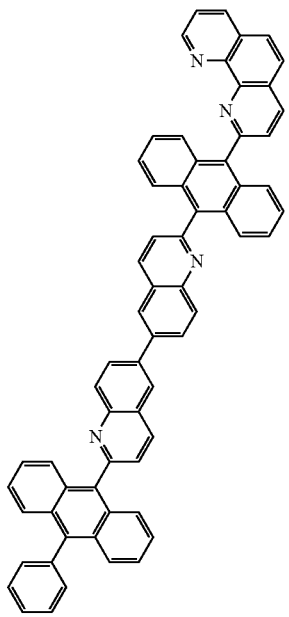

313
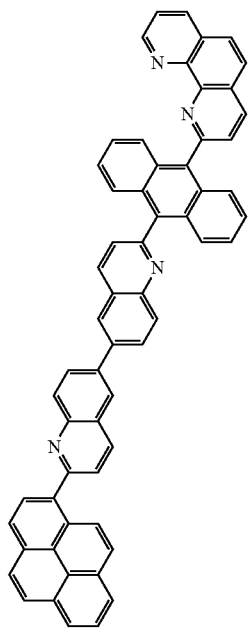
314
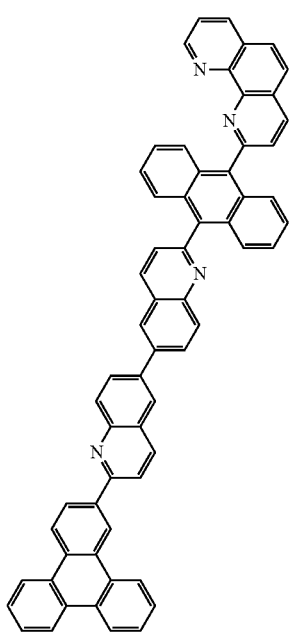
315
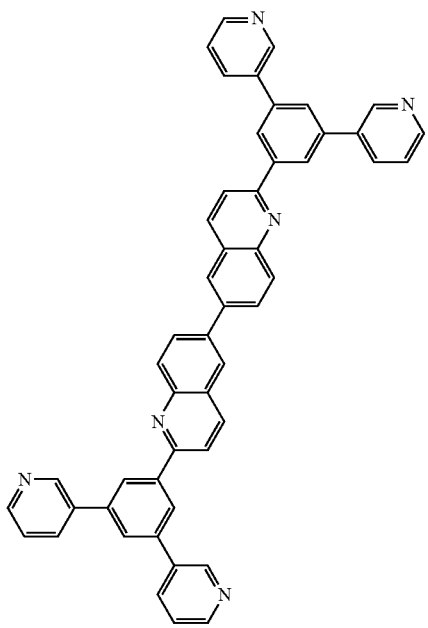
316
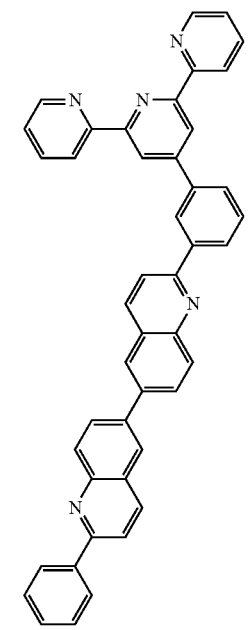

405
-continued
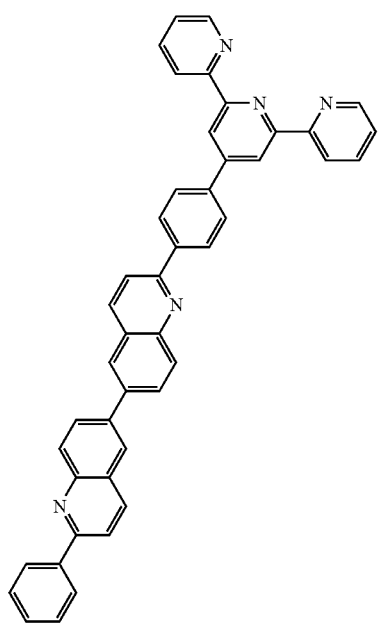
317
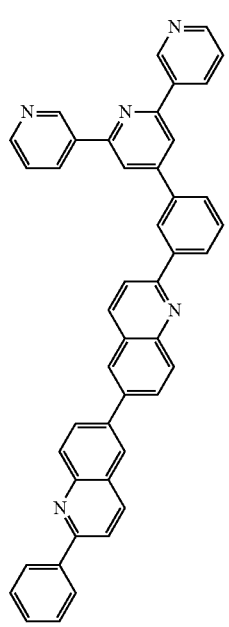
318
406
-continued
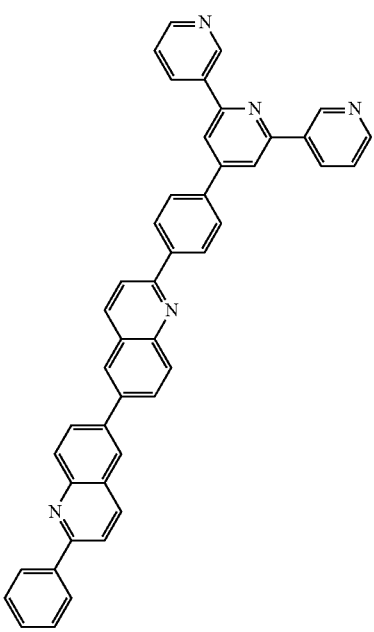
319
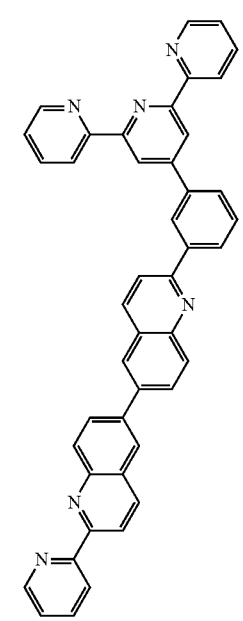
320

407
-continued
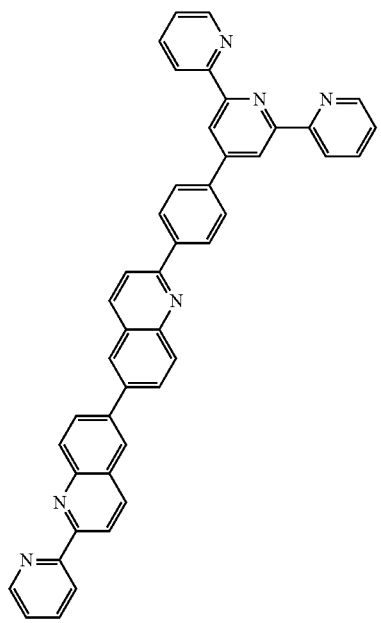
321
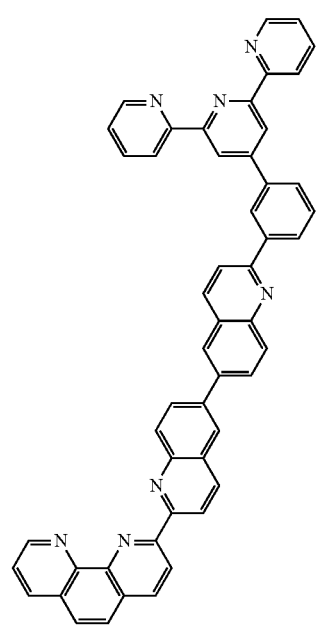
322
408
-continued
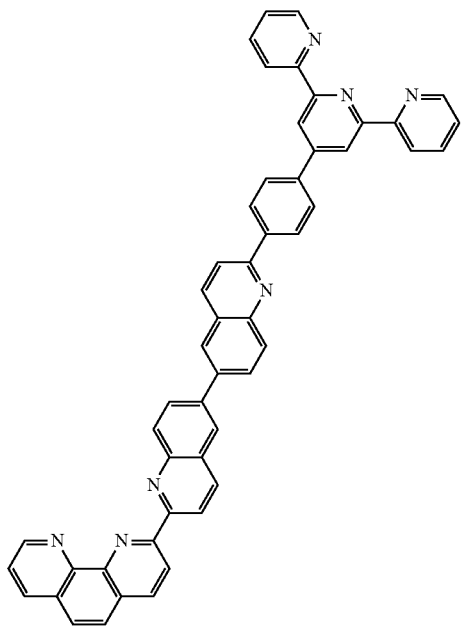
323
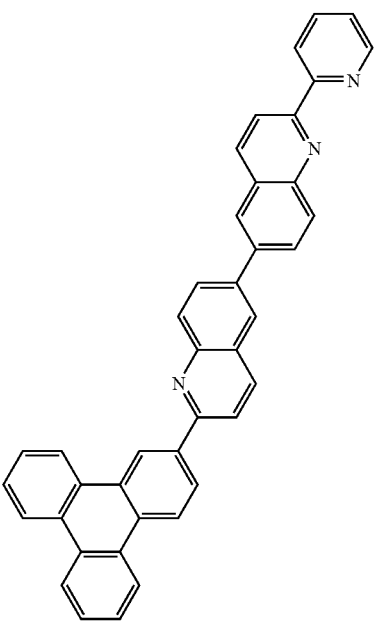
324

409
-continued

325

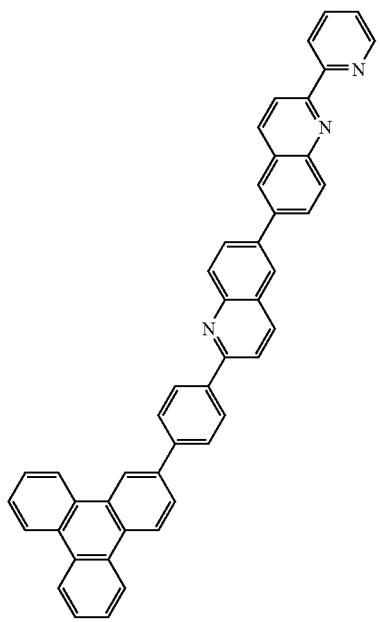

326

410
-continued

327

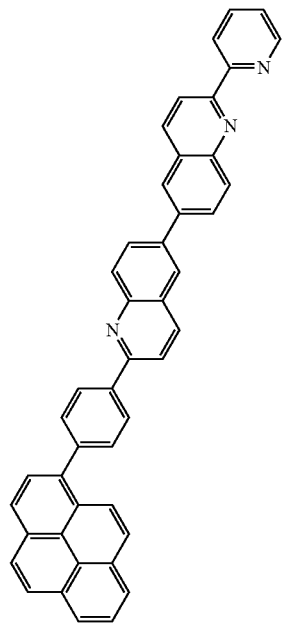

3. An organic light emitting device comprising:
 a positive electrode;
 a negative electrode; and
 an organic material layer having one or more layers disposed between the positive electrode and the negative electrode,
 wherein one or more layers of the organic material layer comprise the hetero-cyclic compound of claim 1.

4. The organic light emitting device of claim 3, wherein the organic material layer comprises at least one layer of a hole blocking layer, an electron injection layer, an electron transferring layer, an electron transporting layer, and a charge producing layer, and at least one layer of the hole blocking layer, the electron injection layer, the electron transferring layer, the electron transporting layer, and the charge producing layer comprises the hetero-cyclic compound.

5. The organic light emitting device of claim 3, wherein the organic material layer comprises a light emitting layer, and the light emitting layer comprises the hetero-cyclic compound.

6. The organic light emitting device of claim 3, wherein the organic material layer comprises one or more layers of a hole injection layer, a hole transporting layer, and a layer which injects and transports holes simultaneously, and one layer of the layers comprises the hetero-cyclic compound.

* * * * *